(12) United States Patent
Christensen et al.

(10) Patent No.: US 9,994,646 B2
(45) Date of Patent: Jun. 12, 2018

(54) COILED COIL AND/OR TETHER CONTAINING PROTEIN COMPLEXES AND USES THEREOF

(71) Applicant: Genentech, Inc., South San Francisco, CA (US)

(72) Inventors: Erin H. Christensen, Tiburon, CA (US); Dan L. Eaton, San Rafael, CA (US); Andrew C. Vendel, San Mateo, CA (US); Bernd Wranik, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days. days.

(21) Appl. No.: 14/735,024

(22) Filed: Jun. 9, 2015

(65) Prior Publication Data

US 2016/0002356 A1    Jan. 7, 2016

Related U.S. Application Data

(62) Division of application No. 13/496,696, filed as application No. PCT/US2010/002546 on Sep. 16, 2010.

(60) Provisional application No. 61/243,105, filed on Sep. 16, 2009, provisional application No. 61/266,992, filed on Dec. 4, 2009.

(51) Int. Cl.
    C07K 16/46    (2006.01)
    C07K 16/28    (2006.01)
    C07K 16/32    (2006.01)

(52) U.S. Cl.
    CPC .......... *C07K 16/468* (2013.01); *C07K 16/283* (2013.01); *C07K 16/2863* (2013.01); *C07K 16/32* (2013.01); *C07K 2317/31* (2013.01); *C07K 2317/51* (2013.01); *C07K 2317/53* (2013.01); *C07K 2317/73* (2013.01); *C07K 2317/92* (2013.01); *C07K 2319/00* (2013.01); *C07K 2319/73* (2013.01)

(58) Field of Classification Search
    CPC ... C07K 16/00–16/468; C07K 2317/31; C07K 2317/60; C07K 2317/62; C07K 2317/64; C07K 2316/00–2316/96; C07K 2319/50; C07K 2319/73
    See application file for complete search history.

(56) References Cited

U.S. PATENT DOCUMENTS

| | | | |
|---|---|---|---|
| 3,773,919 A | 11/1973 | Boswell et al. |
| 3,896,111 A | 7/1975 | Kupchan et al. |
| 4,120,649 A | 10/1978 | Schechter |
| 4,137,230 A | 1/1979 | Hashimoto |
| 4,150,149 A | 4/1979 | Wolfsen et al. |
| 4,151,042 A | 4/1979 | Higashide et al. |
| 4,248,870 A | 2/1981 | Miyashita et al. |
| 4,256,746 A | 3/1981 | Miyashlia et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,544 A | 11/1982 | Goldberg |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,419,446 A | 12/1983 | Howley et al. |
| 4,424,219 A | 1/1984 | Hashimoto et al. |
| 4,444,744 A | 4/1984 | Goldenberg |
| 4,450,254 A | 5/1984 | Isley et al. |
| 4,560,655 A | 12/1985 | Baker |
| 4,601,978 A | 7/1986 | Karin |
| 4,657,866 A | 4/1987 | Kumar |
| 4,665,077 A | 5/1987 | Stringfellow et al. |
| 4,737,456 A | 4/1988 | Weng et al. |
| 4,767,704 A | 8/1988 | Cleveland et al. |
| 4,816,567 A | 3/1989 | Cabilly et al. |
| 4,927,762 A | 5/1990 | Darfler |
| 4,948,882 A | 8/1990 | Ruth |
| 4,965,199 A | 10/1990 | Capon et al. |
| 4,975,278 A | 12/1990 | Senter et al. |
| 5,053,394 A | 10/1991 | Ellestad et al. |

(Continued)

FOREIGN PATENT DOCUMENTS

| | | |
|---|---|---|
| CN | 1176659 A | 3/1993 |
| CN | 1173878 A | 2/1998 |

(Continued)

OTHER PUBLICATIONS

Chang et al. Proc. Nat'l Acad. Sci. 1994 91:11408-12.*
Tso et al., J Hematother. 1995; 4:389-94.*
Arie et al. (Jan. 2001). "Chaperone function of FkpA, a heat shock prolyl isomerase, in the periplasm of *Escherichia coli*," *Mol. Microbiol.* 39(1):199-210.
Arndt et al. (1998) "Factors influencing the dimer to monomer transition of an antibody single-chain Fv fragment," Biochemistry, 15;37(37):12918-26.
Arndt, K.M. et al. (Sep. 7, 2001). "Helix-stabilized Fv (hsFv) antibody fragments: substituting the constant domains of a Fab fragment for a heterodimeric coiled-coil domain," *J. Mol. Biology* 312(1):221-228.

(Continued)

*Primary Examiner* — Jessica H Roark
(74) *Attorney, Agent, or Firm* — Morrison & Foerster LLP

(57) ABSTRACT

The invention provides engineered protein complexes constructed using a coiled coil and/or a tether and methods for making, using, and purifying such complexes, such as multispecific antibodies or other multispecific Fc containing complexes.

50 Claims, 58 Drawing Sheets

(56) References Cited

U.S. PATENT DOCUMENTS

| | | |
|---|---|---|
| 5,114,721 A | 5/1992 | Cohen et al. |
| 5,122,469 A | 6/1992 | Mather et al. |
| 5,143,844 A | 9/1992 | Abrahmsen et al. |
| 5,202,238 A | 4/1993 | Fell, Jr. et al. |
| 5,204,244 A | 4/1993 | Fell et al. |
| 5,208,020 A | 5/1993 | Chari et al. |
| 5,264,365 A | 11/1993 | Georgiou et al. |
| 5,362,852 A | 11/1994 | Geoghegan |
| 5,416,064 A | 5/1995 | Chari et al. |
| 5,451,463 A | 9/1995 | Nelson et al. |
| 5,500,362 A | 3/1996 | Robinson et al. |
| 5,508,192 A | 4/1996 | Georgiou et al. |
| 5,519,142 A | 5/1996 | Hoess et al. |
| 5,541,313 A | 6/1996 | Ruth |
| 5,532,142 A | 7/1996 | Johnston et al. |
| 5,571,894 A | 11/1996 | Wels et al. |
| 5,574,141 A | 11/1996 | Seliger et al. |
| 5,585,481 A | 12/1996 | Arnold, Jr. et al. |
| 5,587,458 A | 12/1996 | King et al. |
| 5,591,828 A | 1/1997 | Bosslet et al. |
| 5,624,821 A | 4/1997 | Winter et al. |
| 5,635,483 A | 6/1997 | Pettit et al. |
| 5,639,635 A | 6/1997 | Joly et al. |
| 5,641,870 A | 6/1997 | Rinderknecht et al. |
| 5,648,237 A | 7/1997 | Carter |
| 5,648,260 A | 7/1997 | Winter et al. |
| 5,663,149 A | 9/1997 | Pettit et al. |
| 5,712,374 A | 1/1998 | Kuntsmann et al. |
| 5,714,586 A | 2/1998 | Kuntsmann et al. |
| 5,731,168 A | 3/1998 | Carter et al. |
| 5,739,113 A | 4/1998 | Lee |
| 5,739,116 A | 4/1998 | Hamann et al. |
| 5,747,654 A | 5/1998 | Pastan et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,798,229 A | 8/1998 | Strittmatter et al. |
| 5,817,786 A | 10/1998 | Ruth |
| 5,821,333 A | 10/1998 | Carter et al. |
| 5,821,337 A | 10/1998 | Carter et al. |
| 5,824,483 A | 10/1998 | Houston et al. |
| 5,840,523 A | 11/1998 | Simmons et al. |
| 5,849,879 A | 12/1998 | Nguyen et al. |
| 5,869,046 A | 2/1999 | Presta et al. |
| 5,877,296 A | 3/1999 | Hamann et al. |
| 5,885,793 A | 3/1999 | Griffiths et al. |
| 5,932,448 A | 8/1999 | Tso et al. |
| 5,959,083 A | 9/1999 | Bosslet et al. |
| 5,959,177 A | 9/1999 | Hein et al. |
| 6,027,888 A | 2/2000 | Georgiou et al. |
| 6,040,498 A | 3/2000 | Stomp et al. |
| 6,083,715 A | 7/2000 | Georgiou et al. |
| 6,136,564 A | 10/2000 | Kopetzki |
| 6,153,190 A | 11/2000 | Young et al. |
| 6,166,185 A | 12/2000 | Davis et al. |
| 6,171,586 B1 | 1/2001 | Lam et al. |
| 6,194,551 B1 | 2/2001 | Idusogie et al. |
| 6,239,259 B1 | 5/2001 | Davis et al. |
| 6,248,516 B1 | 6/2001 | Winter et al. |
| 6,267,958 B1 | 7/2001 | Andya et al. |
| 6,350,860 B1 | 2/2002 | Buyse et al. |
| 6,417,429 B1 | 7/2002 | Hein et al. |
| 6,420,548 B1 | 7/2002 | Vezina et al. |
| 6,511,663 B1 | 1/2003 | King et al. |
| 6,531,581 B1 | 3/2003 | Nardone et al. |
| 6,534,628 B1 | 3/2003 | Nilsson et al. |
| 6,558,672 B1 | 5/2003 | Pastan et al. |
| 6,586,207 B2 | 7/2003 | Tirrell et al. |
| 6,602,684 B1 | 8/2003 | Umana et al. |
| 6,630,579 B2 | 10/2003 | Chari et al. |
| 6,660,843 B1 | 12/2003 | Feige et al. |
| 6,737,056 B1 | 5/2004 | Presta |
| 6,833,441 B2 | 12/2004 | Wang et al. |
| 6,835,809 B1 | 12/2004 | Liu et al. |
| 6,897,044 B1 | 5/2005 | Braslawsky et al. |
| 6,919,426 B2 | 7/2005 | Boone et al. |
| 6,946,292 B2 | 9/2005 | Kanda et al. |
| 6,982,321 B2 | 1/2006 | Winter |
| 7,125,978 B1 | 10/2006 | Vezina et al. |
| 7,129,330 B1 | 10/2006 | Little et al. |
| 7,355,008 B2 | 4/2008 | Stavenhagen et al. |
| 7,381,408 B2 | 6/2008 | Mezo et al. |
| 7,498,298 B2 | 3/2009 | Doronina et al. |
| 7,507,796 B2 | 3/2009 | Little et al. |
| 7,642,228 B2 | 1/2010 | Carter et al. |
| 7,651,688 B2 | 1/2010 | Hanai et al. |
| 7,666,622 B2 | 2/2010 | Sharma et al. |
| 7,695,936 B2 | 4/2010 | Carter et al. |
| 7,919,257 B2 | 4/2011 | Hoogenboom et al. |
| 7,942,042 B2 | 5/2011 | Kawakita et al. |
| 8,216,805 B2 | 7/2012 | Carter et al. |
| 8,227,577 B2 | 7/2012 | Klein et al. |
| 8,242,247 B2 | 8/2012 | Klein et al. |
| 8,268,314 B2 | 9/2012 | Baehner et al. |
| 8,304,713 B2 | 11/2012 | Pradel |
| 8,309,300 B2 | 11/2012 | Jununtula et al. |
| 8,796,424 B2 | 8/2014 | Croasdale et al. |
| 8,871,912 B2 | 10/2014 | Davis et al. |
| 9,688,758 B2 | 6/2017 | Wranik et al. |
| 2002/0051986 A1 | 5/2002 | Baez et al. |
| 2002/0155537 A1 | 10/2002 | Carter et al. |
| 2003/0027751 A1 | 2/2003 | Kovesdi et al. |
| 2003/0124129 A1 | 7/2003 | Oliner |
| 2003/0152987 A1 | 8/2003 | Cohen et al. |
| 2003/0157091 A1* | 8/2003 | Hoogenboom .. A61K 47/48538 424/130.1 |
| 2003/0170230 A1 | 9/2003 | Caterer et al. |
| 2003/0176352 A1 | 9/2003 | Min et al. |
| 2003/0195156 A1 | 10/2003 | Min et al. |
| 2003/0219817 A1 | 11/2003 | Zhu et al. |
| 2003/0229023 A1 | 12/2003 | Oliner et al. |
| 2003/0236193 A1 | 12/2003 | Oliner et al. |
| 2004/0018557 A1 | 1/2004 | Qu et al. |
| 2004/0033561 A1 | 2/2004 | O'Keefe et al. |
| 2004/0038339 A1 | 2/2004 | Kufer et al. |
| 2004/0214988 A1 | 10/2004 | Tirrell et al. |
| 2004/0220388 A1 | 11/2004 | Metens et al. |
| 2004/0224372 A1 | 11/2004 | Li et al. |
| 2005/0054048 A1 | 3/2005 | Grasso et al. |
| 2005/0064509 A1 | 4/2005 | Bradbury et al. |
| 2005/0079170 A1 | 4/2005 | Le Gall et al. |
| 2005/0100543 A1 | 5/2005 | Hansen et al. |
| 2005/0152894 A1 | 7/2005 | Krummen et al. |
| 2005/0163782 A1 | 7/2005 | Glaser et al. |
| 2005/0169933 A1 | 8/2005 | Steeves et al. |
| 2005/0186208 A1 | 8/2005 | Fyfe et al. |
| 2005/0214833 A1 | 9/2005 | Carter et al. |
| 2005/0238649 A1 | 10/2005 | Doronina et al. |
| 2005/0249722 A1 | 11/2005 | Beliard et al. |
| 2005/0260186 A1 | 11/2005 | Bookbinder et al. |
| 2006/0008845 A1 | 1/2006 | Kondejewski et al. |
| 2006/0063921 A1 | 3/2006 | Moulder et al. |
| 2006/0104968 A1 | 5/2006 | Bookbinder et al. |
| 2006/0122370 A1 | 6/2006 | Oliner et al. |
| 2006/0134709 A1 | 6/2006 | Stavenhagen et al. |
| 2006/0160184 A1 | 7/2006 | Hoogenboom et al. |
| 2006/0280747 A1 | 12/2006 | Fuh et al. |
| 2007/0014794 A1 | 1/2007 | Carter et al. |
| 2007/0071675 A1 | 3/2007 | Wu et al. |
| 2007/0071742 A1 | 3/2007 | Fang et al. |
| 2007/0141065 A1 | 6/2007 | Fuh et al. |
| 2007/0178552 A1 | 8/2007 | Arathoon et al. |
| 2007/0196274 A1 | 8/2007 | Sun |
| 2007/0269369 A1 | 11/2007 | Gegg et al. |
| 2007/0274985 A1 | 11/2007 | Dubel et al. |
| 2007/0274998 A1 | 11/2007 | Uktu |
| 2007/0287170 A1 | 12/2007 | Davis et al. |
| 2008/0044834 A1 | 2/2008 | Heyduk |
| 2008/0063641 A1 | 3/2008 | Huang et al. |
| 2008/0187954 A1* | 8/2008 | Kallmeier .............. C07K 16/00 435/68.1 |

(56) References Cited

U.S. PATENT DOCUMENTS

| | | |
|---|---|---|
| 2008/0280778 A1 | 11/2008 | Urdea |
| 2009/0023811 A1 | 1/2009 | Biadatti et al. |
| 2009/0117105 A1 | 5/2009 | Hu et al. |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0194692 A1 | 9/2009 | Kobaru |
| 2009/0232811 A1 | 9/2009 | Klein et al. |
| 2010/0021943 A1 | 1/2010 | An et al. |
| 2010/0062436 A1 | 3/2010 | Jarosch et al. |
| 2010/0081796 A1 | 4/2010 | Brinkman et al. |
| 2010/0111967 A1 | 5/2010 | Baehner et al. |
| 2010/0254989 A1 | 10/2010 | Bossenmaier et al. |
| 2010/0256338 A1 | 10/2010 | Brinkmann et al. |
| 2010/0256339 A1 | 10/2010 | Bossenmaier et al. |
| 2010/0256340 A1 | 10/2010 | Brinkmann et al. |
| 2010/0266617 A1 | 10/2010 | Carven et al. |
| 2010/0316645 A1 | 12/2010 | Imhof-Jung et al. |
| 2010/0322934 A1 | 12/2010 | Imhof-Jung et al. |
| 2010/0322935 A1 | 12/2010 | Croasdale et al. |
| 2011/0054151 A1 | 3/2011 | Lazar et al. |
| 2011/0243966 A1 | 10/2011 | Farrington et al. |
| 2012/0149879 A1 | 6/2012 | Brinkmann et al. |
| 2012/0164726 A1 | 6/2012 | Klein et al. |
| 2012/0184718 A1 | 7/2012 | Bruenker et al. |
| 2012/0225071 A1 | 9/2012 | Klein et al. |
| 2012/0237506 A1 | 9/2012 | Bossenmaier et al. |
| 2012/0237507 A1 | 9/2012 | Bossenmaier et al. |
| 2012/0302737 A1 | 11/2012 | Christensen et al. |
| 2012/0321627 A1 | 12/2012 | Baehner et al. |
| 2013/0022601 A1 | 1/2013 | Brinkmann et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0156772 A1 | 6/2013 | Bossenmaier et al. |
| 2013/0266568 A1 | 10/2013 | Brinkmann et al. |
| 2013/0267686 A1 | 10/2013 | Brinkmann et al. |
| 2013/0273054 A1 | 10/2013 | Bossenmaier et al. |
| 2013/0288267 A1 | 10/2013 | Gerg et al. |
| 2013/0344094 A1 | 12/2013 | Gerg et al. |
| 2014/0249296 A1 | 9/2014 | Ploegh |
| 2014/0294810 A1 | 10/2014 | Lowman et al. |
| 2015/0004166 A1 | 1/2015 | Baehner et al. |
| 2015/0030598 A1 | 1/2015 | Croasdale et al. |
| 2015/0133638 A1 | 5/2015 | Wranik et al. |
| 2015/0232541 A1 | 8/2015 | Fenn et al. |
| 2015/0232560 A1 | 8/2015 | Heindl et al. |
| 2015/0232561 A1 | 8/2015 | Fenn et al. |
| 2015/0291704 A1 | 10/2015 | Beck |

FOREIGN PATENT DOCUMENTS

| | | |
|---|---|---|
| CN | 1232039 A | 10/1999 |
| CN | 1603345 A | 4/2005 |
| CN | 101037671 A | 9/2007 |
| CN | 101052653 A | 10/2007 |
| CN | 101065151 A | 10/2007 |
| CN | 101205255 A | 6/2008 |
| CN | 101218251 A | 7/2008 |
| CN | 101355966 A | 1/2009 |
| CN | 101802197 A | 11/2010 |
| EP | 0 292 128 A1 | 11/1988 |
| EP | 0 307 434 B1 | 3/1989 |
| EP | 0 307 434 B2 | 3/1989 |
| EP | 0 313 219 A2 | 4/1989 |
| EP | 0 339 217 A2 | 11/1989 |
| EP | 0 340 1099 A2 | 11/1989 |
| EP | 0 404 097 A2 | 12/1990 |
| EP | 0 423 839 A2 | 4/1991 |
| EP | 0 425235 A2 | 5/1991 |
| EP | 0 523 978 A1 | 1/1993 |
| EP | 0 618 192 A1 | 10/1994 |
| EP | 0 637 593 A1 | 2/1995 |
| EP | 0 786 468 A2 | 7/1997 |
| EP | 1 074 563 A1 | 2/2001 |
| EP | 1 186 613 A1 | 3/2002 |
| EP | 1 391 213 A1 | 2/2004 |
| EP | 1 431 298 A1 | 6/2004 |
| EP | 1 538 221 A1 | 6/2005 |
| EP | 1 870 459 A1 | 12/2007 |
| EP | 2 050 764 A1 | 4/2009 |
| EP | 2 443 154 B1 | 4/2012 |
| JP | 7-501698 A | 2/1995 |
| JP | 2008-531049 A | 8/2008 |
| RU | 2005/124281 A | 1/2006 |
| RU | 2295537 C2 | 3/2007 |
| WO | WO-87/00195 A1 | 1/1987 |
| WO | WO-89/02439 A1 | 3/1989 |
| WO | WO-89/02931 A1 | 4/1989 |
| WO | WO-89/12642 A1 | 12/1989 |
| WO | WO-90/03430 A1 | 4/1990 |
| WO | WO-90/08156 A1 | 7/1990 |
| WO | WO-90/08187 A1 | 7/1990 |
| WO | WO-90/11294 A1 | 10/1990 |
| WO | WO-91/01133 A1 | 2/1991 |
| WO | WO-91/06305 A1 | 5/1991 |
| WO | WO-92/01047 A1 | 1/1992 |
| WO | WO-92/04053 A1 | 3/1992 |
| WO | WO-92/11388 A1 | 7/1992 |
| WO | WO-93/01161 A1 | 1/1993 |
| WO | WO-93/05060 A1 | 3/1993 |
| WO | WO-93/06217 A1 | 4/1993 |
| WO | WO-93/11161 A1 | 6/1993 |
| WO | WO-93/11162 A1 | 6/1993 |
| WO | WO-93/16185 A2 | 8/1993 |
| WO | WO-93/16185 A3 | 8/1993 |
| WO | WO-93/21232 A1 | 10/1993 |
| WO | WO-94/04550 A1 | 3/1994 |
| WO | WO-94/09131 A1 | 4/1994 |
| WO | WO-94/10202 A1 | 5/1994 |
| WO | WO-94/10308 A1 | 5/1994 |
| WO | WO-94/11026 A2 | 5/1994 |
| WO | WO-94/29350 A2 | 12/1994 |
| WO | WO-94/29350 A3 | 12/1994 |
| WO | WO-95/05399 A1 | 2/1995 |
| WO | WO-95/09917 A1 | 4/1995 |
| WO | WO-95/17886 A1 | 7/1995 |
| WO | WO-96/027011 A1 | 9/1996 |
| WO | WO-96/27612 A1 | 9/1996 |
| WO | WO-97/01580 A1 | 1/1997 |
| WO | WO-97/05156 A1 | 2/1997 |
| WO | WO-97/014719 A1 | 4/1997 |
| WO | WO-97/028267 A1 | 8/1997 |
| WO | WO-97/028267 C1 | 8/1997 |
| WO | WO-97/43451 A1 | 11/1997 |
| WO | WO-98/45331 A2 | 10/1998 |
| WO | WO-98/45331 A3 | 10/1998 |
| WO | WO-98/45332 A2 | 10/1998 |
| WO | WO-98/45332 A3 | 10/1998 |
| WO | WO-98/48032 A2 | 10/1998 |
| WO | WO-98/48032 A3 | 10/1998 |
| WO | WO-98/060431 A2 | 11/1998 |
| WO | WO-99/06587 A2 | 2/1999 |
| WO | WO-99/06587 A3 | 2/1999 |
| WO | WO-99/37791 A1 | 7/1999 |
| WO | WO-99/54342 A1 | 10/1999 |
| WO | WO-1999/51642 A1 | 10/1999 |
| WO | WO-99/66951 A2 | 12/1999 |
| WO | WO-99/66951 A3 | 12/1999 |
| WO | WO-99/66951 C1 | 12/1999 |
| WO | WO-00/24770 A2 | 5/2000 |
| WO | WO-00/29004 A1 | 5/2000 |
| WO | WO-00/35956 A1 | 6/2000 |
| WO | WO-00/61739 A1 | 10/2000 |
| WO | WO-2001/042505 A2 | 6/2001 |
| WO | WO-2001/042505 A3 | 6/2001 |
| WO | WO-01/77342 A1 | 10/2001 |
| WO | WO-01/90192 A2 | 11/2001 |
| WO | WO-2001/085795 A1 | 11/2001 |
| WO | WO-02/02781 A1 | 1/2002 |
| WO | WO-02/051870 A2 | 7/2002 |
| WO | WO-02/072141 A2 | 9/2002 |
| WO | WO-02/072141 A3 | 9/2002 |

(56) References Cited

FOREIGN PATENT DOCUMENTS

| | | |
|---|---|---|
| WO | WO-02/083172 A2 | 11/2002 |
| WO | WO-02/092620 A2 | 11/2002 |
| WO | WO-02/096948 A2 | 12/2002 |
| WO | WO-03/012069 A2 | 2/2003 |
| WO | WO-03/019145 A2 | 3/2003 |
| WO | WO-03/019145 A3 | 3/2003 |
| WO | WO-03/030833 A2 | 4/2003 |
| WO | WO-03/031589 A2 | 4/2003 |
| WO | WO-03/035833 A3 | 4/2003 |
| WO | WO-03/035694 A2 | 5/2003 |
| WO | WO-03/035835 A2 | 5/2003 |
| WO | WO-03/035835 A3 | 5/2003 |
| WO | WO-03/055993 A1 | 7/2003 |
| WO | WO-03/057134 A2 | 7/2003 |
| WO | WO-03/066660 A2 | 8/2003 |
| WO | WO-03/073238 A2 | 9/2003 |
| WO | WO-03/073238 A3 | 9/2003 |
| WO | WO-03/097105 A1 | 11/2003 |
| WO | WO-03/106501 A1 | 12/2003 |
| WO | WO-2003/104249 A1 | 12/2003 |
| WO | WO-2004/032961 A1 | 4/2004 |
| WO | WO-2004/058298 A1 | 7/2004 |
| WO | WO 2004/062602 A2 | 7/2004 |
| WO | WO 2004/062602 A3 | 7/2004 |
| WO | WO-2004/065417 A2 | 8/2004 |
| WO | WO-2004/065540 A2 | 8/2004 |
| WO | WO-2004/065540 A3 | 8/2004 |
| WO | WO-2004/072117 A2 | 8/2004 |
| WO | WO-2004/072117 A3 | 8/2004 |
| WO | WO 2004/081051 A1 | 9/2004 |
| WO | WO-2004/092215 A2 | 10/2004 |
| WO | WO-2004/001025 A3 | 1/2005 |
| WO | WO-2004/004809 A3 | 1/2005 |
| WO | WO-2005/000900 A1 | 1/2005 |
| WO | WO-2005/001025 A2 | 1/2005 |
| WO | WO-2005/004809 A2 | 1/2005 |
| WO | WO-2005/005635 A2 | 1/2005 |
| WO | WO-2005/005635 A3 | 1/2005 |
| WO | WO-2005/011735 A1 | 2/2005 |
| WO | WO-2005/018572 A2 | 3/2005 |
| WO | WO-2005/018572 A3 | 3/2005 |
| WO | WO-2005/027966 A2 | 3/2005 |
| WO | WO-2005/027966 A3 | 3/2005 |
| WO | WO-2005/035572 A2 | 4/2005 |
| WO | WO-2005/035727 A2 | 4/2005 |
| WO | WO-2005/035727 A3 | 4/2005 |
| WO | WO-2005/044853 A2 | 5/2005 |
| WO | WO-2005/044853 A3 | 5/2005 |
| WO | WO-2005/044859 A2 | 5/2005 |
| WO | WO-2005/044859 A3 | 5/2005 |
| WO | WO-2005/051976 A2 | 6/2005 |
| WO | WO-2005/063816 A2 | 7/2005 |
| WO | WO-2005/063816 A3 | 7/2005 |
| WO | WO-2005/074524 A2 | 8/2005 |
| WO | WO-2005/075514 A2 | 8/2005 |
| WO | WO-2006/020258 A2 | 2/2006 |
| WO | WO-2006/020258 A3 | 2/2006 |
| WO | WO-2006/028956 A2 | 3/2006 |
| WO | WO-2006/028956 A3 | 3/2006 |
| WO | WO-2006/031370 A2 | 3/2006 |
| WO | WO-2006/031370 A3 | 3/2006 |
| WO | WO-2006/034488 A2 | 3/2006 |
| WO | WO-2006/034488 A3 | 3/2006 |
| WO | WO-2006/044908 A2 | 4/2006 |
| WO | WO-2006/044908 A3 | 4/2006 |
| WO | WO-2006/045049 A1 | 4/2006 |
| WO | WO-2006/068953 A2 | 6/2006 |
| WO | WO-2006/068953 A3 | 6/2006 |
| WO | WO-2006/082515 A2 | 8/2006 |
| WO | WO-2006/082515 A3 | 8/2006 |
| WO | WO-2006/089364 A1 | 8/2006 |
| WO | WO-2006/091209 A2 | 8/2006 |
| WO | WO-2006/091209 A3 | 8/2006 |
| WO | WO-2006/093794 A1 | 9/2006 |
| WO | WO-2006/103100 A2 | 10/2006 |
| WO | WO-2006/103100 A3 | 10/2006 |
| WO | WO-2006/113665 A2 | 10/2006 |
| WO | WO-2006/114700 A2 | 11/2006 |
| WO | WO-2006/114700 A3 | 11/2006 |
| WO | WO-2006/116260 A2 | 11/2006 |
| WO | WO-2006/116260 A3 | 11/2006 |
| WO | WO 2006/137932 A2 | 12/2006 |
| WO | WO 2006/137932 A3 | 12/2006 |
| WO | WO-2007/024715 A2 | 3/2007 |
| WO | WO-2007/031875 A2 | 3/2007 |
| WO | WO-2007/031875 A3 | 3/2007 |
| WO | WO-2007/038658 A2 | 4/2007 |
| WO | WO-2007/038658 A3 | 4/2007 |
| WO | WO-2007/044887 A2 | 4/2007 |
| WO | WO-2007/044887 A3 | 4/2007 |
| WO | WO-2007/048037 A2 | 4/2007 |
| WO | WO-2007/048037 A3 | 4/2007 |
| WO | WO-2007/059816 A1 | 5/2007 |
| WO | WO-2007/068895 A1 | 6/2007 |
| WO | WO-2007/069092 A2 | 6/2007 |
| WO | WO-2007/069092 A3 | 6/2007 |
| WO | WO-2007/084181 A2 | 7/2007 |
| WO | WO-2007/084181 A3 | 7/2007 |
| WO | WO-2007/085837 A1 | 8/2007 |
| WO | WO-2007/089445 A2 | 8/2007 |
| WO | WO-2007/089445 A3 | 8/2007 |
| WO | WO-2007/095338 A2 | 8/2007 |
| WO | WO-2007/108013 A2 | 9/2007 |
| WO | WO-2007/108013 A3 | 9/2007 |
| WO | WO-2007/109254 A2 | 9/2007 |
| WO | WO-2007/110205 A2 | 10/2007 |
| WO | WO-2007/110205 A3 | 10/2007 |
| WO | WO-2007/147901 A1 | 12/2007 |
| WO | WO-2008/005828 A2 | 1/2008 |
| WO | WO-2008/005828 A3 | 1/2008 |
| WO | WO-2008/017963 A2 | 2/2008 |
| WO | WO-2008/017963 A3 | 2/2008 |
| WO | WO-2008/077077 A2 | 6/2008 |
| WO | WO-2008/077077 A3 | 6/2008 |
| WO | WO-2008/077546 A1 | 7/2008 |
| WO | WO-2008/100624 A2 | 8/2008 |
| WO | WO-2008/100624 A3 | 8/2008 |
| WO | WO-2008/132568 A2 | 11/2008 |
| WO | WO-2008/132568 A3 | 11/2008 |
| WO | WO-2008/143954 A2 | 11/2008 |
| WO | WO-2008/143954 A3 | 11/2008 |
| WO | WO-2009/007124 A1 | 1/2009 |
| WO | WO-2009/018386 A1 | 2/2009 |
| WO | WO-2009/021745 A1 | 2/2009 |
| WO | WO-2009/021754 A2 | 2/2009 |
| WO | WO-2009/021754 A3 | 2/2009 |
| WO | WO-2009/023843 A1 | 2/2009 |
| WO | WO-2009/030780 A2 | 3/2009 |
| WO | WO-2009/032782 A2 | 3/2009 |
| WO | WO-2009/032782 A3 | 3/2009 |
| WO | WO 2009/037659 A2 | 3/2009 |
| WO | WO 2009/037659 A3 | 3/2009 |
| WO | WO-2009/059278 A1 | 5/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO 2009/105671 A2 | 8/2009 |
| WO | WO 2009/105671 A3 | 8/2009 |
| WO | WO-2009/126944 A1 | 10/2009 |
| WO | WO-2010/034441 A1 | 4/2010 |
| WO | WO-2010/040508 A1 | 4/2010 |
| WO | WO-2010/040508 A8 | 4/2010 |
| WO | WO-2010/040508 A9 | 4/2010 |
| WO | WO-2010/045193 A1 | 4/2010 |
| WO | WO-2010/065882 A1 | 6/2010 |
| WO | WO-2010/069532 A1 | 6/2010 |
| WO | WO-2010/087994 A2 | 8/2010 |
| WO | WO-2010/112193 A1 | 10/2010 |
| WO | WO-2010/112194 A1 | 10/2010 |
| WO | WO-2010/115552 A1 | 10/2010 |
| WO | WO-2010/115589 A1 | 10/2010 |
| WO | WO-2010/115589 A8 | 10/2010 |

(56) References Cited

FOREIGN PATENT DOCUMENTS

| WO | WO 2010/118169 A2 | 10/2010 |
|---|---|---|
| WO | WO 2010/118169 A3 | 10/2010 |
| WO | WO-2010/129304 A2 | 11/2010 |
| WO | WO-2010/129304 A3 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/003557 A1 | 1/2011 |
| WO | WO-2011/028952 A1 | 3/2011 |
| WO | WO-2011/034605 A2 | 3/2011 |
| WO | WO-2011/090754 A1 | 7/2011 |
| WO | WO-2011/090762 A1 | 7/2011 |
| WO | WO-2011/143545 A1 | 11/2011 |
| WO | WO-2012/006633 A1 | 1/2012 |
| WO | WO-2012/025525 A1 | 3/2012 |
| WO | WO-2012/025530 A1 | 3/2012 |
| WO | WO-2012/058768 A1 | 5/2012 |
| WO | WO-2012/085069 A2 | 6/2012 |
| WO | WO-2012/085111 A1 | 6/2012 |
| WO | WO-2012/085113 A1 | 6/2012 |
| WO | WO-2012/116927 A1 | 9/2012 |
| WO | WO-2013/003555 A1 | 1/2013 |
| WO | WO-2013/006544 A1 | 1/2013 |
| WO | WO-2013/006544 A8 | 1/2013 |
| WO | WO-2013/026833 A1 | 2/2013 |
| WO | WO-2013/092716 A1 | 6/2013 |
| WO | WO-2013/096291 A2 | 6/2013 |
| WO | WO-2013/096291 A3 | 6/2013 |
| WO | WO-2013/119966 A2 | 8/2013 |
| WO | WO-2013/157953 A1 | 10/2013 |
| WO | WO-2013/157954 A1 | 10/2013 |
| WO | WO-2013/174873 A1 | 11/2013 |
| WO | WO-2014/001326 A1 | 1/2014 |
| WO | WO-2014/012085 A2 | 1/2014 |
| WO | WO-2014/012085 A3 | 1/2014 |
| WO | WO-2014/049003 A1 | 4/2014 |
| WO | WO-2014/144357 A1 | 9/2014 |
| WO | WO-2016/087416 A1 | 6/2016 |

OTHER PUBLICATIONS

Bachman (1987). Cellular and molecuiar bioiogy, vol. 2, Washington, DC, American Society for Microbiology, pp. 1190-1219, ATCC Deposit No. 27,325.
Baldwin et al. (Mar. 15, 1986). "Monoclonal antibodies in cancer treatment," *Lancet* 603-605.
Barnes et al. (1980). "Methods for growth of cultured cells in serum-free medium," *Anal. Biochem.* 102:255-270.
Bass et al. (1990). "Hormone phage: an enrichment method for variant proteins with altered binding properties," *Proteins* 8:309-314.
Booy et al. (Mar.-Apr. 2006). "Monoclonal and bispecific antibodies as novel therapeutics," *Arch. Immunol. Ther. Exp.* 54(2):85-101.
Bothmann et al. (Jun. 2, 2000). "The periplasmic *Escherichia coli* peptidylprolyl cis,trans-isomerase FkpA. I. Increased functional expression of antibody fragments with and without cis-prolines," *J. Biol. Chem.* 275(22):17100-17105.
Burton (1985). "Immunoglobulin G: functional sites," *Molec. Immunol.* 22:161-206.
Cao et al. (Feb. 10, 2003). "Bispecific antibody conjugates in therapeutics," *Adv. Drug Deliv. Rev.* 55(2):171-197.
Capel et al. (1994). "Heterogeneity of human IgG Fc receptors," *Immunomethods* 4:25-34.
Carlsson et al. (1978). "Protein thiolation and reversible protein-protein conjugation. N-Succinimidyl 3-(2-pyridyldithio)propionate, a new heterobifunctional reagent," *Biochem. J.* 173:723-737.
Carter et al. (1992). "Humanization of an anti-p185HER2 antibody for human cancer therapy," *PNAS* 89:4285-4289.
Chari et al. (1992). "Immunoconjugates containing novel maytansinoids: promising anticancer drugs," *Cancer Res.* 52:127-131.
Chen et al. (1999). "Selection and analysis of an optimized anti-VEGF antibody: crystal structure of an affinity-matured Fab in complex with antigen," *J. Mol. Biol.* 293:865-881.

Chen et al. (Jul. 9, 1999). "Chaperone activity of DsbC," *J. Biol. Chem.* 274(28):19601-19605.
Chothia et al. (1987). "Canonical structures for the hypervariable regions of immunoglobulins," *J. Mol Biol.* 196:901-917.
Chow et al. (Jun. 30, 2000). "Studies on the subsite specificity of rat nardilysin (N-arginine dibasic convertase)," *JBC* 275(26):19545-19551.
Clynes et al. (1998). "Fc receptors are required in passive and active immunity to melanoma," *PNAS* 95:652-656.
Daeron (1997). "Fc receptor biology," *Annu. Rev. Immunol.* 15:203-234.
Davies, J. et al. (Feb. 21, 1994). "Camelising human antibody fragments: NMR studies on Vh domains," *FEBS Letters* 339(3):285-290.
De Haas et al. (1995). "Fc gamma receptors of phagocytes," *J. Lab. Clin. Med.* 126:330-341.
Deyev, S.M. et al. (Sep. 1, 2008). "Multivalency: the hallmark of antibodies used for optimization of tumor targeting by design," *Bioessays* 30(9):904-918.
Dooley, H. et al. (2006). "Antibody repertoire development in cartilaginous fish," *Dev. Comp. Immunol.* 30(1-2):43-56.
Doronina et al. (Jul. 2003, e-pub. Jun. 1, 2003). "Development of potent monoclonal antibody auristatin conjugates for cancer therapy," *Nat. Biotechnol.* 21(7):778-784.
Eaton et al. (1986). "Construction and characterization of an active factor VIII variant lacking the central one-third of the molecule," *Biochem.* 25:8343-8347.
Extended European Search Report dated Aug. 5, 2013, for European Patent Application No. 10817575.3, eleven pages.
Fischer et al. (2007). "Bispecific antibodies: molecules that enable novel therapeutic strategies," *Pathobiology* 74:3-14.
Fraker et al. (Feb. 28, 1978). "Protein and cell membrane iodinations with a sparingly soluble chloroamide, 1,3,4,6-tetrachloro-3a,6a-diphrenylglycoluril," *Biochem. Biophys. Res. Commun.* 80(4):849-857.
Gadgil et al. (2006). "Identification of cysteinylation of a free cysteine in the Fab region of a recombinant monoclonal IgG1 antibody using lys-C limited proteolysis coupled with LC/MS analysis," *Analytical biochem.* 2006: 355:185-74.
Gadgil et al. (2006). *Analytical biochem.* 355:185-174.
Gazzano-Santoro et al. (1997). "A non-radioactive complement-dependent cytotoxicity assay for anti-CD20 monoclonal antibody," *J. Immunol. Methods* 202:163-171.
Geoghegan et al. (Mar.-Apr. 1992). "Site-directed conjugation of nonpeptide groups to peptides and proteins via periodate oxidation of a 2-amino alcohol. Application to modification at N-terminal serine," *Bioconjugate Chem.* 3(2):138-146.
Goodman et al (1994). Chapter 6: Basic and Clinical Immunology, 8th edition, Appleton & Lange, Norwalk, CT, pp. 66-79.
Graham et al. (1977). "Characteristics of a human cell line transformed by DNA from human adenovirus type 5," *J. Gen. Virol.* 36:59-72.
Grönwall C. et al. (Jun. 2008). "Generation of Affibody ligands binding interleukin-2 receptor alpha/CD25," Biotechnol. Appl. Biochem. 50(Pt. 2):97-112.
Guss et al. (1986). "Structure of the IgG-binding regions of streptococcal protein G," *EMBO J.* 5:1567-1575.
Guyer et al. (1976). "Immunoglobulin binding by mouse intestinal epithelial cell receptors," *J. Immunol.* 117:587.
Ham et al. (1979). "Media and growth requirements," *Meth. Enz.* 58:44-93.
Hamers-Casterman et al. (1993). "Naturally occurring antibodies devoid of light chains," *Nature* 363:446-448.
Hara et al. (1996). "Overproduction of penicillin-binding protein 7 suppresses thermosensitive growth defect at low osmolarity due to an spr mutation of *Escherichia coli*," *Microbial Drug Resistance* 2:63-72.
Hinman et al. (1993). "Preparation and characterization of monoclonal antibody conjugates of the calicheamicins: a novel and potent family of antitumor antibiotics," *Cancer Res.* 53:3336-3342.
Holliger et al. (1993). "Diabodies: Small bivalent and bispecific antibody fragments," *PNAS* 90:6444-6448.

(56) References Cited

OTHER PUBLICATIONS

Holt, L.J. et al. (Nov. 2003). "Domain antibodies: proteins for therapy," *Trends Biotechnology* 21(11):484-490.
International Search Report dated Jun. 15, 2011 for PCT Patent Applicaion No. PCT/US2010/002546 filed Sep. 16, 2010, five pages.
Janeway, C.A. (Oct. 12, 1989). "Autoimmune disease: immunotherapy by peptides?" *Nature* 341 (6242):482-483.
Johnson et al. (2003). Methods in Molecular Biology 248:11-25. (Lo, ed., Human Press, Totowa, NJ).
Joly et al. (Mar. 17, 1998). "Overexpression of *Escherichia coli* oxidoreductases increases recombinant insulin-like growth factor-I accumulation," *PNAS* 95:2773-2777.
Jones et al. (1986). "Replacing the complementarity-determining regions in a human antibody with those from a mouse," *Nature* 321:522-525.
Kim et al. (1994). "Localization of the site of the murine IgG1 molecule that is involved in binding to the murine intestinal Fc receptor," *Eur. J. Immunol.* 24:2429-2434.
Lee et al. (1996). "Generation and characterization of a novel single-gene-encoded single-chain immunoglobulin molecule with antigen binding activity and effector functions," *Mol. Immunol.* 36:61-71.
Lindmark et al. (1983). "Binding of immunoglobulins to protein A and immunoglobulin levels in mammalian sera," *J. Immunol. Meth.* 62:1-13.
Liu et al. (1996). "Eradication of large colon tumor xenografts by targeted delivery of maytansinoids," *PNAS* 93:8618-8623.
Lode et al. (1998). "Targeted therapy with a novel enediyene antibiotic calicheamicin theta(I)1 effectively suppresses growth and dissemination of liver metastases in a syngeneic model of murine neuroblastoma," *Cancer Res.* 58:2925-2928.
Malmborg et al. (1995). "BIAcore as a tool in antibody engineering," *J. Immunol. Methods* 183:7-13.
Mandler et al. (Jul.-Aug. 2002). "Modifications in synthesis strategy improve the yield and efficacy of geldanamycin-herceptin immunoconjugates," *Bioconjugate Chem.* 13(4):786-791.
Mandler et al. (May 15, 2000). "Synthesis and evaluation of antiproliferative activity of a geldanamycin-Herceptin immunoconjugate," *Bioorganic & Med. Chem. Letters* 10(10):1025-1028.
Mandler et al. (Oct. 4, 2000). "Immunoconjugates of geldanamycin and anti-HER2 monoclonal antibodies: antiproliferative activity on human breast carcinoma cell lines," *J. Nat. Cancer Institute* 92(19):1573-1581.
Marvin et al. (2005). Acta Pharmacol. Sinica 26:649-658.
Marvin et al. (2006). "Bispecific antibodies for dual-modality cancer therapy: killing two signaling cascades with one stone," *Current Opin. Drug Discovery & Dev.* 9(2):184-193.
Mason et al. "Coiled Coil Domains: Stability, Specificity, and Biological Implications,"*ChemBioChem* 5:170-176, (2004).
Mather (Aug. 1980). "Establishment and characterization of two distinct mouse testicular epithellal cell ines," *Biol. Reprod.* 23(1):243-252.
Mather et al. (1982). "Culture of testicular cells in hormone-supplemented serum-free medium,"*Annals N. Y. Acad. Sci.* 383:44-68.
Morrison et al. (1984). "Chimeric human antibody molecules: mouse antigen-binding domains with human constant region domains," *PNAS* 81:6851-6855.
Muller et al. (Dec. 15, 2000). "Processing and sorting of the prohormone convertase 2 propeptide," *JBC* 275:39213-39222.
Müller, D. et al. (Feb. 1, 2008). "Bispecific Antibodies," Handbook of Therapeutic Antibodies, pp. 345-354, retrieved from <http://www3.interscience.wiley.com/cgi-bin/bookhome/117900140>.
Murakami et al. (1995). Chapter 1: "Cell Cycle Regulation, oncogenes, and antineoplastic drugs," The Molecular Basis of Cancer, WB Saunders: Philadelphia, pp. 3-17.

Muyldermans, S. et al. (Apr. 2001). "Recognition of antigens by single-domain antibody fragments: the superfluous luxury of paired domains," *Trends Biochem. Sci.* 26(4):230-235.
Nicolaou et al. (1994)."Calicheamicin $0^1{}_1$ ; A Rationally Designed Molecule with Extremely Potent and Selective DNA Cleaving Properties and Apoptosis Inducing Activity," *Agnew Chem. Int'l. Ed. Engl.* 33(2):183-186.
Niculescu-Duvaz et al. (1997). "Antibody-directed enzyme prodrug therapy (ADEPT): A review," *Adv. Drug Del. Rev.* 26:151-172.
Nieri et al. (Feb. 1, 2009). "Antibodies for Therapeutic Uses and the Evolution of Biotechniques," *Current Med. Chem.* 16(6):753-779.
Nilsson et al. (1987). "A synthetic IgG-binding domain based on staphylococcal protein A," *Prot. Eng.* 1:107-133.
Nord et al. (1995). "A combinatorial library of an α-helical bacterial receptor domain,"*Prot. Eng.* 8:601-608.
Nord et al. (1997), "Binding proteins selected from combinatorial libraries of an α-helical bacterial receptor domain,"*Nat. Biotech.* 15:772-777.
O'Shea et ai. "Peptide 'Velcro': design of a heterodirneric coiled coil," *Current Biology* 3(10):658-667, (1993).
Offner et al. (1991). "T cell receptor peptide therapy triggers autoregulation of experimental encephalomyelitis," *Science* 251:430-432.
Pettit (1997). "The dolastatins," *Fortschr. Chem. Org. Naturst.* 70:1-79.
Pettit et al. (1981). "Marine animal biosynthetic constituents for cancer chemotherapy," *J. Nat. Prod.* 44:482-485.
Pettit et al. (1998). "Antineoplastic agents 360. Synthesis and cancer cell growth inhibitory studies of dolastatin 15 structural modifications," *Anti-Cancer Drug Design* 13:47-66.
Pettit et al. (Nov. 1998). "Specific activities of dolastatin 10 and peptide derivatives against Cryptococcus neoformans," *Antimicrob. Agents Chemother.* 42(11):2961-2965.
Pluckthun (1994). "Antibodies from *Escherichia coli*," Chapter 11 in *The Pharmacology of Monoclonal Antibodies*, vol. 113, Springer-Verlag, New York, pp. 269-315.
Pluckthun, A. et al. (Jun. 1, 1997). "New protein engineering approaches to multivalent and bispecific antibody fragments," *Immunotechnology* 3(2):83-105.
Poncet (1999). "The dolastatins, a family of promising antineoplastic agents," *Curr. Pharm. Des.* 5:139-162.
Presta (1992). "Antibody engineering," *Curr. Opin. Struct. Biol.* 2:593-596.
Presta et al. (1993). "Humanization of an antibody directed against IgE," *J. Immunol.* 151:2623.
Proba et al. (Jul. 4, 1995). "Functional antibody single-chain fragments from the cytoplasm of *Escherichia coli*: influence of thioredoxin reductase (TrxB)," *Gene* 159:203-207.
Ramm et al. (Jun. 2, 2000). "The periplasmic *Escherichia coli* peptidylprolyl cis,trans-isomerase FkpA. II. Isomerase-independent chaperone activity in vitro," *J. Biol. Chem.* 275(22):17106-17113.
Ravetch et al. (1991). "Fc receptors," *Annu. Rev. Immunol.* 9:457-492.
Riechmann et al. (1988). "Reshaping human antibodies for therapy," *Nature* 332:323-329.
Rowland et al. (1986). "Drug localisation and growth inhibition studies of vindesine-monoclonal anti-CEA conjugates in a human tumour xenograft," *Cancer Immunol. Immunother.* 21(3):183-187.
Ruppert et al. (1993). "Cloning and expression of human $TAF_{II}250$: a TBP-associated factor implicated in cell-cycle regulation," *Nature* 362:175-179.
Schroder et al. (1965). "The Peptides," vol. 1, Academic Press, New York and London, pp. 76-136.
Shechter et al. (1976). "Selective chemical cleavage of tryptophanyl peptide bonds by oxidative chlorination with N-chlorosuccinimide," *Biochem.* 15:5071-5075.
Sheriff et al. (1996). "Redefining the minimal antigen-binding fragment," *Nature Struct. Biol.* 3:733-736.
Siebenlist et al. (Jun. 1980). "*E. coli* RNA polymerase interacts homologously with two different promoters," *Cell* 20(2):269-281.
Simmons et al. (2002). "Expression of full-length immunoglobulins in *Escherichia coli*: rapid and efficient production of aglycosylated antibodies," *J. Immunol. Methods* 263:133-147.

(56) References Cited

OTHER PUBLICATIONS

Sims et al. (1993). "A humanized CD18 antibody can block function without cell destruction," *J. Immunol.* 151:2296-2308.
Steiner (1991). "The biosynthesis of biologically active peptides: A perspective," Chapter 1 in *Peptide Biosynthesis and Processing*, CRC Press: Boca Raton, FL, pp. 1-15.
Stella et al. (1985). "Prodrugs: A Chemical Approach to Targeted Drug Delivery," Directed Drug Delivery, pp. 247-267.
Syrigos et al. (1999). "Antibody directed enzyme prodrug therapy (ADEPT): a review of the experimental and clinical considerations," *Anticancer Research* 19(1A):605-614.
Thie, H. et al. (Jul. 22, 2009). "Multimerization domains for antibody phage display and antibody production," *New Biotech.* 26(6):314-321.
Thorpe (1985). Antibody Carriers of Cytotoxic Agents in Cancer Therapy: A Review, in Monoclonal Antibodies '84: Biological and Clinical Applications, pp. 475-506.
Urlaub et al. (1980). "Isolation of Chinese hamster cell mutants deficient in dihydrofolate reductase activity," *PNAS* 77:4216-4220.
Verhoeyen et al. (1988). "Reshaping human antibodies: grafting an antilysozyme activity," *Science* 239:1534-1536.
Vitetta et al. (1987). "Redesigning nature's poisons to create antitumor reagents," *Science* 238:1098-1104.
Ward, E.S. et al. (Oct. 12, 1989). *Nature* 341(6242):544-546.
Wilman (1986). "Prodrugs in Cancer Chemotherapy," Biochemical Society Transactions, pp. 375-382, 615$^{th}$ Meeting Belfast.
Woyke et al. (Dec. 2001). "In vitro activities and postantifungal effects of the potent dolastatin 10 derivative auristatin PHE," *Antimicrob. Agents and Chemother.* 45(12):3580-3584.
Written Opinion of the International Searching Authority dated Jun. 15, 2011 for PCT Patent Application No. PCT/US2010/002545 filed Sep. 16, 2010, seven pages.
Xu et al. (2000). "Diversity in the CDR3 region of V(H) is sufficient for most antibody specificities," *Immunity* 13:37-45.
Yaniv (1982). "Enhancing elements for activation of eukaryotic promoters," *Nature* 297:17-18.
Zapata et al. (1995). "Engineering linear F(ab')2 fragments for efficient production in *Escherichia coli* and enhanced antiproliferative activity," *Protein Eng.* 8(10):1057-1062.
Zhu et al. (Apr. 1997). "Remodeling domain interfaces to enhance heterodimer formation," *Protein Science* 6:781-788.
Adams et al. "Highly specific in vivo tumor targeting by monovalent and divalent forms of 741F8 anti-c-erbB-2 single-chain Fv," *Cancer Res.* 53:4026-4034, (1993).
Aggarwal et al., (Jan. 22, 2008). "Fibroblast Activation Protein Peptide Substrates Identified from Human Collagen I Derived Gelatin Cleavage Sites," *Biochemistry* 47(3):1076-1086.
An et al., "Targeted drug delivery to mesothelioma cells using functionally selected internalizing human single-chain antibodies," *Mol. Cancer Ther.* 7:569-578, (2008).
Anonymous. "Production in yeasts of stable antibody fragments," *Expert Opinion on Therapeutic Patents* 7(2):179-183, (1997).
Anthony, R.M., et al. (2008). "A recombinant IgG Fc that recapitulates the antiinflammatory activity of IVIG", *Science*, 320(5874):373-376.
Armour, K.L. et al. (1999). "Recombinant human IgG molecules lacking Fcγ receptor I binding and monocyte triggering activities", *Eur. J. Immunol.* 29:2613-2624.
Atwell et al., "Stable heterodimers from remodeling the domain interface of a homodimer using a phage display library," *J. Mol. Biol.* 270 (1):26-35 (1997).
Ausubel et al., Short Protocols in Molecular Biology, Greene Publishing and Wiley Interscience, New York, New York, (Table of Contents), (1987).
Avgeris et al., "Kallikrein-related peptidase genes as promising biomarkers for prognosis and monitoring of human malignancies," *Biol. Chem* 391(5):505-511, (May 2010).
Backer et al. "Molecular vehicles for targeted drug delivery," *Bioconjugate Chem.* 13:462-467, (2002).

Bao et al., "HER2-mediated upregulation of MMP-1 is involved in gastric cancer cell invasion," *Arch Biochem Biophys* 499(1-2):49-55, (Jul. 2010).
Barbin et al. (Mar.-Apr. 2006). "Influence of Variable N-Glycosylation on the Cytolytic Potential of Chimeric CD19 Antibodies,"*J. Immunother.* 29(2):122-133.
Barnes et al., "Advances in animal cell recombinant protein production: GS-NS0 expression system," *Cytotechnology* 32 (2):109-23 (Feb. 2000).
Barnes et al., "Characterization of the stability of recombinant protein production in the GS-NS0 expression system," *Biotechnol Bioeng.* 73(4):261-70 (May 2001).
Behrens. "Synthesis of achiral linker reagents for direct labelling of oligonucleotides on solid supports," *Nucleosides & Nucleotides* 18:291-305, (1999).
Bera et al., "A bivalent disulfide-stabilized Fv with improved antigen binding to erbB2," *J. Mol. Biol.* 281(3):475-483, (Aug. 21, 1998).
Bird et al. (Oct. 21, 1988). "Single-Chain Antigen-Binding Proteins," *Science* 242(4877):423-6.
Bird et al. (Apr. 28, 1989). "Single-Chain Antigen-Binding Proteins," *Science* 244(4903):409, *Erratum*.
Boado et al., "IgG-single chain Fv fusion protein therapeutic for Alzheimer's disease: Expression in CHO cells and pharmacokinetics and brain delivery in the rhesus monkey," *Biotechnology and Bioengineering* 105(3):627-635, (Feb. 15, 2010).
Boerner et al., "Production of Antigen—Specific Human Monoclonal Antibodies From in Vitro-Primed Human Splenocytes," *J. Immunol.* 147(1):86-95, (Jul 1991).
Bordusa. in Highlights in Bioorganic Chemistry, Schmuck, C. and Wennemers, H., (eds.), Wiley VCH, Weinheim, pp. 389-403, (2004).
Borgström et al., "Complete Inhibition of Angiogenesis and Growth of Microtumors by Anti-Vascular Endothelial Growth Factor Neutralizing Antibody: Novel Concepts of Angiostatic Therapy from Intravital Videomicroscopy," *Cancer Research* 56:4032-4039, (1996).
Brennan et al. (1985). "Preparation of bispecific antibodies by chemical recombination of monoclonal immunoglobulin G1 fragments," Science 229:81-83.
Briggs et al., "Cystatin E/M suppresses legumain activity and invasion of human melanoma," *BMC Cancer* 10(17):1-13, (Jan. 2010).
Brinkmann. "Disulfide-stabilized Fv fragments," Chapter 14 in 2 in Antibody Engineering, Kontermaan et al. eds., vol. 2, Springer-Verlag, Berlin Heidelberg, Germany, pp. 181-189, (Apr. 30, 2010).
Brinkmann et al., "A recombinant immunotoxin containing a disulfide-stabilized Fv fragment," *PNAS* 90(16):7538-7542, (1993).
Brorson et al., "Mutational Analysis of Avidity and Fine Specificity of Anti-Levan Antibodies," *J. Immunol.* 163:6694-6701 (1994).
Brüggemann et al., "Comparison of the effector functions of human immunoglobulins using a matched set of chimeric antibodies," *J Exp Med.* 166(5):1351-61, (Nov. 1987).
Brüggemann et al., "Designer Mice: The Production of Human Antibody Repertoires in Transgenic Animals," *Year in Immuno.* 7:33-40, (1993).
Brummell et al., "Probing the combining site of an anti-carbohydrate antibody by saturation-mutagenesis: role of the heavy-chain CDR3 residues," *Biochemistry* 32(4):1180-1187 (1993).
Brunhouse et al., "Isotypes of IgG: comparison of the primary structures of three pairs of isotypes which differ in their ability to activate complement," *Mol Immunol.* 16(11): 907-917 (Nov. 1979).
Budtschanow et al. "System of Humoral Immunity Antibodies (Theme 2)," Guidance Manual for General Immunology, Twer (2008) p. 3, English Translation, 3 pages, (5 pages both English Equivalent and Russian Reference.
Burgess et al. "Possible dissociation of the heparin-binding and mitogenic activities of heparin-binding (acidic fibroblast growth factor-1 from its receptor-binding activities by site-directed mutagenesis of a single lysine residue," *Journal of Cell Biology* 111:2129-2138, (Nov. 1990).
Burks et al., "In vitro scanning saturation mutagenesis of an antibody binding pocket," *PNAS* 94(2):412-417 (1997).

(56) References Cited

OTHER PUBLICATIONS

Burton et al., "The C1q Receptor Site on Immunoglobulin G," *Nature* 288(5789):338-344, (Nov. 27, 1980).
Carmichael et al. "Evaluation of a tetrazolium-based semiautomated colorimetric assay: assessment of chemosensitivity testing," *Cancer Res.* 47:936-942, (1987).
Caron et al., "Engineered humanized dimeric forms of IgG are more effective antibodies," *J. Exp. Med.* 176(4):1191-1195, (Oct. 1, 1992).
Carro et al., "Serum insulin-like growth factor I regulates brain amyloid-β levels," *Nature Medicine* 8(12):1390-1397, (2002, e-pub. Nov. 4, 2002).
Carter et al. "High level *Escherichia coli* expression and production of a bivalent humanized antibody fragment," *Bio/Technology* 10:163-167, (1992).
Carter., "Bispecific human IgG by design," *Immunol. Methods* 248:7-15, (2001).
Carter. "Potent antibody therapeutics by design", *Nature Reviews Immunology* 6:343-357, (2006).
Chame et al. "Bispecific antibodies for cancer therapy", *Current Opinion in Drug Discovery & Development*, 12(2):276-283, (2009).
Chan et al., "Variable Region Domain Exchange in Human IgGs Promotes Antibody Complex Formulation with Accompanying Structural Changes and Altered Effector Functions," *Molecular Immunology* 41(5):527-538. (2004).
Chan et al. "Therapeutic antibodies for autoimmunity and inflammation", *Nat. Rev. Immunol.*, 10(5):301-316, (2010).
Charlton. In: *Methods in Molecular Biology*, vol. 248, Lo, B.K.C. (ed.), Humana Press, Totowa, N.J., pp. 245-254, (2003).
Cheong et al. "Affinity enhancement of bispecific antibody against two different epitopes in the same antigen," *Biochem. Biophys. Res. Commun.* 173:795-800, (1990).
Chernaia, "[Cathepsin L from human brain tumor. Purification and contents]." Ukr Biokhim Zh. 70(5):97-103, (Sep.-Oct. 1998). (English Translation of Abstract.).
Chin et al. "Addition of p-azido-L-phenylalanine to the genetic code of *Escherichia coli*", *J. Am. Chem. Soc.*, 124(31):9026-9027, (2002).
Chin et al. "In vivo photocrosslinking with unnatural amino Acid mutagenesis", *ChemBioChem*, 3(11):1135-1137, (2002).
Chin et al. "Addition of a photocrosslinking amino acid to the genetic code of *Escherichia coli*", *Proc. Natl. Acad. Sci. U.S.A.*, 99(17):11020-11024, (2002).
Chitnis et al., "The type 1 insulin-like growth factor receptor pathway," *Clin. Cancer Res.* 14(20):6364-6370, (Oct. 16, 2008).
Chung et al. "Development of a novel albumin-binding prodrug that is cleaved by urokinase-type-plasminogen activator (uPA)," *Bioorg Med Chem Lett.* 16(19):5157-5163 (Oct. 1, 2006).
Clackson et al. "Making antibody fragments using phage display libraries," *Nature* 352:624- 628, (1991).
Clancy et al. "Sortase transpeptidases: insights into mechanism, substrate specificity, and inhibition", *Biopolymers*, 94(4):385-396, (2010).
Cocuzza, "A Phosphoramidite Reagent for automated solid phase synthesis of 5'-biotinylated oligonucleotides," *Tetrahedron Letters* 30:6287-6290, (1989).
Cohen et al., "Nonchromosomal antibiotic resistance in bacteria: Genetic transformation of *Escherichia coli* by R-factor DNA," *Proc. Natl. Acad. Sci. USA* 69(8):2110-2114 (Aug. 1972).
Cole et al., "The EBV-hybridoma technique and its application to human lung cancer," *Monoclonal Antibodies and Cancer Therapy*, New York: Alan R. Liss, Inc. pp. 77-96 (1985).
Coleman., "Effects of amino acid sequence changes on antibody-antigen interactions," *Research in Immunol.* 145(1):33-38, (1994).
Coloma and Morrison., "Design and production of novel tetravalent bispecific antibodies," *Nature Biotechnology* 15(2):159-163 (Feb. 1997).
Cordingley et al., "Substrate requirements of human rhinovirus 3C protease for peptide cleavage in vitro," *J. Biol. Chem.* 265(16):9062-9065, (1990).

Cortesio et al. (Mar. 10, 2008). "Calpain 2 and PTP1B function in a novel pathway with Src to regulate invadopodia dynamics and breast cancer cell invasion," *J. Cell Biol.* 180(5):957-971.
Coxon et al., "Combined treatment of angiopoietin and VEGF pathway antagonists enhances antitumor activity in preclinical models of colon carcinoma," *99th AACR Annual Meeting*, Abstract #1113, (Apr. 2008).
Crawford et al., "Matrix metalloproteinase-7 is expressed by pancreatic cancer precursors and regulates acinar-to-ductal metaplasia in exocrine pancreas," *J. Clin. Invest.* 109(11):1437-1444, (Jun. 2002).
Cudic et al., "Extracellular proteases as targets for drug development," *Curr. Protein Pept Sci* 10(4):297-307, (Aug. 2009).
Cullen et al., "Granzymes in cancer and immunity," *Cell Death Differ* 17(4):616-623, (Apr. 2010).
Dall'Acqua, W. et al. (1998). "Contribution of Domain Interface Residues to the Stability of Antibody CH3 Domain Homodimers", *Biochemistry*, 37:9266-9273.
Davis et al. "SEEDbodies: Fusion Proteins Based on Strand-Exchange Engineered Domain (SEED) $C_H3$ Heterodimers in an Fc Analogue Platform for Asymmetric Binders or Immunofusions and Bispecific Antibodies," *Protein Engineering Design & Selection* 23(4):195-202, (2010, e-pub. Feb. 4, 2010).
Davies et al., "Expression of GnTIII in a recombinant anti-CD20 CHO production cell line: Expression of antibodies with altered glycoforms leads to an increase in ADCC through higher affinity for FcyRIII," *Biotechnol. Bioeng.* 74:288-294, (2001).
De Graaf et al. "Nonnatural amino acids for site specific protein conjugation," *Bioconjug. Chem.* 20:1281-1295, (2009).
Dervan. "Molecular recognition of DNA by small molecules," *Bioorg. Med. Chem.* 9:2215-2235, (2001).
Dimmock, N.J. et al. (2004). "Valency of antibody binding to virions and its determination by surface plasmon resonance", *Rev. Med. Virol.*, 14:123-135.
Ding et al., "Gold Nanorods Coated with Multilayer Polyelectrolyte as Contrast Agents for Multimodal Imaging," *J. Phys. Chem. C* 111 (2007) 12552-12557.
Donaldson et al., "Design and development of masked therapeutic antibodies to limit off-target effects: Application to anti-EGFR antibodies," *Cancer Biology & Therapy* 8(22):2145-2150, (Nov. 15, 2009).
Dubowchik et al. "Doxorubicin immunoconjugates containing bivalent, lysosomally-cleavable dipeptide linkages," *Bioorg. & Med. Chem. Letters* 12:1529-1532, (2002).
Dufner et al., "Harnessing phage and ribosome display for antibody optimization," *Trends Biotechol.* 24(11):523-29 (2006).
Durocher et al., "High-level and high-throughput recombinant protein production by transient transfection of suspension-growing human 293-EBNA1 cells," *Nucleic Acids Research* 30(2 e9):nine pages, (2002).
Edelman et al., "The covalent structure of an entire γG immunoglobulin molecule," *Proc. Natl. Acad. Sci. USA* 63:78-85, (1969).
Ellman et al. "Biosynthetic Method for Introducing Unnatural Amino Acids Site-Specifically into Proteins", *Meth. Enzym.* ,202:301-336, (1991).
Els Conrath et al. (Mar. 9, 2001). "Camel Single-domain Antibodies as Modular Building Units in Bispecific and Bivalent Antibody Constructs," *Journal of Biological Chemistry* 276(19):7346-7350.
Flatman et al., "Process analytics for purification of monoclonal antibodies," *J. Chromatogr B* 848:79-87, (2007).
Frese. "Formylglycine aldehyde Tag—protein engineering through a novel post-translational modification," *ChemBioChem* 10:425-427, (2009).
Friend et al. "Phase I study of an engineered aglycosylated humanized CD3 antibody in renal transplant rejection", *Transplantation*, 68(11):1632-1637, (1999).
Galamb et al., "Inflammation, adenoma and cancer: objective classification of colon biopsy specimens with gene expression signature," *Dis Markers* 25(1):1-16, (2008).
Gautier et al. "An engineered protein tag for multiprotein labeling in living cells," *Chem. Biol.* 15:128-136, (2008).
Geisse et al., "Eukaryotic expression systems: A comparison," *Protein Expression and Purification* 8:271-282 (1996).

(56) References Cited

OTHER PUBLICATIONS

Gerngross. "Advances in the production of human therapeutic proteins in yeasts and filamentous fungi," *Nat. Biotech.* 22:1409-1414, (2004).
Gerspach et al., "Target-selective activation of a TNF prodrug by urokinase-type plasminogen activator (uPA) mediated proteolytic processing at the cell surface," *Cancer Immunol. Immunother* 55:1590-1600 (2006).
Gold et al., "A novel bispecific, trivalent antibody construct for targeting pancreatic carcinoma," *Cancer Res.* 68(12):4819-4826, (2008).
Goldenberg et al. "Multifunctional antibodies by the Dock-and-Lock method for improved cancer imaging and therapy by pretargeting," *J. Nuc. Med.* 49:158-163, (2008).
Goldenberg et al., "Bi-Specific Antibodies that Bind Specific Target Tissue and Targeted Conjugates," Derwent Information Ltd., 12 pages, (2012).
Graham et al., "A new technique for the assay of infectivity of human adenovirus 5 DNA,"*Virology* 52 (2):456-467, (1973).
Greenwood et al. "Structural Motifs Involved in Human IgG Antibody Effector Functions,". *Eur. J. Immunology* 23(5):1098-1104, (May 1993).
Grote et al., "Bispecific Antibody Derivatives Based on Full-Length IgG Formats," Chapter 16 in *Methods in Molecular Biology* 901:247-263, (2012).
Gruber et al. "Efficient tumor cell lysis mediated by a bispecific single chain antibody expressed in *Escherichia coli*," *J. Immunol.* 152:5368-5374, (1994).
Gunasekaran et al., "Enhancing antibody Fc heterodimer formation through electrostatic steering effects: Applications to bispecific molecules and monovalent IgG," *The Journal of Biological Chemistry* 285(25):19637-19646, (Jun. 18, 2010).
Hackenberger. "Chemoselective ligation and modification strategies for peptides and proteins," *Angew. Chem. Int. Ed.* 47:10030-10074, (2008).
Hartog et al., "The Insulin-like growth factor 1 receptor in cancer: Old focus, new future,"European Journal of Cancer, Pergamon Press, Oxford, GB, 43(13):1895-1904, (Aug. 23, 2007).
Hatfield et al. "Antiangiogenic therapy in acute myelogenous leukemia: targeting of vascular endothelial growth factor and interleukin 8 as possible antileukemic strategies" , *Curr. Cancer Drug Targets*, 5(4):229-248, (2005).
Henry et al., "Clinical implications of fibroblast activation protein in patients with colon cancer," *Clin Cancer Res.* 13(6):1736-1741, (Mar. 15, 2007).
Herberman, "Immunodiagnosis of Cancer," in *The Clinical Biochemistry of Cancer*, Fleisher ed., American Association of Clinical Chemists, p. 347, (1979).
Hey et al., "Artificial, non-antibody binding proteins for pharmaceutical and industrial applications," *Trends Biotechnol.* 23:514-522, 2005).
Hezareh et al., "Effector Function Activities of a Panel of Mutants of a Broadly Neutralizing Antibody against Human Immunodeficiency Virus Type 1," *Journal of Virology* 75(24):12161-12168, (Dec. 2001).
Hollander., "Bispecific antibodies for cancer therapy," *Immunotherapy* 1(2):211-222, (Mar. 2009).
Holliger et al., "Engineered antibody fragments and the rise of single domains," *Nat. Biotechnol.* 23(9):1126-1136, (Sep 2005).
Hoogenboom and Winter., "By-passing immunisation. Human antibodies from synthetic repertoires of germline $V_H$ gene segments rearranged in vitro," *J Mol Biol.* 227 (2):381-388, (Sep. 20, 1992).
Hoppe et al. "A parallel three stranded alpha-helical bundle at the nucleation site of collagen triple-helix formation," FEBS Lett. 344:191-195, (1994).
Huber et al. "Crystallographic structure studies of an IgG molecule and an Fc fragment", *Nature*, 264:415-420, (1976).
Hudson et al. "Engineered antibodies," *Nat. Med.* 9:129-134, (2003).
Hust et al., "Single Chain Fab (scFab) Fragment," *BMC Biotechnology* 7(14):1-15, (Mar. 8, 2007).
Huston, J.S. et al. (1993). "Medical Applications of Single-Chain Antibodies," *Intern. Rev. Immunol.* 10(2-3):195-217.
Huston et al. (Aug. 1988). "Protein Engineering of Antibody Binding Sites: Recovery of Specific Activity in an Anti-Digoxin Single-Chain Fv Analogue Produced in *Escherichia coli*," *Proc. Natl. Acad. Sci. U.S.A.* 85(16):5879-5883.
Ibragimova et al., "Stability of the β-Sheet of the WW domain: A molecular dynamics simulation study," *Biophysical Journal* 77:2191-2198, (Oct. 1999).
Idusogie et al., "Mapping of the C1q binding site on rituxan, a Chimeric antibody with a human IgG1 Fc," *The Journal of Immunology* 164:4178-4184, (2000).
Ilangovan et al. (2001). "Structure of sortase, the transpeptidase that anchors proteins to the cell wall of *Staphylococcus aureus*", *Proc. Natl. Acad. Sci. U.S.A.* 98(11):6056-6061, (2001).
Iyer et al. "Abasic oligodeoxyribonucleoside phosphorothioates: synthesis and evaluation as anti-HIV-1 agents," *Nucleic Acids Research* 18:2855-2859, (1990).
Jackman et al. "Development of a Two-part Strategy to Identify a Therapeutic Human Bispedfic Antibody That Inhibits IgE Receptor Signaling," *The Journal of Biological Chemistry* 285(27):20850-20859, (Jul. 2, 2010).
Jakobovits et al., "Analysis of Homozygous Mutant Chimeric Mice: Deletion of the Immunoglobulin Heavy-Chain Joining Region Blocks B-cell Development and Antibody Production," *Proc. Natl. Acad. Sci. USA* 90(6) :2551-2555, (Mar. 15, 1993).
Jakobovits et al., "Germ-line Transmission and Expression of a Human-derived Yeast Artificial Chromosome," *Nature* 362:255-258, (Mar 1993).
Jang et al., "The structural basis for DNA binding by an anti-DNA autoantibody," *Mol. Immunol.* 35(18):1207-1217 (1998).
Jefferis et al., "IgG-Fc-mediated effector functions: molecular definition of interaction sites for effector ligands and the role of glycosylation," *Immunol Rev.*163:59-76, (1998).
Jeffrey et al. "Dipeptide-based highly potent doxorubicin antibody conjugates," *Bioorg. Med. Chem. Lett.* 16:358-362, (2006).
Jendreyko et al., "Simultaneous, Phenotypic Knockout of VEGF-R2 and Tie-2 With an Intradiabody Enhances Antiangiogenic Effects In Vivo," Therapieoptimierung and Risikostratifizierung, Scripps Research Institute, 218:143-151, (2006).
Jia et al., "A novel trifunctional IgG-like bispecific antibody to inhibit HIV-1 infection and enhance lysis of HIV by targeting activation of complement," *Virology Journal* 7(142):1-4, (Jun. 29, 2010).
Jiang et al. "Advances in the assessment and control of the effector functions of therapeutic antibodies", *Nat. Rev. Drug Discov.*, 10(2):101-111, (2011).
Johnson et al., "Kabat Database and its applications: 30 years after the first variability plot," *Nucleic Acids Research* 28(1) :214-218, (2000).
Johnson et al. (1991). "Construction of Single-Chain Fv Derivatives Monoclonal Antibodies and Their Production in *Escherichia coli*," *Methods Enzymol.* 203:88-98.
Kabat et al., "Evolutionary and structural influences on light chain constant ($C_L$) region of human and mouse immunoglobulins," *Proc. Natl. Acad. Sci. USA* 72(7) :2785-2788, (Jul. 1975).
Kabat et al., Sequences of Proteins of Immunological Interest (Table of Contents and Introduction), 5th edition, Bethesda, MD: Public Health Service, NIH, vol. 1, (1991).
Karadag et al., "ADAM-9 (MDC-9/meltrin-γ), a member of the a disintegrin and metalloproteinase family, regulates myeloma-cell-induced interleukin-6 production in osteoblasts by direct interaction with the αvβ5 integrin," *Blood* 107(8):3271-3278, (Apr. 2006).
Kaufman., "Overview of Vector Design for Mammalian Gene Expression," *Molecular Biotechnology* 16:151-160, (2000).
Kazama et al., "Hepsin, a putative membrane-associated serine protease, activates human factor VII and initiates a pathway of blood coagulation on the cell surface leading to thrombin formation," *JBC* 270:66-72, (1995).

(56) References Cited

OTHER PUBLICATIONS

Kim et al., "Inhibition of Vascular Endothelial Growth Factor-Induced Angiogenesis Suppresses Tumour Growth In Vivo," *Nature* 362:841-844, (1993).
Kindt et al., Kuby Immunology, 6th ed., W.H. Freeman and Co., N.Y., p. 91, (2007).
King et al. "Monoclonal antibody conjugates of doxorubicin prepared with branched peptide linkers: inhibition of aggregation by methoxytriethyleneglycol chains," *J. Med. Chem.* 45:4336-4343, (2002).
Klein et al., "Progress in Overcoming the Chain Association Issue in Bispecific Heterodimeric IgG Antibodies" *mAbs* 4(6):653-663, (2012).
Kleinschmidt et al., "Design of a modular immunotoxin connected by polyionic adapter peptides," *J. Mol. Biol.* 327(2):445-452, (Mar. 21, 2003).
Kobayashi et al., "Similarities in the Biodistribution of Iodine-Labeled Anti-Tac Single-Chain Disulfide-Stabilized Fv Fragment and Anti-Tac Disulfide-Stabilized Fv Fragment," *Nuclear Medicine & Biology* 25:387-393, (1998).
Kobayshi et al. "Tryptophan H33 plays an important role in pyrimidine (6-4) pyrimidone photoproduct binding by a high-affinity antibody," *Protein Engineering* 12(10):879-844 (1999).
Kodukula et al., "Biosynthesis of phosphatidylinositol glycan-anchored membrane proteins. Design of a simple protein substrate to characterize the enzyme that cleaves the COOH-terminal signal peptide," *The Journal of Biological Chemistryl* 266(7):4464-4470 (Mar. 5, 1991).
Kostelny et al. "Formation of a bispecific antibody by the use of leucine zippers," *J. Immunol.* 148:1547-1553, (1992).
Kratz et al. "Prodrugs of anthracyclines in cancer chemotherapy," *Current Med. Chem.* 13:477-523, (2006).
Krugmann et al. " Structural Requirements for Assembly of Dimeric IgA Probed by Site-Directed Mutagenesis of J Chain and a Cysteine Residue of the α-chain CH2 Domain," *The Journal of Immunology* 159:244-249, (1997).
Kumar et al. (Nov. 10, 2000). " Molecular Cloning and Expression of the Fabs of Human Autoantibodies in *Escherichia coli*," *J. Biol. Chem.* 275(45):35129-35136.
Lamkanfi et al., "Inflammasomes: guardians of cytosolic sanctity," *Immunol. Rev.* 227(1):95-105, (Jan. 2009).
Landschulz et al. "The leucine zipper: a hypothetical structure common to a new class of DNA binding proteins," *Science* 240:1759-1764, (1988).
Lazar et al., "Transforming growth factor α: Mutation of aspartic acid 47 and leucine 48 results in different biological activities," *Molecular and Cellular Biology* 8(3):1247-1252, (Mar. 1988).
Lee et al., "Using substrate specificity of antiplasmin-cleaving enzyme for fibroblast activation protein inhibitor design," *Biochemistry* 48(23):5149-5158, (Jun. 16, 2009).
Leeman et al., "The Structure, Regulation, and Function of Human Matrix Metalloproteinase-13," *Crit. Rev Biochem Mol. Biol.* 37(3):149-166, (2002).
Levary et al. "Protein-Protein fusion catalyzed by sortase A," PLOS One 6:e18342.1-e18342.1-6, (2011).
Li et al. "Optimization of humanized IgGs in glycoengineered Pichia pastoris," *Nat. Biotech.* 24:210-215, (2006).
Liang et al., "Cross-species Vascular Endothelial Growth Factor (VEGF)-blocking Antibodies Completely Inhibit the Growth of Human Tumor Xenografts and Measure the Contribution of Stromal VEGF," *Journal of Biological Chemistry* 281(2):951-961, (2006).
Lifely et al., "Glycosylation and Biological Activity of CAMPATH-1H Expressed in Different Cell Lines and Grown Under Different Culture Conditions," *Glycobiology* 5(8):813-822, (Dec. 1995).
Lin et al., "Structure-Function relationships in glucagon: Properties of highly purified des-his-, monoiodo-, and [Des-Asn$^{28}$, Thr$^{29}$](homoserine lactone$^{27}$)-glucagon," *Biochemistry USA* 14:1559-1563, (1975).

Liotta et al., "Metastatic potential correlates with enzymatic degradation of basement membrane collagen," *Nature* 284(5751) 67-68, (Mar. 6, 1980).
Liu et al. "Mapping tumor epitope space by direct selection of single-chain Fv antibody libraries on prostate cancer cells," *Cancer Res.* 64 704-710, (2004).
Liu et al. "Heterogeneity of Monoclonal Antibodies," *Journal of Pharmaceutical Sciences* 97(7):2426-2447, (Jul. 2008).
Liu et al., "Clinical and imaging diagnosis of primary hepatic lymphoma," *J First Mil Med. Univ*, 25(10):1290-1292, three pages, (2005). (Translation of the Abstract Only.).
Lopez-Otin et al., "The regulatory crosstalk between kinases and proteases in cancer," *Nat. Rev. Cancer* 10(4):278-292, (Apr. 2010).
Love et al., "Recombinant antibodies possessing novel effector functions," *Methods in Enzymology* 178:515-527, (1989).
Lu et al., "A Fully Human Recombinant IgG-Like Bispecific Antibody to Both the Epidermal growth Factor Receptor and the Insulin-Like Growth Factor Receptor for Enhanced Antitumor Activity," *The Journal of Biological Chemistry* 280(20):19665-19672, (May 20, 2005).
Lu et al. (2002). "Fab-scFv Fusion Protein: an Efficient Approach to Production of Bispecific Antibody Fragments" *J. Immunol Methods* 267(2):213-26.
Lu et al., "Simultaneous blockage of both the epidermal growth factor receptor and the insulin-like growth factor receptor signaling pathways in cancer cells with a fully human recombinant bispecific antibody" J. Biol. Chem. 279(4):2856-65 (2004).
Lu et al. (2004. E-pub. Apr. 22, 2004). "The Effect of Variable Domain Orientation and Arrangement on the Antigen-Binding Activity of a Recombinant Human Bispecific Diabody" *Biochem. Biophys. Res. Commun.* 318(2):507-513.
Lu et al., "ADAMTS1 and MMP1 proteolytically engage EGF-like ligands in an osteolytic signaling cascade for bone metastasis," *Genes Dev.* 23(16):1882-1894, (Aug. 2009).
Lukas et al., "Inhibition of C1-Mediated Immune Hemolysis by Monomeric and Dimeric Peptides from the Second Constant Domain of Human Immunoglobulin G," *The Journal of Immunolgy* 127(6):2555-2560, (Dec. 1981).
Lund et al., "Oligosaccharide-protein interactions in IgG can modulate recognition by Fcγ receptors," *FASEB Journal* 9:115-119, (1995).
Maccallum et al. (1996)."Antibody-antigen Interactions: Contact Analysis and Binding Site Topography," *J. Mol. Biol.* 262:732-745.
Madej et al. "Engineering of an anti-epidermal growth factor receptor antibody to single chain format and labeling by sortase A-mediated protein ligation", *Biotechnology and Bioengineering*, 109(6):1461-1470, (2012).
Makrides., "Components of Vectors for Gene Transfer and Expression in Mammalian Cells," *Protein Expression and Purification* 17:183-202, (1999).
Mamoune et al., "Calpain-2 as a target for limiting prostate cancer invasion," *Cancer Res.* 63(15):4632-4640, (Aug. 2003).
Mann. "Proteomic analysis of post-translational modifications," *Biochemistry* 21:255-261, (2003).
Marks et al., "By-Passing Immunization: Human Antibodies From V-gene Libraries Displayed on Phage," *J Mol Biol.* 222(3) :581-597, (Dec. 5, 1991).
Matrisian. "Cancer biology: extracellular proteinases in malignancy," *Curr. Biol.* 9(20):R776-R778, (Oct. 1999).
Mccarron et al. "Antibody conjugates and therapeutic strategies," *Mol. Interventions* 5:368-380, (2005).
Mckeen et al. "Synthesis of fluorophore and quencher monomers for use in scorpion primers and nucleic acid structural probes," *Organic & Biomol. Chem.* 1: 2267-2275, (2003).
Mclean, G.R. et al. (2005). "A point mutation in the CH3 domain of human IgG3 inhibits antibody secretion without affecting antigen specificity", *Molecular Immunology*, 42:1111-1119.
Meissner et al., "Transient Gene Expression: Recombinant Protein Production with Suspension-Adapted HEK293-EBNA Cells," *Biotechnology and Bioengineering* 75:197-203, (2001).
Melnyk et al., "Vascular Endothelial Growth Factor Promotes Tumor Dissemination by a Mechanism Distinct from Its Effect on Primary Tumor Growth," Cancer Research 56:921-924, (1996).

(56) References Cited

OTHER PUBLICATIONS

Merchant et al., "An efficient route to human bispecific IgG," *Nature Biotechnology* 16:677-681, (1998).
Meyer et al. "Oligonucleotide sequential bis-conjugation via click-oxime and click-Huisgen procedures," *Journal of Organic Chemistry* 75:3927-3930, (2010).
Michaelson et al., "Anti-tumor activity of stability-engineered IgG-like bispecific antibodies targeting TRAIL-R2 and LTβR," *MAbs* 1(2):128-141, (Mar. 2009, e-pub. Mar. 11, 2009).
Miller et al., "Design, Construction, and In Vitro Analyses of Multivalent Antibodies," *J. Immunol.* 170:4854-4861, (2003).
Milstein et al., "Hybrid Hybridomas and Their Use in Immunohistochemistry," *Nature* 305:537-540, (Oct. 6, 1983).
Mimura et al., "Role of Oligosaccharide Residues of IgG1-Fc in FcγRIIb Binding," *The Journal of Biological Chemistry* 276(49): 45539-45547, (Dec. 7, 2001).
Minn et al., "Genes that Mediate Breast Cancer Metastasis to Lung," *Nature* 436(7050):518-524, (Jul. 2005).
Mirny et al. "Protein Folding Theory: From Lattice to All-Atom Models", *Annu. Rev. Biophys. Biomol. Struct.*, 30:361-96, (2001).
Mizukami et al. "Induction of interleukin-8 preserves the angiogenic response in HIF-1alpha-deficient colon cancer cells", *Nat. Med.*, 11(9):992-997, (2005).
Möhlmann et al. "In vitro sortagging of an antibody fab fragment: overcoming unproductive reactions of sortase with water and lysine side chains," *Chembiochem: A European Journal of Chemical Biology*, 12(11):1774-1780, (2011).
Morgan et al., "The N-terminal End of the $C_H 2$ Domain of Chimeric Human IgG1 anti-HLA-DR is Necessary for C1q, FcγRI and FcγRIII Binding," *Immunology* 86:319-324, (1995).
Morimoto et al. "Single-step purification of F(ab')2 fragments of mouse monoclonal antibodies (immunoglobulins G1) by hydrophobic interaction high performance liquid chromatography using TSKgel Phenyl-5PW," *J. Biochem. Biophys. Meth.* 24:107-117, (1992).
Morocho et al., "Novel biotin phosphoramidites with super-long tethering arms,"*Nucleosides, Nucleotides & Nucleic Acids* 22:1439-1441, (2003).
Morrison et al., "Variable region domain exchange influences the functional properties of IgG," *Journal of Immunology, American Association of Immunologists* 160:2802-2808, (Jan. 1, 1998).
Morrison. "Two Heads are Better than One," *Nature Biotechnology* 25(11):1233-1234, (Nov. 2007).
Morrison. "Success in Specification," *Nature* 368:812-813, (Apr. 1994).
Müller et al., "Recombinant Bispecific Antibodies for Cellular Cancer Immunotherapy," *Current Opinion in Molecular Therapeutics* 9:319-326, (2007).
Müller et al., "The first constant domain ($C_H 1$ and $C_L$) of an antibody used as heterodimerization domain for bispecific miniantibodies," *FEBS Letters* 422:259-264, (1998).
Muller et al. "A dimeric bispecific miniantibody combines two specificities with avidity," *FEBS Lett.* 432:45-49, (1998).
Mukhopadhyay et al., "Matrix metalloproteinase-12 is a therapeutic target for asthma in children and young adults," *J. Allergy Clin Immunol.* 126:70-76, (2010).
Nagy et al., "Stability of cytotoxic luteinizing hormone-releasing hormone conjugate (AN-152) containing doxorubicin 14-O-hemiglutarate in mouse and human serum in vitro: implications for the design of preclinical studies," Proc. Natl. Acad. Sci. USA 97:829-834, (2000).
Natsume et al. (Sep. 1, 2006). "Fucose Removal From Complex-type Oligosaccharide Enhances the Antibody-dependent Cellular Cytotoxicity of Single-gene-encoded Bispecific Antibody Comprising of Two Single-Chain Antibodies Linked to the Antibody Constant Region," *Journal of Biochemistry* 140(3):359-368.
Nelson et al. "Oligonucleotide labeling methods. 3. Direct labeling of oligonucleotides employing a novel, non-nucleosidic, 2-aminobutyl-1,3-propanediol backbone," *Nucleic Acids Research* 20:6253-6259, (1992).

Netzel-Arnett et al., "Sequence Specificities of Human Fibroblast and Neutrophil Collagenases," *J. Biol. Chem.* 266(11):6747-6755, (Apr. 15, 1991).
Netzel-Arnett et al., "Comparative sequence specificities of human 72- and 92-kDa gelatinases (type IV collagenases) and PUMP (matrilysin)," *Biochemistry* 32(25):6427-6432, (Jun. 29, 1993).
Neuberger et al., "A hapten-specific chimaeric IgE antibody with human physiological effector function," *Nature* 314:268-270, (Mar. 21, 1985).
Nielsen et al. "Therapeutic efficacy of anti-ErbB2 immunoliposomes targeted by a phage antibody selected for cellular endocytosis," *Biochim. Biophys. Acta* 1591:109-118, (2002).
Niwa et al., "IgG subclass-independent improvement of antibody-dependent cellular cytotoxicity by fucose removal from $Asn^{297}$-linked oligosaccharides," *J. Immunol. Methods* 306:151-160, (2005).
Norderhaug et al., "Versatile Vectors for Transient and Stable Expression of Recombinant Antibody Molecules in Mammalian Cells," *Journal of Immunological Methods* 204:77-87, (1997).
Noren et al. "A General Method for Site-Specific Incorporation of Unnatural Amino Acids into Proteins", *Science*, 244:182-188, (1989).
Novellino et al. "A listing of human tumor antigens recognized by T cells: Mar. 2004 update", *Cancer Immunol. Immunother*, 54(3):187-207, (2005).
Novotný, J. et al. (1985). "Structural invariants of antigen binding: Comparison of immunoglobulin $V_L$-$V_H$ and $V_L$- $V_L$ domain dimmers", *Proc. Natl. Acad. Sci. USA*, 82:4592-4596.
Ohno et al., "Antigen-binding specificities of antibodies are primarily determined by seven residues of $V_H$," *Proc. Natl. Acad. Sci. USA* 82(9):2945-2949, (May 1985).
Oliner et al., "Suppression of Angiogenesis and Tumor Growth by Selective Inhibition of Angiopoietin-2," *Cancer Cell* 6:507-516, (2004).
Orcutt, et al., "A modular IgG-scFv bispecific antibody topology," *Protein Engineering, Design & Selection* 23(4):221-228, (Apr. 2010, e-pub. Dec. 17, 2009).
Orlandi et al., "Cloning Immunoglobulin Variable Domains for Expression by the Polymerase Chain Reaction," *Proc. Natl. Acad. Sci. USA* 86:3833-3837, (May 1989).
Pace et al., "How to Measure and Predict the Molar Absorption Coefficient of a Protein," *Protein Science* 4(11): 2411-2423, (Nov. 1995).
Pack et al. "Miniantibodies: use of amphipathic helices to produce functional, flexibly linked dimeric FV fragments with high avidity in *Escherichia coli*," *Biochem.* 31:1579-1584, (1992).
Pakula et al., "Genetic analysis of protein stability and function," *Annu. Rev. Genet.* 23:289-310, (1989).
Pan et al. (Jan. 2007). "Blocking Neuropilin-1 Function Has an Additive Effect with nti-VEGF to Ihibit Tumor Growth," *Cancer Cell* 11:53-67.
Parmiani et al. "Unique human tumor antigens: immunobiology and use in clinical trials", *J. Immunol*, 178(4):1975-1979, (2007).
Pleass et al. (Aug. 13, 1999). "Identification of Residues in the CH2/CH3 Domain Interface of IgA Essential for Interaction With the Human fcα Receptor (Fcα R) CD89," *The Journal of Biology Chemistry* 274(33):23508-23514.
Pon. "A long chain biotin phosphoramidite reagent for the automated synthesis of 5'-biotinylated oligonucleotides," *Tetrahedron Letters* 32:1715-1718, (1991).
Popp et al. "Making and breaking peptide bonds: protein engineering using sortase", *Angewandte Chemie*, 50(22):5024-5032, (2011).
Portolano et al. "Lack of promiscuity in autoantigen-specific H and L chain combinations as revealed by human H and L chain roulette," J. Immunol. 150:880-887, (1993).
PreScission Protease, GE Healthcare Catalogue No. 27-0843-01, located at http://www.gelifesciences.com/webapp/wcs/stores/servlet/productByld/en/GELifeScience, last visited on Jul. 10, 2013, one page.
Presta et al. "Humanization of an anti-vascular endothelial growth factor monoclonal antibody for the therapy of solid tumors and other disorders," *Cancer Res.* 57:4593-4599, (1997).

(56) References Cited

OTHER PUBLICATIONS

Presta. "Molecular engineering and design of therapeutic antibodies," *Current Opinion in Immunology* 20:460-470, (2008).
Prokhorenko et al. "Incorporation of a Pyrene Nucleoside Analogue Into Synthetic Oligodeoxynucleotides Using a Nucleoside-Like Synthon," *Bioorganic & Medicinal Chemistry Letters* 5:2081-2084, (1995).
Putnam et al. "Synthesis and evaluation of RNA transesterification efficiency using stereospecific serinol-terpyridine conjugates," *Nucleosides, Nucleotides & Nucleic Acids* 24:1309-1323, (2005).
Raag et al. "Single-chain Fvs," *The FASEB Journal* 9:73-80, (Jan. 1995).
Radaev et al., "Recognition of IgG by Fcγ Receptor," *The Journal of Biological Chemistry* 276(19): 16478-16483, (May 11, 2001).
Rajagopal et al., "A Form of Anti-Tac(Fv) Which is Both Single-chain and Disulfide Stabilized: Comparison with its single-chain and Disulfide-stabilized Homologs," *Protein Engineering* 10(12):1453-1459, (1997).
Raju. "Glycosylation Variations with Expression Systems and Their Impact on Biological Activity of Therapeutic Immunoglobulins," *BioProcess International* 1(4): 44-53, (Apr. 2003).
Ramzaeva et al. Oligonucleotides fuctionalized by fluorescein and rhodamine dyes: Michael addition of methyl acrylate to 2'-deoxypseudouridine, *Helv. Chim. Acta* 83:1108-1126, (2006).
Rawlings., "A large and accurate collection of peptidase cleavages in the MEROPS database," Database (Oxford), pp. 1-14, (2009, e-pub. Nov. 2, 2009).
Reiter et al. (1994). "Stabilization of the Fv Fragments in Recombinant Immunotoxins by Disulfide Bonds Engineered into Conserved Framework Regions," *Biochemistry* 33(18):5451-5449.
Reiter et al. (Jul. 15, 1994). "Improved Binding and Antitumor Activity of a Recombinant Anti-erbB2 Immunotoxin by Disulfide Stabilization of the Fv Fragment," *J. Biol. Chem.* 269(28):18327-18331.
Reiter et al., "Cytotoxic and antitumor activity of a recombinant immunotoxin composed of disulfide-stabilized anti-Tac Fv fragment and truncated Pseudomonas exotoxin," *International Journal of Cancer* 58:142-149, (1994).
Reiter et al., "Antitumor activity and pharmacokinetics in mice of a recombinant immunotoxin containing a disulfide-stabilized Fv fragment," *Cancer Research* 54:2714-2718, (1994).
Reiter et al., "Antibody engineering of recombinant Fv immunotoxins for improved targeting of cancer: disulfide-stabilized Fv immunotoxins," *Clin. Cancer Res.* 2(2):245-252, (Feb. 1, 1996).
Reiter et al., "Disulfide stabilization of antibody Fv: computer predictions and experimental evaluation," *Protein Engineering* 8:1323-1331, (1995).
Reiter et al., "Construction of a functional disulfide-stabilized TCR Fv indicates that antibody and TCR Fv frameworks are very similar in structure," *Immunity* 2:281-287, (1995).
Reiter et al., "Engineering antibody Fv fragments for cancer detection and therapy: disulfide-stabilized Fv fragments," *Nature Biotechnology* 14:1239-1245, (1996).
Remacle et al. "Substrate Cleavage Analysis of Furin and Related Proprotein Convertases," *Journal of Biological Chemistry* 283(30):20897-20906, (Jul. 25, 2008).
Ren et al. "Macrophage migration inhibitory factor stimulates angiogenic factor expression and correlates with differentiation and lymph node status in patients with esophageal squamous cell carcinoma," *Ann. Surg.* 242:55-63, (2005).
Ren et al. "A biocompatible condensation reaction for the labeling of terminal cysteine residues on proteins," *Angew. Chem. Int. Ed.* 48:9658-9662, (2009).
Ridgway et al., "'Knobs-into-holes' Engineering of antibody $C_H3$ domains for heavy chain heterodimerization," *Protein Engineering* 9(7):617-621, (1996).
Roget et al. "Synthesis and use of labelled nucleoside phosphoramidite building blocks bearing a reporter group: biotinyl, dinitrophenyl, pyrenyl and dansyl," *Nucleic Acids Research* 17:7643-7651, (1989).

Roitt et al. "Multispecific Antibodies Comprising Full Length Antibodies and Single Chain Fab Fragments," *Immunology*, English Translation, Moscow:Mir, pp. 388-389, (2000).
Roitt et al. (2000). "Immunology," Moscow, Mir., pp. 100-101 (English Translation).
Rossi et al., "Multivalent Anti-CD20/Anti-CD22 Bispecific Antibody Fusion Proteins Made by the DNL Method Show Potent Lymphoma Cytotoxicity," *Blood, American Society of Hematology* 8:11, pp. 707A, (2006).
Routier et al., "The Glycosylation Pattern of a Humanized IgGI Antibody (D1.3) Expressed in CHO Cells," *Glycoconjugate Journal* 14:201-207, (1997).
Roux et al. "Comparisons of the ability of human IgG3 hinge mutants, IgM, IgE, and IgA2, to form small immune complexes: a role for flexibility and geometry," *J. Immunol.*, 161(8):4083-4090, (1998).
Rupert et al. (Mar. 11, 1993). "Cloning and Expression of Human $TAF_{II}250$: a TBP-Associated Factor Implicated in Cell-Cycle Regulation," *Nature* 362:175-179.
Ruppert et al., "Protease levels in breast, ovary and other gynecological tumor tissues: prognostic importance in breast cancer," *Cancer Detect. Prev.* 21(5):452-459, (1997).
Sakamoto et al. "Enzyme-Mediated Site-Specific Antibody-Protein Modification Using a ZZ Domain as a Linker,"*BioConjugate Chem.*. 21 :2227-2293 (2010, e-pub. Nov. 11, 2010).
Salfeld, J.G. (Dec. 2007). "Isotype Selection in Antibody Engineering," *Nat. Biotechnol.* 25(12):1369-1372.
Sambrook et al., Molecular Cloning: A Laboratory Manual "The Table of Contents" Cold Spring Harbor, New York: Cold Spring Harbor Laboratory Press, (1989).
Santos et al. (Oct. 1999) "Generation and Characterization of a Single Gene-Encoded Single-Chain-tetravalent Antitumor Antibody" *Clinical Cancer Research* 5(10 Suppl):3118s-3123s.
Schaefer et al., "Immunoglobulin domain crossover as a generic approach for the production of bispecific IgG antibodies," *Proc. Natl. Acad. Sci. U.S.A.* 108(27):11187-11192, (Jul. 5, 2011, e-pub. Jun. 20, 2011).
Schirrmann et al. (Jan./Feb. 2010). "Oligomeric Forms of Single Chain Immunoglobulin (sclgG)," *Landes Bioscience* 2(1):73-76.
Schmidt et al., "Suppression of Metastasis Formation by a Recombinant Single Chain Antibody-Toxin Targeted to Full-length and Oncogenic Variant EGF Receptors," *Oncogene* 18:1711-1721, (1999).
Schmiedl et al., "Expression of a bispecific dsFv-dsFy' antibody fragment in *Escherichia coli*," *Protein Engineering* 13(10):725-734, (Oct. 2000).
Schoonjans, et al., "Fab Chains as an Efficient Heterodimerization Scaffold for the Production of Recombinant Bispecific and Trispecific Antibody Derivatives," *Journal of Immunology* 165:7050-7057, (2000).
Schoonjans et al. (2000). "Efficient Heterodimerization of Recombinant Bi- and Trispecific antibodies" *Bioseparation* 9(3):179-183.
Schwartz et al., "A superactive insulin: (B10-aspartic acid]insulin(human)," *Proc. Natl. Acad. Sci. USA* 84:6408-6411, (Sep. 1987).
Scott et al., "Biologic protease inhibitors as novel therapeutic agents," *Biochimie* 92(11):1681-1688, (Nov. 2010).
Seela. "Oligodeoxyribonucleotides containing 1,3-propanediol as nucleoside substitute," *Nucleic Acids Research* 15:3113-3129, (1987).
Sensi et al. "Unique tumor antigens: evidence for immune control of genome integrity and immunogenic targets for T cell-mediated patient-specific immunotherapy," *Clin. Cancer Res.* 12:5023-5032, (2006).
Senter. "Potent antibody drug conjugates for cancer therapy," *Curr. Opin. Chem. Biol.* 13:235-244, (2009).
Seo. "Post-translational modifications and their biological functions: proteomic analysis and systematic approaches," *Biochemistry and Molecular Biology* 37(1):35-44, (2004).
Shen et al., "Single variable domain antibody as a versatile building block for the construction of IgG-like bispecific antibodies," *Journal of Immunological Methods* 318:65-74, (2007).

(56) References Cited

OTHER PUBLICATIONS

Shen et al., "Single variable domain-IgG fusion: A novel recombinant approach to Fc domain-containing bispecific antibodies," *J. of Biological Chemistry* 281(16):10706-10714, (Apr. 21, 2006, e-pub. Feb. 15, 2006).
Shi et al. "A stereospecific synthesis of L-deoxyribose, L-ribose and L-ribosides," *Tetrahed.* 58:3287-3296, (2002).
Shields et al., "High Resolution Mapping of the Binding Site on Human IgG1 for FcγRI, FcγRII, FcγRIII and FcRn and Design of IgG1 Variants with Improved Binding to the FcγR," *Journal of Biological Chemistry* 276 (9):6591-6604, (2001).
Shields et al., "Lack of Fucose on Human IgG1 N-Linked Oligosaccharide Improves Binding to Human FcγRIII and Antibody-dependent Cellular Toxicity," *J Biol Chem.* 277(30):26733-26740, (Jul. 26, 2002).
Shinkawa et al., "The Absence of Fucose but Not the Presence of galactose or Bisecting N-Acetylglucosamine of Human IgG1 Complex-Type Oligosaccharides Shows the Critical Role of Enhancing Antibody-Dependent Cellular cytotoxicity," *J. Biol. Chem.* 278 (5) 3466-3473, (2003).
Silva et al. " Synthesis of a new phosphoramidite nucleoside Biotinylated for the Preparation Oligonucleotide Multibiotinilado," *Biotecnologia Aplicada* 15:154-158, (1998).(Translation of English Abstract Only).
Simon et al., "Antibody Domain Mutants Demonstrate Autonomy of the Antigen Binding Site,"*The EMBO Journal* 9(4):1051-1056, (1990).
Singer, M. and Berg, P. "Genes and genomes," Moscoer, MIR 1(1998) 63-64 (With English Translation.) (per J. Xiao order translation).
Smith-Gill et al. (Dec. 15, 1987). "Contributions of Immunoglobulin Heavy and Light Chain to Antibody Specificity for Lysozyme and Two Haptens," *J. Immunol.* 139(12):4135-4144.
Sondermann et al. "The 3.2-A crystal structure of the human IgG1 Fc fragment-FcγRIII complex", *Nature*, 406:267-273, (2000).
Song et al. (2000). "Light Chain of Natural Anibody Plays a Dominant Role in Protein Antigen Binding, " *Biochem. Biophys. Res. Comm.* 268(2):390-394.
Stella et al. (1985). "Prodrugs: A Chemical Approach to Target Drug Delivery" *Directed Drug Delivery*, Borchardt et al (ed.), Human Press, pp. 247-267.
Stetler-Stevenson et al., "Progelatinase A activation during tumor cell invasion," *Invasion Metastasis* 14(1-6):259-268, (1994-1995).
Stevenson et al., "A chimeric antibody with dual Fc regions (bisFabFc) prepared by manipulations at the IgG hinge," *Anticancer Drug Des.* 3(4):219-230, (Mar. 1989).
Stites et al. (1994). "Immunoglobulin Protiens," Chapter 6 in *Basic Clinical Immunology*, 8th Edition, Appleton & Lange, Norwalk, CT, pp. 66-79.
Stork et al. (Nov. 2007, e-pub. Nov. 3, 2007 ). "A Novel Tri-Functional Antibody Fusion Protein With Improved Pharmacokinetic Properties Generated by Fusing a Bispecific Single-Chain Diabody With an Albumin-Binding Domain From Streptococcal Protein G," *Protein Eng. Des. Sel.* 20(11):569-576.
Strop . et al. (2012). "Generating Bispecific Human IgG1 and IgG2 Antibodies from Any Antibody Pair", *Journal of Molecular Biology*, 420(3):204-219.
Su et al. "Novel non-nucleosidic phosphoramidites for oligonucleotide modification and labeling," *Bioorganic & Medicinal Chemistry Letters* 7:1639-1644, (1997).
Sunbul. "Site specific protein labeling by enzymatic post-translational modification," *Org. Biomol. Chem.* 7:3361-3371, (2009).
Ta et al. "Enzymatic Single-Chain Antibody Tagging a Universal Approach to Targeted Molecular Imaging and Cell Homing in Cardiovascular Disease", *Circulation Research*, 109(4):365-373, (2011).
Taki et al., "Transglutaminase-mediated N- and C-terminal fluorescein labeling of a protein can support the native activity of the modified protein," *Prot. Eng. Des. Sel.* 17:119-126, (2004).

Tao et al. (Apr. 1991). "The Differential Ability of Human IgG1 and IgG4 to Activate Complement is Determined by the COOH-terminal Sequence of the $C_H2$ Domain," *J. Exp. Med* 173:1025-1028.
Taylor et al., "Native chemical ligation: semisynthesis of post-translationally modified proteins and biological probes,"*Nucl. Acids Mol. Biol.* 22:65-96, (2009).
Thies et al. "Folding and association of the antibody domain CH3: prolyl isomerization preceeds dimerization," *J. Mol. Biol.*, 293:67-79, (1999).
Theisen et al. "Fluorescent dye phosphoramidite labelling of oligonucleotides," *Nineteenth Symposium on Nucleic Acids Chemistry*, Fukuoka, Japan, Nov. 11-13, 1992, Nucleic Acids Symposium Series 27, 27:99-100, (1992).
Thommesen et al., "Lysine 322 in the human IgG3 $C_H2$ domain is crucial for antibody dependent complement activation," *Molecular Immunology* 37:995-1004, (2000).
Ton-That et al. "Purification and characterization of sortase, the transpeptidase that cleaves surface proteins of Staphylococcus aureus at the LPXTG motif", *Proc. Natl. Acad. Sci. U.S.A.*, 96(22):12424-12429, (1999).
Torres, M. et al. (2005). "Variable-Region-Identical Antibodies Differing in Isotype Demonstrate Differences in Fine Specificity and Idiotype", *The Journal of Immunology*, 174:2132.
Torgov et al., "Generation of an intensely potent anthracycline by a monoclonal antibody-beta-galactosidase conjugate," *Bioconjug. Chem.* 16 (2005) 717-721.
Tripathi et al., "Laminin-332 is a substrate for hepsin, a protease associated with prostate cancer progression," *JBC* 283:30576-30584, (2008).
Tsukiji et al. "Sortase-Mediated Ligation: A Gift from Gram-Positive Bacteria to Protein Engineering", *Chembiochem*, 10(5):787-798, (2009).
Umaña et al., "Engineered Glycoforms of an Antineuroblastoma IgG1 with Optimized Antibody-Dependent Cellular Cytotoxic Activity," *Nature Biotechnology* 17(2):176-180 (Feb. 1999).
Urata et al., "Synthesis and properties of mirror-image DNA," *Nucl. Acids Res.* 20:3325-3332, (1992).
Vallböhmer et al "Molecular determinants of cetuximab efficacy", *J Clin. Oncol.*, 23(15):3536-3544, (2005).
Van Dijk and Van de Winkel., "Human antibodies as next generation therapeutics," *Curr Opin Chem Biol.* 5(4): 368-74, (Aug. 2001).
Van Spriel et al., "Immunotherapeutic perspective for bispecific antibodies," *Immunology Today* 21(8):391-397, (Aug. 2000).
Van't Veer et al., "Gene expression profiling predicts clinical outcome of breast cancer,"*Nature* 415(6871):530-536, (Jan. 2002).
Vazquez-Ortiz et al., "Overexpression of cathepsin F, matrix metalloproteinases 11 and 12 in cervical cancer," *BMC Cancer* 5:68, (Jun. 30, 2005).
Velasco et al., "Human cathepsin O. Molecular cloning from a breast carcinoma, production of the active enzyme in *Escherichia coli*, and expression analysis in human tissues," *J. Biol Chem* 269(43):27136-27142, (Oct. 28, 1994).
Veveris-Lowe et al., "Seminal Fluid Characterization for Male Fertility and Prostate Cancer: Kallikrein-Related Serine Proteases and whole Proteome Approaches," *Semin Thromb Hemost.* 33(1):87-99, (2007).
Vijayalakshmi., "Antibody Purification Methods," *Applied Biochemistry and Biotechnology* 75:93-102, (1998).
Wagner et al. "Bispecific antibody generated with sortase and click chemistry has broad antiinfluenza virus activity," *Proc. Natl. Acad. Sci. USA* 111:16820-16825, (Nov. 25, 2014).
Walker et al., "Efficient and Rapid Affinity Purification of Proteins Using Recombinant Fusion Proteases," *Bio/Technology* 12:601-605, (1994).
Walker et al. (Jun. 5, 2009, e-pub. Apr. 16, 2009). "Efficient Recovery of High-Affinity Antibodies From a Single-Chain Fab Yeast Display Library," *J. Mol. Biol.* 389(2):365-375.
Ward et al. "The effector functions of immunoglobulins: implications for theraty," *Ther. Immunol.* 2:77-94, (1995).
Wang et al. "Expanding the genetic code", *Chem. Commun (Camb.* ), 7:1-11, (2002).

(56) References Cited

OTHER PUBLICATIONS

Warren et al., "Regulation of Vascular Endothelial Growth Factor of Human Colon Cancer Tumorigenesis in a Mouse Model of Experimental Liver Metastasis," *J. Clin. Invest.* 95:1789-1797, (1995).
Webber et al., "Preparation and characterization of a disulfide-stabilized Fv fragment of the anti-Tac antibody: comparison with its single-chain analog," *Molecular Immunology* 32:249-258, (1995).
Werner et al., "Appropriate Mammalian Expression Systems for Biopharmaceuticals," *Drug Research* 48(8):870-880, (1998).
Wielockx et al., "Matrilysin (matrix metalloproteinase-7): a new promising drug target in cancer and inflammation?," *Cytokine Growth Factor Rev.* 15(2-3):111-115, (Apr.-Jun. 2004).
Willems et al., "Optimizing expression and purification from cell culture medium of trispecific recombinant antibody derivatives," *Journal of Chromatography B* 786:161-176, (2003).
Witte et al. "Preparation of unnatural N-to-N and C-to-C protein fusions", *Proceedings of the National Academy of Sciences of the United States of America*, 109(30):11993-11998, (2012).
Wojczewski et al. "Fluorescent oligonucleotides—versatile tools as probes and primers for DNA and RNA analysis," *Synlett* 10:1667-1678, (1999).
Woof et al., "Human antibody-FC receptor interactions illuminated by crystal structures," *Nat. Rev. Immunol.* 4:1-11, (2004).
Wranik et al. (Dec. 21, 2012). "Luz-Y: A Novel Platform for the Mammalian Cell Production of Full-length IgG Bispeciic Antibodies," *Journal of Biological Chemistry* 287(52):43331-4339.
Wright et al. "Phage display of chelating recombinant antibody libraries," *Molecular Immunology* 44:2860-2869, (2007).
Wright et al., "ADAM28: a potential oncogene involved in asbestos-related lung adenocarcinomas," *Genes Chromosomes Cancer* 49(8);688-698, (Aug. 2010).
Wright and Morrison, "Effect of Glycosylation on Antibody Function: Implications for Genetic Engineering," *Trends in Biotechnology* 15:26-32, (1997).
Wu et al., "Simultaneous Targeting of Multiple Disease Mediators by a Dual-Variable-Domain Immunoglobulin," *Nature Biotechnology* 25(11):1290-1297, (Nov. 2007).
Xie et al., "A New format of bispecific antibody: Highly efficient heterodimerization, expression and tumor cell lysis," *J. of Immunol. Methods* 296:95-101, (2005).
Yamaguchi et al. "Proteolytic Fragmentation With High Specificity of Mouse Immunoglobulin G," *Journal of Immunological Methods* 181:259-267, (1995).
Yazaki et al. Methods in Molecular Biology, vol. 248, Lo, B.K.C. (ed.), Humana Press, Totowa, NJ (2004), pp. 255-268, (2004).
Zahn et al. "Alternative heterocycles for DNA recognition: a 3-pyrazole/pyrrole pair specifies for G.C base pairs," Bioorg. Med. Chem. 8:2467-2474, (2000).
Zeidler et al., "Simultaneous activation of T cells and accessory cells by a new class of intact bispecific antibody results in efficient tumor cell killing," *Journal of Immunology* 163:1246-1252, (1999).
Zuo et al., "An efficient route to the production of an IgG-like bispecific antibody," *Protein Engineering* 13(5):361-367, (2000).
International Search Report dated Dec. 6, 2011, for PCT Patent Application No. PCT/EP2011/064476 filed on Aug. 23, 2011, seven pages.
International Search Report dated Dec. 6, 2011, for PCT Patent Application No. PCT/EP2011/064468 filed on Aug. 23, 2011, seven pages.
Written Opinion of the International Searching Authority dated Dec. 6, 2011, for PCT Patent Application No. PCT/EP2011/064476 filed on Aug. 23, 2011, four pages.
Written Opinion of the International Searching Authority dated Dec. 6, 2011, for PCT Patent Application No. PCT/EP2011/064468 filed on Aug. 23, 2011, four pages.
International Search Report dated Aug. 5, 2014, for PCT Patent Application No. PCT/EP2013/063258, filed on Jun. 25, 2013, seven pages.
International Search Report dated Aug. 6, 2013, PCT Patent Application No. PCT/EP2013/063260, filed on Jun. 25, 2013, seven pages.
Written Opinion of the International Searching Authority dated Aug. 5, 2014, for PCT Patent Application No. PCT/EP2013/063258, filed on Jun. 25, 2013, seven pages.
Written Opinion of the International Searching Authority dated Aug. 6, 2013, PCT Patent Application No. PCT/EP2013/063260, filed on Jun. 25, 2013, eight pages.
International Search Report dated Aug. 6, 2013, for PCT Application No. PCT/US2013/025365, filed on Feb. 8, 2013, 6 pages.
Written Opinion dated Aug. 6, 2013, for PCT Application No. PCT/US2013/025365, filed Feb. 8, 2013, 9 pages.
International Preliminary Report on Patentability for PCT/EP2011/054505, dated Oct. 2, 2012, filed on Mar. 24, 2011, 8 pages.
International Preliminary Report on Patentability dated Aug. 21, 2014, for PCT Patent Application No. PCT/US2013/025365, filed on Feb. 8, 2013, 11 pages.
International Search Report for PCT/EP2011/054505 dated Jun. 28, 2011, filed on Mar. 24, 2011, 7 pages.
European Search Report dated Mar. 14, 2006, for European Patent Application No. 07024864.6, 8 pages.
European Search Report dated Aug. 31, 2009, for European Patent Application No. 09005108.7, 6 pages.
International Search Report dated Aug. 5, 2010, for PCT Application No. PCT/EP2010/003559, filed on Jun. 14, 2010, 10 pages.
Labrijn et al. "Species-Specific Determinants in the IgG CH3 Domain Enable Fab-Arm Exhange by Affecting the Noncovalent CH3-CH3 Interaction Strength," *The Journal of lmmmunology* 187:3238-3246, (2011, e-pub. Aug. 12, 2011).
U.S. Appl. No. 14/551,957, filed Nov. 24, 2014 for Castoldi et al.
U.S. Appl. No. 14/579,165, filed Dec. 22, 2014, by Dieter et al.
U.S. Appl. No. 14/579,192, filed Dec. 22, 2014, by Fenn et al.
U.S. Appl. No. 14/579,218, filed Dec. 22, 2014, by Fenn et al.
Alt et al. "Novel Tetravalent and Bispecific IgG-Like Antibody Molecules Combining Single-chain Diabodies With the Immunoglobulin γ1 Fc or CH3 Region," *FEBS Lett.* 454(1-2):90-94, (Jul. 2, 1999).
Chen et al. "Improved Variants of SrtA for Site-Specific Conjugation on Antibodies and Proteins With High Efficiency," *Scientific Reports* 6(31899):1-12, (Aug. 18, 2016).
Koerber et al. "An Improved Single-Chain Fab Platform for Efficient Display and Recombinant Expression," *J. Mol. Biol.* 427(2):576-586, (Jan. 30, 2015).
Metz, S. et al. "Bispecific Digoxigenin-Binding Antibodies for targeted Payload Delivery," *Proc. Natl. Acad. Sci. U.S.A.* 108(20):8194-8199, (May 17, 2011).
Metz, S. et al. "Bispecific Antibody Derivatives with Restricted Binding Functionalities that are Activated by Proteolytic Processing," *Protein Engineering Design and Selection* 25(10):571-580, (2012, e-pub. Sep. 13, 2012).
Schlaeger, E.-J. "The Protein Hydrolysate, Primatone RL, is a Cost-Effective Multiple Growth Promoter of Mammalian Cell Culture in Serum-Containing and Serum-Free Media and Displays Anti-Apoptosis Properties," *J. Immunol. Methods* 194:191-199, (1996).
Schlaeger, E.-J. et al. "Transient Gene Expression in Mammalian Cells Grown in Serum-Free Suspension Culture," *Cytotechnology* 30:71-83, (1999).
Wörn et al. "Stability Engineering of Antibody Single-Chain Fv Fragments," *J. Mol. Biol.* 305:989-1010, (2001).

\* cited by examiner

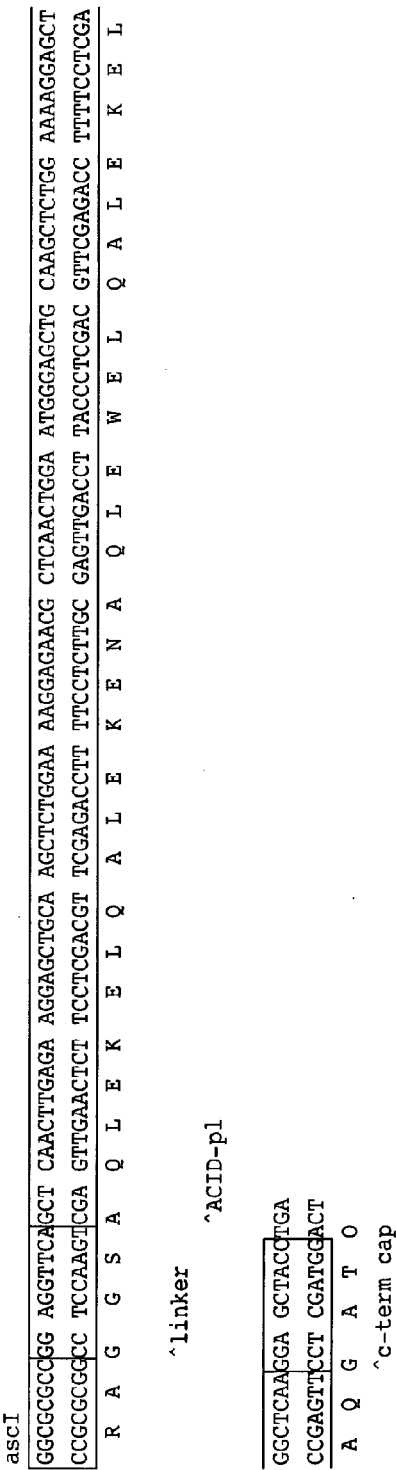
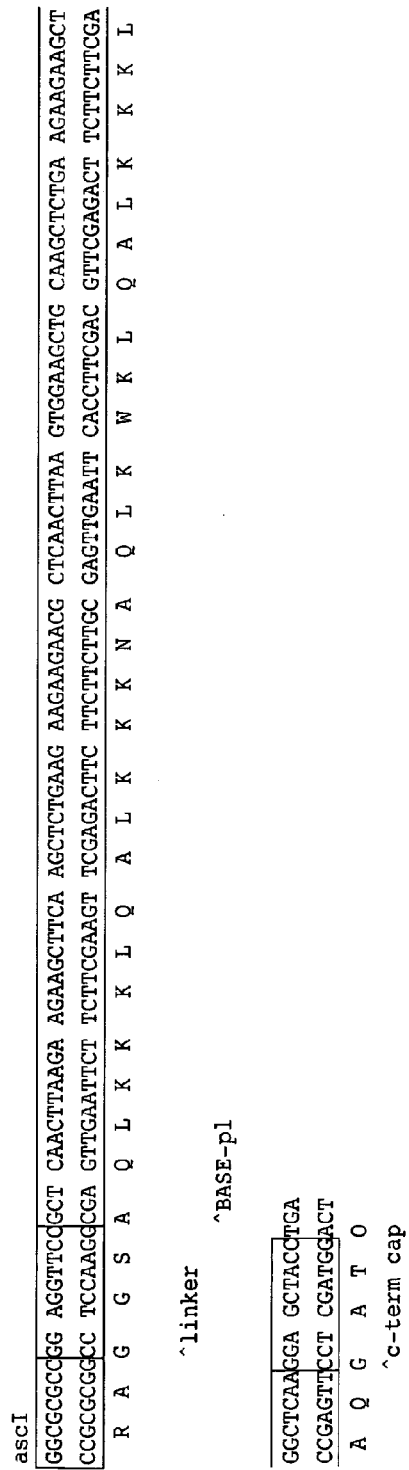
FIG. 2A

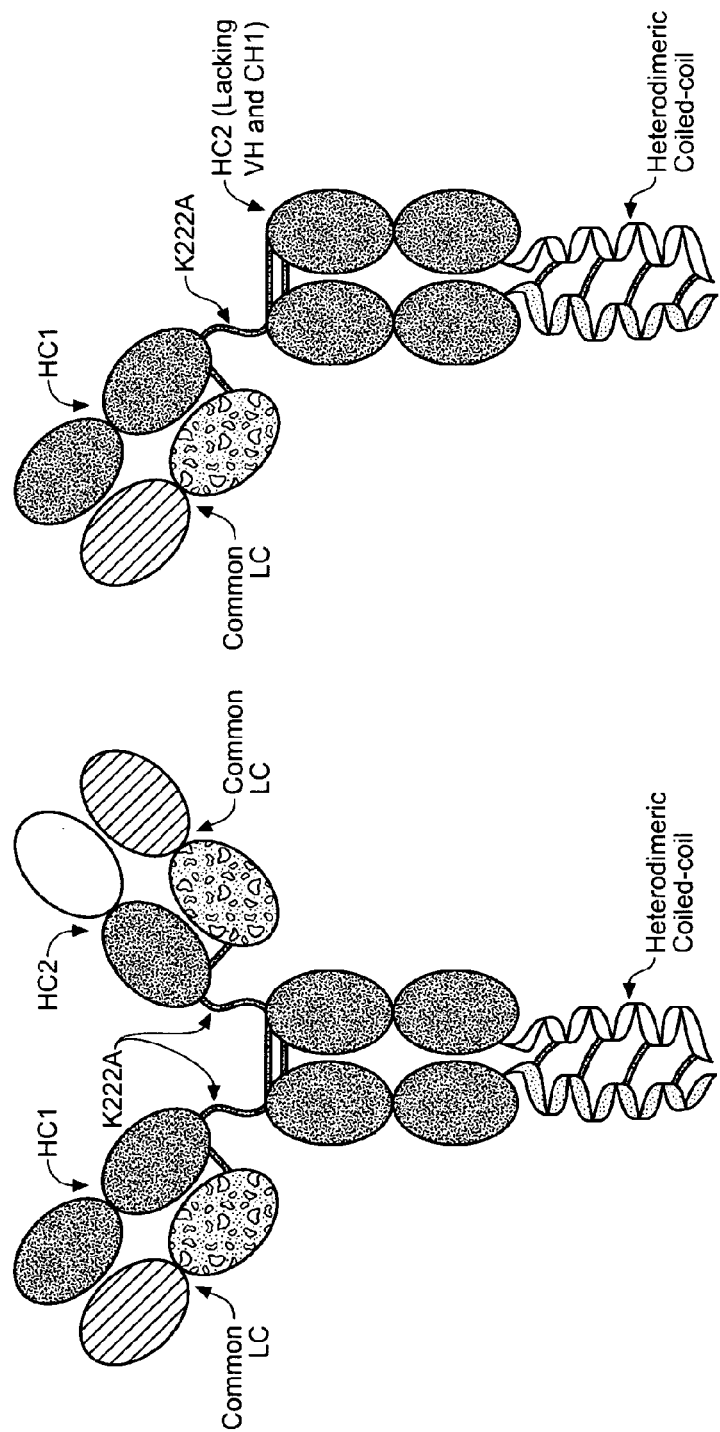

Example: Furin-cleavable 26aa Tether

LC RGRCRRGSGGGSGGGSGGGSGGGSGRSRKRREVQ HC

Example: LysC-cleavable 26aa Tether

LC RGECKGGSGGGSGGGSGGGSGGGSGGSKEVQ HC

FIG. 7B

Common LC
Anti-FcεR1/anti-FcγR2b bispecific Ab with common light chain

Anti-FcγR2b-Bp1 sequence: (anti human FcγR2b HC with BASE.p1 coiled coil heterodimerization domain and K222A mutation)

EVQLVESGGGLVQPGGSLRLSCAASGFTFTNYWIHWVRQAPGKGLEWVGGITPDGGATDYADSV
KGRFTISADTSKNTAYLQMNSLRAEDTAVYYCANDLGSREFYAMDYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDATHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLS
PGKWRAGGSAQLKKKLQALKKKNAQLKWKLQALKKKLAQGAT (SEQ ID NO:1)

Anti-FcεR1-Ap1 sequence (anti human FcεR1 HC with ACID.p1 coiled coil heterodimerization domain and K222A mutation)

EVQLVESGGGLVQPGGSLRLSCAASGFTIYANSIHWVRQAPGKGLEWVAYIGPNFGRSYYADSV
KGRFTISADTSKNTAYLQMNSLRAEDTAVYYCARVWRRSLMSVMDYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDATHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLS
PGKWRAGGSAQLEKELQALEKENAQLEWELQALEKELAQGAT (SEQ ID NO:2)

4d5 LC (common LC for Anti-FcγR2b and Anti-FcεR1)

DIQMTQSPSSLSASVGDRVTITCRASQDVSTAVAWYQQKPGKAPKLLIYSASFLYSGVPSRFSG
SGSGTDFTLTISSLQPEDFATYYCQQSYTTPPTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC (SEQ ID NO:3)

FIG. 8

One-armed anti-HER2 antibody 1 and anti-EGFR (D1.5)

Anti-HER2 antibody 1.ACID.p1 (Anti-HER2 antibody 1 HC with ACID.p1 coiled coil heterodimerization domain and K222A mutation)

EVQLVESGGGLVQPGGSLRLSCAASGFNIKDTYIHWVRQAPGKGLEWVARIYPTNGYTRYADSV
KGRFTISADTSKNTAYLQMNSLRAEDTAVYYCSRWGGDGFYAMDYWGQGTLVTVSSASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKKVEPKSCDATHTCPPCPAPELLGGPSVFLFPPKPKDTLMI
SRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSP
GKWRAGGSAQLEKELQALEKENAQLEWELQALEKELAQGAT (SEQ ID NO:4)

Anti-EGFR (D1.5).ACID.p1 (anti-EGFR (D1.5) HC with ACID.p1 coiled coil heterodimerization domain and K222A mutation)

EVQLVESGGGLVQPGGSLRLSCAASGFTFTGNWIHWVRQAPGKGLEWVGEISPSGGYTDYADSV
KGRFTISADTSKNTAYLQMNSLRAEDTAVYYCARESRVSYEAAMDYWGQGTLVTVSSASTKGPS
VFPLAPSSKSTSGGTAALGCLVKDYFPEPVTVSWNSGALTSGVHTFPAVLQSSGLYSLSSVVTV
PSSSLGTQTYICNVNHKPSNTKVDKKVEPKSCDATHTCPPCPAPELLGGPSVFLFPPKPKDTLM
ISRTPEVTCVVVDVSHEDPEVKFNWYVDGVEVHNAKTKPREEQYNSTYRVVSVLTVLHQDWLNG
KEYKCKVSNKALPAPIEKTISKAKGQPREPQVYTLPPSREEMTKNQVSLTCLVKGFYPSDIAVE
WESNGQPENNYKTTPPVLDSDGSFFLYSKLTVDKSRWQQGNVFSCSVMHEALHNHYTQKSLSLS
PGKWRAGGSAQLEKELQALEKENAQLEWELQALEKELAQGAT (SEQ ID NO:7)

truncFC.Bp1 (HC lacking VH and CH1 with BASE.p1 coiled coil heterodimerization domain)

ECPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLTVDKSR
WQQGNVFSCSVMHEALHNHYTQKSLSLSPGKWRAGGSAQLKKKLQALKKKNAQLKWKLQALKKKLAQGAT
(SEQ ID NO:5)

Anti-HER2 antibody 1 LC

DIQMTQSPSSLSASVGDRVTITCRASQDVNTAVAWYQQKPGKAPKLLIYSASFLYSGVPSRFSG
SRSGTDFTLTISSLQPEDFATYYCQQHYTTPPTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC (SEQ ID NO:6)

*FIG. 9-1*

Anti-EGFR (D1.5) LC

DIQMTQSPSSLSASVGDRVTITCRASQDVSTAVAWYQQKPGKAPKLLIYSASFLYSGVPSRFSG
SGSGTDFTLTISSLQPEDFATYYCQQSYPTPYTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC (SEQ ID NO:8)

*FIG. 9-2*

Tethered example
Anti-HER2 antibody 1 /anti-EGFR (D1.5) antibody

Anti-HER2 (antibody 1)26.ACID.p1 (Anti-HER2 antibody 1 LC tethered to HC via 26aa GGS tether with ACID.p1 coiled coil heterodimerization domain and K222A mutation)

```
DIQMTQSPSSLSASVGDRVTITCRASQDVNTAVAWYQQKPGKAPKLLIYSASFLYSGVPSRFSG
SRSGTDFTLTISSLQPEDFATYYCQQHYTTPPTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGECGGGSGGSGGSGGSGGSGGSGGSGGSGEVQLVESGGGLVQPGG
SLRLSCAASGFNIKDTYIHWVRQAPGKGLEWVARIYPTNGYTRYADSVKGRFTISADTSKNTAY
LQMNSLRAEDTAVYYCSRWGGDGFYAMDYWGQGTLVTVSSASTKGPSVFPLAPSSKSTSGGTAA
LGCLVKDYFPEPVTVSWNSGALTSGVHTFPAVLQSSGLYSLSSVVTVPSSSLGTQTYICNVNHK
PSNTKVDKKVEPKSCDATHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGKWRAGGSAQLEKELQ
ALEKENAQLEWELQALEKELAQGAT (SEQ ID NO:9)
```

D1.5.26.BASE.p1 (anti-EGFR LC tethered to HC via 26aa GGS tether with BASE.p1 coiled coil heterodimerization domain and K222A mutation)

```
DIQMTQSPSSLSASVGDRVTITCRASQDVSTAVAWYQQKPGKAPKLLIYSASFLYSGVPSRFSG
SGSGTDFTLTISSLQPEDFATYYCQQSYPTPYTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGECGGGSGGSGGSGGSGGSGGSGGSGGSGEVQLVESGGGLVQPGG
SLRLSCAASGFTFTGNWIHWVRQAPGKGLEWVGEISPSGGYTDYADSVKGRFTISADTSKNTAY
LQMNSLRAEDTAVYYCARESRVSYEAAMDYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNH
KPSNTKVDKKVEPKSCDATHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPI
EKTISKAKGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGKWRAGGSAQLKKKL
QALKKKNAQLKWKLQALKKKLAQGAT (SEQ ID NO:10)
```

FIG. 10

Tethered example
HER1/HER2

Anti-HER2 (antibody 2).26.ACID.p1 (anti-HER2 antibody 2 LC tethered to HC via 26aa GGS tether with ACID.p1 coiled coil heterodimerization domain and K222A mutation)

DIQMTQSPSSLSASVGDRVTITCKASQDVSIGVAWYQQKPGKAPKLLIYSASYRYTGVPSRFSG
SGSGTDFTLTISSLQPEDFATYYCQQYYIYPYTTFGQGTKVEIKRTVAAPSVFIFPPSDEQLKS
GTASVVCLLNNFYPREAKVQWKVDNALQSGNSQESVTEQDSKDSTYSLSSTLTLSKADYEKHKV
YACEVTHQGLSSPVTKSFNRGECGGGSGGSGGSGGSGGSGGSGGSGGSGEVQLVESGGGLVQPG
GSLRLSCAASGFTFTDYTMDWVRQAPGKGLEWVADVNPNSGGSIYNQRFKGRFTLSVDRSKNTL
YLQMNSLRAEDTAVYYCARNLGPSFYFDYWGQGTLVTVSSASTKGPSVFPLAPSSKSTSGGTAA
LGCLVKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGKWRAGGSAQLEKELQ
ALEKENAQLEWELQALEKELAQGAT (SEQ ID NO:11)

D1.5.26.BASE.p1 (anti-EGFR LC tethered to HC via 26aa GGS tether with BASE.p1 coiled coil heterodimerization domain and K222A mutation)

DIQMTQSPSSLSASVGDRVTITCRASQDVSTAVAWYQQKPGKAPKLLIYSASFLYSGVPSRFSG
SGSGTDFTLTISSLQPEDFATYYCQQSYPTPYTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGECGGGSGGSGGSGGSGGSGGSGCSGGSGEVQLVESGGGLVQPGG
SLRLSCAASGFTFTGNWIHWVRQAPGKGLEWVGEISPSGGYTDYADSVKGRFTISADTSKNTAY
LQMNSLRAEDTAVYYCARESRVSYEAAMDYWGQGTLVTVSSASTKGPSVFPLAPSSKSTSGGTA
ALGCLVKDYFPEPVTVSWNSGALTSGVHTFPAVLQSSGLYSLSSVVTVPSSSLGTQTYICNVNH
KPSNTKVDKKVEPKSCDATHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKALPAPI
EKTISKAKGQPREPQVYTLPPSREEMTKNQVSLTCLVKGFYPSDIAVEWESNGQPENNYKTTPP
VLDSDGSFFLYSKLTVDKSRWQQGNVFSCSVMHEALHNHYTQKSLSLSPGKWRAGGSAQLKKKL
QALKKKNAQLKWKLQALKKKLAQGAT (SEQ ID NO:10)

FIG. 11

```
                   claI/bsp106
 901 ACCTCGGTTC TATCGATTGA ATTCCACCAT GGGATGGTCA TGTATCATCC TTTTTCTAGT AGCAACTGCA ACTGGAGTAC ATTCAGAAGT TCAGCTGTGT
     TGGAGCCAAG ATACCTAACT TAAGGTGGTA CCCTACCAGT ACATAGTAGG AAAAAGATCA TCGTTGACGT TGACCTCATG TAAGTCCTTCA AGTCGACCAC
   1                    M  G  W  S  C  I  I  L  F  L  V  A  T  A  T  G  V  H  S  E  V  Q  L  V
                        ^start of signal sequence for Anti-HER2 antibody 1 HC 1001 GAGTCTGGCG GTGGCCTGGT GCAGCCAGGG GGCTCACTCC GTTTGTCCTG TGCAGCTTCT GGCTTCAACA TTAAAGACAC CTATATACAC TGGGTGCGTC
     CTCAGACCGC CACCGGACCA CGTCGGTCCC CCGAGTGAGG CAAACAGGAC ACGTCGAAGA CCGAAGTTGT AATTTCTGTG GATATATGTG ACCCACGCAG
  25 E  S  G  G  G  L  V  Q  P  G  G  S  L  R  L  S  C  A  A  S  G  F  N  I  K  D  T  Y  I  H  W  V  R  Q 1101 AGGGCCCCGGG TAAGGGCCTG GAATGGGTTG CAAGGATTTA TCCTACGAAT GGTTATACTA GATATGCCGA TAGCGTCAAG GGCCGTTTCA CTATAAGCGC
     TCCGGGGCCC ATTCCCGGAC CTTACCCAAC GTTCCTAAAT AGGATGCTTA CCAATATGAT CTATACGGCT ATCGCAGTTC CCGGCAAAGT GATATTCGCG
  59 A  P  G  K  G  L  E  W  V  A  R  I  Y  P  T  N  G  Y  T  R  Y  A  D  S  V  K  G  R  F  T  I  S  A 1201 AGACACATCC AAAAACACAG CCTACCTGCA GATGAACAGC CTGCGTGCTG AGGACACTGC CGTCTATTAT TGTTCTAGAT GGGGAGGGGA CGGCTTCTAT
     TCTGTGTAGG TTTTTGTGTC GGATGGACGT CTACTTGTCG GACGCACGAC TCCTGTGACG GCAGATAATA ACAAGATCTA CCCCTCCCCT GCCGAAGATA
  92 D  T  S  K  N  T  A  Y  L  Q  M  N  S  L  R  A  E  D  T  A  V  Y  Y  C  S  R  W  G  G  D  G  F  Y apaI
1301 GCTATGGACT ACTGGGGTCA AGGAACCCTG GTCACCGTCT CCTCGGCCTC CACCAAGGGC CCATCGGTTC TTCCCCTCGC ACCCTCCTCC AAGAGCACCT
     CGATACCTGA TGACCCCAGT TCCTTGGGAC CAGTGGCAGA GGAGCCGGAG GTGGTTCCCG GGTAGCCAAG AAGGGGACCG TGGGAGGAGG TTCTCGTGGA
 125 A  M  D  Y  W  G  Q  G  T  L  V  T  V  S  S  A  S  T  K  G  P  S  V  F  P  L  A  P  S  S  K  S  T  S 1401 CTGGGGGCAC AGCGGCCCTG GGCTGCCTGG TCAAGGACTA CTTCCCCGAA CCGGTGACGG TGTCGTGGAA CTCAGGCGCC CTGACCAGCG GCGTGCACAC
     GACCCCCGTG TCGCCGGGAC CCGACGGACC AGTTCCTGAT GAAGGGGCTT GGCCACTGCC ACAGCACCTT GAGTCCGCGG GACTGGTCGC CGCACGTGTG
 159 G  G  T  A  A  L  G  C  L  V  K  D  Y  F  P  E  P  V  T  V  S  W  N  S  G  A  L  T  S  G  V  H  T
```

FIG. 12A-1

```
1501 CTTCCCGGCT GTCCTACAGT CCTCAGGACT CTACTCCCTC AGCAGCGTGG TGACTGTGCC CTCTAGCAGC TTGGGCACCC AGACCTACAT CTGCAACGTG
     GAAGGGCCGA CAGGATGTCA GGAGTCCTGA GATGAGGGAG TCGTCGCACC ACTGACACGG GAGATCGTCG AACCCGTGGG TCTGGATGTA GACGTTGCAC
 192  F  P  A   V  L  Q  S   S  G  L   Y  S  L   S  S  V  V   T  V  P   S  S  S   L  G  T  Q   T  Y  I   C  N  V

1601 AATCACAAGC CCAGCAACAC CAAGGTGGAC AAGAAAGTTG AGCCCAAATC TTGTGACGCA ACTCACACAT GCCCACCGTG CCCAGCACCT GAACTCCTGG
     TTAGTGTTCG GGTCGTTGTG GTTCCACCTG TTCTTTCAAC TCGGGTTTAG AACACTGCGT TGAGTGTGTA CGGGTGGCAC GGGTCGTGGA CTTGAGGACC
 225  N  H  K  P   S  N  T   K  V  D   K  K  V  E   P  K  S   C  D  A   T  H  T  C   P  P  C   P  A  P   E  L  L  G
                                                                        ^K222A mut 1701 GGGGACCGTC AGTCTTCCTC TTCCCCCCAA AACCCAAGGA CACCCTCATG ATCTCCCGGA CCCCTGAGGT CACATGCGTG GTGGTGGACG TGAGCCACGA
     CCCCTGGCAG TCAGAAGGAG AAGGGGGGTT TTGGGTTCCT GTGGGAGTAC TAGAGGGCCT GGGGACTCCA GTGTACGCAC CACCACCTGC ACTCGGTGCT
 259  G  P  S   V  F  L   F  P  P  K   P  K  D   T  L  M   I  S  R  T   P  E  V   T  C  V   V  V  D  V   S  H  E
```

*FIG. 12A-2*

```
                  claI/bspI06
 901 ACCTCGGTTC TATCGATTGA ATTCCACCAT GGGATGGTCA TGTATCATCC TTTTTCTAGT AGCAACTGCA ACTGGAGTAC ATTCAGATAT CCAGATGACC
     TGGAGCCAAG ATAGCTAACT TAAGGTGGTA CCCTACCAGT ACATAGTAGG AAAAAGATCA TCGTTGACGT TGACCTCATG TAAGTCTATA GGTCTACTGG
   1                       M   G   W   S   C   I   I   L   F   L   V   A   T   A   T   G   V   H   S   D   I   Q   M   T
                                            Anti-HER2 antibody 1 VL begin^

1001 CAGTCCCCGA GCTCCCTGTC CGCCTCTGTG GGCGATAGGG TCACCATCAC CTGCCGTGCC AGTCAGGATG TGAATACTGC TGTAGCCTGG TATCAACAGA
     GTCAGGGGCT CGAGGGACAG GCGGAGACAC CCGCTATCCC AGTGGTAGTG GACGGCACGG TCAGTCCTAC ACTTATGACG ACATCGGACC ATAGTTGTCT
  25  Q   S   P   S   S   L   S   A   S   V   G   D   R   V   T   I   T   C   R   A   S   Q   D   V   N   T   A   V   A   W   Y   Q   Q   K

1101 AACCAGGAAA AGCTCCGAAA CTACTGATTT ACTCCGGCAT CTTCCTCTAC TCTGGAGTCC CTTCTCGCTT CTCCGGTTCC AGATCTGGGA CGGATTTCAC
     TTGGTCCTTT TCGAGGCTTT GATGACTAAA TGAGCGGTAG GAAGGAGATG AGACCTCAGG GAAGAGCGAA GAGGCCAAGG TCTAGACCCT GCCTAAAGTG
  59  P   G   K   A   P   K   L   L   I   Y   S   A   S   F   L   Y   S   G   V   P   S   R   F   S   G   S   R   S   G   T   D   F   T

1201 TCTGACAATC AGCAGTCTGC AGCCGGAAGA CTTCGCAACT TATTACTGTC AGCAACATTA TACTACTCCT CCCACGTTCG GACAGGGTAC CAAGGTGGAG
     AGACTGTTAG TCGTCAGACG TCGGCCTTCT GAAGCGTTGA ATAATGACAG TCGTTGTAAT ATGATGAGGA GGGTGCAAGC CTGTCCCATG GTTCCACCTC
  92  L   T   I   S   S   L   Q   P   E   D   F   A   T   Y   Y   C   Q   Q   H   Y   T   T   P   P   T   F   G   Q   G   T   K   V   E

1301 ATCAAACGAA CTGTGGCTGC ACCATCTGTC TTCATCTTCC CGCCATCTGA TGAGCAGTTG AAATCTGGAA CTGCCTCTGT TGTGTGCCTG CTGAATAACT
     TAGTTTGCTT GACACCGACG TGGTAGACAG AAGTAGAAGG GCGGTAGACT ACTCGTCAAC TTTAGACCTT GACGGAGACA ACACACGGAC GACTTATTGA
 125  I   K   R   T   V   A   A   P   S   V   F   I   F   P   P   S   D   E   Q   L   K   S   G   T   A   S   V   V   C   L   L   N   N   F

1401 TCTATCCCAG AGAGGCCAAA GTACAGTGGA AGGTGGATAA CGCCCTCCAA TCGGGTAACT CCCAGGAGAG TGTCACAGAG CAGGACAGCA AGGACAGCAC
     AGATAGGGTC TCTCCGGTTT CATGTCACCT TCCACCTATT GCGGGAGGTT AGCCCATTGA GGGTCCTCTC ACAGTGTCTC GTCCTGTCGT TCCTGTCGTG
 159  Y   P   R   E   A   K   V   Q   W   K   V   D   N   A   L   Q   S   G   N   S   Q   E   S   V   T   E   Q   D   S   K   D   S   T

1501 CTACAGCCTC AGCAGCACCC TGACGCTGAG CAAAGCAGAC TACGAGAAAC ACAAAGTCTA CGCCTGCGAA GTCACCCATC AGGGCCTGAG CTCCCCCGTC
     GATGTCGGAG TCGTCGTGGG ACTGCGACTC GTTTCGTCTG ATGCTCTTTG TGTTTCAGAT GCGGACGCTT CAGTGGGTAG TCCCGGACTC GAGCGGGCAG
 192  Y   S   L   S   S   T   L   T   L   S   K   A   D   Y   E   K   H   K   V   Y   A   C   E   V   T   H   Q   G   L   S   S   P   V

FIG. 12B-1
```

```
                                                                                                    bamHI[M.mspI-]
1601 ACAAAGAGCT TCAACAGGGG AGAGTGTGGA GGAGGTTCAG GAGGTTCTGG TGGTTCGGGA GATCTGGAGG TTCAGGAGGT TCTGGTGGT
     TGTTTCTCGA AGTTGTCCCC TCTCACACCT CCTCCAAGTC CTCCAAGACC ACCAAGCCCT CTAGACCTCC AAGTCCTCCA AGACCACCA
225 T  K  S  F  N  R  G  E  C  G  G  S  G  G  S  G  G  S  G  G  S  G  G  S  G  G  S  G  G  S
                              ^Anti-HER2 antibody 1 LC end 1701 CAGGAGAAGT TCAGCTGGTG GAGTCTGGCG GTGGCCTGGT GCAGCCAGGG GGCTCACTCC GTTTGTCCCTG TGCAGCTTCT GGCTTCAACA TTAAAGACAC
     GTCCTCTTCA AGTCGACCAC CTCAGACCGC CACCGGACCA CGTCGGTCCC CCGAGTGAGG CAAACAGGAC ACGTCGAAGA CCGAAGTTGT AATTTCTGTG
259 G  E  V  Q  L  V  E  S  G  G  G  L  V  Q  P  G  G  S  L  R  L  S  C  A  A  S  G  F  N  I  K  D  T
     ^Anti-HER2 antibody 1 VH begin 1801 CTATATACAC TGGTGCGTC AGGCCCCGGG TAAGGGCCTG GAATGGGTTG CAAGGATTTA TCCTACGAAT GGTTATACTA GATATGCCGA TAGCGTCAAG
     GATATATGTG ACCCACGCAG TCCGGGGCCC ATTCCCGGAC CTTACCCAAC GTTCCTAAAT AGGATGCTTA CCAATATGAT CTATACGGCT ATCGCAGTTC
292 Y  I  H  W  V  R  Q  A  P  G  K  G  L  E  W  V  A  R  I  Y  P  T  N  G  Y  T  R  Y  A  D  S  V  K 1901 GCCCGTTCA CTATAAGCGC AGACACATCC AAAAACACAG CCTACCTGCA GATGAACAGC CTGCGTGCTG AGGACACTGC CGTCTATTAT TGTTCTAGAT
     CGGGCAAAGT GATATTCGCG TCTGTGTAGG TTTTTGTGTC GGATGGACGT CTACTTGTCG GACGCACGAC TCCTGTGACG GCAGATAATA ACAAGATCTA
325 G  R  F  T  I  S  A  D  T  S  K  N  T  A  Y  L  Q  M  N  S  L  R  A  E  D  T  A  V  Y  Y  C  S  R  W
                                                                                                        apaI
2001 GGGGAGGGGA CGGCTTCTAT GCTATGGACT ACTGGGGTCA AGGAACCCTG GTCACCGTCT CCTCGGCCTC CACCAAGGGC CCATCGGTCT TCCCCCTGGC
     CCCCTCCCCT GCCGAAGATA CGATACCTGA TGACCCCAGT TCCTTGGGAC CAGTGGCAGA GGAGCCGGAG GGTGGTTCCCG GGTAGCCAGA AGGGGGACCG
359 G  G  D  G  F  Y  A  M  D  Y  W  G  Q  G  T  L  V  T  V  S  S  A  S  T  K  G  P  S  V  F  P  L  A 2101 ACCCTCCTCC AAGAGCACCT CTGGGGGCAC AGCGGCCCTG GGCTGCCTGG TCAAGGACTA CTTCCCCGAA CCGGTGACGG TGTCGTGGAA CTCAGGCGCC
     TGGGAGGAGG TTCTCGTGGA GACCCCCGTG TCGCCGGGAC CCGACGGACC AGTTCCTGAT GAAGGGGCTT GGCCACTGCC ACAGCACCTT GAGTCCGCGG
392 P  S  S  K  S  T  S  G  G  T  A  A  L  G  C  L  V  K  D  Y  F  P  E  P  V  T  V  S  W  N  S  G  A
                                                                                                    ^Anti-HER2 antibody 1 VH end
```

FIG. 12B-2

```
2201 CTGACCAGCG GCGTGCACAC CTTCCCGGCT GTCCTACAGT CCTCAGGACT CTACTCCCTC AGCAGCGTGG TGACTGTGCC CTCTAGCAGC TTGGGCACCC
     GACTGGTCGC CGCACGTGTG GAAGGGCCGA CAGGATGTCA GGAGTCCTGA GATGAGGGAG TCGTCGCACC ACTGACACGG GAGATCGTCG AACCCGTGGG
425  L  T  S  G  V  H  T  F  P  P  A  V  L  Q  S  S  G  L  Y  S  L  S  S  V  V  T  V  P  S  S  S  L  G  T  Q

2301 AGACCTACAT CTGCAACGTG AATCACAAGC CCAGCAACAC CAAGGTGGAC AAGAAAGTTG AGCCCAAATC TTGTGACGCA ACTCACACAT GCCCACCGTG
     TCTGGATGTA GACGTTGCAC TTAGTGTTCG GGTCGTTGTG GTTCCACCTG TTCTTTCAAC TCGGGTTTAG AACACTGCGT TGAGTGTGTA CGGGTGGCAC
459  T  Y  I  C  N  V  N  H  K  P  S  N  T  K  V  D  K  K  V  E  P  K  S  C  D  A  T  H  T  C  P  P  C
                                                                                    ^K to A mut 2401 CCCAGCACCT GAACTCCTGG GGGGACCGTC AGTCTTCCTC TTCCCCCCAA AACCCAAGGA CACCCTCATG ATCTCCCGGA CCCCTGAGGT CACATGCGTG
     GGGTCGTGGA CTTGAGGACC CCCCTGGCAG TCAGAAGGAG AAGGGGGGTT TTGGGTTCCT GTGGGAGTAC TAGAGGGCCT GGGGACTCCA GTGTACGCAC
492  P  A  P  E  L  L  G  G  P  S  V  F  L  F  P  P  K  P  K  D  T  L  M  I  S  R  T  P  E  V  T  C  V
```

FIG. 12B-3

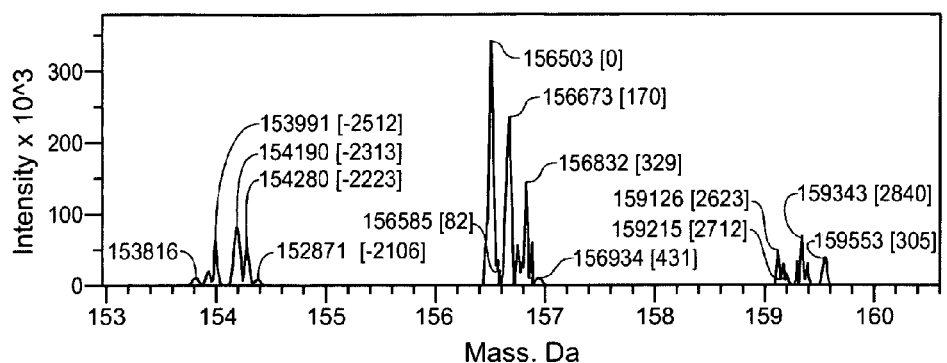
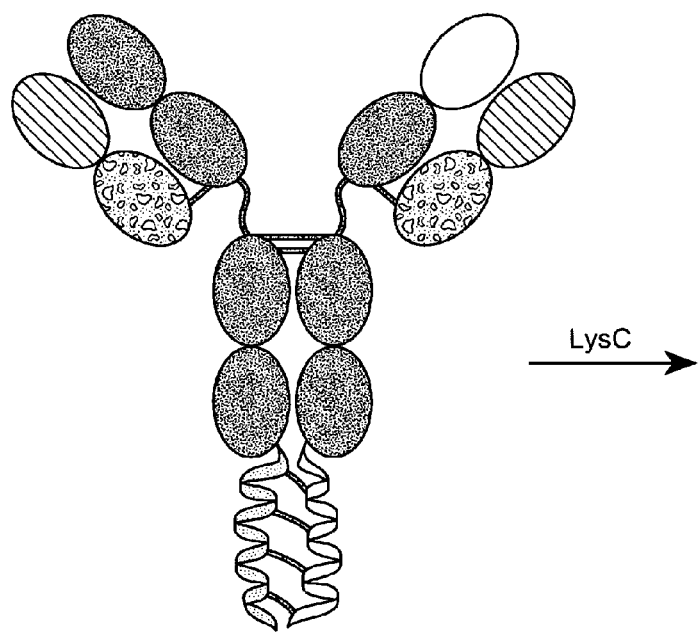
Theoretical MW = 156491
FIG. 13A

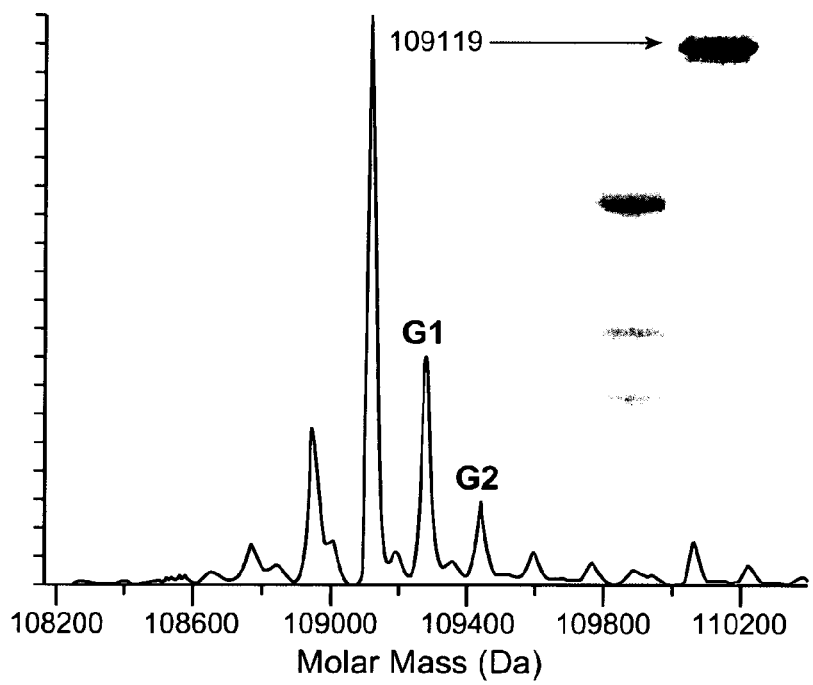
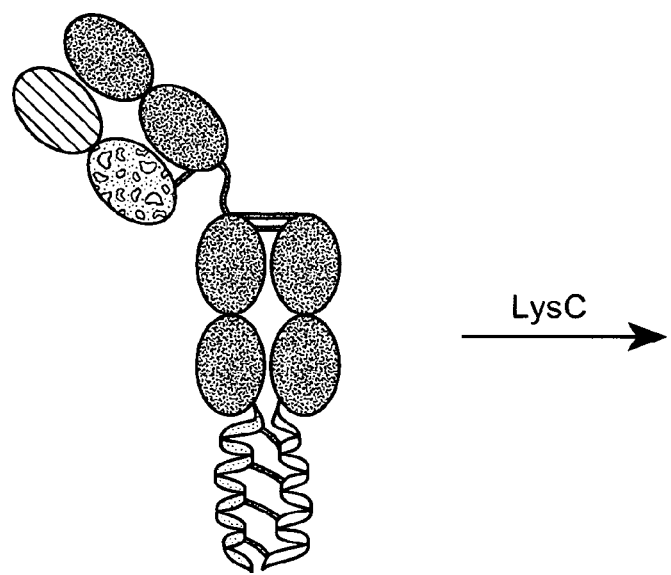
FIG. 17A

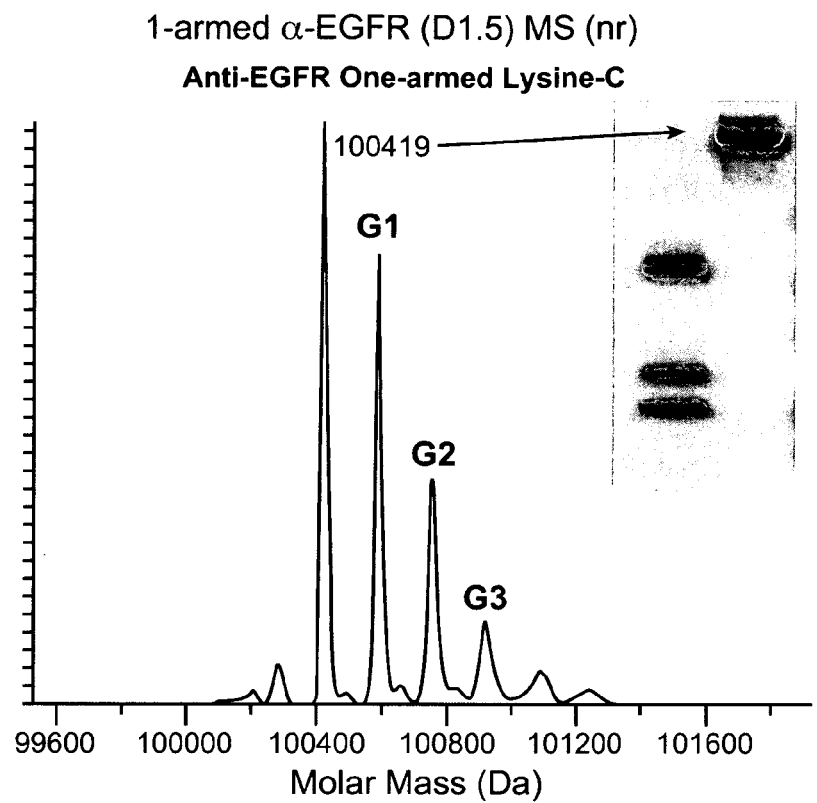
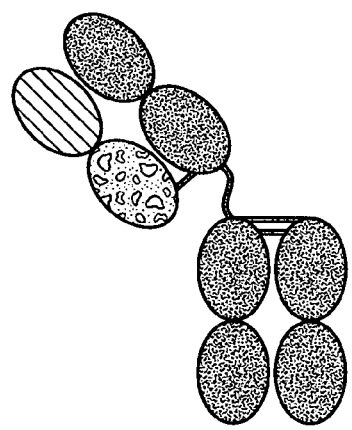
FIG. 17B

```
                         SEQUENCE LISTING

<160> NUMBER OF SEQ ID NOS: 39

<210> SEQ ID NO 1
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Trp Ile His Trp Val Arg Gln Ala Pro Gly Lys Gly Leu Glu Trp Val
        35                  40                  45

Gly Gly Ile Thr Pro Asp Gly Ala Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Asn Asp Leu Gly Ser Arg Glu Phe Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Ala Thr His Thr Cys Pro Pro Cys Pro Ala Pro Glu Leu Leu Gly
225                 230                 235                 240
```

Gly Pro Ser Val Phe Leu Phe Pro Pro Lys Pro Asp Thr Leu Met
            245                 250                 255

Ile Ser Arg Thr Pro Glu Val Thr Cys Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys Trp Arg Ala Gly Gly Ser Ala Gln Leu Lys Lys Lys Leu
450                 455                 460

Gln Ala Leu Lys Lys Lys Asn Ala Gln Leu Lys Trp Lys Leu Gln Ala
465                 470                 475                 480

Leu Lys Lys Lys Leu Ala Gln Gly Ala Thr
            485                 490

<210> SEQ ID NO 2
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Tyr Ala Asn
            20                  25                  30

Ser Ile His Trp Val Arg Gln Ala Pro Gly Lys Gly Leu Glu Trp Val
        35                  40                  45

Ala Tyr Ile Gly Pro Asn Phe Gly Arg Ser Tyr Tyr Ala Asp Ser Val
    50                  55                  60

Lys Gly Arg Phe Thr Ile Ser Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Val Trp Arg Arg Ser Leu Met Ser Val Met Asp Tyr Trp Gly
        100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Ala Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Trp Arg Ala Gly Gly Ser Ala Gln Leu Glu Lys Glu Leu
450                 455                 460

Gln Ala Leu Glu Lys Glu Asn Ala Gln Leu Glu Trp Glu Leu Gln Ala
465                 470                 475                 480

Leu Glu Lys Glu Leu Ala Gln Gly Ala Thr
                485                 490

<210> SEQ ID NO 3
<211> LENGTH: 214
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Ala Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Trp Arg Ala Gly Gly Ser Ala Gln Leu Glu Lys Glu Leu Gln
450                 455                 460

Ala Leu Glu Lys Glu Asn Ala Gln Leu Glu Trp Glu Leu Gln Ala Leu
465                 470                 475                 480

Glu Lys Glu Leu Ala Gln Gly Ala Thr
                485

<210> SEQ ID NO 5
<211> LENGTH: 262
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 5

Glu Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys Trp
    210                 215                 220

Arg Ala Gly Gly Ser Ala Gln Leu Lys Lys Lys Leu Gln Ala Leu Lys
225                 230                 235                 240

Lys Lys Asn Ala Gln Leu Lys Trp Lys Leu Gln Ala Leu Lys Lys Lys
                245                 250                 255

Leu Ala Gln Gly Ala Thr
            260

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro

```
             65                  70                  75                  80
Glu Asp Phe Ala Thr Tyr Tyr Cys Gln Gln His Tyr Thr Thr Pro Pro
                     85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 7
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asn
                20                  25                  30

Trp Ile His Trp Val Arg Gln Ala Pro Gly Lys Gly Leu Glu Trp Val
            35                  40                  45

Gly Glu Ile Ser Pro Ser Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Tyr Glu Ala Ala Met Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205
```

Lys Pro Ser Asn Thr Lys Val Asp Lys Lys Val Glu Pro Lys Ser Cys
            210                 215                 220

Asp Ala Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Trp Arg Ala Gly Gly Ser Ala Gln Leu Glu Lys Glu Leu
    450                 455                 460

Gln Ala Leu Glu Lys Glu Asn Ala Gln Leu Glu Trp Glu Leu Gln Ala
465                 470                 475                 480

Leu Glu Lys Glu Leu Ala Gln Gly Ala Thr
                485                 490

<210> SEQ ID NO 8
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Ser Tyr Pro Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 9
<211> LENGTH: 729
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys Gly Gly Gly Ser Gly Gly Ser Gly Gly Ser
```

```
              210                 215                 220
Gly Gly Ser Gly Gly Ser Gly Ser Gly Gly Ser Gly Gly Ser Gly
225                 230                 235                 240

Glu Val Gln Leu Val Glu Ser Gly Gly Gly Leu Val Gln Pro Gly Gly
                245                 250                 255

Ser Leu Arg Leu Ser Cys Ala Ala Ser Gly Phe Asn Ile Lys Asp Thr
                260                 265                 270

Tyr Ile His Trp Val Arg Gln Ala Pro Gly Lys Gly Leu Glu Trp Val
            275                 280                 285

Ala Arg Ile Tyr Pro Thr Asn Gly Tyr Thr Arg Tyr Ala Asp Ser Val
        290                 295                 300

Lys Gly Arg Phe Thr Ile Ser Ala Asp Thr Ser Lys Asn Thr Ala Tyr
305                 310                 315                 320

Leu Gln Met Asn Ser Leu Arg Ala Glu Asp Thr Ala Val Tyr Tyr Cys
                325                 330                 335

Ser Arg Trp Gly Gly Asp Gly Phe Tyr Ala Met Asp Tyr Trp Gly Gln
            340                 345                 350

Gly Thr Leu Val Thr Val Ser Ser Ala Ser Thr Lys Gly Pro Ser Val
        355                 360                 365

Phe Pro Leu Ala Pro Ser Ser Lys Ser Thr Ser Gly Gly Thr Ala Ala
    370                 375                 380

Leu Gly Cys Leu Val Lys Asp Tyr Phe Pro Glu Pro Val Thr Val Ser
385                 390                 395                 400

Trp Asn Ser Gly Ala Leu Thr Ser Gly Val His Thr Phe Pro Ala Val
                405                 410                 415

Leu Gln Ser Ser Gly Leu Tyr Ser Leu Ser Ser Val Val Thr Val Pro
            420                 425                 430

Ser Ser Ser Leu Gly Thr Gln Thr Tyr Ile Cys Asn Val Asn His Lys
        435                 440                 445

Pro Ser Asn Thr Lys Val Asp Lys Lys Val Glu Pro Lys Ser Cys Asp
450                 455                 460

Ala Thr His Thr Cys Pro Pro Cys Pro Ala Pro Glu Leu Leu Gly Gly
465                 470                 475                 480

Pro Ser Val Phe Leu Phe Pro Pro Lys Pro Lys Asp Thr Leu Met Ile
                485                 490                 495

Ser Arg Thr Pro Glu Val Thr Cys Val Val Val Asp Val Ser His Glu
            500                 505                 510

Asp Pro Glu Val Lys Phe Asn Trp Tyr Val Asp Gly Val Glu Val His
        515                 520                 525

Asn Ala Lys Thr Lys Pro Arg Glu Glu Gln Tyr Asn Ser Thr Tyr Arg
    530                 535                 540

Val Val Ser Val Leu Thr Val Leu His Gln Asp Trp Leu Asn Gly Lys
545                 550                 555                 560

Glu Tyr Lys Cys Lys Val Ser Asn Lys Ala Leu Pro Ala Pro Ile Glu
                565                 570                 575

Lys Thr Ile Ser Lys Ala Lys Gly Gln Pro Arg Glu Pro Gln Val Tyr
            580                 585                 590

Thr Leu Pro Pro Ser Arg Glu Glu Met Thr Lys Asn Gln Val Ser Leu
        595                 600                 605

Thr Cys Leu Val Lys Gly Phe Tyr Pro Ser Asp Ile Ala Val Glu Trp
    610                 615                 620

Glu Ser Asn Gly Gln Pro Glu Asn Asn Tyr Lys Thr Thr Pro Pro Val
625                 630                 635                 640
```

```
Leu Asp Ser Asp Gly Ser Phe Phe Leu Tyr Ser Lys Leu Thr Val Asp
                645                 650                 655

Lys Ser Arg Trp Gln Gln Gly Asn Val Phe Ser Cys Ser Val Met His
            660                 665                 670

Glu Ala Leu His Asn His Tyr Thr Gln Lys Ser Leu Ser Leu Ser Pro
        675                 680                 685

Gly Lys Trp Arg Ala Gly Ser Ala Gln Leu Glu Lys Glu Leu Gln
    690                 695                 700

Ala Leu Glu Lys Glu Asn Ala Gln Leu Glu Trp Glu Leu Gln Ala Leu
705                 710                 715                 720

Glu Lys Glu Leu Ala Gln Gly Ala Thr
                725

<210> SEQ ID NO 10
<211> LENGTH: 729
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Ser Gly Gly Ser
    210                 215                 220

Gly Gly Ser Gly Gly Ser Gly Gly Ser Gly Gly Ser Gly Gly Ser Gly
225                 230                 235                 240

Glu Val Gln Leu Val Glu Ser Gly Gly Gly Leu Val Gln Pro Gly Gly
                245                 250                 255

Ser Leu Arg Leu Ser Cys Ala Ala Ser Gly Phe Asn Ile Lys Asp Thr
```

-continued

```
              260                 265                 270
Tyr Ile His Trp Val Arg Gln Ala Pro Gly Lys Gly Leu Glu Trp Val
            275                 280                 285

Ala Arg Ile Tyr Pro Thr Asn Gly Tyr Thr Arg Tyr Ala Asp Ser Val
290                 295                 300

Lys Gly Arg Phe Thr Ile Ser Ala Asp Thr Ser Lys Asn Thr Ala Tyr
305                 310                 315                 320

Leu Gln Met Asn Ser Leu Arg Ala Glu Asp Thr Ala Val Tyr Tyr Cys
                325                 330                 335

Ser Arg Trp Gly Gly Asp Gly Phe Tyr Ala Met Asp Tyr Trp Gly Gln
            340                 345                 350

Gly Thr Leu Val Thr Val Ser Ser Ala Ser Thr Lys Gly Pro Ser Val
            355                 360                 365

Phe Pro Leu Ala Pro Ser Ser Lys Ser Thr Ser Gly Gly Thr Ala Ala
370                 375                 380

Leu Gly Cys Leu Val Lys Asp Tyr Phe Pro Glu Pro Val Thr Val Ser
385                 390                 395                 400

Trp Asn Ser Gly Ala Leu Thr Ser Gly Val His Thr Phe Pro Ala Val
                405                 410                 415

Leu Gln Ser Ser Gly Leu Tyr Ser Leu Ser Ser Val Val Thr Val Pro
                420                 425                 430

Ser Ser Ser Leu Gly Thr Gln Thr Tyr Ile Cys Asn Val Asn His Lys
            435                 440                 445

Pro Ser Asn Thr Lys Val Asp Lys Lys Val Glu Pro Lys Ser Cys Asp
450                 455                 460

Ala Thr His Thr Cys Pro Pro Cys Pro Ala Pro Glu Leu Leu Gly Gly
465                 470                 475                 480

Pro Ser Val Phe Leu Phe Pro Pro Lys Pro Lys Asp Thr Leu Met Ile
                485                 490                 495

Ser Arg Thr Pro Glu Val Thr Cys Val Val Val Asp Val Ser His Glu
            500                 505                 510

Asp Pro Glu Val Lys Phe Asn Trp Tyr Val Asp Gly Val Glu Val His
            515                 520                 525

Asn Ala Lys Thr Lys Pro Arg Glu Glu Gln Tyr Asn Ser Thr Tyr Arg
530                 535                 540

Val Val Ser Val Leu Thr Val Leu His Gln Asp Trp Leu Asn Gly Lys
545                 550                 555                 560

Glu Tyr Lys Cys Lys Val Ser Asn Lys Ala Leu Pro Ala Pro Ile Glu
                565                 570                 575

Lys Thr Ile Ser Lys Ala Lys Gly Gln Pro Arg Glu Pro Gln Val Tyr
            580                 585                 590

Thr Leu Pro Pro Ser Arg Glu Glu Met Thr Lys Asn Gln Val Ser Leu
            595                 600                 605

Thr Cys Leu Val Lys Gly Phe Tyr Pro Ser Asp Ile Ala Val Glu Trp
610                 615                 620

Glu Ser Asn Gly Gln Pro Glu Asn Asn Tyr Lys Thr Thr Pro Pro Val
625                 630                 635                 640

Leu Asp Ser Asp Gly Ser Phe Phe Leu Tyr Ser Lys Leu Thr Val Asp
                645                 650                 655

Lys Ser Arg Trp Gln Gln Gly Asn Val Phe Ser Cys Ser Val Met His
            660                 665                 670

Glu Ala Leu His Asn His Tyr Thr Gln Lys Ser Leu Ser Leu Ser Pro
            675                 680                 685
```

```
Gly Lys Trp Arg Ala Gly Gly Ser Ala Gln Leu Glu Lys Glu Leu Gln
        690                 695                 700

Ala Leu Glu Lys Glu Asn Ala Gln Leu Glu Trp Glu Leu Gln Ala Leu
705                 710                 715                 720

Glu Lys Glu Leu Ala Gln Gly Ala Thr
                725

<210> SEQ ID NO 11
<211> LENGTH: 729
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Gly Gly Ser Gly Gly
210                 215                 220

Ser Gly Gly Ser Gly Gly Ser Gly Gly Ser Gly Gly Ser Gly Gly Ser
225                 230                 235                 240

Gly Glu Val Gln Leu Val Glu Ser Gly Gly Gly Leu Val Gln Pro Gly
                245                 250                 255

Gly Ser Leu Arg Leu Ser Cys Ala Ala Ser Gly Phe Thr Phe Thr Asp
            260                 265                 270

Tyr Thr Met Asp Trp Val Arg Gln Ala Pro Gly Lys Gly Leu Glu Trp
        275                 280                 285

Val Ala Asp Val Asn Pro Asn Ser Gly Gly Ser Ile Tyr Asn Gln Arg
290                 295                 300

Phe Lys Gly Arg Phe Thr Leu Ser Val Asp Arg Ser Lys Asn Thr Leu
```

```
            305                 310                 315                 320
Tyr Leu Gln Met Asn Ser Leu Arg Ala Glu Asp Thr Ala Val Tyr Tyr
                325                 330                 335
Cys Ala Arg Asn Leu Gly Pro Ser Phe Tyr Phe Asp Tyr Trp Gly Gln
                340                 345                 350
Gly Thr Leu Val Thr Val Ser Ser Ala Ser Thr Lys Gly Pro Ser Val
                355                 360                 365
Phe Pro Leu Ala Pro Ser Ser Lys Ser Thr Ser Gly Gly Thr Ala Ala
        370                 375                 380
Leu Gly Cys Leu Val Lys Asp Tyr Phe Pro Glu Pro Val Thr Val Ser
385                 390                 395                 400
Trp Asn Ser Gly Ala Leu Thr Ser Gly Val His Thr Phe Pro Ala Val
                405                 410                 415
Leu Gln Ser Ser Gly Leu Tyr Ser Leu Ser Ser Val Val Thr Val Pro
                420                 425                 430
Ser Ser Ser Leu Gly Thr Gln Thr Tyr Ile Cys Asn Val Asn His Lys
                435                 440                 445
Pro Ser Asn Thr Lys Val Asp Lys Lys Val Glu Pro Lys Ser Cys Asp
        450                 455                 460
Lys Thr His Thr Cys Pro Pro Cys Pro Ala Pro Glu Leu Leu Gly Gly
465                 470                 475                 480
Pro Ser Val Phe Leu Phe Pro Pro Lys Pro Lys Asp Thr Leu Met Ile
                485                 490                 495
Ser Arg Thr Pro Glu Val Thr Cys Val Val Val Asp Val Ser His Glu
                500                 505                 510
Asp Pro Glu Val Lys Phe Asn Trp Tyr Val Asp Gly Val Glu Val His
                515                 520                 525
Asn Ala Lys Thr Lys Pro Arg Glu Glu Gln Tyr Asn Ser Thr Tyr Arg
        530                 535                 540
Val Val Ser Val Leu Thr Val Leu His Gln Asp Trp Leu Asn Gly Lys
545                 550                 555                 560
Glu Tyr Lys Cys Lys Val Ser Asn Lys Ala Leu Pro Ala Pro Ile Glu
                565                 570                 575
Lys Thr Ile Ser Lys Ala Lys Gly Gln Pro Arg Glu Pro Gln Val Tyr
                580                 585                 590
Thr Leu Pro Pro Ser Arg Glu Glu Met Thr Lys Asn Gln Val Ser Leu
                595                 600                 605
Thr Cys Leu Val Lys Gly Phe Tyr Pro Ser Asp Ile Ala Val Glu Trp
        610                 615                 620
Glu Ser Asn Gly Gln Pro Glu Asn Asn Tyr Lys Thr Thr Pro Pro Val
625                 630                 635                 640
Leu Asp Ser Asp Gly Ser Phe Phe Leu Tyr Ser Lys Leu Thr Val Asp
                645                 650                 655
Lys Ser Arg Trp Gln Gln Gly Asn Val Phe Ser Cys Ser Val Met His
                660                 665                 670
Glu Ala Leu His Asn His Tyr Thr Gln Lys Ser Leu Ser Leu Ser Pro
                675                 680                 685
Gly Lys Trp Arg Ala Gly Gly Ser Ala Gln Leu Glu Lys Glu Leu Gln
        690                 695                 700
Ala Leu Glu Lys Glu Asn Ala Gln Leu Glu Trp Glu Leu Gln Ala Leu
705                 710                 715                 720
Glu Lys Glu Leu Ala Gln Gly Ala Thr
                725
```

-continued

```
<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Arg Ala Gly Gly Ser Ala Gln Leu Glu Lys Glu Leu Gln Ala Leu Glu
1               5                   10                  15

Lys Glu Asn Ala Gln Leu Glu Trp Glu Leu Gln Ala Leu Glu Lys Glu
                20                  25                  30

Leu Ala Gln Gly Ala Thr
        35

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Arg Ala Gly Gly Ser Ala Gln Leu Lys Lys Lys Leu Gln Ala Leu Lys
1               5                   10                  15

Lys Lys Asn Ala Gln Leu Lys Trp Lys Leu Gln Ala Leu Lys Lys Lys
                20                  25                  30

Leu Ala Gln Gly Ala Thr
        35

<210> SEQ ID NO 14
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Ser Gly Gly Ser Gly Gly Ser Gly Gly Ser Gly Gly Ser
1               5                   10                  15

Gly Gly Ser Gly Gly Ser Gly Gly Ser Gly
                20                  25

<210> SEQ ID NO 15
<211> LENGTH: 291
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
                20                  25                  30

Pro Gly Gly Ser Leu Arg Leu Ser Cys Ala Ala Ser Gly Phe Asn Ile
            35                  40                  45

Lys Asp Thr Tyr Ile His Trp Val Arg Gln Ala Pro Gly Lys Gly Leu
```

```
              50                  55                  60
Glu Trp Val Ala Arg Ile Tyr Pro Thr Asn Gly Tyr Thr Arg Tyr Ala
 65                  70                  75                  80

Asp Ser Val Lys Gly Arg Phe Thr Ile Ser Ala Asp Thr Ser Lys Asn
                 85                  90                  95

Thr Ala Tyr Leu Gln Met Asn Ser Leu Arg Ala Glu Asp Thr Ala Val
            100                 105                 110

Tyr Tyr Cys Ser Arg Trp Gly Gly Asp Gly Phe Tyr Ala Met Asp Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Ala Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu
    290

<210> SEQ ID NO 16
<211> LENGTH: 524
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gly Trp Ser Cys Ile Ile Leu Phe Leu Val Ala Thr Ala Thr Gly
  1               5                  10                  15

Val His Ser Asp Ile Gln Met Thr Gln Ser Pro Ser Ser Leu Ser Ala
             20                  25                  30

Ser Val Gly Asp Arg Val Thr Ile Thr Cys Arg Ala Ser Gln Asp Val
         35                  40                  45

Asn Thr Ala Val Ala Trp Tyr Gln Gln Lys Pro Gly Lys Ala Pro Lys
 50                  55                  60

Leu Leu Ile Tyr Ser Ala Ser Phe Leu Tyr Ser Gly Val Pro Ser Arg
 65                  70                  75                  80

Phe Ser Gly Ser Arg Ser Gly Thr Asp Phe Thr Leu Thr Ile Ser Ser
                 85                  90                  95

Leu Gln Pro Glu Asp Phe Ala Thr Tyr Tyr Cys Gln Gln His Tyr Thr
            100                 105                 110
```

```
Thr Pro Pro Thr Phe Gly Gln Gly Thr Lys Val Glu Ile Lys Arg Thr
            115                 120                 125
Val Ala Ala Pro Ser Val Phe Ile Phe Pro Pro Ser Asp Glu Gln Leu
    130                 135                 140
Lys Ser Gly Thr Ala Ser Val Val Cys Leu Leu Asn Asn Phe Tyr Pro
145                 150                 155                 160
Arg Glu Ala Lys Val Gln Trp Lys Val Asp Asn Ala Leu Gln Ser Gly
                165                 170                 175
Asn Ser Gln Glu Ser Val Thr Glu Gln Asp Ser Lys Asp Ser Thr Tyr
            180                 185                 190
Ser Leu Ser Ser Thr Leu Thr Leu Ser Lys Ala Asp Tyr Glu Lys His
        195                 200                 205
Lys Val Tyr Ala Cys Glu Val Thr His Gln Gly Leu Ser Ser Pro Val
    210                 215                 220
Thr Lys Ser Phe Asn Arg Gly Glu Cys Gly Gly Gly Ser Gly Gly Ser
225                 230                 235                 240
Gly Gly Ser Gly Gly Ser Gly Gly Ser Gly Gly Ser Gly Gly Ser Gly
                245                 250                 255
Gly Ser Gly Glu Val Gln Leu Val Glu Ser Gly Gly Gly Leu Val Gln
            260                 265                 270
Pro Gly Gly Ser Leu Arg Leu Ser Cys Ala Ala Ser Gly Phe Asn Ile
        275                 280                 285
Lys Asp Thr Tyr Ile His Trp Val Arg Gln Ala Pro Gly Lys Gly Leu
    290                 295                 300
Glu Trp Val Ala Arg Ile Tyr Pro Thr Asn Gly Tyr Thr Arg Tyr Ala
305                 310                 315                 320
Asp Ser Val Lys Gly Arg Phe Thr Ile Ser Ala Asp Thr Ser Lys Asn
                325                 330                 335
Thr Ala Tyr Leu Gln Met Asn Ser Leu Arg Ala Glu Asp Thr Ala Val
            340                 345                 350
Tyr Tyr Cys Ser Arg Trp Gly Gly Asp Gly Phe Tyr Ala Met Asp Tyr
        355                 360                 365
Trp Gly Gln Gly Thr Leu Val Thr Val Ser Ser Ala Ser Thr Lys Gly
    370                 375                 380
Pro Ser Val Phe Pro Leu Ala Pro Ser Ser Lys Ser Thr Ser Gly Gly
385                 390                 395                 400
Thr Ala Ala Leu Gly Cys Leu Val Lys Asp Tyr Phe Pro Glu Pro Val
                405                 410                 415
Thr Val Ser Trp Asn Ser Gly Ala Leu Thr Ser Gly Val His Thr Phe
            420                 425                 430
Pro Ala Val Leu Gln Ser Ser Gly Leu Tyr Ser Leu Ser Ser Val Val
        435                 440                 445
Thr Val Pro Ser Ser Ser Leu Gly Thr Gln Thr Tyr Ile Cys Asn Val
    450                 455                 460
Asn His Lys Pro Ser Asn Thr Lys Val Asp Lys Lys Val Glu Pro Lys
465                 470                 475                 480
Ser Cys Asp Ala Thr His Thr Cys Pro Pro Cys Pro Ala Pro Glu Leu
                485                 490                 495
Leu Gly Gly Pro Ser Val Phe Leu Phe Pro Pro Lys Pro Lys Asp Thr
            500                 505                 510
Leu Met Ile Ser Arg Thr Pro Glu Val Thr Cys Val
        515                 520
```

```
<210> SEQ ID NO 17
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Gly Ser Gly Gly Ser Gly Gly Ser Gly Gly Ser Gly Gly Ser
1               5                   10                  15

Gly Gly Ser Gly Arg Ser Arg Lys Arg Arg
            20                  25

<210> SEQ ID NO 18
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Gly Gly Ser Gly Gly Ser Gly Gly Ser Gly Gly Ser Gly Gly Ser
1               5                   10                  15

Gly Gly Ser Gly Gly Ser Gly Gly Ser Lys
            20                  25

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu Asn Leu Tyr Phe Gln Gly
1               5

<210> SEQ ID NO 20
<211> LENGTH: 9
<212> TYPE: PRT
<213> ORGANISM: Unknown
<220> FEATURE:
<223> OTHER INFORMATION: Description of Unknown: Hedgehog peptide

<400> SEQUENCE: 20

Gly Asp Trp Asn Ala Arg Trp Cys Phe
1               5

<210> SEQ ID NO 21
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (3)..(116)

<400> SEQUENCE: 21 gg cgc gcc gga ggt tca gct caa ctt gag aag gag ctg caa gct ctg        47
   Arg Ala Gly Gly Ser Ala Gln Leu Glu Lys Glu Leu Gln Ala Leu
   1               5                   10                  15 gaa aag gag aac gct caa ctg gaa tgg gag ctg caa gct ctg gaa aag       95
```

```
Glu Lys Glu Asn Ala Gln Leu Glu Trp Glu Leu Gln Ala Leu Glu Lys
            20                  25                  30 gag ctg gct caa gga gct acc tga                                    119
Glu Leu Ala Gln Gly Ala Thr
        35

<210> SEQ ID NO 22
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (3)..(116)

<400> SEQUENCE: 22 gg cgc gcc gga ggt tcc gct caa ctt aag aag aag ctt caa gct ctg       47
   Arg Ala Gly Gly Ser Ala Gln Leu Lys Lys Lys Leu Gln Ala Leu
   1               5                   10                  15 aag aag aag aac gct caa ctt aag tgg aag ctg caa gct ctg aag aag      95
Lys Lys Lys Asn Ala Gln Leu Lys Trp Lys Leu Gln Ala Leu Lys Lys
            20                  25                  30 aag ctg gct caa gga gct acc tga                                    119
Lys Leu Ala Gln Gly Ala Thr
        35

<210> SEQ ID NO 23
<211> LENGTH: 900
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
acctcggttc tatcgattga attccaccat gggatggtca tgtatcatcc tttttctagt    60
agcaactgca actggagtac attcagaagt tcagctggtg gagtctggcg gtggcctggt   120
gcagccaggg ggctcactcc gtttgtcctg tgcagcttct ggcttcaaca ttaaagacac   180
ctatatacac tgggtgcgtc aggccccggg taagggcctg gaatggggttg caaggattta  240 tcctacgaat ggttatacta gatatgccga tagcgtcaag ggccgtttca ctataagcgc   300
agacacatcc aaaaacacag cctacctgca gatgaacagc ctgcgtgctg aggacactgc   360
cgtctattat tgttctagat ggggagggga cggcttctat gctatggact actggggtca   420
aggaaccctg gtcaccgtct cctcggcctc caccaagggc ccatcggtct tccccctggc   480
accctcctcc aagagcacct ctgggggcac agcggccctg ggctgcctgg tcaaggacta   540
cttccccgaa ccggtgacgg tgtcgtggaa ctcaggcgcc ctgaccagcg gcgtgcacac   600
cttcccggct gtcctacagt cctcaggact ctactccctc agcagcgtgg tgactgtgcc   660
ctctagcagc ttgggcaccc agacctacat ctgcaacgtg aatcacaagc ccagcaacac   720
caaggtggac aagaaagttg agcccaaatc ttgtgacgca actcacacat gcccaccgtg   780
cccagcacct gaactcctgg ggggaccgtc agtcttcctc ttccccccaa acccaagga    840 caccctcatg atctccccgga cccctgaggt cacatgcgtg gtggtggacg tgagccacga   900

<210> SEQ ID NO 24
<211> LENGTH: 1600
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<221> NAME/KEY: CDS
<222> LOCATION: (29)..(1600)

<400> SEQUENCE: 24
acctcggttc tatcgattga attccacc atg gga tgg tca tgt atc atc ctt        52
                                Met Gly Trp Ser Cys Ile Ile Leu
                                  1               5 ttt cta gta gca act gca act gga gta cat tca gat atc cag atg acc      100
Phe Leu Val Ala Thr Ala Thr Gly Val His Ser Asp Ile Gln Met Thr
     10                  15                  20 cag tcc ccg agc tcc ctg tcc gcc tct gtg ggc gat agg gtc acc atc      148
Gln Ser Pro Ser Ser Leu Ser Ala Ser Val Gly Asp Arg Val Thr Ile
 25                  30                  35                  40 acc tgc cgt gcc agt cag gat gtg aat act gct gta gcc tgg tat caa      196
Thr Cys Arg Ala Ser Gln Asp Val Asn Thr Ala Val Ala Trp Tyr Gln
                 45                  50                  55 cag aaa cca gga aaa gct ccg aaa cta ctg att tac tcg gca tcc ttc      244
Gln Lys Pro Gly Lys Ala Pro Lys Leu Leu Ile Tyr Ser Ala Ser Phe
             60                  65                  70 ctc tac tct gga gtc cct tct cgc ttc tct ggt tcc aga tct ggg acg      292
Leu Tyr Ser Gly Val Pro Ser Arg Phe Ser Gly Ser Arg Ser Gly Thr
         75                  80                  85 gat ttc act ctg acc atc agc agt ctg cag ccg gaa gac ttc gca act      340
Asp Phe Thr Leu Thr Ile Ser Ser Leu Gln Pro Glu Asp Phe Ala Thr
     90                  95                 100 tat tac tgt cag caa cat tat act act cct ccc acg ttc gga cag ggt      388
Tyr Tyr Cys Gln Gln His Tyr Thr Thr Pro Pro Thr Phe Gly Gln Gly
105                 110                 115                 120 acc aag gtg gag atc aaa cga act gtg gct gca cca tct gtc ttc atc      436
Thr Lys Val Glu Ile Lys Arg Thr Val Ala Ala Pro Ser Val Phe Ile
                125                 130                 135 ttc ccg cca tct gat gag cag ttg aaa tct gga act gcc tct gtt gtg      484
Phe Pro Pro Ser Asp Glu Gln Leu Lys Ser Gly Thr Ala Ser Val Val
            140                 145                 150 tgc ctg ctg aat aac ttc tat ccc aga gag gcc aaa gta cag tgg aag      532
Cys Leu Leu Asn Asn Phe Tyr Pro Arg Glu Ala Lys Val Gln Trp Lys
        155                 160                 165 gtg gat aac gcc ctc caa tcg ggt aac tcc cag gag agt gtc aca gag      580
Val Asp Asn Ala Leu Gln Ser Gly Asn Ser Gln Glu Ser Val Thr Glu
    170                 175                 180 cag gac agc aag gac agc acc tac agc ctc agc agc acc ctg acg ctg      628
Gln Asp Ser Lys Asp Ser Thr Tyr Ser Leu Ser Ser Thr Leu Thr Leu
185                 190                 195                 200 agc aaa gca gac tac gag aaa cac aaa gtc tac gcc tgc gaa gtc acc      676
Ser Lys Ala Asp Tyr Glu Lys His Lys Val Tyr Ala Cys Glu Val Thr
                205                 210                 215 cat cag ggc ctg agc tcg ccc gtc aca aag agc ttc aac agg gga gag      724
His Gln Gly Leu Ser Ser Pro Val Thr Lys Ser Phe Asn Arg Gly Glu
            220                 225                 230 tgt gga gga ggt tca gga ggt tct ggt ggt tcg gga gga tcc gga gga      772
Cys Gly Gly Gly Ser Gly Gly Ser Gly Gly Ser Gly Gly Ser Gly Gly
        235                 240                 245 tct gga ggt tca gga ggt tct ggt ggg tca gga gaa gtt cag ctg gtg      820
Ser Gly Gly Ser Gly Gly Ser Gly Gly Ser Gly Glu Val Gln Leu Val
    250                 255                 260 gag tct ggc ggt ggc ctg gtg cag cca ggg ggc tca ctc cgt ttg tcc      868
Glu Ser Gly Gly Gly Leu Val Gln Pro Gly Gly Ser Leu Arg Leu Ser
```

```
265                 270                 275                 280
tgt gca gct tct ggc ttc aac att aaa gac acc tat ata cac tgg gtg      916
Cys Ala Ala Ser Gly Phe Asn Ile Lys Asp Thr Tyr Ile His Trp Val
                285                 290                 295
cgt cag gcc ccg ggt aag ggc ctg gaa tgg gtt gca agg att tat cct      964
Arg Gln Ala Pro Gly Lys Gly Leu Glu Trp Val Ala Arg Ile Tyr Pro
            300                 305                 310
acg aat ggt tat act aga tat gcc gat agc gtc aag ggc cgt ttc act     1012
Thr Asn Gly Tyr Thr Arg Tyr Ala Asp Ser Val Lys Gly Arg Phe Thr
        315                 320                 325
ata agc gca gac aca tcc aaa aac aca gcc tac ctg cag atg aac agc     1060
Ile Ser Ala Asp Thr Ser Lys Asn Thr Ala Tyr Leu Gln Met Asn Ser
    330                 335                 340
ctg cgt gct gag gac act gcc gtc tat tat tgt tct aga tgg gga ggg     1108
Leu Arg Ala Glu Asp Thr Ala Val Tyr Tyr Cys Ser Arg Trp Gly Gly
345                 350                 355                 360
gac ggc ttc tat gct atg gac tac tgg ggt caa gga acc ctg gtc acc     1156
Asp Gly Phe Tyr Ala Met Asp Tyr Trp Gly Gln Gly Thr Leu Val Thr
                365                 370                 375
gtc tcc tcg gcc tcc acc aag ggc cca tcg gtc ttc ccc ctg gca ccc     1204
Val Ser Ser Ala Ser Thr Lys Gly Pro Ser Val Phe Pro Leu Ala Pro
            380                 385                 390
tcc tcc aag agc acc tct ggg ggc aca gcg gcc ctg ggc tgc ctg gtc     1252
Ser Ser Lys Ser Thr Ser Gly Gly Thr Ala Ala Leu Gly Cys Leu Val
        395                 400                 405
aag gac tac ttc ccc gaa ccg gtg acg gtg tcg tgg aac tca ggc gcc     1300
Lys Asp Tyr Phe Pro Glu Pro Val Thr Val Ser Trp Asn Ser Gly Ala
    410                 415                 420
ctg acc agc ggc gtg cac acc ttc ccg gct gtc cta cag tcc tca gga     1348
Leu Thr Ser Gly Val His Thr Phe Pro Ala Val Leu Gln Ser Ser Gly
425                 430                 435                 440
ctc tac tcc ctc agc agc gtg gtg act gtg ccc tct agc agc ttg ggc     1396
Leu Tyr Ser Leu Ser Ser Val Val Thr Val Pro Ser Ser Ser Leu Gly
                445                 450                 455
acc cag acc tac atc tgc aac gtg aat cac aag ccc agc aac acc aag     1444
Thr Gln Thr Tyr Ile Cys Asn Val Asn His Lys Pro Ser Asn Thr Lys
            460                 465                 470
gtg gac aag aaa gtt gag ccc aaa tct tgt gac gca act cac aca tgc     1492
Val Asp Lys Lys Val Glu Pro Lys Ser Cys Asp Ala Thr His Thr Cys
        475                 480                 485
cca ccg tgc cca gca cct gaa ctc ctg ggg gga ccg tca gtc ttc ctc     1540
Pro Pro Cys Pro Ala Pro Glu Leu Leu Gly Gly Pro Ser Val Phe Leu
    490                 495                 500
ttc ccc cca aaa ccc aag gac acc ctc atg atc tcc cgg acc cct gag     1588
Phe Pro Pro Lys Pro Lys Asp Thr Leu Met Ile Ser Arg Thr Pro Glu
505                 510                 515                 520
gtc aca tgc gtg                                                     1600
Val Thr Cys Val
```

```
<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (2)..(2)
<223> OTHER INFORMATION: Any amino acid
<220> FEATURE:
<221> NAME/KEY: MISC_FEATURE

```

```
<222> LOCATION: (4)..(4)
<223> OTHER INFORMATION: Any amino acid

<400> SEQUENCE: 25

Arg Xaa Arg Xaa Arg Arg
1               5

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: Any hydrophobic amino acid residue or
      Asparagine
<220> FEATURE:
<221> NAME/KEY: misc_feature
<222> LOCATION: (1)..(14)
<223> OTHER INFORMATION: This sequence consists of 2 heptad repeats; see
      specification as filed for detailed description of preferred
      embodiments
<220> FEATURE:
<221> NAME/KEY: MISC_FEATURE
<222> LOCATION: (2)..(3)
<223> OTHER INFORMATION: Any amino acid residue
<220> FEATURE:
<221> NAME/KEY: MISC_FEATURE
<222> LOCATION: (4)..(4)
<223> OTHER INFORMATION: Any hydrophobic amino acid residue
<220> FEATURE:
<221> NAME/KEY: MISC_FEATURE
<222> LOCATION: (5)..(5)
<223> OTHER INFORMATION: Any charged amino acid residue
<220> FEATURE:
<221> NAME/KEY: MISC_FEATURE
<222> LOCATION: (6)..(6)
<223> OTHER INFORMATION: Any amino acid residue
<220> FEATURE:
<221> NAME/KEY: MISC_FEATURE
<222> LOCATION: (7)..(7)
<223> OTHER INFORMATION: Any amino acid residue
<220> FEATURE:
<221> NAME/KEY: MISC_FEATURE
<222> LOCATION: (8)..(8)
<223> OTHER INFORMATION: Any hydrophobic amino acid residue or
      Asparagine
<220> FEATURE:
<221> NAME/KEY: MISC_FEATURE
<222> LOCATION: (9)..(10)
<223> OTHER INFORMATION: Any amino acid residue
<220> FEATURE:
<221> NAME/KEY: MISC_FEATURE
```

```
<222> LOCATION: (11)..(11)
<223> OTHER INFORMATION: Any hydrophobic amino acid residue
<220> FEATURE:
<221> NAME/KEY: MISC_FEATURE
<222> LOCATION: (12)..(12)
<223> OTHER INFORMATION: Any charged amino acid residue
<220> FEATURE:
<221> NAME/KEY: MISC_FEATURE
<222> LOCATION: (13)..(13)
<223> OTHER INFORMATION: Any amino acid residue
<220> FEATURE:
<221> NAME/KEY: MISC_FEATURE
<222> LOCATION: (14)..(14)
<223> OTHER INFORMATION: Any charged amino acid residue

<400> SEQUENCE: 29

Xaa Xaa Xaa Xaa Xaa Xaa Xaa Xaa Xaa Xaa Xaa Xaa Xaa Xaa
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: Any hydrophobic amino acid residue or
      Asparagine
<220> FEATURE:
<221> NAME/KEY: misc_feature
<222> LOCATION: (1)..(14)
<223> OTHER INFORMATION: This sequence consists of 2 heptad repeats; see
      specification as filed for detailed description of preferred
      embodiments
<220> FEATURE:
<221> NAME/KEY: MISC_FEATURE
<222> LOCATION: (2)..(3)
<223> OTHER INFORMATION: Any amino acid residue
<220> FEATURE:
<221> NAME/KEY: MISC_FEATURE
<222> LOCATION: (4)..(4)
<223> OTHER INFORMATION: Any hydrophobic amino acid residue
<220> FEATURE:
<221> NAME/KEY: MISC_FEATURE
<222> LOCATION: (5)..(5)
<223> OTHER INFORMATION: Any charged amino acid residue
<220> FEATURE:
<221> NAME/KEY: MISC_FEATURE
<222> LOCATION: (6)..(6)
<223> OTHER INFORMATION: Any amino acid residue
<220> FEATURE:
<221> NAME/KEY: MISC_FEATURE
<222> LOCATION: (7)..(7)
<223> OTHER INFORMATION: Any charged amino acid residue
<220> FEATURE:
<221> NAME/KEY: MISC_FEATURE
<222> LOCATION: (8)..(8)
<223> OTHER INFORMATION: Any hydrophobic amino acid residue or
      Asparagine
<220> FEATURE:
<221> NAME/KEY: MISC_FEATURE
<222> LOCATION: (9)..(10)
<223> OTHER INFORMATION: Any amino acid residue
<220> FEATURE:
<221> NAME/KEY: MISC_FEATURE
<222> LOCATION: (11)..(11)
<223> OTHER INFORMATION: Any hydrophobic amino acid residue
<220> FEATURE:
<221> NAME/KEY: MISC_FEATURE
<222> LOCATION: (12)..(12)
<223> OTHER INFORMATION: Any charged amino acid residue
<220> FEATURE:
<221> NAME/KEY: MISC_FEATURE
<222> LOCATION: (13)..(13)
```

```
<223> OTHER INFORMATION: Any amino acid residue
<220> FEATURE:
<221> NAME/KEY: MISC_FEATURE
<222> LOCATION: (14)..(14)
<223> OTHER INFORMATION: Any charged amino acid residue

<400> SEQUENCE: 30

Xaa Xaa Xaa Xaa Xaa Xaa Xaa Xaa Xaa Xaa Xaa Xaa Xaa Xaa
1               5                   10

<210> SEQ ID NO 31
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Arg Gly Arg Cys Arg Arg Gly Ser Gly Gly Ser Gly Gly Ser Gly Gly
1               5                   10                  15

Ser Gly Gly Ser Gly Gly Ser Gly Arg Ser Arg Lys Arg Arg Glu Val
            20                  25                  30

Gln

<210> SEQ ID NO 32
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Arg Gly Glu Cys Lys Gly Gly Ser Gly Gly Ser Gly Gly Ser Gly Gly
1               5                   10                  15

Ser Gly Gly Ser Gly Gly Ser Gly Gly Ser Gly Gly Ser Lys Glu Val
            20                  25                  30

Gln

<210> SEQ ID NO 33
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gly Gly Ser Ala Gln Leu Glu Lys Glu Leu Gln Ala Leu Glu Lys Glu
1               5                   10                  15

Asn Ala Gln Leu Glu Trp Glu Leu Gln Ala Leu Glu Lys Glu Leu Ala
            20                  25                  30

Gln Gly Ala Thr
        35

<210> SEQ ID NO 34
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34
```

```
Gly Gly Ser Ala Gln Leu Lys Lys Leu Gln Ala Leu Lys Lys
1               5                   10                  15

Asn Ala Gln Leu Lys Trp Lys Leu Gln Ala Leu Lys Lys Leu Ala
            20                  25                  30

Gln Gly Ala Thr
        35

<210> SEQ ID NO 35
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Cys Arg Arg Gly Ser Gly Gly Ser Gly Gly Ser Gly Gly Ser
1               5                   10                  15

Gly Ser Gly Gly Ser Gly Arg Ser Arg Lys Arg Arg
            20                  25

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Arg Lys Arg Lys Arg Arg Gly Ser Gly Gly Ser Gly Gly Ser Gly Gly
1               5                   10                  15

Ser Gly Gly Ser Gly Gly Ser Gly Arg Ser Arg Lys Arg Arg
            20                  25                  30

<210> SEQ ID NO 37
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Arg Gly Arg Ala Arg Arg Gly Ser Gly Gly Ser Gly Gly Ser Gly Gly
1               5                   10                  15

Ser Gly Gly Ser Gly Gly Ser Gly Arg Ser Arg Lys Arg Arg Glu Val
            20                  25                  30

Gln

<210> SEQ ID NO 38
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Arg Gly Glu Cys Arg Lys Arg Lys Arg Arg Gly Ser Gly Gly Ser Gly
1               5                   10                  15

Gly Ser Gly Gly Ser Gly Gly Ser Gly Gly Ser Gly Arg Ser Arg Lys
            20                  25                  30
```

```
Arg Arg Glu Val Gln
        35

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Gly Glu Cys Arg Lys Arg Lys Arg Arg
1               5                   10
```

COILED COIL AND/OR TETHER CONTAINING PROTEIN COMPLEXES AND USES THEREOF

CROSS-REFERENCE TO RELATED APPLICATIONS

This application is a division of U.S. patent application Ser. No. 13/496,696, filed Mar. 16, 2012 which is the U.S. national stage filing under 35 U.S.C. § 371 of international application PCT/US2010/002546, filed Sep. 16, 2010, which claims benefit of U.S. Provisional Applications 61/243,105, filed Sep. 16, 2009 and 61/266,992, filed Dec. 4, 2009. The contents of each are incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392016010SEQLIST.txt, date recorded: Sep. 21, 2015 size: 72 KB).

FIELD OF THE INVENTION

This invention relates to novel engineered proteins, multispecific protein complexes, including multispecific antibodies, methods of constructing them and producing them. This invention also relates to the new application of technologies useful in obtaining the multispecific protein complexes.

BACKGROUND OF THE INVENTION

Finding technologies for building mulitspecific antibodies that are useful and scalable for commercial and therapeutic purposes has been elusive. Many methods have been tried, but nearly all suffer significant drawbacks such as being poorly soluble; inexpressible in mammalian cells, demonstrating low yield of heterodimer formation, technically challenging to manufacture, immunogenic, short half-life in vivo, unstable among other problems (e.g., Hollinger et al., (1993) PNAS 90:6444-6448; U.S. Pat. Nos. 5,932,448; 6,833,441; 5,591,828; 7,129,330; 7,507,796; Fischer et al., (2007) Pathobiology 74:3-14; Booy (2006) Arch. Immunol. Ther. Exp. 54:85-101; Cao et al (2003) 55:171-197; and Marvin et al., (2006) Current Opinion in Drug Discovery & Development 9(2):184-193. Thus, there is a need for improved technologies and processes to make multispecific antibodies.

SUMMARY OF THE INVENTION

The present invention provides novel protein complexes and methods of creating and manufacturing protein complexes. In one aspect, the invention involves a coiled coil domain that is linked to an Fc CH component, which coiled coil domain may or may not be cleavable from the Fc containing protein if desired. In another aspect, the invention involves a protein comprising a tether and an Fc CH component complex, which tether may or may not be cleavable from the protein. In another aspect, the invention involves a protein comprising a coiled coil, a tether and an Fc CH component, optimally able to form a protein complex, which tether and/or coiled coil may or may not be cleavable from the protein depending on the desired effect.

In another aspect, the invention provides a process of preparing the protein comprising a tether, wherein the tether is cleaved by a host cell or cleaved by a chemical or enzymatic reaction in vitro. In another aspect, the invention involves a protein comprising a coiled coil, a tether and an Fc CH component, optimally able to form a protein complex, which tether and/or coiled coil are cleavable from the protein by a host cell that expresses the protein and overexpresses enzymes capable of cleaving the tether and/or coiled coil from the protein.

In another aspect, the invention provides a process of making a protein or protein complex comprising a coiled coil and a tether, wherein the tether and/or the coiled coil is cleaved by a host cell or cleaved by a chemical or enzymatic reaction in vitro. In one specific embodiment the protein complex further comprises an Fc CH component. In another aspect, the invention involves a method for manufacturing a heteromeric protein complex comprising the step of culturing a host cell under conditions that express two different proteins from the same or different recombinant nucleic acid sequences, wherein each protein comprises a coiled coil domain and a tether. In a further embodiment, the host cell comprises a recombinant nucleic acid sequence encoding an enzyme capable of cleaving the tether and/or the coiled coil. In one embodiment, the manufacturing method further comprises the step of isolating the proteins made by the host cell. In another embodiment, the manufacturing method further comprises the step of cleaving the tether and/or the coiled coil from a protein produced by the host cell.

In another aspect, the invention involves the protein complexes described herein with or without the tether and/or the coiled coil. In addition to the many advances and advantages provided herein, the invention provides a simple, efficient, high yield production process for manufacturing substantially homogenous heteromultimeric complexes.

In one preferred embodiment, the present invention provides a protein complex comprising two or more polypeptides, wherein a first polypeptide comprises a first coiled coil domain (CC) and a first Fc CH component (FcCH); and a second polypeptide comprises (1) a second coiled coil domain (CC) and a second FcCH, wherein the first CC and the second CC complex with each other; and the first FcCH and second FcCH complex with each other.

In one embodiment, the first CC comprises the sequence of Formula I herein and the second CC comprises the sequence of Formula II herein.

In a second aspect, the invention features a protein complex comprising (a) a first polypeptide comprising a first coiled coil domain (CC), where the first CC comprises a heptad repeat of Formula I; and (b) a second polypeptide comprising an Fc CH component and a second coiled coil (CC), where the second CC comprises a heptad repeat of Formula II where n in Formula I and II is greater than or equal to 2, and where, in each heptad repeat, the first CC comprises an $X_5$ residue that is opposite in charge to the $X'_7$ residue in the second CC and the first CC comprises an $X_7$ residue that is opposite in charge to the $X'_5$ residue in the second CC.

In one embodiment, the first polypeptide further comprises a VH domain and a VL domain and the second polypeptide further comprises a VH and VL domain, wherein the VH and VL domains of each polypeptide are linked to each other in the N-terminal to C-terminal order: VL-CL-tether-VH.

In a further embodiment, the VH domain of each polypeptide is different from each other. In another embodiment, the VL domain of each polypeptide is different from each other.

In one embodiment, the protein complex of this invention comprises a hinge region, wherein the hinge region comprises a K222A mutation in its hinge region, a C220A mutation in its hinge region or a K222A and a C220A mutation in its hinge region.

In one embodiment, the protein complex is selected from the group consisting of an antibody, an immunoadhesin, a peptibody or an affibody. Thus, according to a further embodiment, the first and/or second polypeptides can further comprise a target binding sequence of an antibody (e.g., VH or VL domain), peptibody (e.g., peptide), immunoadhesin (e.g., extracellular domain) or a scaffold protein comprising a sequence that binds the target.

According to one embodiment, the protein complex is a one armed antibody.

In one aspect, the invention provides a protein complex comprising a coiled coil comprising (a) a first polypeptide comprising a first coiled coil domain (CC), where the first CC comprises a heptad repeat of Formula I:

$$(X_1 X_2 X_3 X_4 X_5 X_6 X_7)_n \quad \text{(Formula I)} \quad \text{(SEQ ID NO: 29)}$$

$X_1$ is a hydrophobic amino acid residue or Asparagine,
$X_2$, $X_3$, and $X_6$ are each any amino acid residue,
$X_4$ is a hydrophobic amino acid residue, and
$X_5$ and $X_7$ are each a charged amino acid residue; and
(b) a second polypeptide comprising a second coiled coil domain (CC), where the second CC comprises a heptad repeat of Formula II:

$$(X'_1 X'_2 X'_3 X'_4 X'_5 X'_6 X'_7)_n \quad \text{(Formula II)} \quad \text{(SEQ ID NO: 30)}$$

$X'_1$ is a hydrophobic amino acid residue or Asparagine,
$X'_2$, $X'_3$, and $X'_6$ are each any amino acid residue,
$X'_4$ is a hydrophobic amino acid residue, and
$X'_5$ and $X'_7$ are each a charged amino acid residue;
where n in Formula I and II is greater than or equal to 2; and where, in each heptad repeat, the first CC comprises an $X_5$ residue that is opposite in charge to the $X'_7$ residue in the second CC and the first CC comprises an $X_7$ residue that is opposite in charge to the $X'_5$ residue in the second CC.

In an embodiment, the first and second polypeptides each comprise a VH and a CH1 domain, and may each further comprise a hinge domain. In another embodiment, the first and second polypeptides each further comprise a CH2 and a CH3 domain. In yet another embodiment, the first and second polypeptides each comprise VH, CH1, hinge, CH2, and CH3 domains positioned relative to each other in an N-terminal to C-terminal direction: VH-CH1-hinge-CH2-CH3.

In one aspect, the invention provides an antibody comprising (a) a first polypeptide comprising a VH domain and a first coiled coil domain (CC), where the first CC comprises a heptad repeat of Formula I:

$$(X_1 X_2 X_3 X_4 X_5 X_6 X_7)_n \quad \text{(Formula I) (SEQ ID NO:29)}$$

$X_1$ is a hydrophobic amino acid residue or Asparagine,
$X_2$, $X_3$, and $X_6$ are each any amino acid residue,
$X_4$ is a hydrophobic amino acid residue, and
$X_5$ and $X_7$ are each a charged amino acid residue; and
(b) a second polypeptide comprising a VH domain and a second coiled coil domain (CC), where the second CC comprises a heptad repeat of Formula II:

$$(X'_1 X'_2 X'_3 X'_4 X'_5 X'_6 X'_7)_n \quad \text{(Formula II) (SEQ ID NO:30)}$$

$X'_1$ is a hydrophobic amino acid residue or Asparagine,
$X'_2$, $X'_3$, and $X'_6$ are each any amino acid residue,
$X'_4$ is a hydrophobic amino acid residue, and
$X'_5$ and $X'_7$ are each a charged amino acid residue;
where n in Formula I and II is greater than or equal to 2; and where, in each heptad repeat, the first CC comprises an $X_5$ residue that is opposite in charge to the $X'_7$ residue in the second CC and the first CC comprises an X7 residue that is opposite in charge to the X' 5 residue in the second CC.

In an embodiment, the first and second polypeptides each comprise a VH and a CH1 domain, and may each further comprise a hinge domain. In another embodiment, the first and second polypeptides each further comprise a CH2 and a CH3 domain. In yet another embodiment, the first and second polypeptides each comprise VH, CH1, hinge, CH2, and CH3 domains positioned relative to each other in an N-terminal to C-terminal direction: VH-CH1-hinge-CH2-CH3.

In a particular embodiment the antibody further comprises a third and a fourth polypeptide, where the third polypeptide comprises a first VL domain and the fourth polypeptide comprises a second VL domain. In an embodiment, the VH domain of the first polypeptide is linked to the VL domain of the third polypeptide by a tether and the VH domain of the second polypeptide is linked to the VL domain of the fourth polypeptide by a tether. In another embodiment, the third polypeptide further comprises a first CL domain where the first VL and CL domains are positioned relative to each other within the third polypeptide in an N-terminal to C-terminal direction: VL-CL, and the fourth polypeptide further comprises a second CL domain, and where the second VL and CL domains are positioned relative to each other within the fourth polypeptide in an N-terminal to C-terminal direction: VL-CL.

In an additional embodiment, the sequences of the first VL domain and the second VL domain are the same. In a further embodiment, the N-terminus of the VH of at least one of the first or the second polypeptides is connected to the C-terminus of a CL with a tether.

In a second aspect, the invention features an antibody comprising (a) a first polypeptide comprising a VH domain and a first coiled coil domain (CC), where the first CC comprises a heptad repeat of Formula I; and (b) a second polypeptide comprising a CH2 and CH3 domain and a second coiled coil (CC), where the second CC comprises a heptad repeat of Formula II, where n in Formula I and II is greater than or equal to 2, and where, in each heptad repeat, the first CC comprises an $X_5$ residue that is opposite in charge to the $X'_7$ residue in the second CC and the first CC comprises an $X_7$ residue that is opposite in charge to the $X'_5$ residue in the second CC.

In one embodiment of the second aspect of the invention, the first polypeptide comprises a VH and CH1 domain, and may further comprise a hinge domain. In another embodiment, the first polypeptide further comprises a CH2 and a CH3 domain. In a further embodiment of the second aspect of the invention, the first polypeptide comprises. VH, CH1, hinge, CH2, and CH3 domains positioned relative to each other in an N-terminal to C-terminal direction: VH-CH1-hinge-CH2-CH3. In yet another embodiment of the second aspect of the invention, the antibody further comprises a third polypeptide, where the third polypeptide comprises a VL domain. In one example, the third polypeptide further comprises a CL domain, and the VL and CL domains are positioned relative to each other in an N-terminal to C-terminal direction: VL-CL. In yet another embodiment of the second aspect of the invention, the N-terminus of the VH of the first polypeptide is connected to the C-terminus of a CL with a tether.

In one embodiment, a two armed antibody of this invention comprises one, not two tethers such that the antibody comprises (1) a polypeptide comprising a coiled coil domain and a heavy chain tethered to a light chain according to this invention, (2) a polypeptide comprising a coiled coil domain and a heavy chain and (3) a polypeptide comprising a light chain. In another embodiment, a host cell that expresses such two armed antibody is contemplated.

In other embodiments, the hydrophobic amino acid residue in any of $X_1$, $X'_1$, $X_4$, and $X'_4$ is selected from the group Alanine, Valine, Leucine, Isoleucine, Tryptophan, Phenylalanine, and Methionine. In another embodiment, the charged amino acid residue in any of $X_5$, $X'_5$, $X_7$, and $X'_7$ is selected from the group Lysine, Arginine, Histidine, Aspartic Acid, and Glutamic Acid. In a further embodiment, in at least one heptad repeat of the first CC, $X_1$ is Asparagine, and the respective $X'_1$ is Asparagine in at least one heptad repeat of the second CC.

In yet other embodiment, the first CC comprises a heptad repeat where $X_1$ is Leucine or Asparagine, $X_2$ is Alanine or Glutamine, $X_3$ is Alanine or Glutamine, $X_4$ is Leucine, $X_5$ is Glutamic Acid, $X_6$ is Lysine or Tryptophan, and $X_7$ is Glutamic Acid; and the second CC comprises a heptad repeat where $X'_1$, is Leucine or Asparagine, $X'_2$ is Alanine or Glutamine, $X'_3$ is Alanine or Glutamine, $X'_4$ is Leucine, $X'_5$ is Lysine, $X'_6$ is Lysine or Tryptophan, and $X'_7$ is Lysine.

In further embodiments, n in Formula I and II is greater than or equal to 3, for example, greater than or equal to 4, 5, 6, 7, 8, 9, 10, 20, 30, 40, 50, 60, 70, 80, 90, or 100.

In additional embodiments, at least one of the first or the second CC is linked C-terminal to a constant domain of the protein. For example, the constant domain is a CH3 domain and the first CC is linked C-terminal to a CH3 domain of the first polypeptide and the second CC is linked C-terminal to a CH3 domain of the second polypeptide. The linkage, for example, is by a cleavable linker sequence. In other embodiments, a Lys-C endopeptidase cleavage site is located N-terminal to at least one of the first or the second CC.

In another aspect, the invention features an antibody comprising a first polypeptide comprising a VL, CL, tether, VH, CH1, CH2, and CH3 domain positioned relative to each other in an N-terminal to C-terminal direction: VL-CL-tether-VH-CH1-CH2-CH3 (Formula III). In one embodiment, the antibody further comprises a second polypeptide of Formula III.

In a particular embodiment, the antibody of the invention is multispecific. For example, the antibody is capable of binding at least 2 antigens, or the antibody a capable of binding at least 2 epitopes on the same antigen. In another embodiment, the antibody is bispecific.

In an additional embodiment, the proteins of this invention comprise a tether comprising Glycine (G) and Serine (S) residues. In one embodiment, the tether, for example, is between 15 and 50 amino acids in length. In a particular embodiment, the tether is between 20 and 32 amino acids in length, for example, 20, 21, 22, 23, 24, 25, 26, 27, 28, 29, 30, 31 or 32 amino acids in length. The tether, in one embodiment, comprises GGS repeats. In another embodiment, the tether is cleavable. In one preferred embodiment, the tether is cleavable in two sites at or near the N and C terminus of the tether by the same enzyme. In one embodiment, the tether comprises the cleavage site for furin. In a further embodiment, the furin cleavage site is RXRXRR (SEQ ID NO:25), wherein X is any amino acid.

In a further embodiment, the antibody of the invention comprises a mutation that removes a Lys-C endopeptidase cleavage site. In one example, the mutation that removes a Lys-C endopeptidase cleavage site is in a hinge domain. For instance, the antibody has a K222A substitution (EU numbering system).

In another embodiment, the tether or the linker is cleavable by one or more of the following endopeptidases: Furin, Thrombin, Genenase, Lys-C, Arg-C, Asp-N, Glu-C, Factor Xa, Tobacco Etch Virus Protease (TEV), Enterokinase, Human Rhinovirus C3 protease (HRV C3), or Kininogenase. In a particular embodiment, the tether or the linker comprises an Asparagine-Glycine peptide bond, for example, a Asparagine-Glycine peptide bond that is cleavable by hydroxylamine.

In one embodiment, an antibody of the invention further comprises mutations in a CL/CH1 and or in a VH/VL interface using KnH technology. In one embodiment, a multispecific antibody of this invention was constructed using a coiled coil of this invention and a knob and hole at a CL/CH1 interface.

In an additional embodiment, the antibody of the invention comprises a constant region conjugated to a cytotoxic agent.

In yet another embodiment, the antibody of the invention is expressed by eukaryotic cell, for example, a mammalian cell such as a CHO cell. In an alternative embodiment, the antibody is expressed by a prokaryotic cell, for example, an *E. coli* cell.

In a further aspect, the invention features method for producing a protein complex, such as an antibody. Accordingly, the invention provides several new aspects. In one embodiment, this method comprises the step of culturing a cell comprising a vector encoding a protein of this invention in a culture medium. In one embodiment, the method further comprises recovering the protein from the cell or the culture medium. In another embodiment, the method further comprises the steps of (a) capturing the antibody on a column comprising Protein A, (b) eluting the antibody from the column, and (c) diluting the eluted antibody into a solution containing a chaotropic agent or mild detergent.

In yet another aspect, the invention features a method of maintaining a coiled coil containing antibody in solution. This method comprises maintaining the antibody in the presence of a chaotropic agent or mild detergent. Examples, of chaotropic agents or mild detergents that may be used in this method include Arginine, Guanidine-HCl, urea, lithium perchlorate, Histidine, Sodium Dodecyl Sulfate (SDS), Tween, Triton, and NP-40.

In one embodiment, a heteromultimeric complex of this invention binds to two or more target molecules. In another embodiment, each polypeptide in the heteromultimeric complex binds to a different target molecule. In yet another embodiment, the heteromultimeric complex inhibits the biological activity of the target molecule(s) to which it binds. In one embodiment, when a desired biological effect is to bring a cell to be depleted or inactivated in close proximity to an effector cell (e.g., T lymphocyte, natural killer cell (NK), macrophage or other mononuclear cells, one of the target molecules can be CD3, CD16, or CD64.

According to one embodiment, a heteromultimeric complex of this invention binds to at least two target molecules selected from the group consisting of: IL-1alpha and IL-1beta, IL-12 and IL-18; IL-13 and IL-9; IL-13 and IL-4; IL-13 and IL-5; IL-5 and IL-4; IL-13 and IL-1beta; IL-13 and IL-25; IL-13 and TARC; IL-13 and MDC; IL-13 and MEF; IL-13 and TGF-β; IL-13 and LHR agonist; IL-12 and TWEAK, IL-13 and CL25; IL-13 and SPRR2a; IL-13 and SPRR2b; IL-13 and ADAM8, IL-13 and PED2, IL17A and IL17F, CD3 and CD19, CD138 and CD20; CD138 and CD40; CD19 and CD20; CD20 and CD3; CD38 and CD138; CD38 and CD20; CD38 and CD40; CD40 and CD20; CD-8 and IL-6; CD20 and BR3, TNFalpha and TGF-beta, TNFalpha and IL-1beta; TNFalpha and IL-2, TNF alpha and IL-3, TNFalpha and IL-4, TNFalpha and IL-5, TNFalpha and IL6, TNFalpha and IL8, TNFalpha and IL-9, TNFalpha and IL-10, TNFalpha and IL-11, TNFalpha and IL-12, TNFalpha and IL-13, TNFalpha and IL-14, TNFalpha and IL-15, TNFalpha and IL-16, TNFalpha and IL-17, TNFalpha and IL-18, TNFalpha and IL-19, TNFalpha and IL-20, TNFalpha and IL-23, TNFalpha and IFNalpha, TNFalpha and CD4, TNFalpha and VEGF, TNFalpha and MIF, TNFalpha and ICAM-1, TNFalpha and PGE4, TNFalpha and PEG2, TNFalpha and RANK ligand, TNFalpha and Te38; TNFalpha and BAFF; TNFalpha and CD22; TNFalpha and CTLA-4; TNFalpha and GP130; TNFα and IL-12p40; VEGF and HER2, VEGF-A and HER2, VEGF-A and PDGF, HER1 and HER2, VEGF-A and VEGF-C, VEGF-C and VEGF-D, HER2 and DR5, VEGF and IL-8, VEGF and MET, VEGFR and MET receptor, VEGFR and EGFR, HER2 and CD64, HER2 and CD3, HER2 and CD16, HER2 and HER3; EGFR and HER2, EGFR and HER3, EGFR and HER4, IL-13 and CD40L, IL4 and CD40L, TNFR1 and IL-1R, TNFR1 and IL-6R and TNFR1 and IL-18R, EpCAM and CD3, MAPG and CD28, EGFR and CD64, CSPGs and RGM A; CTLA-4 and BTNO2; IGF1 and IGF2; IGF1/2 and Erb2B; MAG and RGM A; NgR and RGM A; NogoA and RGM A; OMGp and RGM A; PDL-I and CTLA-4; and RGM A and RGM B.

In a further embodiment, the invention features an isolated antibody comprising a first heavy chain comprising the sequence of SEQ ID NO:1, a second heavy chain comprising the sequence of SEQ ID NO:2, and a light chain comprising the sequence of SEQ ID NO:3, where the antibody specifically binds FcεR1 and FcγR2b.

In another embodiment, the invention features an isolated antibody comprising a first heavy chain comprising the sequence of SEQ ID NO:4, a second heavy chain comprising the sequence of SEQ ID NO:5, and a light chain comprising the sequence of SEQ ID NO:6, where the antibody specifically binds HER2.

In yet another embodiment, the invention features an isolated antibody comprising a first heavy chain comprising the sequence of SEQ ID NO:7, a second heavy chain comprising the sequence of SEQ ID NO:5, and a light chain comprising the sequence of SEQ ID NO:8, where the antibody specifically binds EGFR.

In an additional embodiment, the invention features an isolated antibody comprising a first light chain sequence and a first heavy chain sequence comprising the sequence of SEQ ID NO:9, and a second light chain sequence and a second heavy chain sequence comprising the sequence of SEQ ID NO:10, where the antibody specifically binds HER2 and EGFR.

In a further embodiment, the invention features an isolated antibody comprising a first light chain sequence and a first heavy chain sequence comprising the sequence of SEQ ID NO:11, and a second light chain sequence and a second heavy chain sequence comprising the sequence of SEQ ID NO:10, where the antibody specifically binds HER2 and EGFR.

The invention also features use of antibodies made according to the methods described herein in methods of treatment. In one embodiment the invention features use of an antibody that specifically binds FcεR1 and FcγR2b in a method of treating an allergic or inflammatory response (e.g., an autoimmune disease) in a subject. This method includes administering an antibody or antibody fragment to a subject for a time and in an amount sufficient to treat the allergic or inflammatory respone in the subject. In another embodiment, the invention features use of an antibody that specifically binds HER2 or EGFR (or both HER2 and EGFR) in a method of treating a tumor in a subject. This method includes administering an antibody or antibody fragment to a subject for a time and in an amount sufficient to treat the tumor in the subject.

In particular embodiments, the methods of treatment described herein involve the use of an antibody fragment that lacks a coiled coil and/or a tether. In this embodiment, the coiled coil and/or tether sequences are cleaved from the antibody following production and the resultant engineered antibody used for therapeutic administration. In further embodiments, the methods of treatment involve administering to the subject an effective amount of a second drug. The second drug may contain another antibody or antibody fragment, a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, or a growth-inhibitory agent. The second drug can be administered prior or subsequent to the administration of the first drug (e.g., the antibody or antibody fragment). In another embodiment, the second drug is administered concurrently with the first drug.

In additional embodiments, the invention features an isolated polynucleotide encoding the sequence of any one of SEQ ID NO:1, 2, 3, 4, 5, 6, 7, 8, 9, 10, 11, 17-18, 26, 31-32 or 35-36 or a combination thereof, a vector comprising a polynucleotide including the sequence of any one of SEQ ID NO:1, 2, 3, 4, 5, 6, 7, 8, 9, 10, 11, 17-18, 26, 31-32 or 35-36 or a combination thereof, and a host cell comprising such a vector. The host cell can be a eukaryotic cell, such as a yeast, insect, or mammalian cell. In one embodiment the mammalian cell is a Chinese Hamster Ovary (CHO cell). The host cell can also be a prokaryotic cell, such as an *E. coli* cell. In other embodiments, the invention features an isolated polypeptide comprising any one of the sequence of SEQ ID NO:1, 2, 3, 4, 5, 6, 7, 8, 9, 10, 11, 17-18, 26, 31-32 or 35-36 or a combination thereof.

Other features and advantages of the invention will be apparent from the following Detailed Description, the Drawings, and the Claims.

BRIEF DESCRIPTION OF THE DRAWINGS

FIG. 2A shows the amino acid sequences of the exemplary ACID.p1 (SEQ ID NO:12) and BASE.p1 (SEQ ID NO:13) coiled coil heterodimerization domains and DNA sequences encoding them (SEQ ID NO:21 and SEQ ID NO:22, respectively).

FIG. 7B is a series of schematic diagrams showing exemplary cleavable tethers. The top diagram shows an exemplary 26 amino acid tether sequence (SEQ ID NO:17) in SEQ ID NO:31 that can be cleaved by Furin and links the N-terminus of the light chain (LC) and the C-terminus of the heavy chain (HC). Furin can cleave the tether sequence at di-basic sites (Arginine-Arginine) at the N- and C-termini of the tether. The bottom diagram shows an exemplary 26 amino acid tether sequence (SEQ ID NO:18) in SEQ ID NO:32 that can be cleaved by Lys-C endopeptidase at Lysine residues at the N- and C-termini of the tether sequence.

FIG. 8 shows the sequences of the heavy chains (HC; Anti-FcγR2b-BASE.p1 sequence and Anti-FcεR1-ACID.p1 sequence) and common light chain (4d5 LC) of a bispecific antibody that binds to both FcεR1 and FcγR2b. The Anti-FcγR2b-BASE.p1 sequence (SEQ ID NO:1) contains the heavy chain sequence of anti-human FcγR2b with a BASE.p1 coiled coil heterodimerization domain sequence and K222A mutation in the hinge region. The Anti-FcεR1-ACID.p1 sequence (SEQ ID NO:2) contains the heavy chain sequence of anti-human FcεR1 with an ACID.p1 coiled coil heterodimerization domain sequence and K222A mutation in the hinge region. The 4d5 antibody light chain (SEQ ID NO:3) is common to both the FcγR2b and FcεR1 HCs of this bispecific antibody.

FIGS. 9-1 and 9-2 are the sequences of used to generate exemplary one-armed antibodies. One exemplary one-armed antibody specifically binds HER2 and contains the Anti-HER2 antibody 1.ACID.p1 sequence (Anti-HER2 antibody 1 HC with an ACID.p1 coiled coiled heterodimerization domain sequence and K222A mutation; SEQ ID NO:4), the truncFC.BASE.p1 sequence (a heavy chain lacking the VH and CH1 domains with a BASE.p1 coiled coil heterodimerization domain sequence; SEQ ID NO:5), and the anti-HER2 antibody 1 LC sequence (SEQ ID NO:6). Another exemplary one-armed antibody specifically binds EGFR and contains the Anti-EGFR (D1.5).ACID.p1 sequence (anti-EGFR (D1.5) HC with an ACID.p1 coiled coiled heterodimerization domain sequence and K222A mutation in the hinge region; SEQ ID NO:7), the truncFC.BASE.p1 sequence (a heavy chain lacking the VH and CH1 domains with a BASE.p1 coiled coil heterodimerization domain sequence; SEQ ID NO:5), and anti-EGFR (D1.5) antibody LC sequence (SEQ ID NO:8).

FIG. 10 shows the sequences of the tethered HC and LC (Anti-HER2 (antibody 1)26.ACID.p1 and D1.5.26.BASE.p1) of a bispecific antibody that binds both HER2 and EGFR/HER1. The Anti-HER2 (antibody 1)26.ACID.p1 sequence contains the anti-HER2 antibody 1 LC sequence tethered to the anti-HER2 antibody 1 HC sequence by a 26 amino acid Glycine Glycine Serine (GGS) tether with an ACID.p1 coiled coil heterodimerization domain and K222A mutation (SEQ ID NO:9). The D1.5.26.BASE.p1 sequence contains the D1.5 anti-EGFR antibody LC sequence tethered to the D1.5 anti-EGFR antibody HC sequence by a 26 amino acid GGS tether with a BASE.p1 coiled coil heterodimerization domain and K222A mutation (SEQ ID NO:10).

FIG. 11 shows the sequences of the tethered HC and LC (anti-HER2 (antibody 2).26.ACID.p1 and D1.5.26.BASE.p1) of another exemplary antibody that binds both HER2 and EGFR/HER1. The anti-HER2 (antibody 2).26.ACID.p1 sequence contains the anti-HER2 antibody 2 LC sequence tethered to the anti-HER2 antibody 2 HC sequence by a 26 amino acid GGS tether with a ACID.p1 coiled coil heterodimerization domain and K222A mutation (SEQ ID NO:11). The D1.5.26.BASE.p1 sequence contains the D1.5 anti-EGFR antibody LC sequence tethered to the D1.5 anti-EGFR antibody HC sequence by a 26 amino acid GGS tether with a BASE.p1 coiled coil heterodimerization domain and K222A mutation (SEQ ID NO:10).

FIGS. 12A-1 and 12A-2 and 12B-1, 12B-2, and 12B-3 are partial HC (SEQ ID NO:15) and LC (SEQ ID NO:16) amino acid sequences and DNA sequences SEQ ID NO:23 and SEQ ID NO:24, respectively of the anti-HER2 antibody 1 used to construct coiled coil heterodimerization domain containing antibodies. The start of the anti-HER2 antibody 1 HC sequence is indicated in FIG. 12A, as is the location of the K222A mutation in the sequence. The start of the anti-HER2 antibody 1 variable light chain (VL), the end of the anti-HER2 antibody 1 LC, the start of the anti-HER2 antibody 1 variable heavy chain (VH), the end of the anti-HER2 antibody 1 VH, and the location of the K to A mutation is indicated in FIG. 12B. The locations of ClaI/Bsp106, BamH1, and ApaI restriction sites useful in constructing vectors containing these sequences are also indicated in FIGS. 12A and 12B.

FIGS. 13A and 13B are a series of graphs of mass spectrometry results and schematic diagrams showing that the heterodimeric coiled coil can be cleaved from an exemplary α-FcεR1/α-FcγR2b bispecific antibody using Lys-C endopeptidase. The theoretical masses of the antibody with the coiled coil (left diagram) and the antibody without the coiled coil (right diagram) are indicated and are within the margin of error of the experimentally observed masses indicated in the graphs of the mass spectrometry results above the respective diagram, showing that the coiled coil was cleaved from the antibody.

FIGS. 17A and 17B are a series of graphs of mass spectrometry results and schematic diagrams showing that the coiled coil can be cleaved from an exemplary one-armed α-EGFR antibody using Lys-C endopeptidase. The theoretical masses of the one-armed antibody with a coiled coil (MW=109112), and the one-armed antibody without a coiled coil (MW=100419) are within the margin of error of the experimentally observed masses indicated in the graph of the mass spectrometry results for the respective construct.

The theoretical molecular mass for the respective constructs is indicated below the graph showing the mass spectrometry results and, in each case, is within the margin of error of the experimentally observed molecular mass.

Figure 19A:
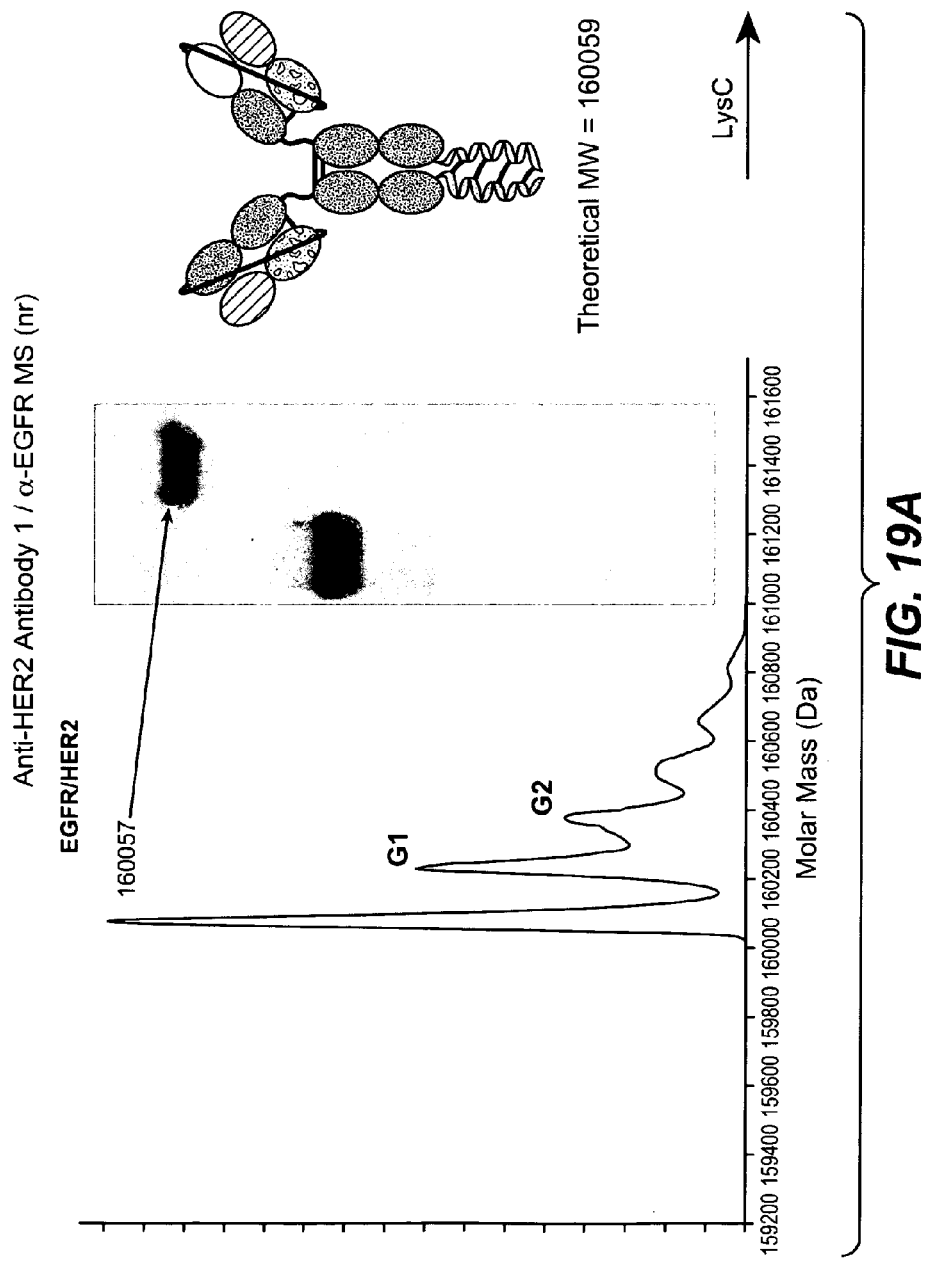
Figure 19B:
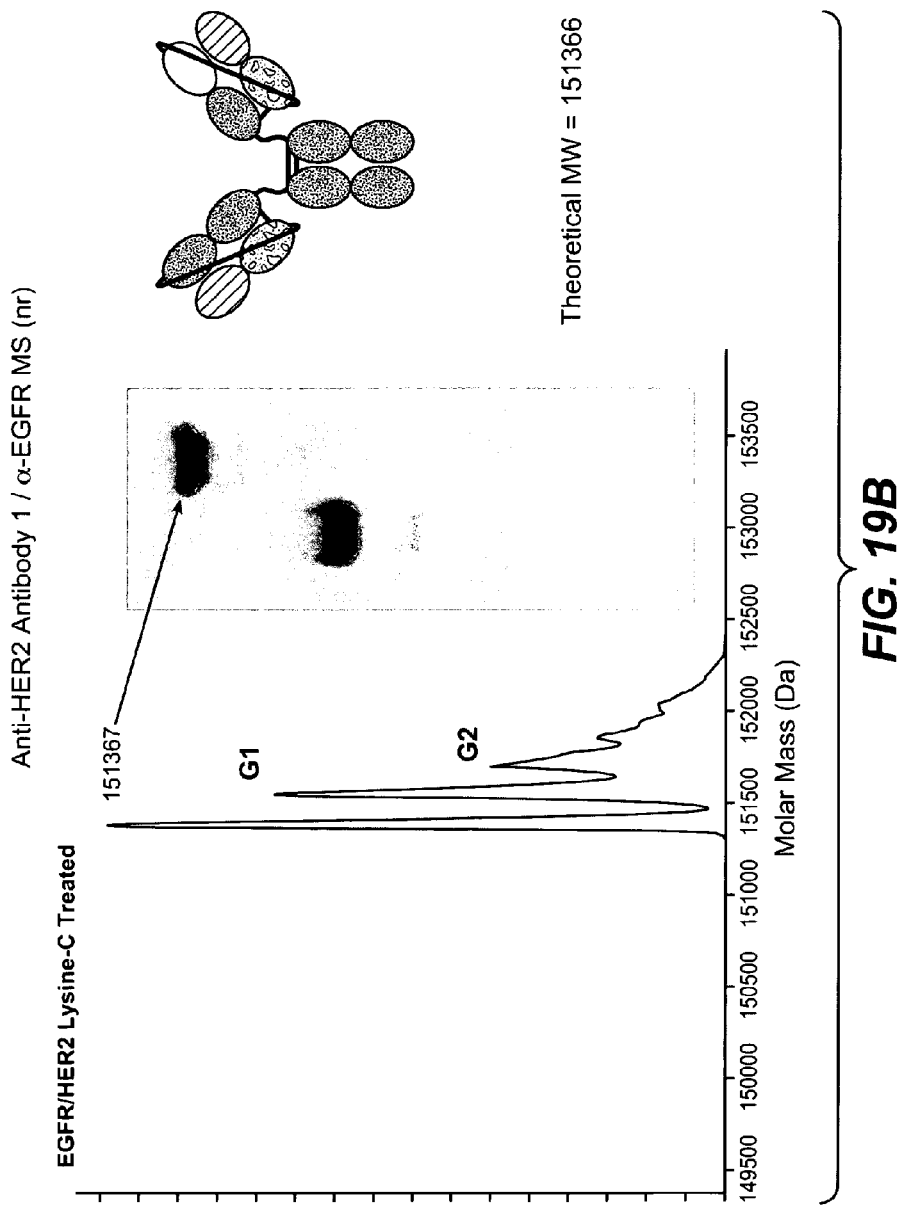

FIGS. 19A and 19B are a series of graphs of mass spectrometry results and schematic diagrams showing that the coiled coil can be cleaved from an exemplary tethered α-EGFR/α-HER2 bispecific antibody using Lys-C endopeptidase. The theoretical molecular mass of the cleaved and uncleaved antibodies is also indicated in the figure and is within the margin of error of the respective experimentally observed molecular mass indicated in the mass spectrometry results.

Figure 20A:
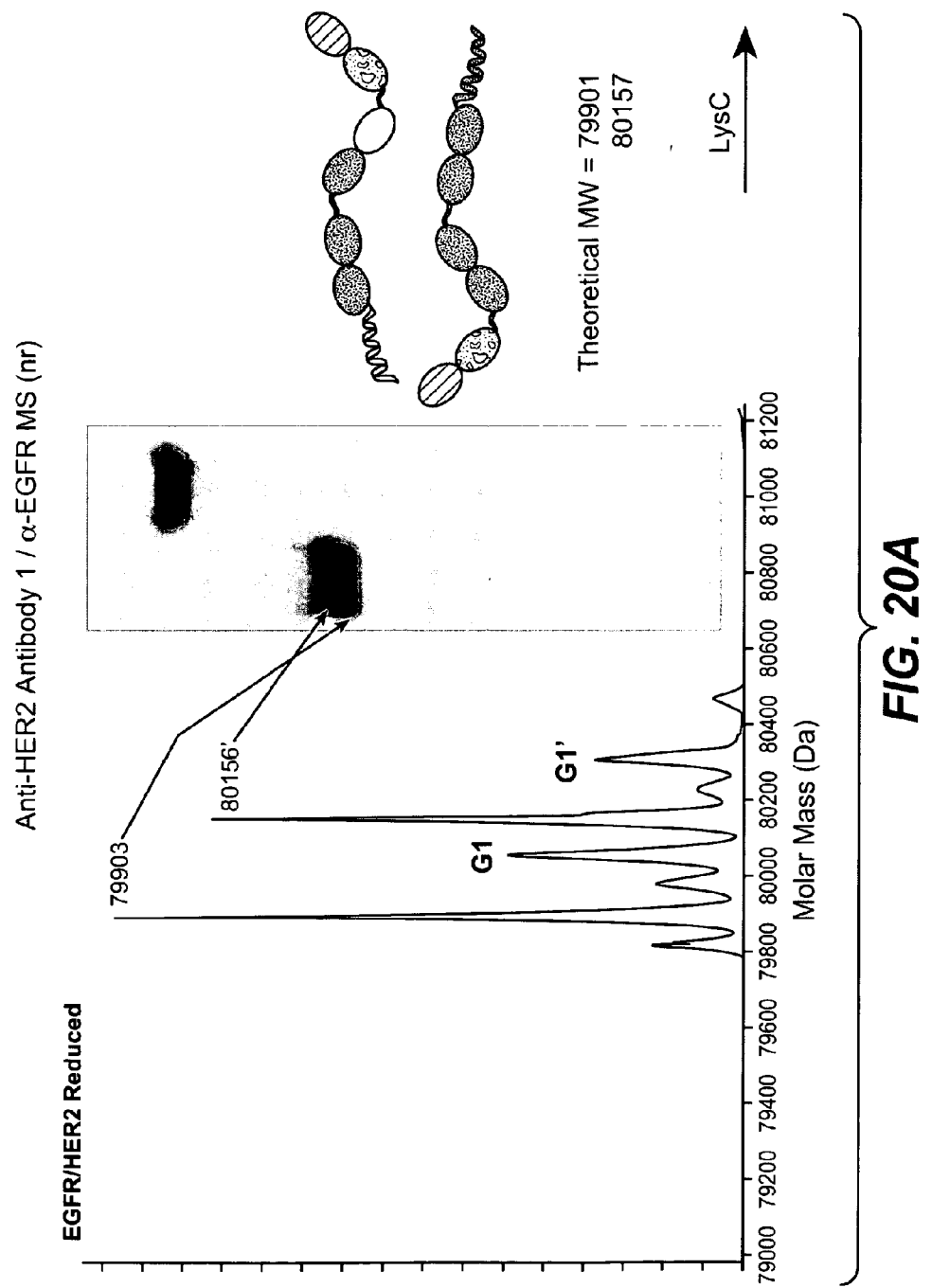
Figure 20B:
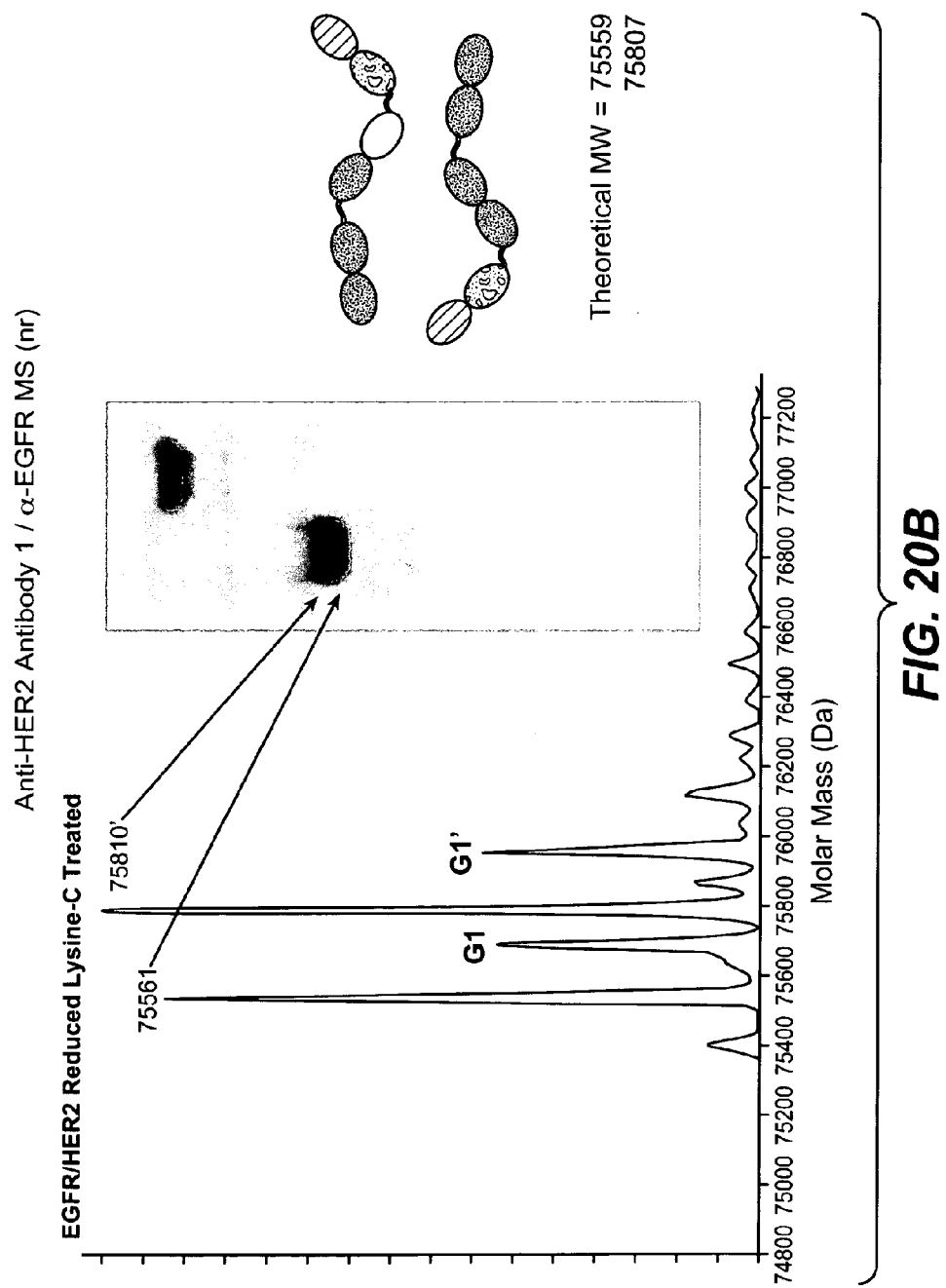

FIGS. 20A and 20B are a series of graphs of mass spectrometry results and schematic diagrams showing that the coiled coil can be cleaved from an exemplary tethered α-EGFR/α-HER2 bispecific antibody using Lys-C endopeptidase where the antibody has first been treated with Lys-C endopeptidase and the sample then subjected to mass spectrometry analysis. The theoretical molecular masses of the cleaved and uncleaved HC/LC complexes are also indicated in the figure and the theoretical molecular mass for each construct is within the margin of error of the experimentally observed molecular mass shown in the mass spectrometry results.

Figure 21:
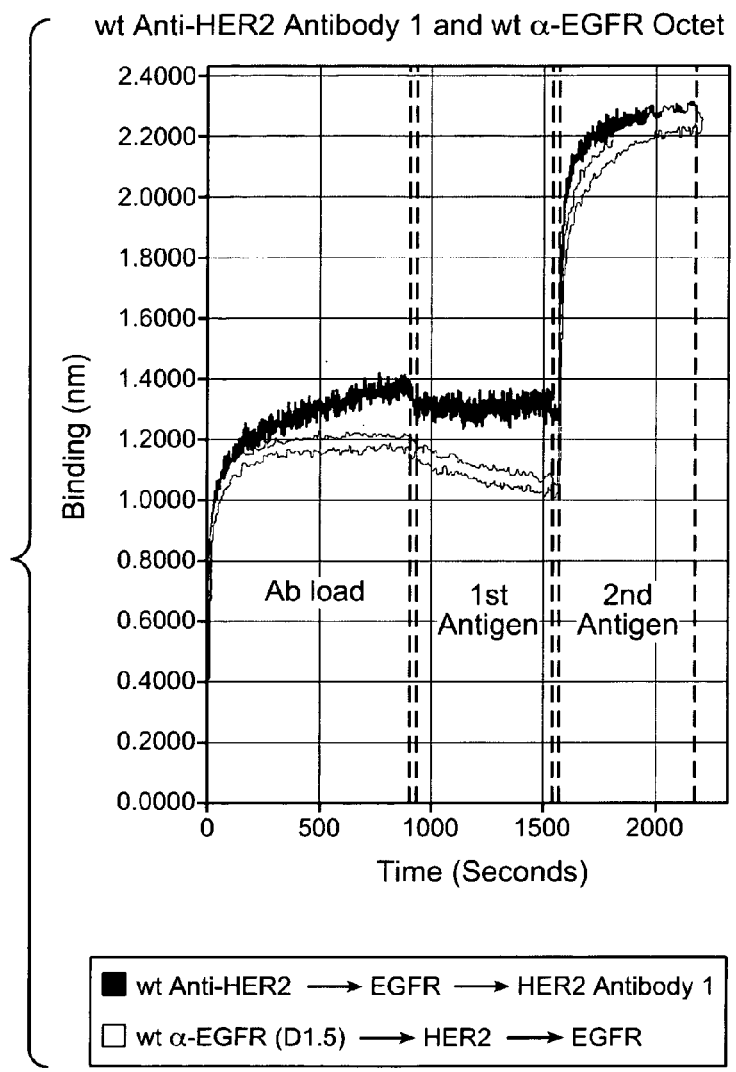

FIG. 21 is a graph showing the results from an Octet analysis indicating that the wild-type anti-HER2 antibody 1 and wild-type α-EGFR antibody do not cross react with each other's antigen, but do bind their respective antigen.

Figure 22:
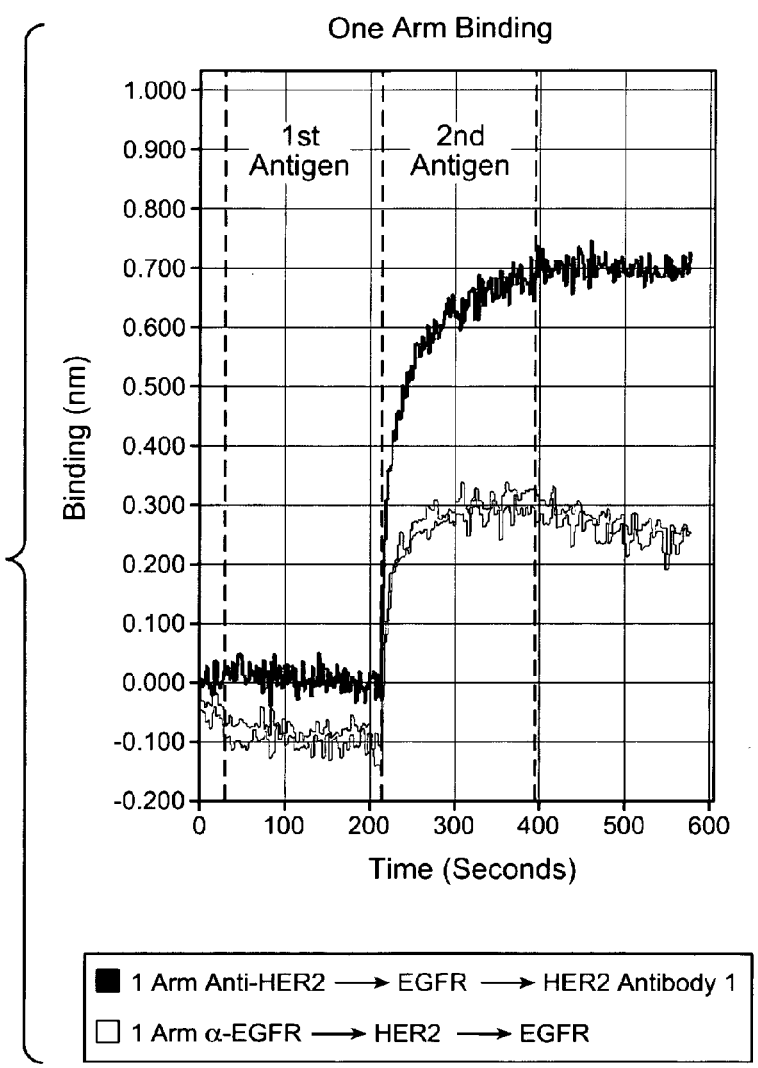

FIG. 22 is a graph showing the results from an Octet analysis indicating that the one-armed anti-HER2 antibody 1 and one-armed α-EGFR antibody do not cross react with each other's antigen, but do bind their respective antigen.

Figure 23A:
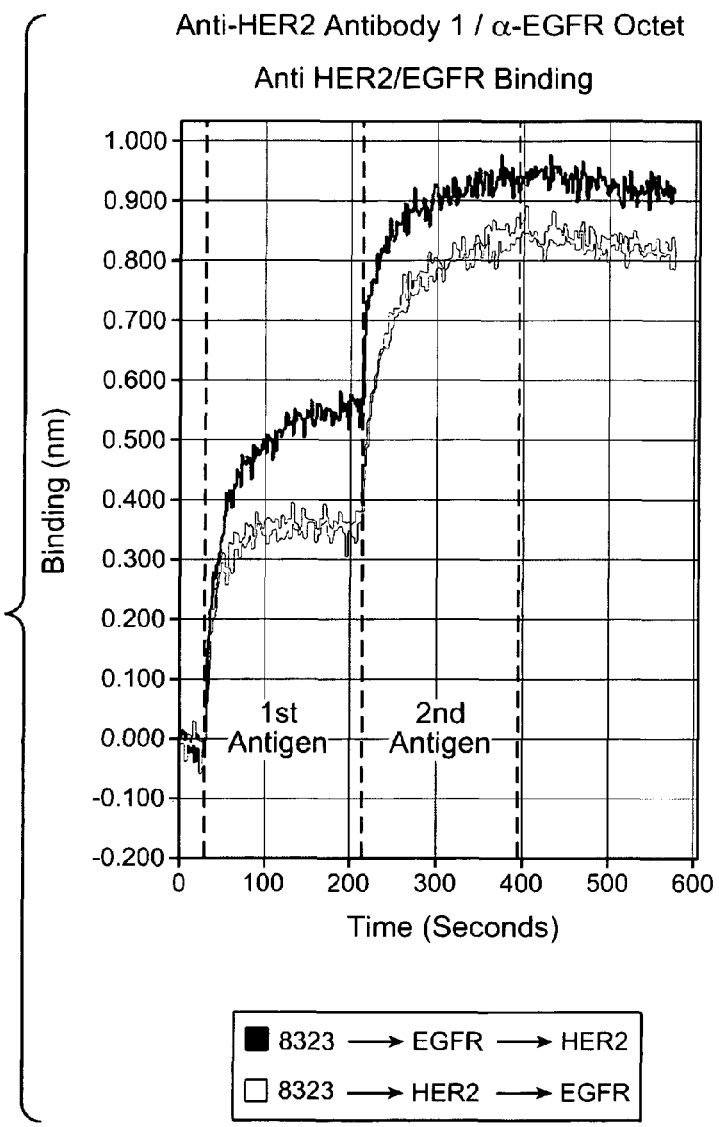

FIG. 23A is a graph showing the results from an Octet analysis indicating that the exemplary tethered bispecific Anti-HER2 antibody 1/α-EGFR antibody (8323) binds both HER2 and EGFR simultaneously. In the top trace, the antibody was first incubated with the EGFR extracellular domain (ECD) and then with the HER2 receptor ECD and in the bottom trace, the antibody was first incubated with the HER2 receptor ECD and then with the EGFR ECD.

Figure 23B:
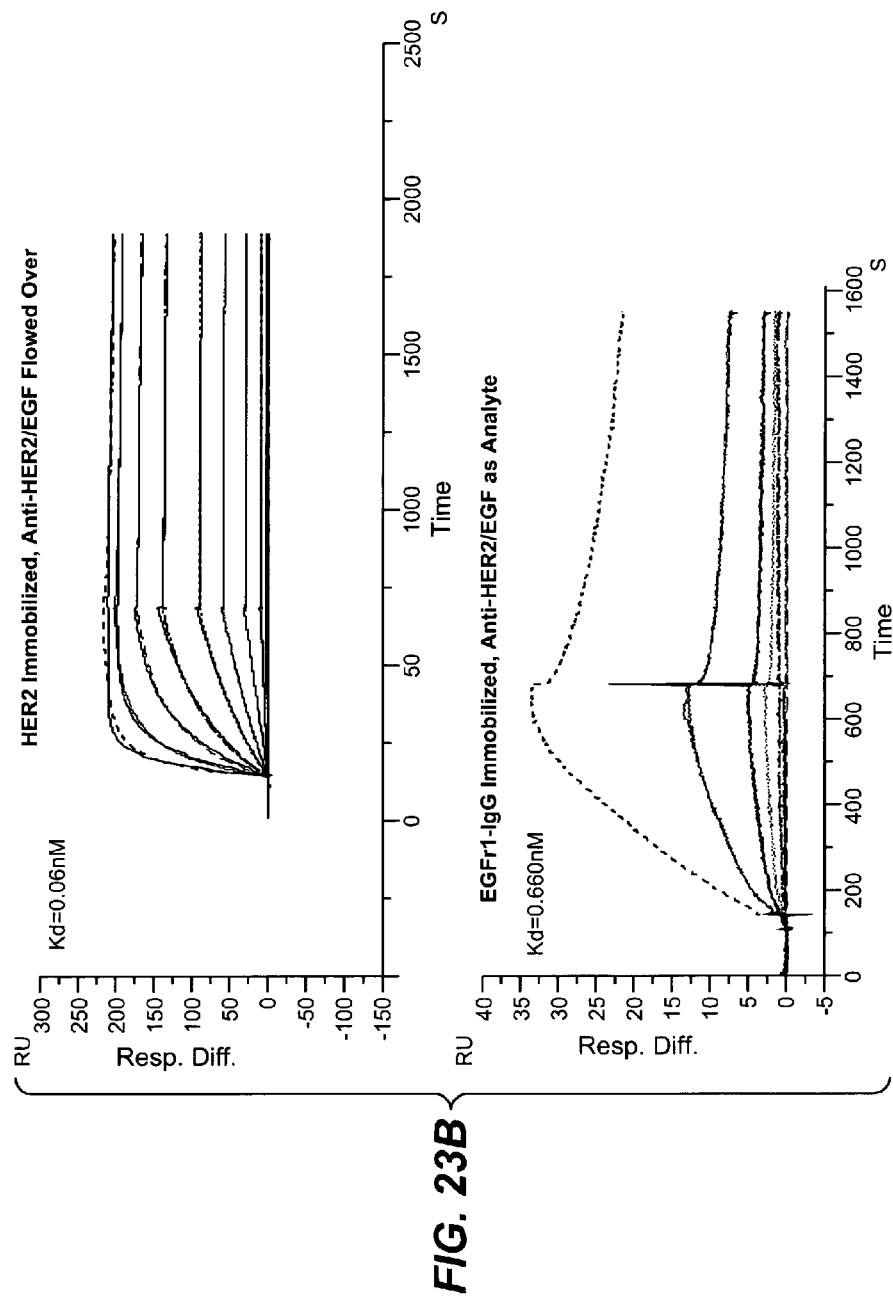

FIG. 23B is a series of graphs showing the binding affinities of an exemplary bispecific Anti-HER2 antibody 1/α-EGFR antibody for HER2 (top) and EGFR1 (bottom).

Figure 24:
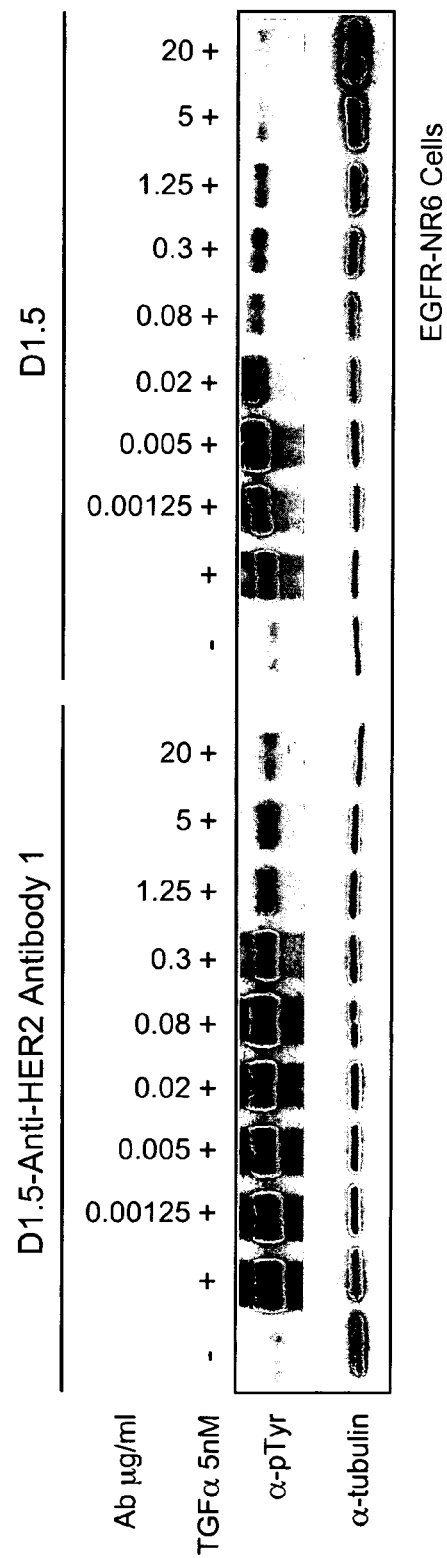

FIG. 24 is an image of immunoblots showing that the exemplary bispecific Anti-HER2 antibody 1/α-EGFR (D1.5) antibody inhibits transforming growth factor alpha (TGFα) mediated EGFR (epidermal growth factor receptor) phosphorylation in a dose dependent manner in EGFR expressing NR6 cells (left side). The D1.5 anti-EGFR antibody is used as a control (right side). Phosphorylation levels are determined using an anti-phospho-tyrosine (α-pTyr) antibody and an anti-tubulin antibody (α-tubulin) is used as a loading control.

Figure 25:
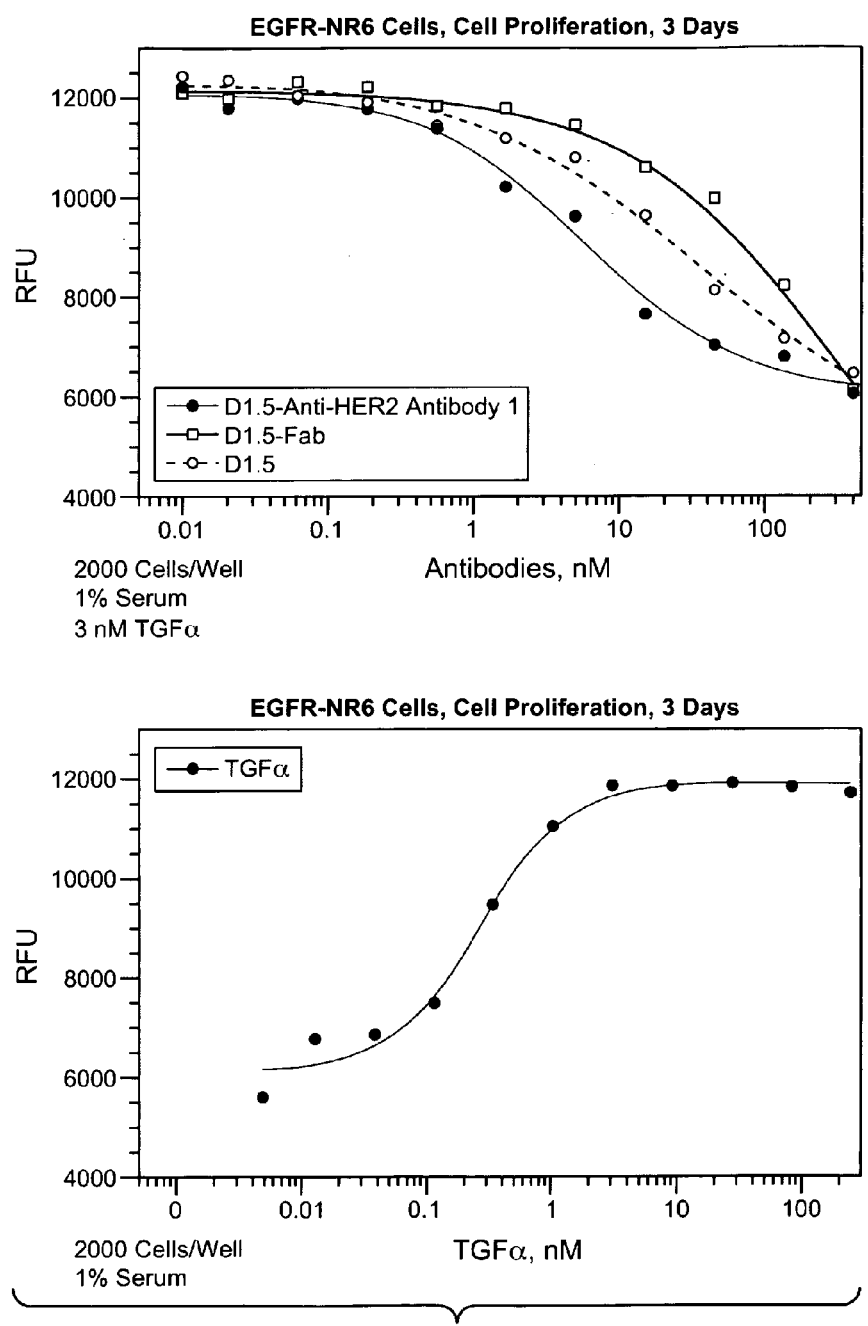

FIG. 25 is a series of graphs showing that the bispecific Anti-HER2 antibody 1/α-EGFR(D1.5) antibody inhibits TGFα-induced growth, over a three-day period, in NR6 cells that are stably transfected to express EGFR.

Figure 26:
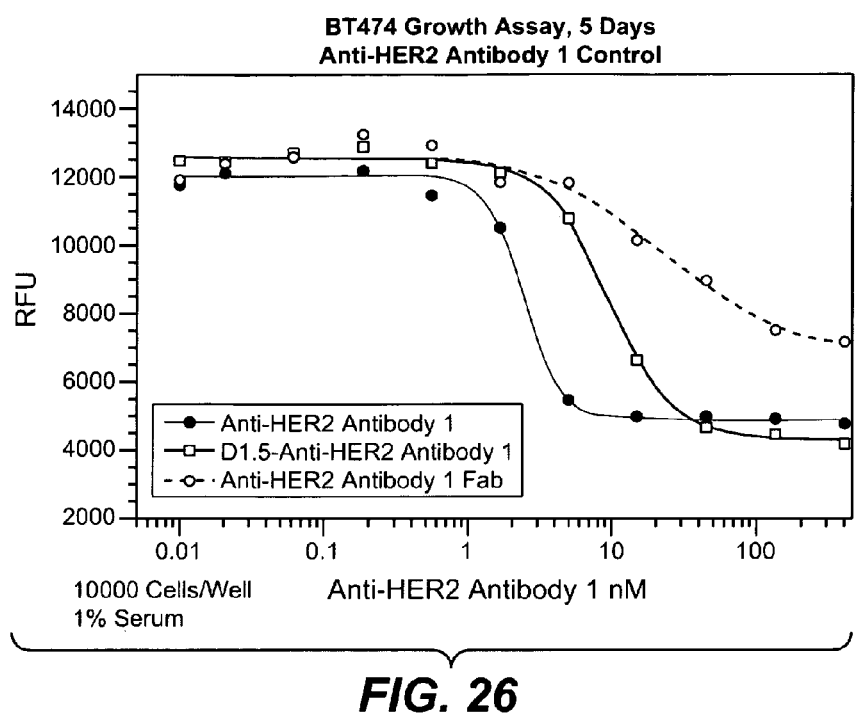

FIG. 26 is a graph showing that the exemplary bispecific Anti-HER2 antibody 1/α-EGFR(D1.5) antibody inhibits growth of HER2 amplified BT474 cells over a five-day period in a manner similar to the anti-HER2 antibody 1 control.

Figure 27:
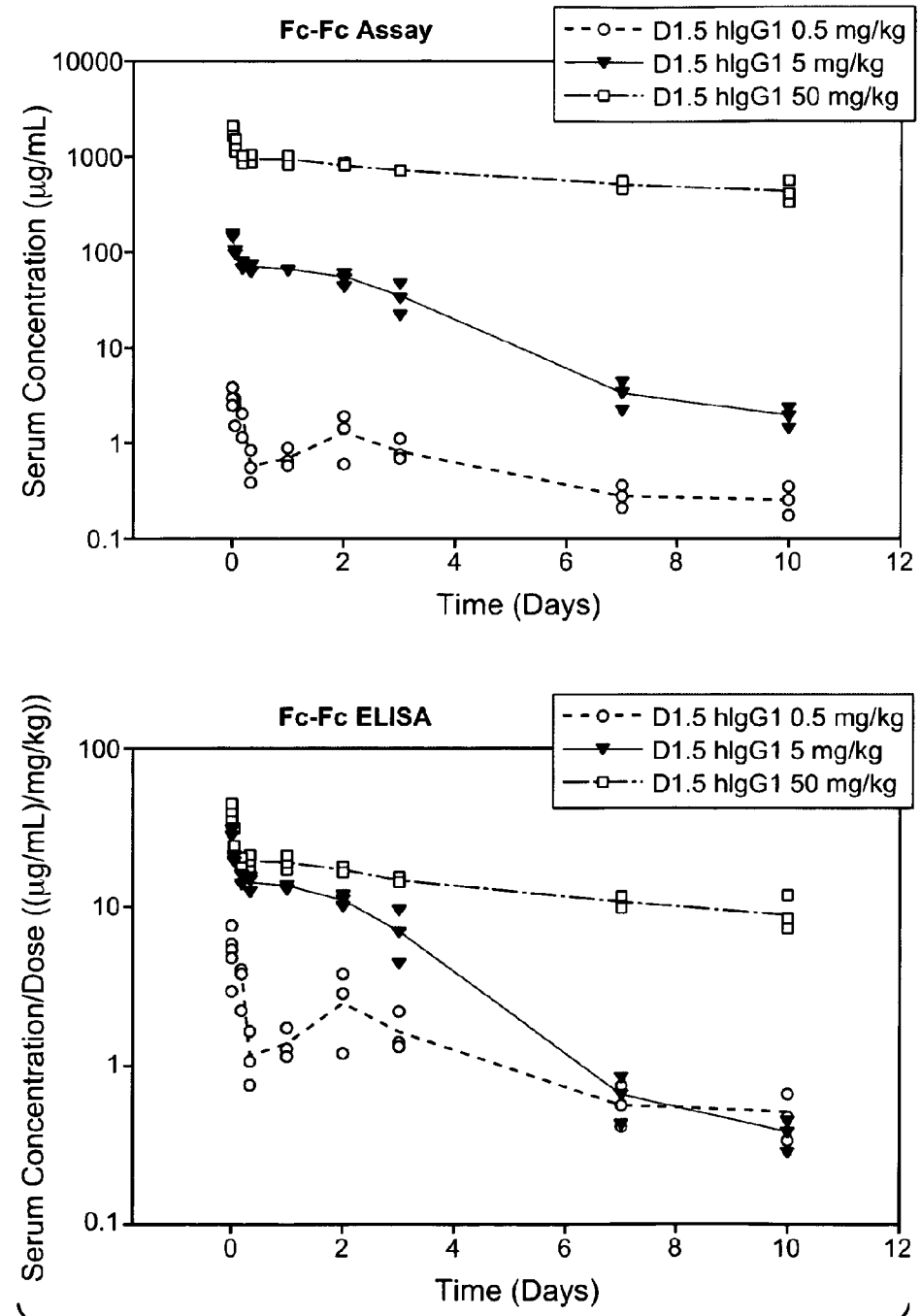

FIG. 27 is a series of graphs showing Fc-Fc assay and Fc-Fc ELISA assay results of a ten-day pharmacokinetics (PK) analysis of the D1.5 human IgG1 control antibody (anti-EGFR) using SCID Beige mice.

Figure 28A:
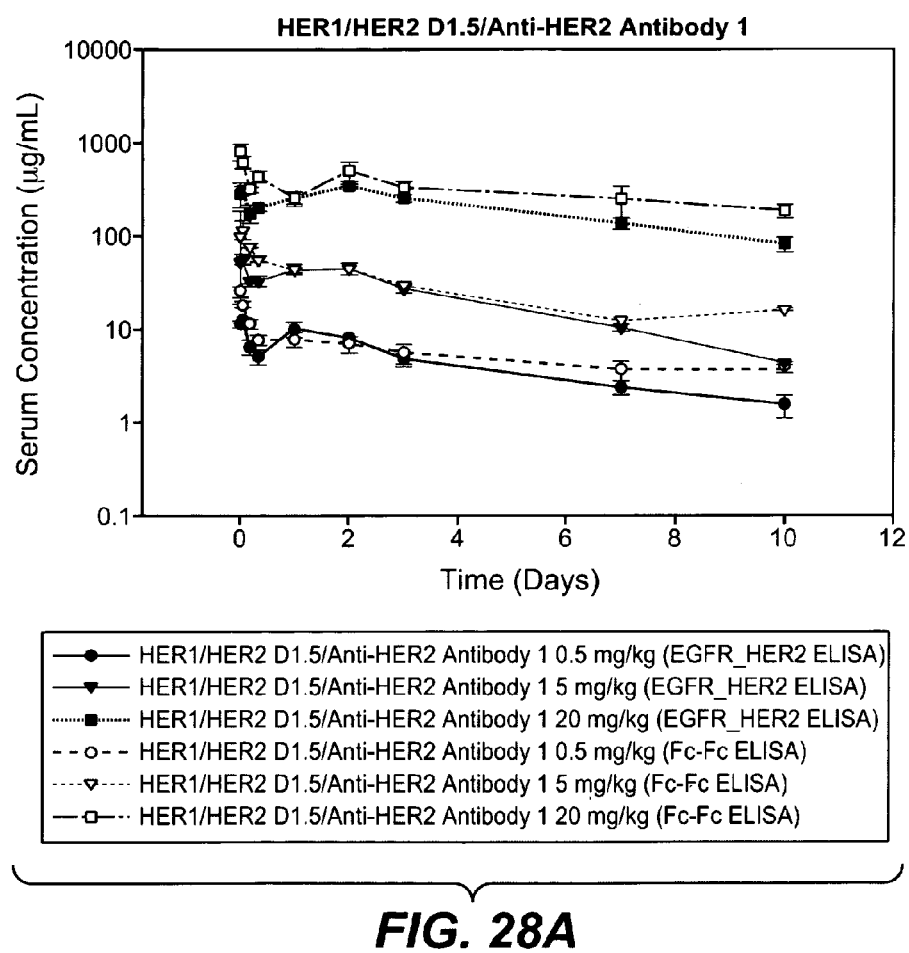
Figure 28B:
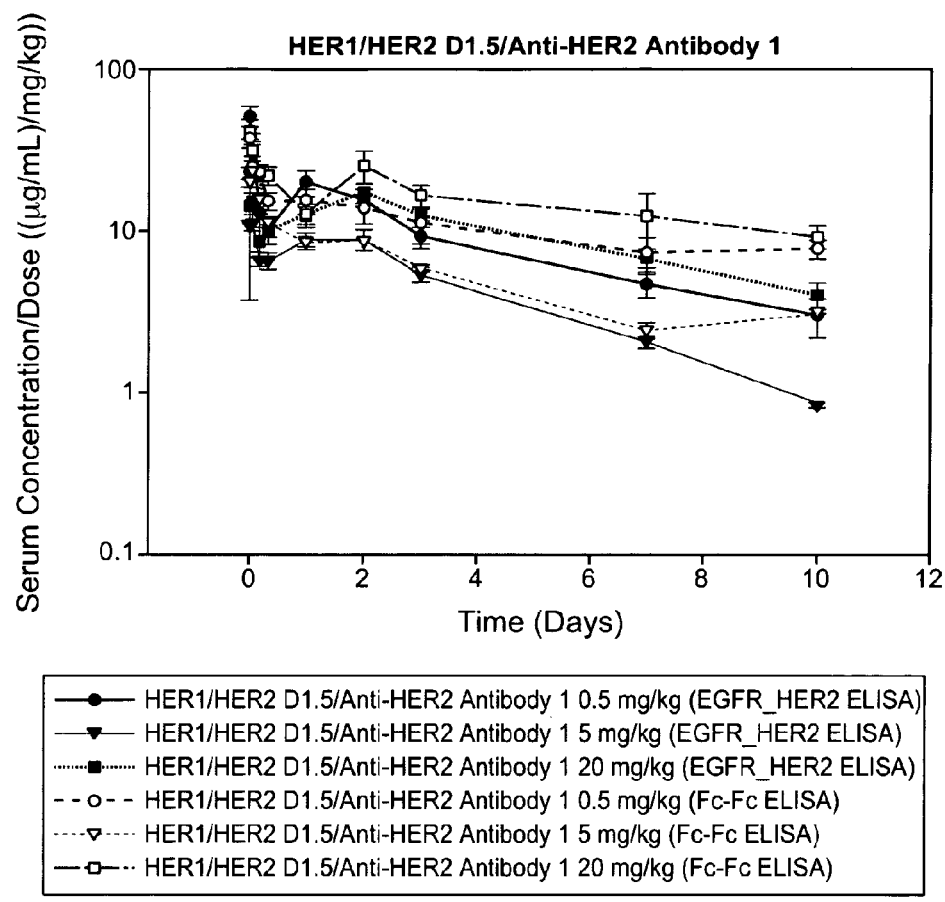

FIGS. 28A and 28B are a series of graphs showing EGFR-HER2 ELISA and Fc-Fc ELISA assay results of a ten-day PK analysis of the exemplary bispecific Anti-HER2 antibody 1/α-EGFR(D1.5) antibody using SCID Beige mice.

Figure 29:
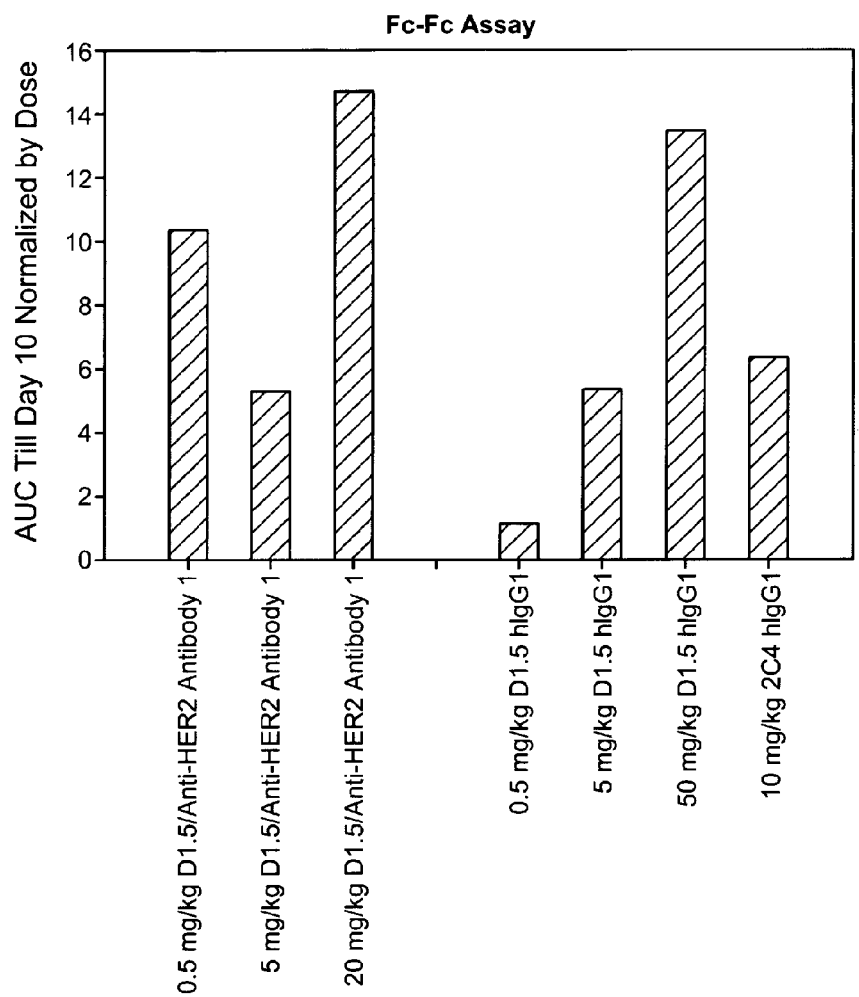

FIG. 29 is a graph showing a comparison of the exposure of the exemplary bispecific Anti-HER2 antibody 1/α-EGFR (D1.5) antibody to the control D1.5 (anti-EGFR) and control (anti-HER2 antibody 2) antibodies in mice. The exemplary bispecific Anti-HER2 antibody 1/α-EGFR(D1.5) antibody has an exposure in mice over the tested time period that is similar to the control antibodies.

Figure 1:
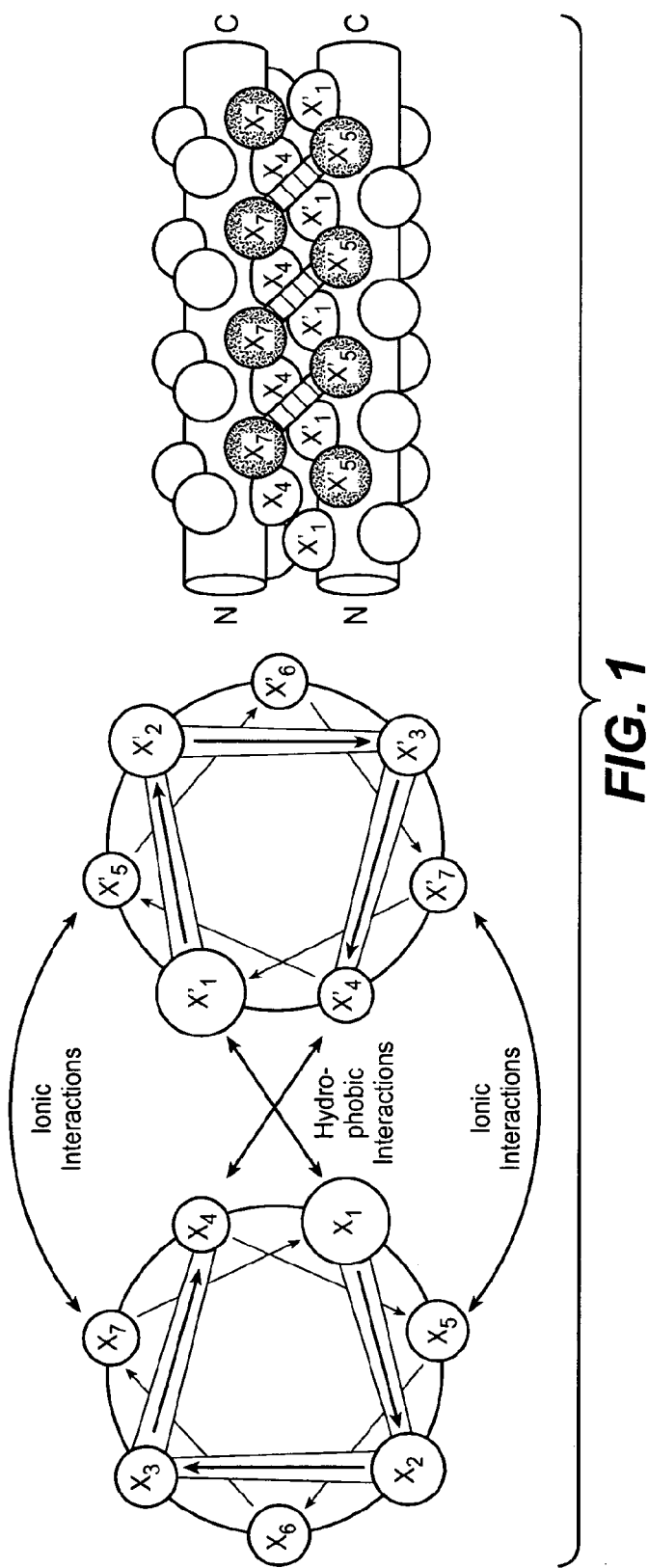
FIG. 1 is a schematic diagram showing ionic and hydrophobic interactions between amino acids in an exemplary coiled coil (CC) structure. The residues in the first CC are labeled $X_1$ through $X_7$ and the residues in the second CC are labeled $X'_1$, through $X'_7$. Ionic interactions between the $X_5$ residue of the first CC and the $X'_7$ residue of the second CC and the $X_7$ residue of the first CC and the $X'_5$ residue of the second CC are indicated. In addition, hydrophobic interactions between the $X_4$ and $X'_4$ and $X_1$ and $X'_1$, residues are shown.
Figures 1, 30A:
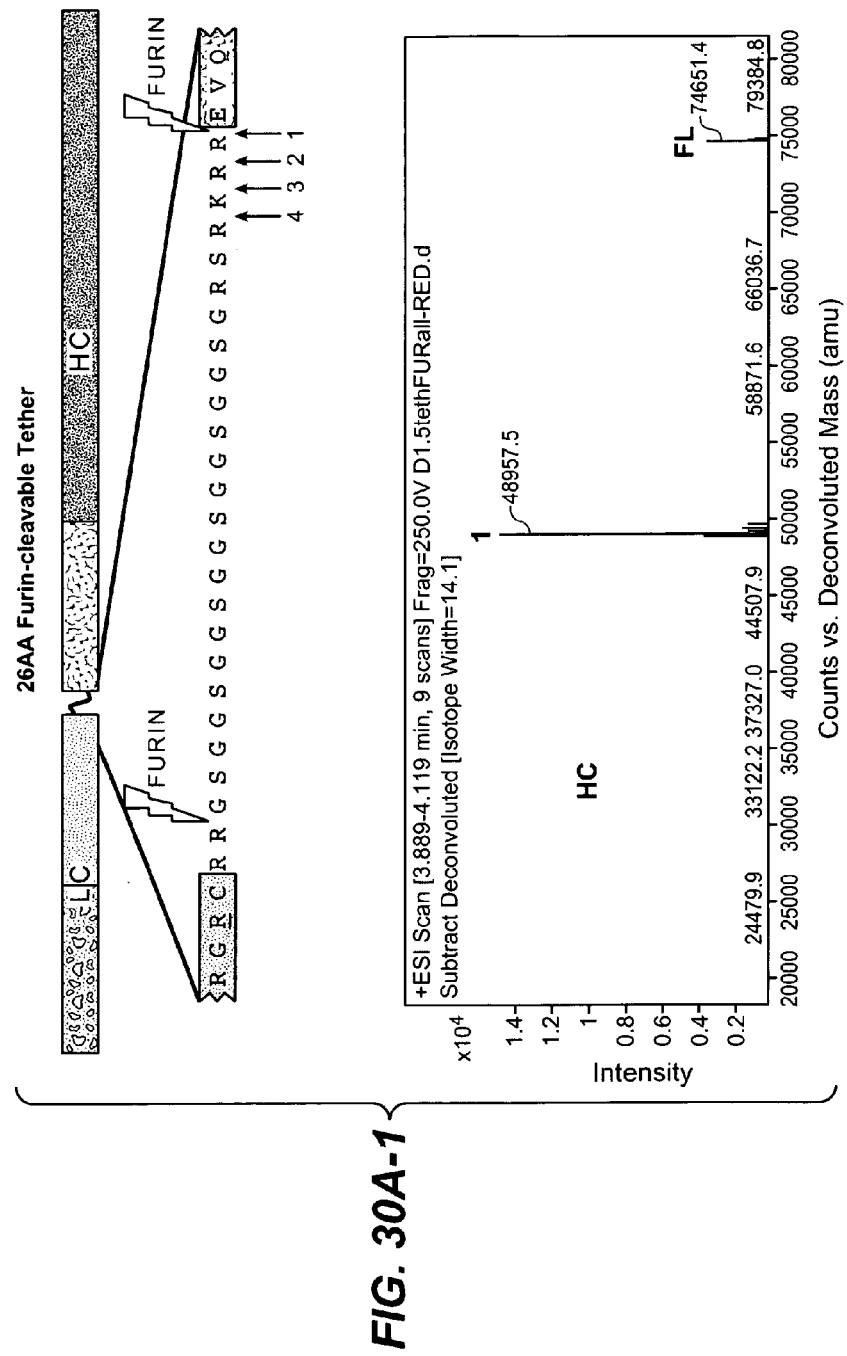
Figures 2, 30A:
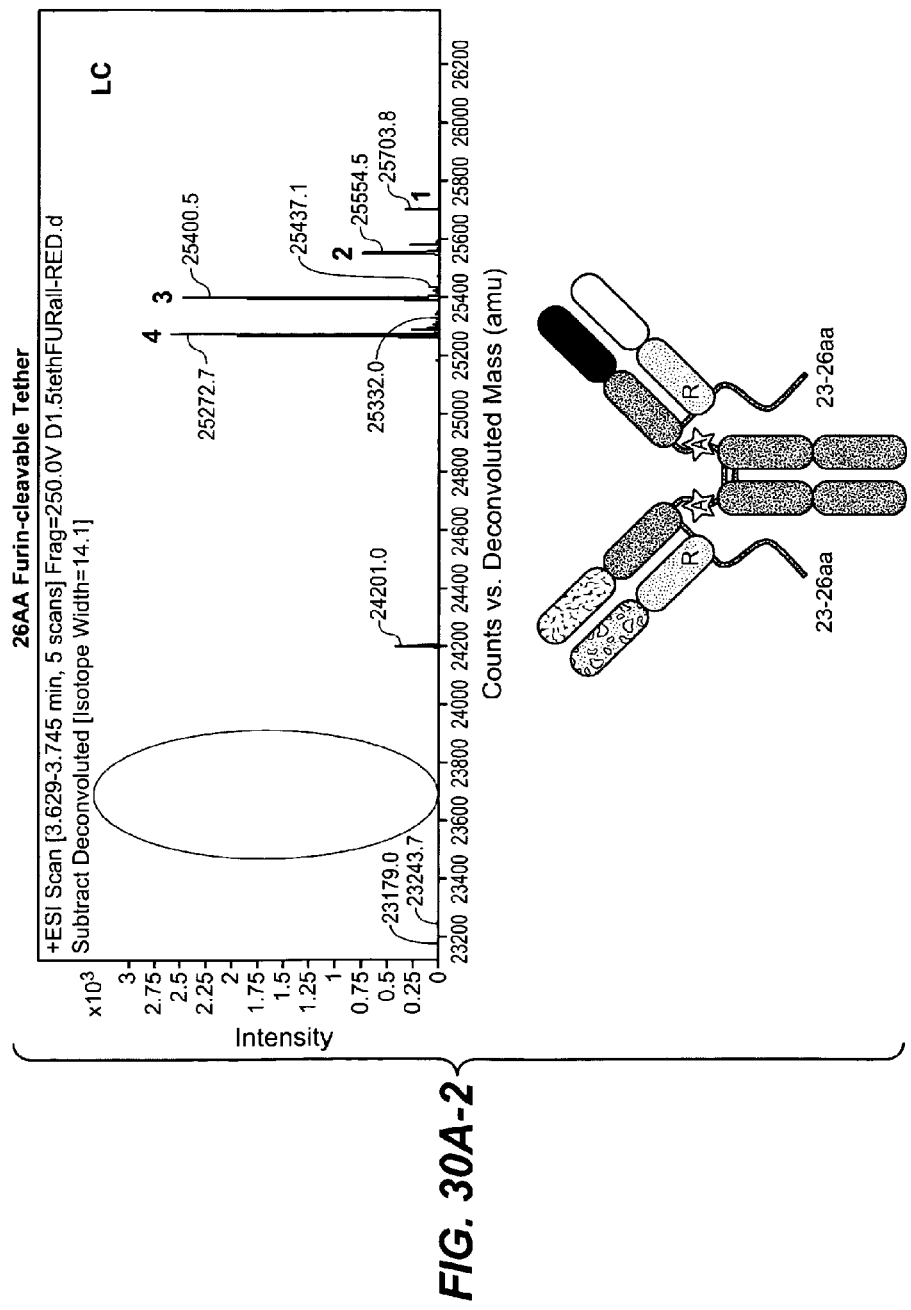
Figures 1, 30B:
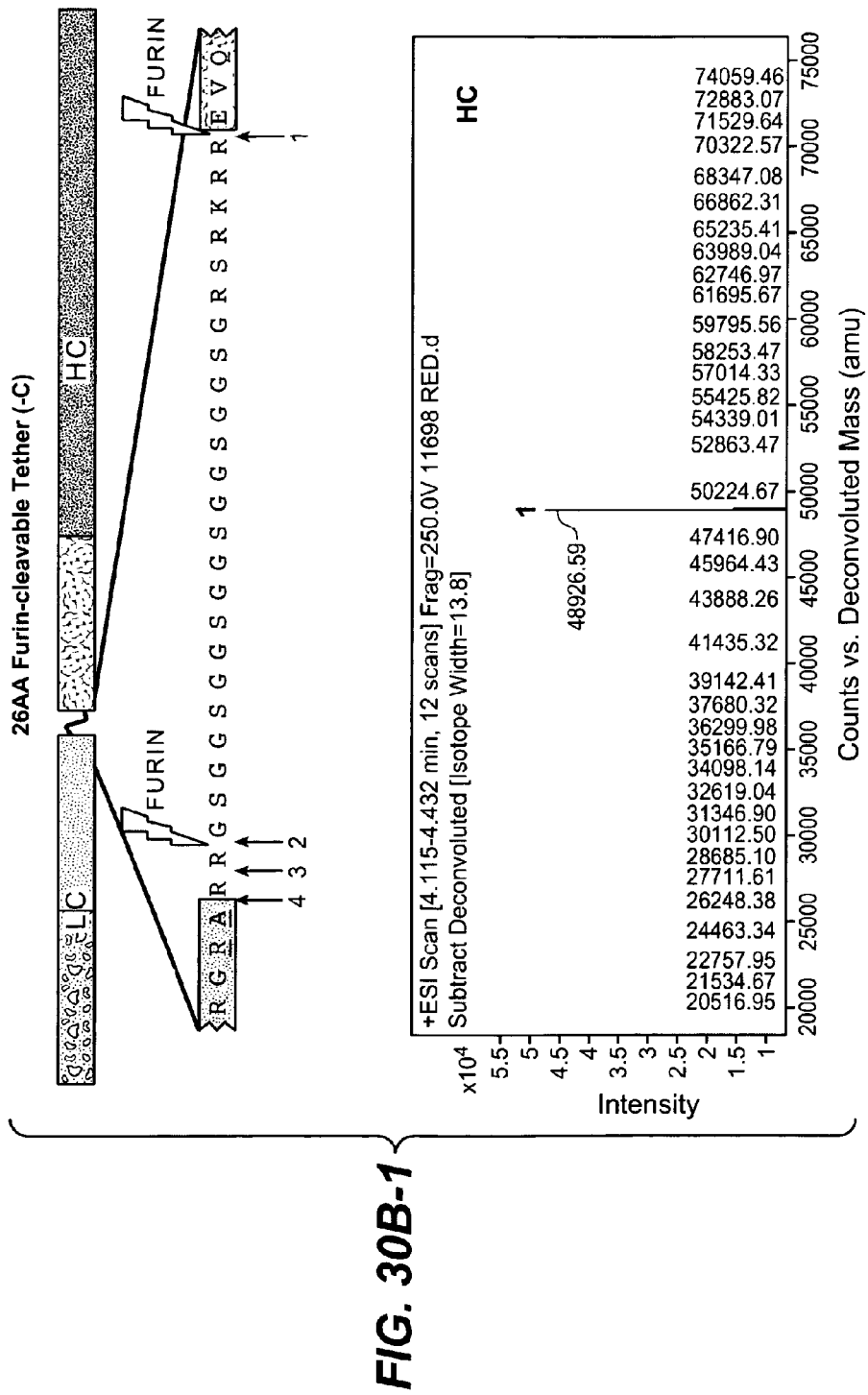
Figures 2, 30B:
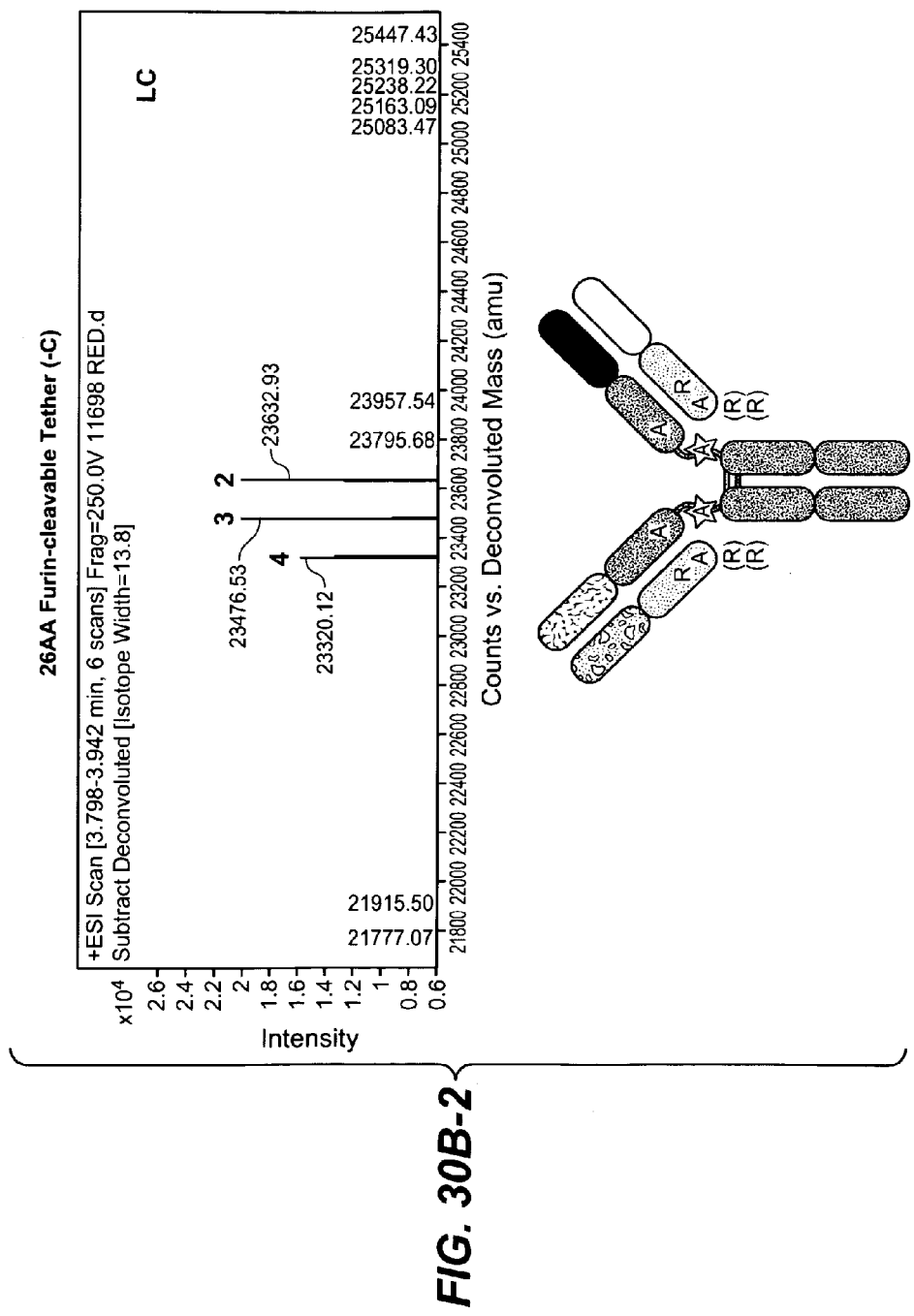
Figures 1, 30C:
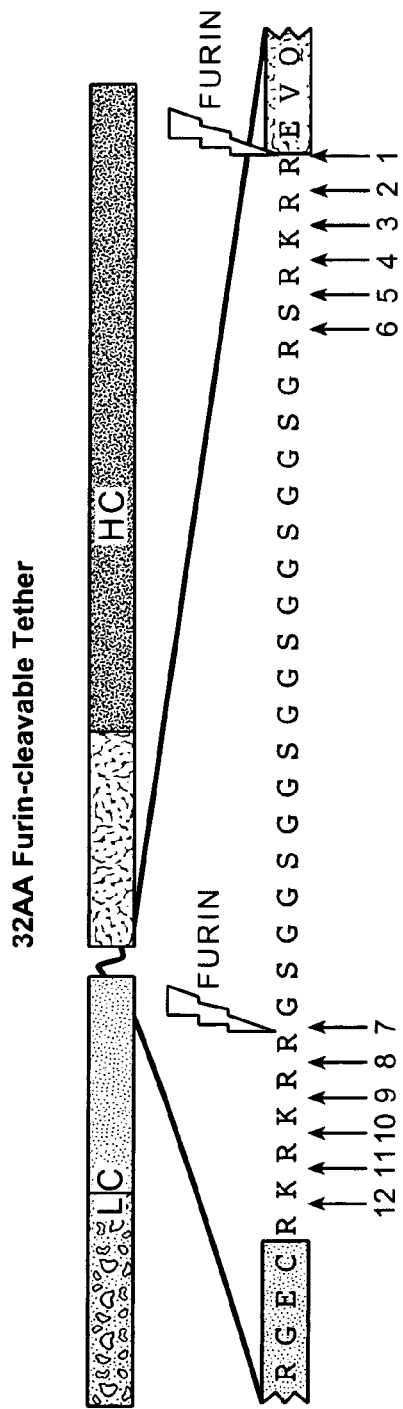
Figures 2, 30C:
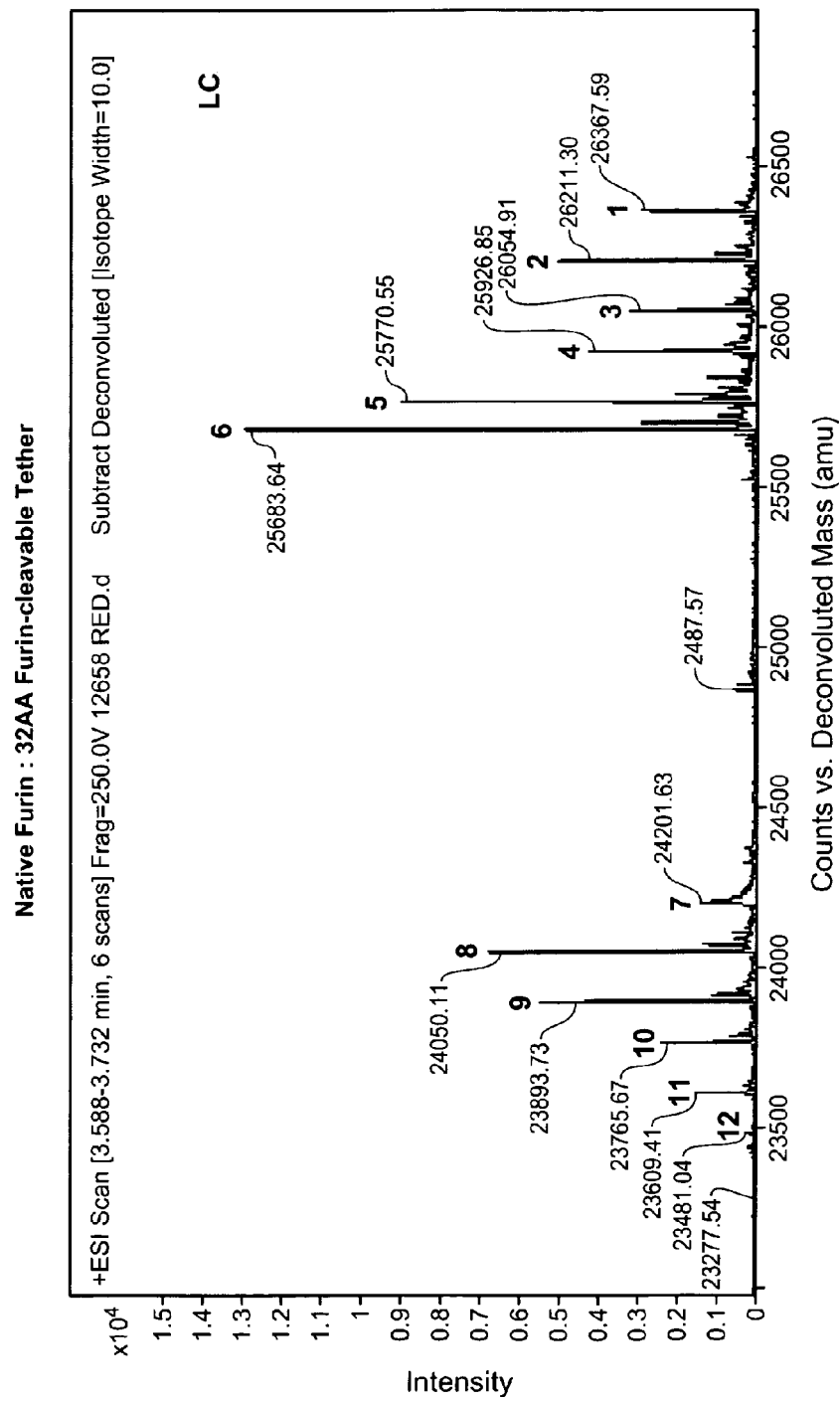
Figures 3, 30C:
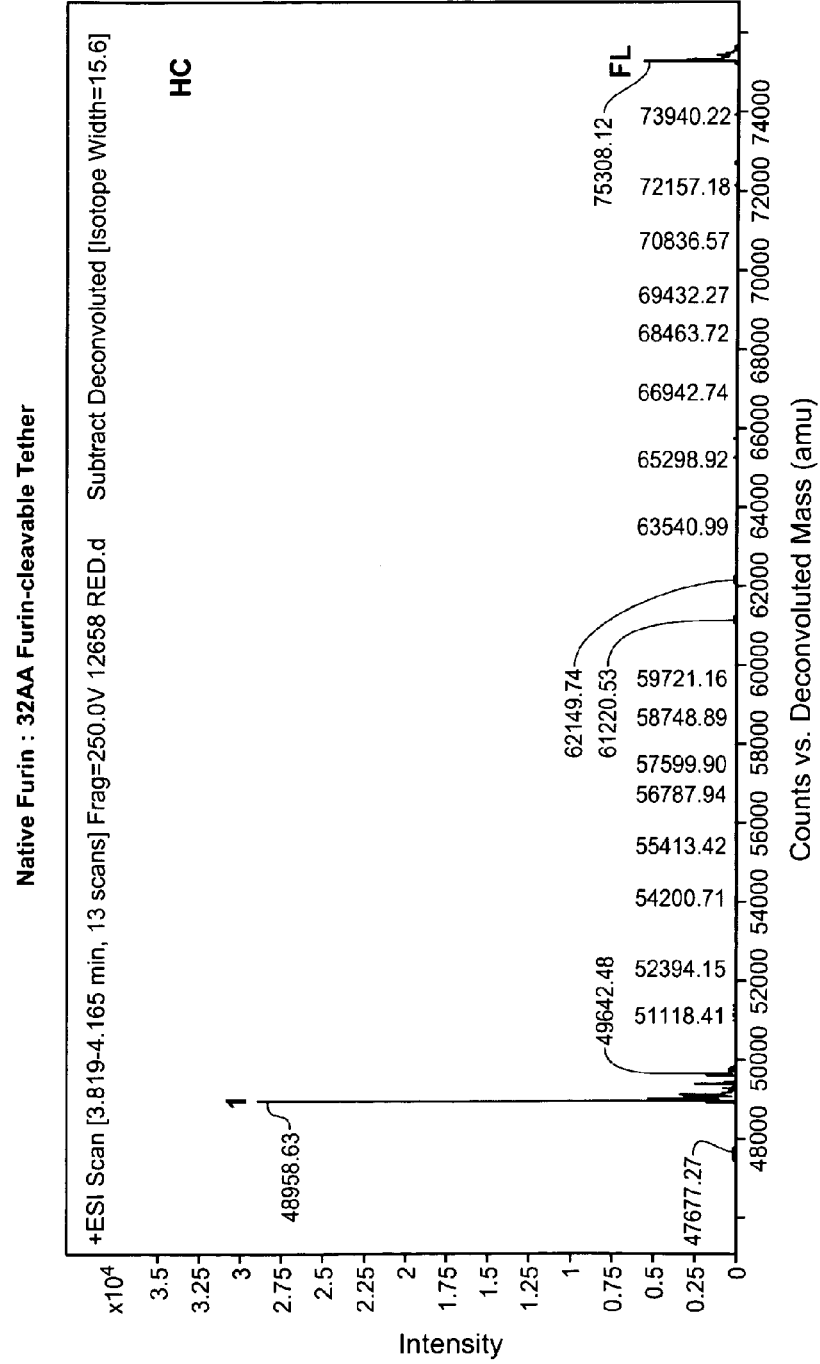
FIG. 3 is a schematic diagram showing the structure of an exemplary bispecific antibody containing a common light chain (common LC), a heterodimeric coiled coil, and a mutation in the hinge region (K222A; Kabat numbering system) of the first and second heavy chains (HC1 and HC2) that removes a Lys-C endopeptidase cleavage site.
Figures 4, 30C:
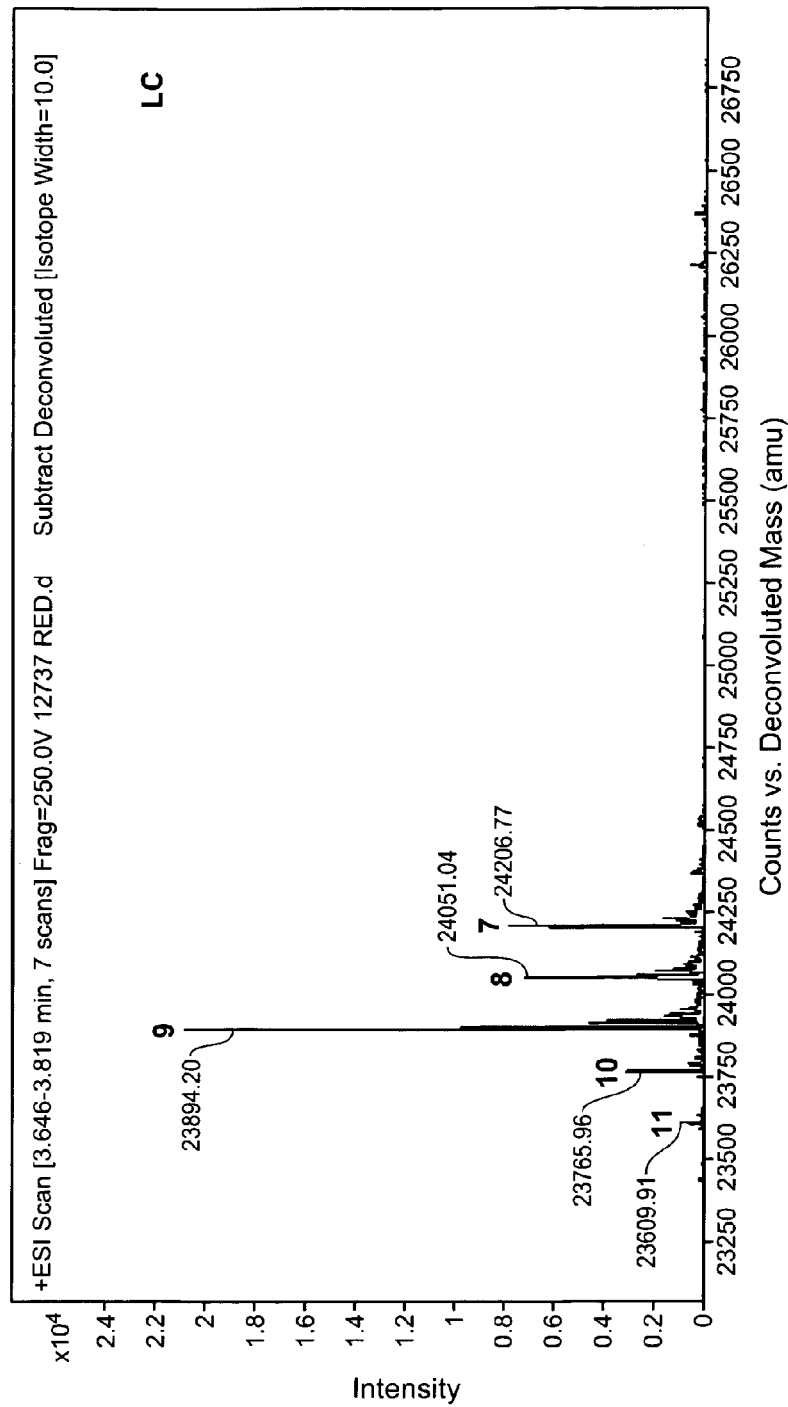
FIG. 4A is a schematic diagram showing the structure of an exemplary one-armed antibody containing a full-length heavy chain (HC1), a partial heavy chain (HC2) lacking the VH and CH1 domains, a light chain (common LC), a heterodimeric coiled coil, and a mutation in the hinge region (K222A) of HC1 that removes a Lys-C endopeptidase cleavage site.
Figures 5, 30C:
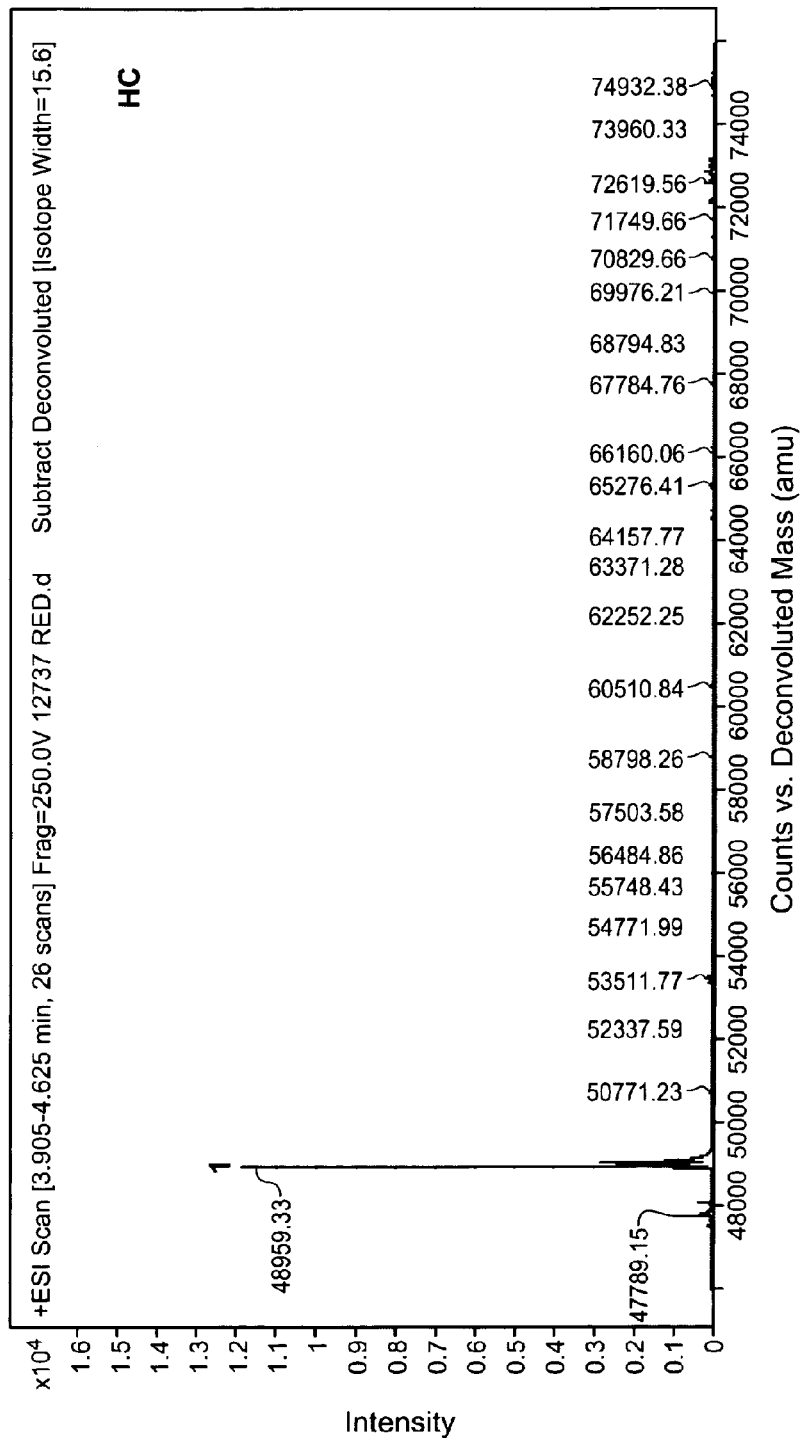
Figures 1, 30D:
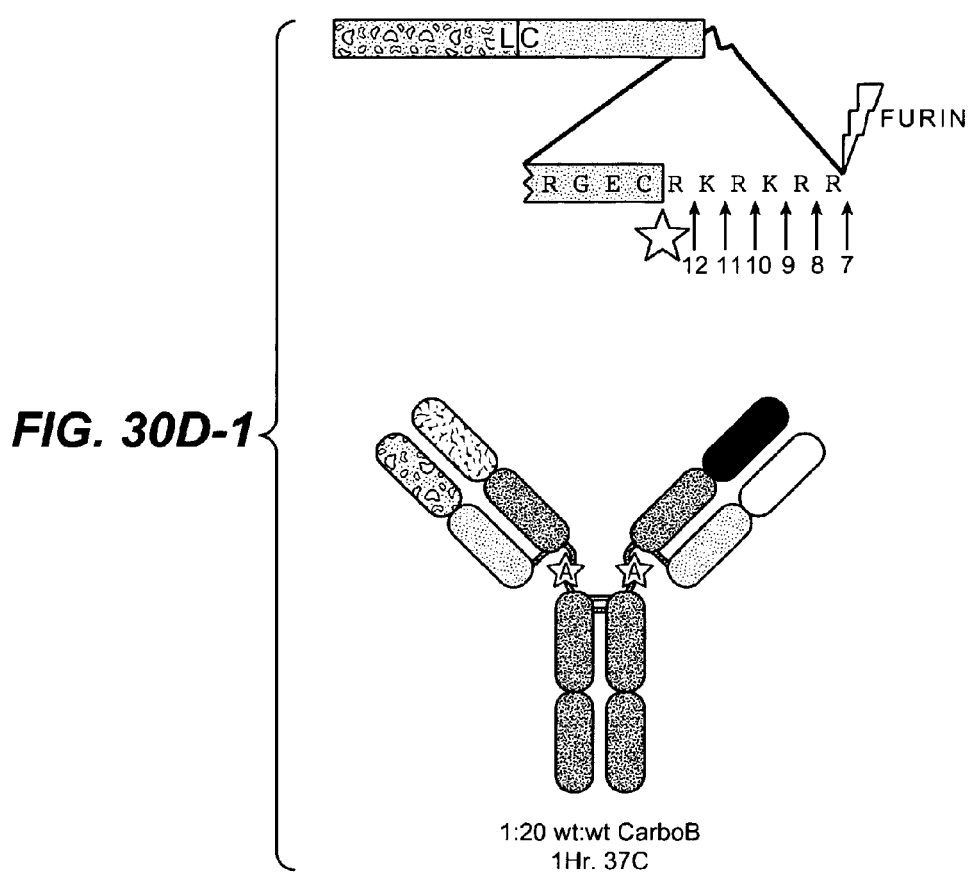
Figures 2, 30D:
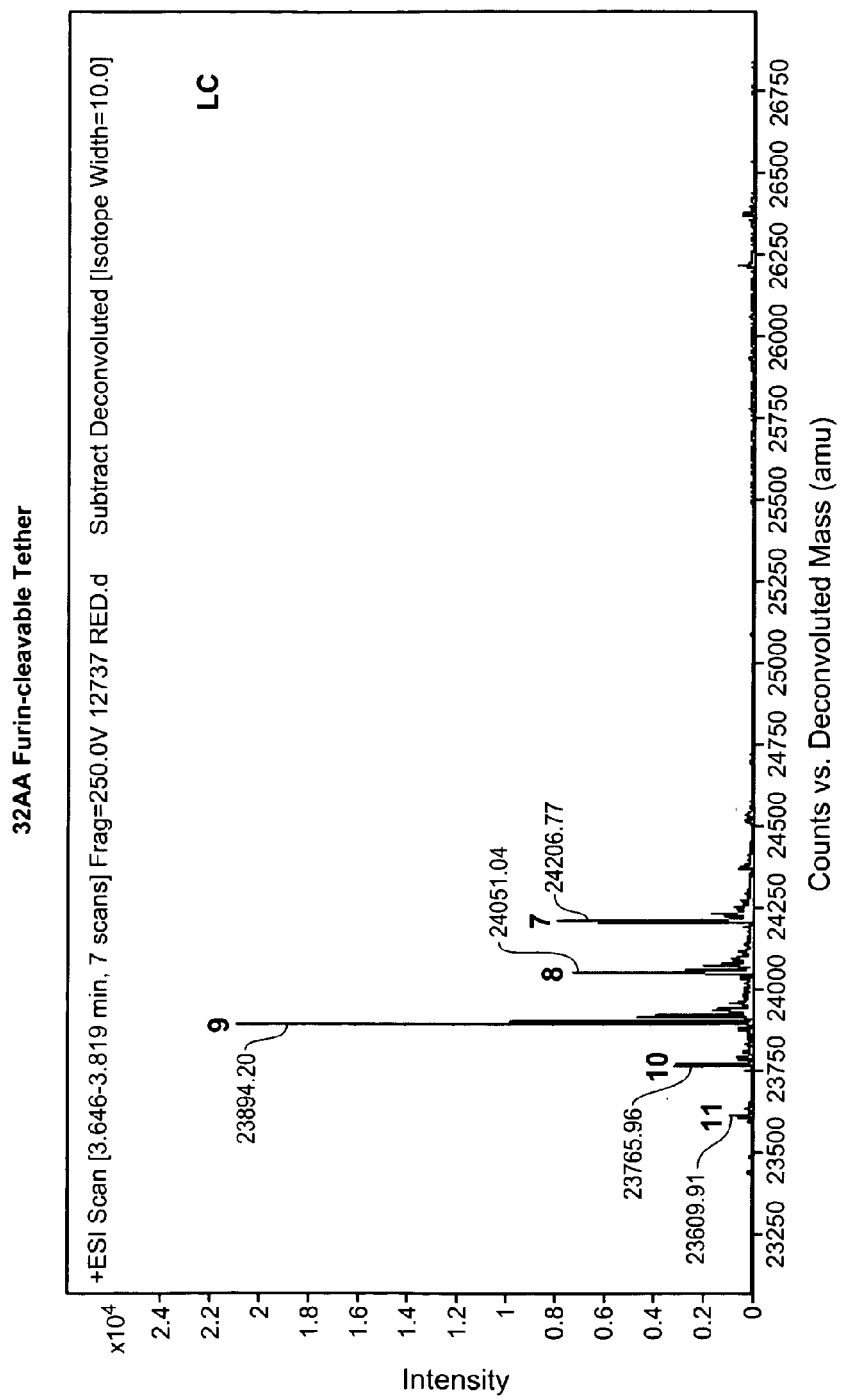
Figures 3, 30D:
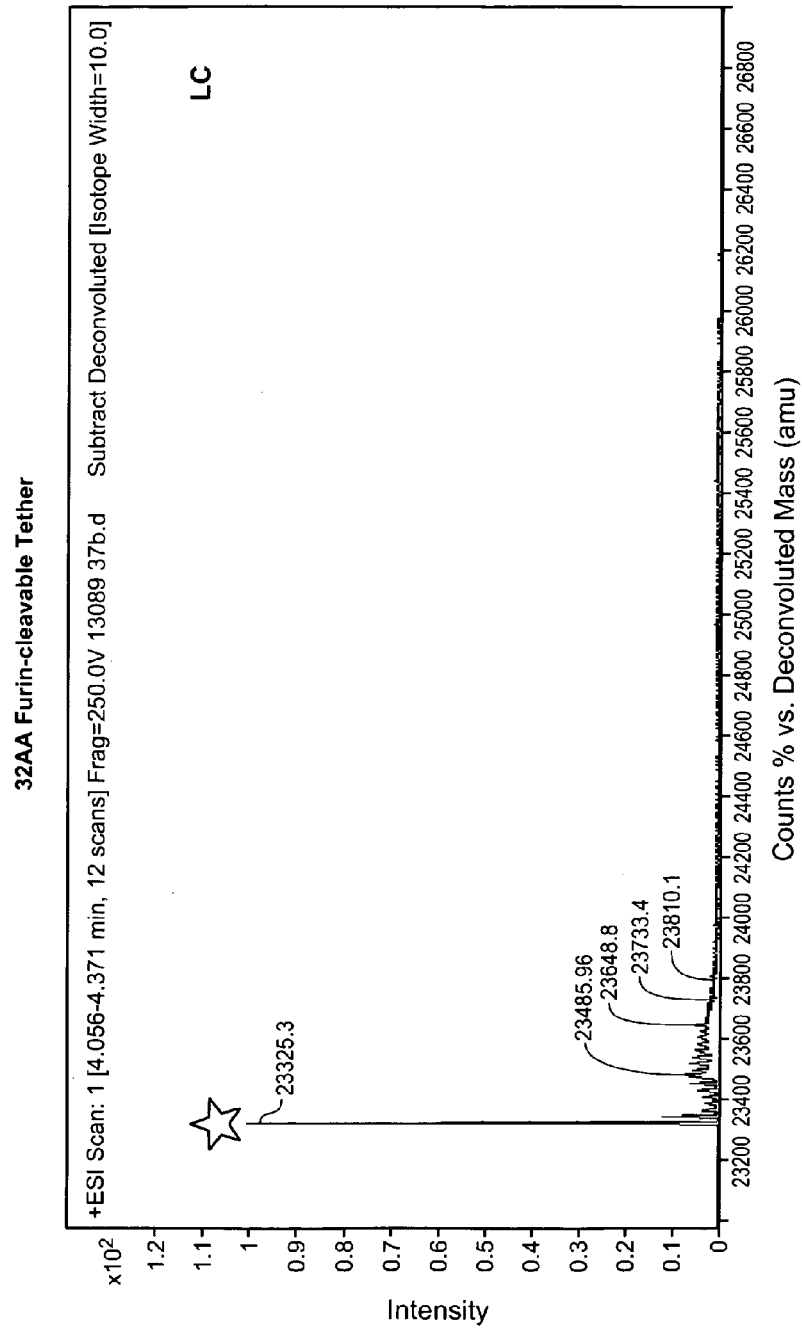

FIGS. 30A-1 and 30A-2, 30B-1 and 30B-2, 30C-1, 30C-2, 30C-3, 30C-4, and 30C-5, 30D-1, 30D-2, and 30D-3 are mass spectroscopy graphs showing the cleavage products of the heavy chain and the light chain of an antibody after cleavage by furin by a cell co-expressing furin. The sequence presented in FIGS. 30A-1, 30B-1, and 20C-1 is SEQ ID NO:38. The sequence presented in FIGS. 30D-1 is SEQ ID NO:39.

Figure 31:
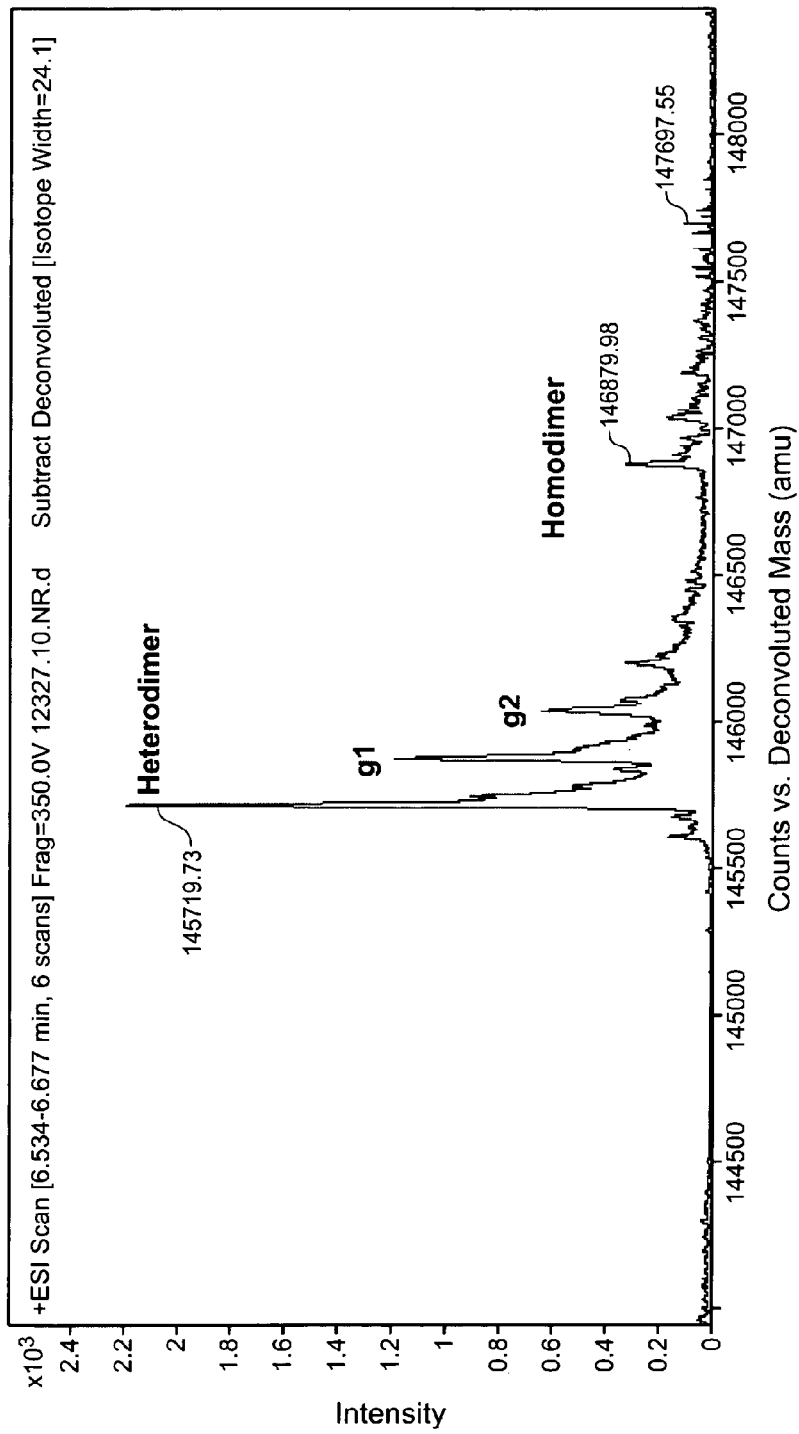

FIG. 31 is a non-reduced mass spectroscopy graph showing a bispecific antibody made by expressing a furin-cleavable, tethered coiled-coil antibody in a CHO cell that coexpressed furin and exposing the antibody to carboxypeptidase digestion.

Figure 32A:
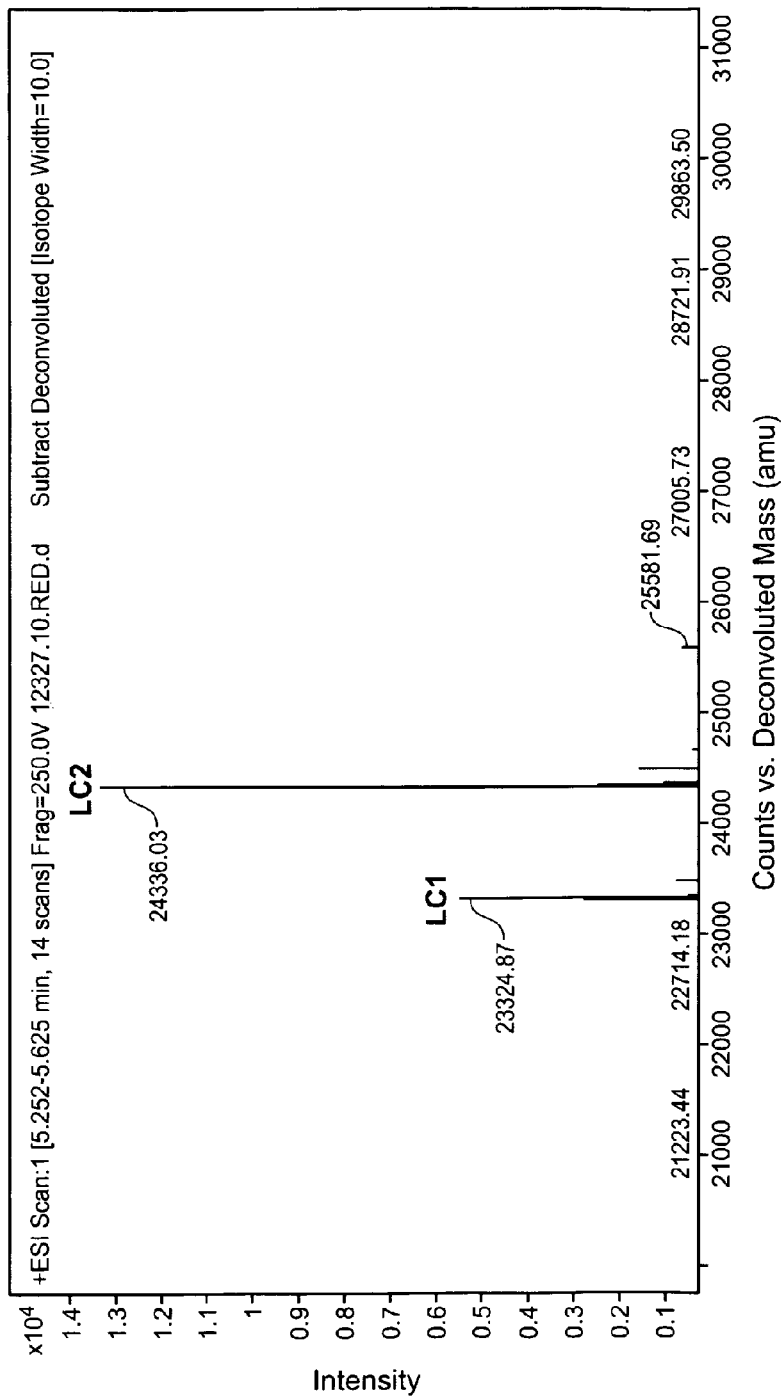
Figure 32B:
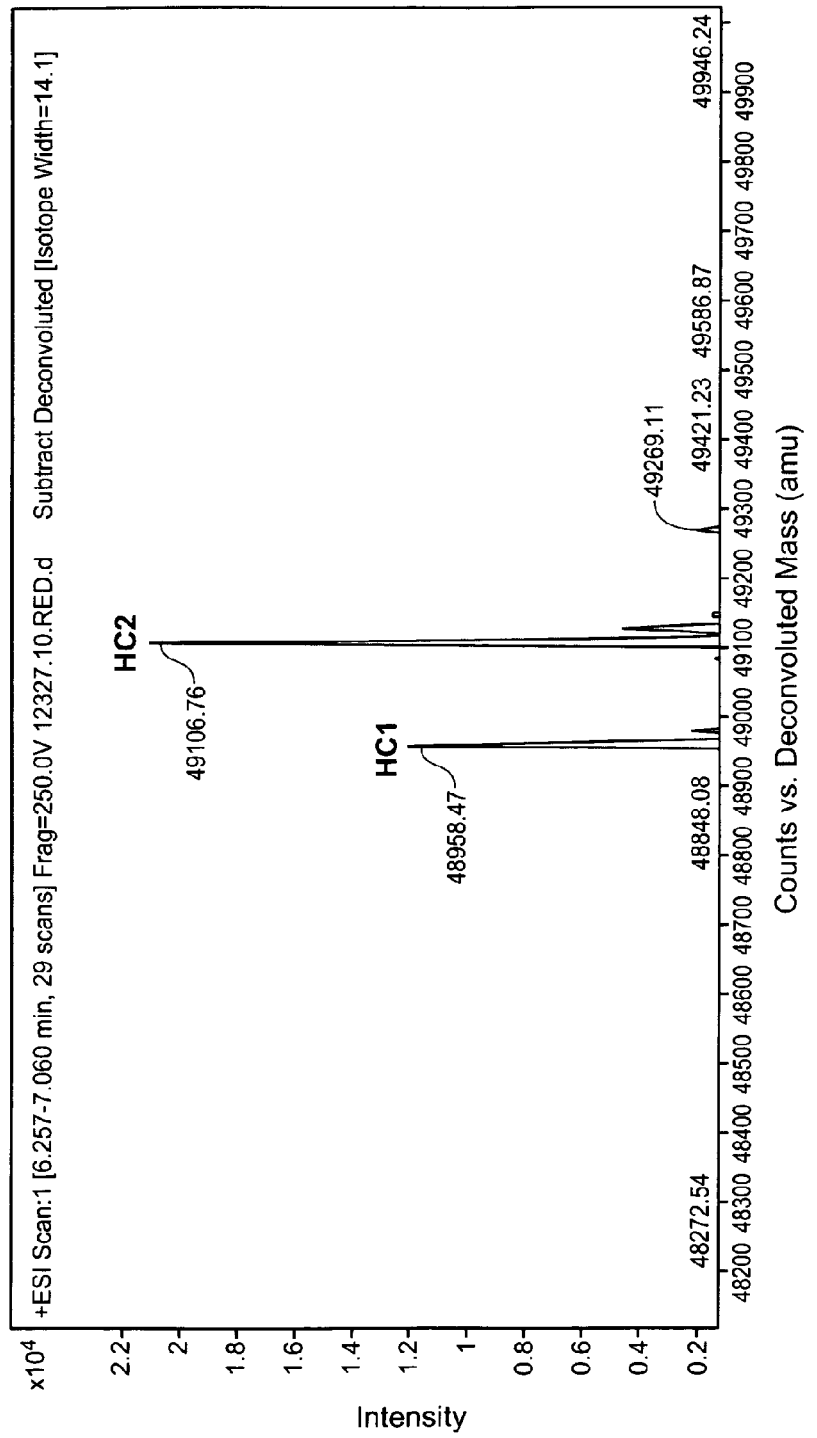

FIGS. 32 (A) and (B) is a reduced mass spectroscopy graph showing a bispecific antibody made by expressing a furin-cleavable, tethered coiled-coil antibody in a CHO cell that coexpressed furin and exposing the antibody to carboxypeptidase digestion.

DETAILED DESCRIPTION

Without being bound by theory, applicants believe that the coiled coil dimerization domains described herein provide the initial trigger that drives the binding of two or more molecules together with a high degree of accuracy and efficiency surprisingly even in the presence of Fc regions of an immunoglobulin, which Fc regions are also naturally attracted to each other under cell culture conditions.

By reducing homodimerization of heavy chains, use of the coiled coil heterodimerization domains described herein provides a breakthrough in the ability to produce a homogeneous population of protein complexes comprising a Fc CH component (e.g., multispecific or one-armed antibodies, etc.). Multispecific complexes are advantageous for use in therapeutic applications because, for example, they can direct the co-localization of a target (e.g., a tumor cell) and an agent directed against the target (e.g., a T cell) or they can eliminate the need for combination therapy and the risk associated with providing two or more therapeutics to a subject. Further, to facilitate the construction of antibodies, including multispecific antibodies, tethers according to the present invention can be used to link the light and heavy chains of an antibody and thereby aid in the proper association of each light chain to its cognate heavy chain.

I. Definitions

The term "antibody" herein is used in the broadest sense and refers to any immunoglobulin (Ig) molecule comprising two heavy chains and two light chains, and any fragment, mutant, variant or derivation thereof which so long as they exhibit the desired biological activity (e.g., epitope binding activity). Examples of antibodies include monoclonal antibodies, polyclonal antibodies, multispecific antibodies and antibody fragments.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the heavy chain constant domain of antibodies means residue numbering by the EU numbering system.

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

A naturally occurring basic 4-chain antibody unit is a heterotetrameric glycoprotein composed of two identical light (L) chains and two identical heavy (H) chains (an IgM antibody consists of 5 of the basic heterotetramer units along with an additional polypeptide called J chain, and therefore contains 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has, at the N-terminus, a variable domain ($V_H$) followed by three constant domains ($C_H$) for each of the α and γ chains and four $C_H$ domains for µ and ε isotypes. Each L chain has, at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Ten and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N. J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework regions" (FR) are those variable domain residues other than the CDR residues. Each variable domain typically has four FRs identified as FR1, FR2, FR3, and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat. In one embodiment, for the VL, the subgroup is subgroup kappa I as in Kabat. In one embodiment, for the VH, the subgroup is subgroup III as in Kabat.

One example of an "intact" antibody is one that comprises an antigen-binding site as well as a $C_L$ and at least heavy chain constant domains, $C_H1$, $C_H2$, and $C_H3$. The constant domains can be native sequence constant domains (e.g., human native sequence constant domains) or amino acid sequence variant thereof.

"Antibody fragments" comprise a portion of an intact antibody, preferably the antigen binding or a variable region of the intact antibody. Examples of antibody fragments include Fab, Fab', F(ab')$_2$, and Fv fragments; diabodies (Db); tandem diabodies (taDb), linear antibodies (e.g., U.S. Pat. No. 5,641,870, Example 2; Zapata et al., Protein Eng. 8(10):1057-1062 (1995)); one-armed antibodies, single variable domain antibodies, minibodies, single-chain antibody molecules; and multispecific antibodies formed from antibody fragments (e.g., including but not limited to, Db-Fc, taDb-Fc, taDb-CH3 and (scFV)4-Fc).

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003): 21:484-490; WO 2005/035572; WO 03/035694; Febs Lett (1994) 339:285-290; WO00/29004; WO 02/051870).

The expression "linear antibodies" generally refers to the antibodies described in Zapata et al., Protein Eng. 8(10): 1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

The term "knob-into-hole" or "KnH" technology as mentioned herein refers to the technology directing the pairing of two polypeptides together in vitro or in vivo by introducing a pertuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (e.g., US2007/0178552, WO 96/027011, WO 98/050431 and Zhu et al. (1997) Protein Science 6:781-788). This is especially useful in driving the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions). Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H$1). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H$1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region; this region is also the part recognized by Fc receptors (FcR) found on certain types of cells.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains, which enables the sFv to form the desired structure for antigen binding. For a review of sFv, see Pluckthun, The Pharmacology of Monoclonal Antibodies, vol. 113, Rosenburg and Moore eds., Springer-Verlag, New York, pp. 269-315 (1994); Malmborg et al., J. Immunol. Methods 183:7-13, 1995.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA 90:6444-6448 (1993).

The term "one-armed antibody" or "one-armed antibodies" refers to an antibody that comprises (1) a variable domain joined by a peptide bond to a polypeptide comprising a CH2 domain, a CH3 domain or a CH2-CH3 domain and (2) a second CH2, CH3 or CH2-CH3 domain, wherein a variable domain is not joined by a peptide bond to a polypeptide comprising the second CH2, CH3 or CH2-CH3 domain. In one embodiment, the one-armed antibody comprises 3 polypeptides (1) a first polypeptide comprising a variable domain (e.g., VH), CH1, CH2 and CH3, (2) a second polypeptide comprising a variable domain (e.g., VL) and a CL domain, and (3) a third polypeptide comprising a CH2 and CH3 domain. In an embodiment, the third polypeptide does not comprise a variable domain. In another embodiment, the one-armed antibody has a partial hinge region containing the two cysteine residues which form disulphide bonds linking the constant heavy chains. In one embodiment, the variable domains of the one armed antibody form an antigen binding region. In another embodiment, a variable domain of the one armed antibody is a single variable domain, wherein each single variable domain is an antigen binding region.

Antibodies of the invention can be "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. USA 81:6851-6855 (1984)). Chimeric antibodies of interest herein include primatized antibodies comprising variable domain antigen-binding sequences derived from a non-human primate (e.g., Old World Monkey, Ape, etc.) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Complex" or "complexed" as used here in refers to the association of two or more molecules that interact with each other through bonds and/or forces (e.g., van der waals, hydrophobic, hydrophilic forces) that are not peptide bonds. In one embodiment, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

The term "heteromultimer" or "heteromultimeric" as used herein describes two or more polypeptides that interact with each other by a non-peptidic, covalent bond (e.g., disulfide bond) and/or a non-covalent interaction (e.g., hydrogen bonds, ionic bonds, Van der Waals forces, and hydrophobic interactions), wherein at least two of the molecules have different sequences from each other.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., CH2 and/or CH3 sequence of an IgG). Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG-1, IgG-2, IgG-3, or IgG-4 subtypes, IgA (including IgA-1 and IgA-2), IgE, IgD, or IgM.

An antibody of this invention "which binds" an antigen of interest is one that binds the antigen with sufficient affinity such that the antibody is useful as a diagnostic and/or therapeutic agent in targeting a protein or a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA) or ELISA. With regard to the binding of an antibody to a target molecule, the term "specific binding" or "specifically binds to" or is "specific for" a particular polypeptide or an epitope on a particular polypeptide target means binding that is measurably different from a non-specific interaction (e.g., a non-specific interaction may be binding to bovine serum albumin or casein). Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In one embodiment, the term "specific binding" refers to binding where a molecule binds to a particular polypeptide or epitope on a particular polypeptide without substantially binding to any other polypeptide or polypeptide epitope.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

In one embodiment, the "Kd" or "Kd value" according to this invention is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-Aminco spectrophotometer (ThermoSpectronic) with a stir red cuvette.

An "on-rate" or "rate of association" or "association rate" or "$k_{on}$," according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol. 293:865-881 (1999). However, if the on-rate exceeds $10^6$ $M^{-1}$ $S^{-1}$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

"Biologically active" and "biological activity" and "biological characteristics" with respect to a polypeptide of this invention, such as an antibody, fragment, or derivative thereof, means having the ability to bind to a biological molecule, except where specified otherwise.

"Peptibody" or "peptibodies" refers to a fusion of randomly generated peptides with an Fc domain. See U.S. Pat. No. 6,660,843, issued Dec. 9, 2003 to Feige et al. (incorporated by reference in its entirety). They include one or more peptides linked to the N-terminus, C-terminus, amino acid sidechains, or to more than one of these sites. Peptibody technology enables design of therapeutic agents that incorporate peptides that target one or more ligands or receptors, tumor-homing peptides, membrane-transporting peptides, and the like. Peptibody technology has proven useful in design of a number of such molecules, including linear and disulfide-constrained peptides, "tandem peptide multimers" (i.e., more than one peptide on a single chain of an Fc domain). See, for example, U.S. Pat. No. 6,660,843; U.S. Pat. App. No. 2003/0195156, published Oct. 16, 2003 (corresponding to WO 02/092620, published Nov. 21, 2002); U.S. Pat. App. No. 2003/0176352, published Sep. 18, 2003 (corresponding to WO 03/031589, published Apr. 17, 2003); U.S. Ser. No. 09/422,838, filed Oct. 22, 1999 (corresponding to WO 00/24770, published May 4, 2000); U.S. Pat. App. No. 2003/0229023, published Dec. 11, 2003; WO 03/057134, published Jul. 17, 2003; U.S. Pat. App. No. 2003/0236193, published Dec. 25, 2003 (corresponding to PCT/US04/010989, filed Apr. 8, 2004); U.S. Ser. No. 10/666,480, filed Sep. 18, 2003 (corresponding to WO 04/026329, published Apr. 1, 2004), each of which is hereby incorporated by reference in its entirety.

"Affibodies" or "Affibody" refers to the use of a protein liked by peptide bond to an Fc region, wherein the protein is used as a scaffold to provide a binding surface for a target molecule. The protein is often a naturally occurring protein such as staphylococcal protein A or IgG-binding B domain, or the Z protein derived therefrom (see Nilsson et al (1987), Prot Eng 1, 107-133, and U.S. Pat. No. 5,143,844) or a fragment or derivative thereof. For example, affibodies can be created from Z proteins variants having altered binding affinity to target molecule(s), wherein a segment of the Z protein has been mutated by random mutagenesis to create a library of variants capable of binding a target molecule. Examples of affibodies include U.S. Pat. No. 6,534,628, Nord K et al, Prot Eng 8:601-608 (1995) and Nord K et al, Nat Biotech 15:772-777 (1997). Biotechnol Appl Biochem. 2008 June; 50(Pt 2):97-112.

"Isolated" heteromultimer or complex means a heteromultimer or complex which has been separated and/or recovered from a component of its natural cell culture environment. Contaminant components of its natural environment are materials which would interfere with diagnostic or therapeutic uses for the heteromultimer, and may include enzymes, hormones, and other proteinaceous or nonproteinaceous solutes. In preferred embodiments, the heteromultimer will be purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain.

The heteromultimers of the present invention are generally purified to substantial homogeneity. The phrases "substantially homogeneous", "substantially homogeneous form" and "substantial homogeneity" are used to indicate that the product is substantially devoid of by-products originated from undesired polypeptide combinations (e.g. homomultimers).

Expressed in terms of purity, substantial homogeneity means that the amount of by-products does not exceed 10%, 9%, 8%, 7%, 6%, 4%, 3%, 2% or 1% by weight or is less than 1% by weight. In one embodiment, the by-product is below 5%.

"Biological molecule" refers to a nucleic acid, a protein, a carbohydrate, a lipid, and combinations thereof. In one embodiment, the biologic molecule exists in nature.

"Isolated," when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or nonproteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

By "linked" or "links" as used herein is meant either a direct peptide bond linkage between a first and second amino acid sequence or a linkage that involves a third amino acid sequence that is peptide bonded to and between the first and second amino acid sequences. For example, a linker peptide bonded to the C-terminal end of one amino acid sequence and to the N-terminal end of the other amino acid sequence.

By "linker" as used herein is meant an amino acid sequence of two or more amino acids in length. The linker can consist of neutral polar or nonpolar amino acids. A linker can be, for example, 2 to 100 amino acids in length, such as between 2 and 50 amino acids in length, for example, 3, 5, 10, 15, 20, 25, 30, 35, 40, 45, or 50 amino acids in length. A linker can be "cleavable," for example, by auto-cleavage, or enzymatic or chemical cleavage. Cleavage sites in amino acid sequences and enzymes and chemicals that cleave at such sites are well known in the art and are also described herein.

By a "tether" as used herein is meant an amino acid linker that joins two other amino acid sequences. A tether as described herein can link the N-terminus of an immunoglobulin heavy chain variable domain with the C-terminus of an immunoglobulin light chain constant domain. In particular embodiments, a tether is between about 15 and 50 amino acids in length, for example, between 20 and 26 amino acids in length (e.g., 20, 21, 22, 23, 24, 25, or 26 amino acids in length). A tether may be "cleavable," for example, by auto-cleavage, or enzymatic or chemical' cleavage using methods and reagents standard in the art.

Enzymatic cleavage of a "linker" or a "tether" may involve the use of an endopeptidase such as, for example, Lys-C, Asp-N, Arg-C, V8, Glu-C, chymotrypsin, trypsin, pepsin, papain, thrombin, Genenase, Factor Xa, TEV (tobacco etch virus cysteine protease), Enterokinase, HRV C3 (human rhinovirus C3 protease), Kininogenase, as well as subtilisin-like proprotein convertases (e.g., Furin (PC1), PC2, or PC3) or N-arginine dibasic convertase. Chemical cleavage may involve use of, for example, hydroxylamine, N-chlorosuccinimide, N-bromosuccinimide, or cyanogen bromide.

A "Lys-C endopeptidase cleavage site" as used herein is a Lysine residue in an amino acid sequence that can be cleaved at the C-terminal side by Lys-C endopeptidase. Lys-C endopeptidase cleaves at the C-terminal side of a Lysine residue.

By a "heptad repeat" as used herein is meant a sequence of 7 consecutive amino acids that are repeated at least once in an amino acid sequence. The heptad repeats may be arranged consecutively in the amino acid sequence with the C-terminus of the first repeat being immediately adjacent to the N-terminus of the second repeat. In one embodiment, the heptad repeat has the sequence of Formula I or Formula II as defined herein.

By a "coiled coil domain," "coiled coil heterodimerization domain," "coil," or "coil heterodimerization domain" as used herein is meant an amino acid sequence that forms an alpha-helical structure that can interact with a second alpha-helical structure (a second "coiled coil domain") to form a "coiled coil" or "heterodimeric coiled coil." The alpha helical structures may be right-handed alpha helices. In one embodiment, the alpha helical structures are made up of heptad repeats. In one particular example, the coil coil domain has a structure as shown in FIG. 1 where residues at the "$X_1$" and "$X_1$'" positions of a first and a second alpha helical structure form hydrophobic interactions with each other, residues at the "$X_4$" and "$X_4$'" positions of the first and the second alpha helical structure form hydrophobic interactions with each other, residues at the "$X_5$" positions of the first alpha helical structure form ionic interactions with residues at the "$X_7$'" position of the second alpha helical structure, and residues at the "$X_7$" positions of the first alpha helical structure form ionic interactions with residues at the "$X_5$'" position of the second alpha helical structure. The coiled coil domain may be made up of 2 or more heptad repeats of Formula I or Formula II as defined herein.

By a "hydrophobic residue" is meant Alanine, Valine, Leucine, Isoleucine, Tryptophan, Phenylalanine, Proline, or Methionine. In a particular embodiment, the hydrophobic residue is not Proline.

By a "charged residue" is meant an acidic or basic amino acid. Lysine, Arginine, and Histidine are basic amino acids, and Aspartic Acid and Glutamic Acid are acidic amino acids.

By a "chaotropic agent" is meant a water-soluble substance which disrupts the three-dimensional structure of a protein (e.g., an antibody) by interfering with stabilizing intra-molecular interactions (e.g., hydrogen bonds, van der Waals forces, or hydrophobic effects). Exemplary chaotropic agents include, but are not limited to, urea, Guanidine-HC1, lithium perchlorate, Histidine, and Arginine.

By a "mild detergent" is meant a water-soluble substance which disrupts the three-dimensional structure of a protein (e.g., an antibody) by interfering with stabilizing intra-molecular interactions (e.g., hydrogen bonds, van der Waals forces, or hydrophobic effects), but which does not permanently disrupt the protein structure as to cause a loss of biological activity (i.e., does not denature the protein). Exemplary mild detergents include, but are not limited to, Tween (e.g., Tween-20), Triton (e.g., Triton X-100), NP-40 (nonyl phenoxylpolyethoxylethanol), Nonidet P-40 (octyl phenoxylpolyethoxylethanol), and Sodium Dodecyl Sulfate (SDS).

"Hinge region" is generally defined as stretching from Glu216 to Pro230 of human IgG1 (Burton, Molec. Immunol.

22:161-206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region. Prior to the present invention, FcgammaR binding was generally attributed to amino acid residues in the lower hinge region of an IgG Fc region.

The "CH2 domain" of a human IgG Fc region usually extends from about residues 231 to about 340 of the IgG. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, Molec. Immunol. 22:161-206 (1985).

The "CH3 domain" comprises the stretch of residues C-terminal to a CH2 domain in an Fc region (i.e. from about amino acid residue 341 to about amino acid residue 447 of an IgG).

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc complex" as used herein refers to two CH2 domains of an Fc region interacting together and/or two CH3 domains of an Fc region interacting together, wherein the CH2 domains and/or the CH3 domains interact through bonds and/or forces (e.g., van der waals, hydrophobic, hydrophilic forces) that are not peptide bonds.

"Fc component" as used herein refers to a hinge region, a CH2 domain or a CH3 domain of an Fc region.

"Fc CH component" or "FcCH" as used here in refers to a polypeptide comprising a CH2 domain, a CH3 domain, or CH2 and CH3 domains of an Fc region.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxic agents. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. Nos. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al., Proc. Natl. Acad. Sci. USA 95:652-656 (1998).

"Fc receptor" or "FcR" describes a receptor that binds to the Fc region of an antibody. The preferred FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), can be performed.

The term "therapeutically effective amount" refers to an amount of an antibody, antibody fragment, or derivative to treat a disease or disorder in a subject. In the case of tumor (e.g., a cancerous tumor), the therapeutically effective amount of the antibody or antibody fragment (e.g., a multispecific antibody or antibody fragment) may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The terms "cancer" and "cancerous" refer to or describe the physiological condition in mammals that is typically characterized by unregulated cell growth/proliferation. Included in this definition are benign and malignant cancers. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastric or stomach cancer including gastrointestinal cancer, pancreatic cancer, glioblastoma, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer (e.g., renal cell carcinoma), liver cancer, prostate cancer, vulval cancer, thyroid cancer, hepatic carcinoma, anal carcinoma, penile carcinoma, melanoma, and various types of head and neck cancer. By "early stage cancer" is meant a cancer that is not invasive or metastatic or is classified as a Stage 0, I, or II cancer. The term "precancerous" refers to a condition or a growth that typically precedes or develops into a cancer. By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

A "non-malignant disease or disorder involving abnormal activation of HER2" is a condition that does not involve a cancer where abnormal activation of HER2 is occurring in cells or tissue of the subject having, or predisposed to, the disease or disorder. Examples of such diseases or disorders include autoimmune disease (e.g., psoriasis), see definition below; endometriosis; scleroderma; restenosis; polyps such as colon polyps, nasal polyps or gastrointestinal polyps; fibroadenoma; respiratory disease (e.g., chronic bronchitis, asthma including acute asthma and allergic asthma, cystic fibrosis, bronchiectasis, allergic or other rhinitis or sinusitis, al-anti-trypsin deficiency, coughs, pulmonary emphysema, pulmonary fibrosis or hyper-reactive airways, chronic obstructive pulmonary disease, and chronic obstructive lung disorder); cholecystitis; neurofibromatosis; polycystic kidney disease; inflammatory diseases; skin disorders including psoriasis and dermatitis; vascular disease; conditions involving abnormal proliferation of vascular epithelial cells; gastrointestinal ulcers; Menetrier's disease, secreting adenomas or protein loss syndrome; renal disorders; angiogenic disorders; ocular disease such as age related macular degeneration, presumed ocular histoplasmosis syndrome, retinal neovascularization from proliferative diabetic retinopathy, retinal vascularization, diabetic retinopathy, or age related macular degeneration; bone associated pathologies such as osteoarthritis, rickets and osteoporosis; damage following a cerebral ischemic event; fibrotic or edemia diseases such as hepatic cirrhosis, lung fibrosis, carcoidosis, throiditis, hyperviscosity syndrome systemic, Osler Weber-Rendu disease, chronic occlusive pulmonary disease, or edema following burns, trauma, radiation, stroke, hypoxia or ischemia; hypersensitivity reaction of the skin; diabetic retinopathy and diabetic nephropathy; Guillain-Barre syndrome; graft versus host disease or transplant rejection; Paget's disease; bone or joint inflammation; photoaging (e.g. caused by UV radiation of human skin); benign prostatic hypertrophy; certain microbial infections including microbial pathogens selected from adenovirus, hantaviruses, *Borrelia burgdorferi, Yersinia* spp. and *Bordetella pertussis*; thrombus caused by platelet aggregation; reproductive conditions such as endometriosis, ovarian hyperstimulation syndrome, preeclampsia, dysfunctional uterine bleeding, or menometrorrhagia; synovitis; atheroma; acute and chronic nephropathies (including proliferative glomerulonephritis and diabetes-induced renal disease); eczema; hypertrophic scar formation; endotoxic shock and fungal infection; familial adenomatosis polyposis; neurodedenerative diseases (e.g. Alzheimer's disease, AIDS-related dementia, Parkinson's disease, amyotrophic lateral sclerosis, retinitis pigmentosa, spinal muscular atrophy and cerebellar degeneration); myelodysplastic syndromes; aplastic anemia; ischemic injury; fibrosis of the lung, kidney or liver; T-cell mediated hypersensitivity disease; infantile hypertrophic pyloric stenosis; urinary obstructive syndrome; psoriatic arthritis; and Hashimoto's thyroiditis.

An "allergic or inflammatory disorder" herein is a disease or disorder that results from a hyper-activation of the immune system of an individual. Exemplary allergic or inflammatory disorders include, but are not limited to, asthma, psoriasis, rheumatoid arthritis, atopic dermatitis, multiple sclerosis, systemic lupus, erythematosus, eczema, organ transplantation, age-related mucular degeneration, Crohn's disease, ulcerative colitis, eosinophilic esophagitis, and autoimmune diseases associated with inflammation.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis *nodosa*), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AMA), pernicious anemia (anemia pemiciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, *pemphigus* (including *pemphigus vulgaris, pemphigus foliaceus, pemphigus* mucus-membrane pemphigoid, and *pemphigus* erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiffman or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampler's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes *dorsalis*, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis *acuta*, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as *Leishmania*, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

The term "cytotoxic agent" as used herein refers to a substance that inhibits or prevents the function of a cell and/or causes destruction of a cell. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu), chemotherapeutic agents, e.g., methotrexate, adriamicin, *vinca* alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor, anticancer, and chemotherapeutic agents disclosed herein. Other cytotoxic agents are described herein. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1 (see, e.g., Agnew, Chem Intl. Ed. Engl. 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylarnine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylomithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Anti-cancer therapy" as used herein refers to a treatment that reduces or inhibits cancer in a subject. Examples of anti-cancer therapy include cytotoxic radiotherapy as well as the administration of a therapeutically effective amount of a cytotoxic agent, a chemotherapeutic agent, a growth inhibitory agent, a cancer vaccine, an angiogenesis inhibitor, a prodrug, a cytokine, a cytokine antagonist, a corticosteroid, an immunosuppressive agent, an anti-emetic, an antibody or antibody fragment, or an analgesic to the subject.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone (HGH), N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor (EGF); hepatic growth factor; fibroblast growth factor (FGF); prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-1beta, IL-2, IL-3, IL-4, IL-5, IL-6, IL-7, IL-8, IL-9, IL-10, IL-11, IL-12; IL-18 a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

By "cytokine antagonist" is meant a molecule that partially or fully blocks, inhibits, or neutralizes a biological activity of of at least one cytokine. For example, the cytokine antagonists may inhibit cytokine activity by inhibiting cytokine expression and/or secretion, or by binding to a cytokine or to a cytokine receptor. Cytokine antagonists include antibodies, synthetic or native-sequence peptides, immunoadhesins, and small-molecule antagonists that bind to a cytokine or cytokine receptor. The cytokine antagonist is optionally conjugated with or fused to a cytotoxic agent. Exemplary TNF antagonists are etanercept (ENBREL®), infliximab (REMICADE®), and adalimumab (HUMIRA™).

The term "immunosuppressive agent" as used herein refers to substances that act to suppress or mask the immune system of the subject being treated. This includes substances that suppress cytokine production, downregulate or suppress self-antigen expression, or mask the MHC antigens. Examples of immunosuppressive agents include 2-amino-6-aryl-5-substituted pyrimidines (see U.S. Pat. No. 4,665,077); mycophenolate mofetil such as CELLCEPT®; azathioprine (IMURAN®, AZASAN®/6-mercaptopurine; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids and glucocorticosteroids, e.g., prednisone, prednisolone such as PEDIAPRED® (prednisolone sodium phosphate) or ORAPRED® (prednisolone sodium phosphate oral solution), methylprednisolone, and dexamethasone; methotrexate (oral or subcutaneous) (RHEUMATREX®, TREXALL™); hydroxycloroquine/chloroquine; sulfasalazine; leflunomide; cytokine or cytokine receptor antagonists including anti-interferon-γ, -β, or -α antibodies, anti-tumor necrosis factor-α antibodies (infliximab or adalimumab), anti-TNFα immunoadhesin (ENBREL®, etanercept), anti-tumor necrosis factor-β antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; polyclonal or pan-T antibodies, or monoclonal anti-CD3 or anti-CD4/CD4a antibodies; soluble peptide containing a LFA-3 binding domain (WO 90/08187); streptokinase; TGF-β; streptodornase; RNA or DNA from the host; FK506; RS-61443; deoxyspergualin; rapamycin; T-cell receptor (Cohen et at, U.S. Pat. No. 5,114,721); T-cell receptor fragments (Offner et al. Science 251: 430-432 (1991); WO 90/11294; Ianeway, Nature 341:482 (1989); and WO 91/01133); T cell receptor antibodies (EP 340,109) such as T10B9; cyclophosphamide (CYTOXAN®); dapsone; penicillamine (CUPRIMINE®); plasma exchange; or intravenous immunoglobulin (IVIG). These may be used alone or in combination with each other, particularly combinations of steroid and another immunosuppressive agent or such combinations followed by a maintenance dose with a non-steroid agent to reduce the need for steroids.

An "analgesic" refers to a drug that acts to inhibit or suppress pain in a subject. Exemplary analgesics include non-steroidal anti-inflammatory drugs (NSAIDs) including ibuprofen (MOTRIN®), naproxen (NAPROSYN®), acetylsalicylic acid, indomethacin, sulindac, and tolmetin, including salts and derivatives thereof, as well as various other medications used to reduce the stabbing pains that may occur, including anticonvulsants (gabapentin, phenyloin, carbamazepine) or tricyclic antidepressants. Specific examples include acetaminophen, aspirin, amitriptyline (ELAVIL®), carbamazepine (TEGRETOL®), phenyltoin (DILANTIN®), gabapentin (NEURONTIN®), (E)-N-Vanillyl-8-methyl-6-noneamid (CAPSAICIN®), or a nerve blocker.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone triamcinolone, and betamethasone.

A "cancer vaccine," as used herein is a composition that stimulates an immune response in a subject against a cancer. Cancer vaccines typically consist of a source of cancer-associated material or cells (antigen) that may be autologous (from self) or allogenic (from others) to the subject, along with other components (e.g., adjuvants) to further stimulate and boost the immune response against the antigen. Cancer vaccines can result in stimulating the immune system of the subject to produce antibodies to one or several specific antigens, and/or to produce killer T cells to attack cancer cells that have those antigens.

"Cytotoxic radiotherapy" as used herein refers to radiation therapy that inhibits or prevents the function of cells and/or causes destruction of cells. Radiation therapy may include, for example, external beam irradiation or therapy with a radioactive labeled agent, such as an antibody. The term is intended to include use of radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu).

"Target molecule" refers to a molecule which can bind to a protein complex of this invention (preferably with affinity higher than 1 uM Kd according to scatchard analysis). Examples of target molecules include, but are not limited to, serum soluble proteins and their receptors, such as cytokines and cytokine receptors, adhesins, growth factors and their receptors, hormones, viral particles (e.g., RSV F protein, CMV, StaphA, influenza, hepatitis C virus), micoorganisms (e.g., bacterial cell proteins, fungal cells), adhesins, CD proteins and their receptors.

An "anti-emetic" is a compound that reduces or prevents nausea in a subject. Anti-emetic compounds include, for example, neurokinin-1 receptor antagonists, 5HT3 receptor antagonists (such as ondansetron, granisetron, tropisetron, and zatisetron), GABAB receptor agonists, such as baclofen, a corticosteroid such as dexamethasone, KENALOG®, ARISTOCORT®, or NASALIDE®, an antidopaminergic, phenothiazines (for example prochlorperazine, fluphenazine, thioridazine and mesoridazine), dronabinol, metroclopramide, domperidone, haloperidol, cyclizine, lorazepam, prochlorperazine, and levomepromazine.

A "subject" is a vertebrate, such as a mammal, e.g., a human. Mammals include, but are not limited to, farm animals (such as cows), sport animals, pets (such as cats, dogs and horses), primates, mice, and rats.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., Current Protocols in Molecular Biology (Green Publishing Associates and Wiley Interscience, N Y, 1989); Innis et al., PCR Protocols: A Guide to Methods and Applications (Academic Press, Inc., NY, 1990); Harlow et al., Antibodies: A Laboratory Manual (Cold Spring Harbor Press, Cold Spring Harbor, 1988); Gait, Oligonucleotide Synthesis (IRL Press, Oxford, 1984); Freshney, Animal Cell Culture, 1987; Coligan et al., Current Protocols in Immunology, 1991.

Throughout this specification and claims, the word "comprise," or variations such as "comprises" or "comprising," will be understood to imply the inclusion of a stated integer or group of integers but not the exclusion of any other integer or group of integers.

II. Construction Of Coiled Coil Containing And Tethered Antibodies

Protein complexes described herein may be constructed by using a heterodimerizing domain (e.g., a coiled coil domain) and/or a tether.

Use of a heterodimerizing domain enables the construction of a relatively pure population of antibodies that have different heavy chains within a single antibody. In particular, as described above, antibodies typically include two identical heavy chains, which are each paired with an identical light chain. Use of the coiled coil heterodimerization domain technology of the invention enables different antibody heavy chains to preferentially dimerize with each other in the formation of a single antibody. The resulting antibody thus includes two different heavy chains, each of which is typically (but need not be) paired with an identical light chain. Each pair of heavy and light chains within such an antibody has different binding specificity, due to the presence of the different heavy chains, and thus the antibody can be considered as a multispecific antibody. Tethers can also be exploited to engineer antibodies of the invention, either alone or in combination with the coiled-coil technology. The tethers can connect the C-terminus of a constant light chain to the N-terminus of a variable heavy chain, thus enabling proper light chain and heavy chain association, as well as recombinant antibody production using a single antibody-encoding plasmid. Antibodies including coiled coils and/or tethers are further described below.

A. Coiled Coil Domains

Figure 2B:
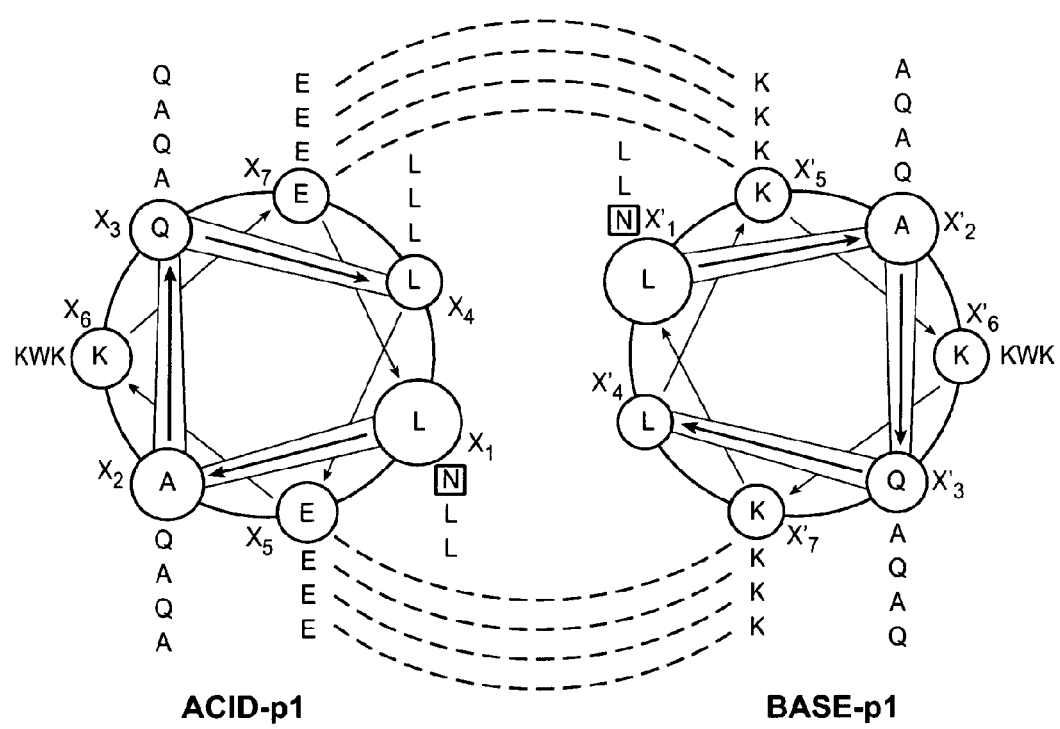
FIG. 2B is a schematic diagram showing interactions between the exemplary ACID.p1 and BASE.p1 coiled coil heterodimerization domains and DNA sequences SEQ ID NO:21 and SEQ ID NO:22, respectively.

The heterodimerizing domain used to generate the protein complexes described herein can be an alpha helix (e.g., a right-handed alpha helix) that can form a coiled coil upon association with a second alpha helix containing oppositely charged residues. To generate homogeneous or nearly homogeneous populations of heterodimeric molecules, the heterodimerization domain must have a strong preference for forming heterodimers over homodimers. In this respect, the heterodimerization domains described herein provide a significant advantage over Fos/jun leucine zipper domains because jun readily forms homodimers. Exemplary alpha-helical heterodimerization domains are illustrated in FIGS. 1, 2A, and 2B. In particular embodiments, the first coiled coil domain contains a heptad repeat of Formula I:

$$(X_1X_2X_3X_4X_5X_6X_7)_n \quad \text{(Formula I) (SEQ ID NO:29)}$$

$X_1$ is a hydrophobic amino acid residue or Asparagine,
$X_2$, $X_3$, and $X_6$ are each any amino acid residue,
$X_4$ is a hydrophobic amino acid residue, and
$X_5$ and $X_7$ are each a charged amino acid residue.
and the second coiled coil domain contains a heptad repeat of Formula II:

$$(X'_1 X'_2 X'_3 X'_4 X'_5 X'_6 X'_7)_n \quad \text{(Formula II) (SEQ ID NO:30)}$$

$X'_1$ is a hydrophobic amino acid residue or Asparagine,
$X'_2$, $X'_3$, and $X'_6$ are each any amino acid residue,
$X'_4$ is a hydrophobic amino acid residue, and
$X'_5$ and $X'_7$ are each a charged amino acid residue.
In both Formula I and Formula II, n is greater than or equal to 2 (e.g., greater than or equal to 3 or 4), and less than or equal to 100. In one embodiment, n is between 2 and 20.

The $X_5$ and $X_7$ residues of the first coiled coil domain and the $X'_5$ and $X'_7$ residues of the second coiled coil domain may have, but need not have, the same charge. Thus, in one example, the $X_5$ and $X_7$ residues of the first coiled coil domain are basic residues, and the $X'_5$ and $X'_7$ residues of the second coiled coil domain are acidic residues. In another example, $X_5$ in the first coiled coil domain is a basic residue, and $X_7$ of the first coiled coil domain is an acidic residue. In this example, the second coiled coil domain has a basic residue in the $X'_5$ position, and an acidic residue in the $X'_7$ position. As shown in FIG. 1, an ionic interaction occurs between the $X_5$ residue of the first coiled coil domain and the $X'_7$ residue of the second coiled coil domain, as well as between the $X_7$ residue of the first coiled coil domain and the $X'_5$ residue of the second coiled coil domain. In a related example, $X_5$ in the first coiled coil domain is an acidic residue, $X_7$ in the first coiled coil domain is a basic residue, $X'_5$ in the second coiled coil domain is an acidic residue, and $X'_7$ in the second coiled coil domain is a basic residue. In addition, inclusion of at least one heptad repeat with an Asparagine at the $X_1/X'_1$ position of both the first and second coiled coil domains may be used to ensure a parallel orientation of the first and second coiled coil domains.

The hydrophobic residues in the heptad repeats are preferably chosen from Alanine, Valine, Leucine, Isoleucine, Tryptophan, Phenylalanine, and Methionine. Proline, while hydrophobic, is in one embodiment not included in a coiled coil domain of Formula I or Formula II because the presence of Proline in an amino acid sequence can limit its ability to form an alpha helical structure. In addition, in other embodiments, the coiled coil domain of Formula I or Formula II does not contain a Glycine residue because, due to its conformational flexibility, Glycine does not readily adopt the constrained alpha helical structure. Charged residues that may be included in a coiled coil domain of Formula I or Formula II include Lysine, Arginine, Histidine, Aspartic Acid, and Glutamic Acid, where Lysine, Arginine, and Histidine are basic residues, and Aspartic Acid and Glutamic Acid are acidic residues.

Construction of an antibody described herein may use a coiled coil domain of Formula I and a coiled coil domain of Formula II (a first and a second coiled coil domain) where the first coiled coil domain is linked to a first constant domain of the antibody (e.g., CH3 of a first heavy chain) and the second coiled coil domain is linked to a second constant domain of the antibody (e.g., CH3 of a second heavy chain). The linkage may be a direct linkage by a peptide bond or may be through a linker sequence. A linker can be peptide bonded to the C-terminal end of one amino acid sequence (e.g., the constant region) and to the N-terminal end of the other amino acid sequence (e.g., the coiled coil domain). The linker can be long enough to allow for cleavage of the coiled coil domain from the antibody constant region, as described further elsewhere herein, but short enough to confer heterodimeric association of two antibody constant regions (e.g., two heavy chain constant regions). As such, a linker may be an amino acid sequence of 2 to 100 amino acids in length. In a particular embodiment, the linker is between 2 and 50 amino acids in length, for example, 3, 5, 10, 15, 20, 25, 30, 35, 40, 45, or 50 amino acids in length. The linker can consist of, for example, neutral polar or nonpolar amino acids.

B. Multispecific Antibodies

It should be understood that the variable domains of such antibodies can be derived from several methods. For example, the variable domains of the antibodies of this invention can be the same as existing antibodies known in the art.

A coiled coil domain may be used to generate a multispecific antibody (an antibody that binds to at least two antigens or to at least two epitopes on the same antigen). In one example, the multispecific antibody is a bispecific antibody. Typically, in naturally occurring IgG antibodies, the variable regions of each pair of heavy and light chains in the antibody are identical. Use of coiled coil domains according to the present invention enables the two heavy chains within an antibody to be different, resulting in antibodies having antigen binding domains with different binding specificities. In particular, coiled coil heterodimerization domains on each heavy chain (e.g., C-terminal to CH3) promote binding between different heavy chains. Optionally the coiled coil domains are linked to the heavy chain constant regions by a linker that can be cleaved so that the coiled coil can be removed from the antibody after assembly.

A schematic representation of an exemplary bispecific antibody, which includes two different heavy chains (HC1 and HC2) and two identical or common light chains, is shown in FIG. 3. The exemplary bispecific antibody in FIG. 3 also contains a heterodimeric coiled coil. The antibody may also contain a Lys-C endopeptidase cleavage site N-terminal to each coiled coil heterodimerization domain that allows for the removal of the coiled coil from the antibody once the antibody has been assembled. Both of the heavy chains in this exemplary bispecific antibody also contain a K222A mutation in the hinge region to remove a Lys-C endopeptidase cleavage site, so that Lys-C endopeptidase treatment results only in removal of the coiled coil and not cleavage within the heavy chain constant regions.

While the exemplary antibody contains a mutation that removes a Lys-C endopeptidase cleavage site in the hinge region, the location of Lys-C endopeptidase cleavage sites can vary depending on the antibody sequence used. One skilled in the art can readily scan the sequence of an antibody to determine whether there are any cleavage sites (e.g., a Lys-C endopeptidase cleavage site) in the heavy or light chain sequences that would need to be removed to avoid cleavage of the antibody itself upon removal of the coiled coil or tether sequences.

Further, multispecific antibodies may be constructed using the methods described herein where the heavy chain lacks the CH1 domain (the VH is directly connected to the hinge-CH2 domain) and the corresponding light chain lacks the CL domain. Such antibodies can be used to bring to different antigens together or to associate B and T cells.

C. One-armed Antibodies

Heterodimerizing coiled coil domains can also be used to generate one-armed antibodies A schematic diagram illustrating an example of a one-armed antibody is shown in FIG.

4A. The exemplary antibody shown in FIG. 4A includes a light chain (LC), one full-length heavy chain (HC1), and a second heavy chain (HC2) lacks the VH and CH1 domains and part of the hinge region. Both the HC1 and the HC2 include a coiled coil heterodimerization domain at the C-terminus. The HC1 sequence in this example contains a K222A mutation in the hinge region to remove a Lys-C endopeptidase cleavage site, so that Lys-C cleavage only removes the coiled coil and does not result in cleavage within the heavy chain.

D. Conjugated Protein Complexes

Figure 4B:
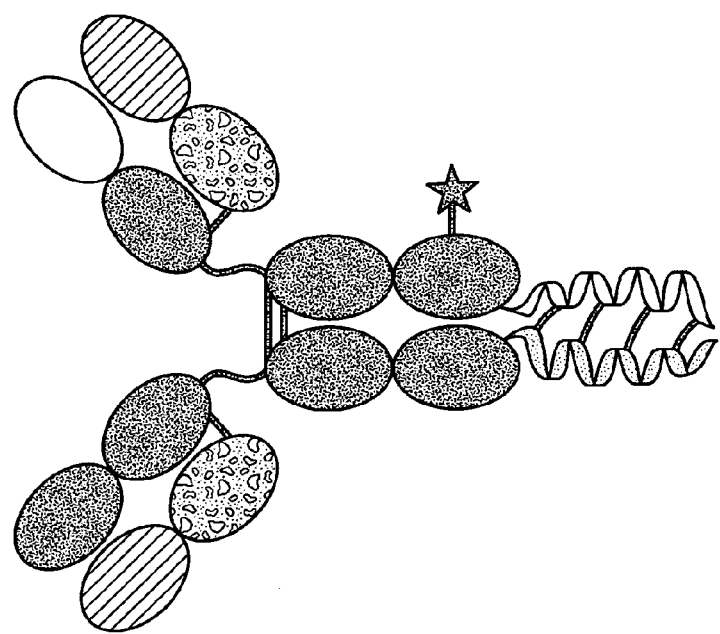
FIG. 4B is a schematic diagram showing the structure of an exemplary conjugated antibody containing two full-length heavy chains, a common light chain, a coiled coil, and a cytotoxic agent conjugated to one of the heavy chain constant regions. The cytotoxic agent is indicated by the star.

Coiled coil heterodimerization domains may also be used to generate protein complexes such as antibodies (e.g., monospecific, bispecific, multispecific, one-armed, or tethered antibodies) in which a constant region is modified by conjugation to a cytotoxic agent. For instance, the coiled coil heterodimerization domain enables the construction of antibodies where one of the heavy chain constant regions (HC1 or HC2) contains a modification that allows for conjugation to a cytotoxic agent, while the other heavy chain constant region does not. In one example, HC1 is conjugated to a cytotoxic agent while HC2 is not. A schematic diagram illustrating an example of a conjugated antibody is shown in FIG. 4B. The exemplary antibody includes two full-length heavy chains and two identical light chains (common light chain), as well as a coiled coil. As indicated by the star, one of the heavy chains has been conjugated to a cytotoxic agent (for example, a toxin). Similarly, in an alternative antibody construct, one of the light chain constant regions may be conjugated to a cytotoxic agent, while the other light chain constant region is not (e.g., LC1 is conjugated to a cytotoxic agent and LC2 is not).

In one particular example, a constant region of the antibody may be modified to introduce electrophilic moieties which can react with nucleophilic substituents on a linker reagent used to conjugate the cytotoxic agent to the antibody or on the cytotoxic agent itself. The sugars of glycosylated antibodies may be oxidized, e.g., with periodate oxidizing reagents, to form aldehyde or ketone groups which may react with the amine group of linker reagents or a cytotoxic agent. The resulting imine Schiff base groups may form a stable linkage, or may be reduced, e.g., by borohydride reagents, to form stable amine linkages. Nucleophilic groups on a cytotoxic agent include, but are not limited to, amine, thiol, hydroxyl, hydrazide, oxime, hydrazine, thiosemicarbazone, hydrazine carboxylate, and arylhydrazide groups capable of reacting to form covalent bonds with electrophilic groups on antibody regions and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups.

E. Tethered Protein Complexes

Figure 5:
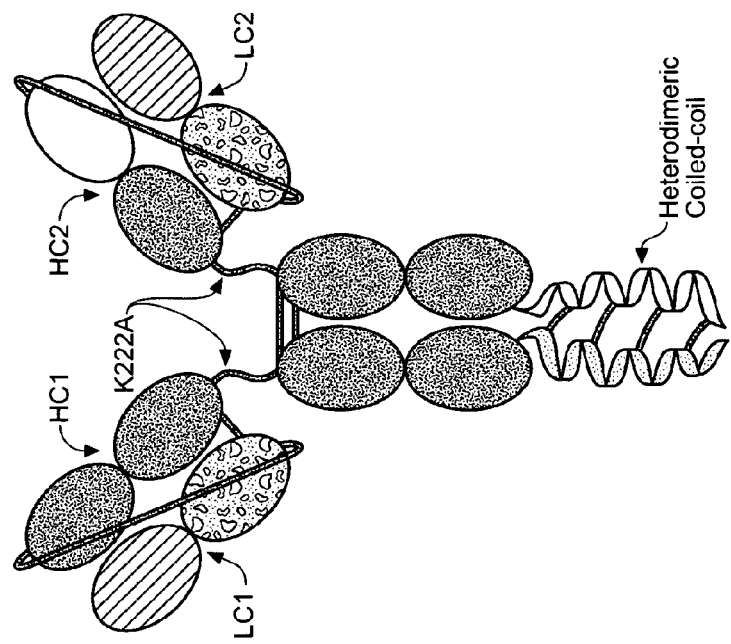
FIG. 5 is a schematic diagram showing the structure of an exemplary tethered bispecific antibody. The antibody contains two heavy chains (HC1 and HC2) and two light chains (LC1 and LC2). A tether links the N-terminus of the variable heavy chain of HC1 with the C-terminus of the constant light chain of LC1 and a second tether links the N-terminus of the variable heavy chain of HC2 with the C-terminus of the constant light chain of LC2. In this example, the tethers include Glycine Glycine Serine (GGS) repeats. In this figure, the light chains (LC1 and LC2) are different, but a tethered antibody could also contain a common light chain. The exemplary tethered antibody further contains a heterodimeric coiled coil and a mutation in the hinge region (K222A) of HC1 and HC2 that removes a Lys-C endopeptidase cleavage site.

The invention also provides protein complexes constructed using tethers, for example, an antibody can have a tether that links the C-terminus of a constant light chain to the N-terminus of a variable heavy chain. The tether aids in proper association of the light chain and the heavy chain (i.e., association of the light chain with the heavy chain to which it is tethered). Such a tethered antibody can be constructed with or without a heterodimerizing domain, as described above. A schematic diagram of an exemplary tethered antibody containing a coiled coil is shown in FIG. 5. The exemplary antibody shown in FIG. 5 contains two different heavy chains (HC1 and HC2), as well as two different light chains (LC1 and LC2). Tethered antibodies can also be constructed to contain common light chains and/or common heavy chains. In the exemplary antibody, HC1 and HC2 contain a K222A mutation in the hinge region to remove a Lys-C endopeptidase cleavage site, as described above, as well as coiled coil heterodimerization domains at their C-termini.

Figure 6:
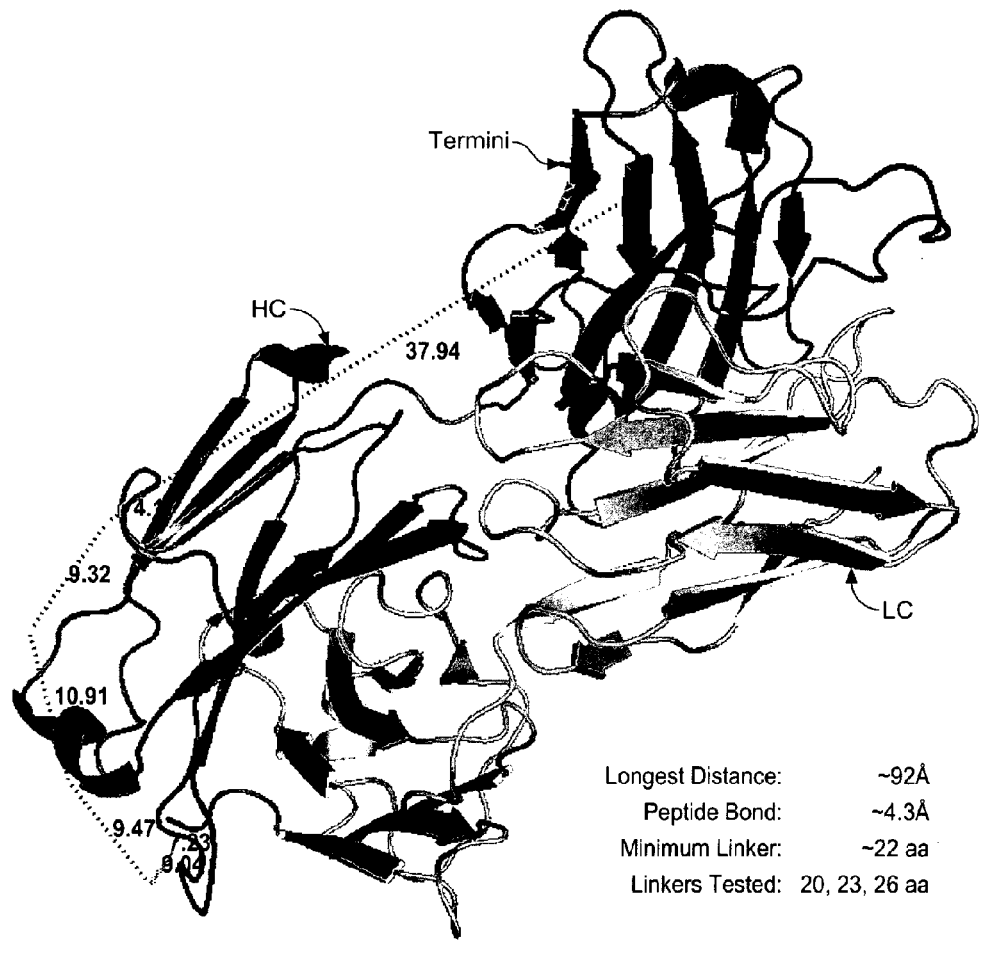
FIG. 6 is a schematic diagram showing the structure of an exemplary heavy chain (HC) and light chain (LC), as well as an exemplary tether linking the N-terminus of the variable heavy chain with the C-terminus of the constant light chain. In this example, the distance spanned by the tether is approximately 92Å, or approximately 22 amino acids in length. Tethers of 20, 23, and 26 amino acids in length were tested.

The addition of a heterodimerizing domain to a tethered antibody aids in bringing the heavy chain/light chain complexes together and thereby reduces or eliminates homodimerization of such complexes. In a particular embodiment, tethers are long enough to span the distance between the N-terminus of the variable heavy chain and the C-terminus of the constant light chain in the assembled antibody (FIG. 6) to allow for the proper light chain/heavy chain association, but are short enough to prevent interchain association (i.e., association of the light chain with a heavy chain to which it is not tethered). In the example shown in FIG. 6, the distance between the N-terminus of the variable heavy chain and the C-terminus of the constant light chain is approximately 92Å. A peptide bond spans about 4.3Å. In this example, a tether should be about 22 amino acids in length to span the distance between the N-terminus of the variable heavy chain and the C-terminus of the constant light chain. The distance between the C-terminus of the constant light chain and the N-terminus of the variable heavy chain can differ between antibodies and the length of a tether therefore can also vary between antibodies. Tethers of 20, 23, and 26 amino acids in length were tested and, in general, tethers of 15-50 amino acids are effective. A tether may remain flexible and not form secondary structures, and for this purpose a tether containing Glycine (G) and Serine (S) residues can be used. A tether may consist solely of G and S residues, but also may include other residues, as long as the tether remains flexible to allow for the assembly of the light chain and heavy chain of the antibody. In a particular embodiment, the tether contains GGS repeats (FIG. 5). For a tether of 15-30 amino acids in length, the tether, in one embodiment, contains at least 5 GGS repeats. An exemplary tether described herein and having the sequence of SEQ ID NO:14 contains 8 GGS repeats and contains an additional Glycine residue at both the N- and C-termini. Other exemplary tether sequences are show in in FIG. 7B and contain either Furin or Lys-C endopeptidase cleavage sites at their N- and C-termini.

F. Cleavage of Tether and Linker Sequences

Once a protein complex is assembled, the tether may no longer be required and can, if desired, be cleaved, from the antibody. Cleavage sites found in the tether, but not in the antibody sequence, can be used to remove the tether. Similarly, the coiled coil is also no longer required once the antibody has been assembled and can also, if desired, be cleaved from the antibody.

Figure 7A:
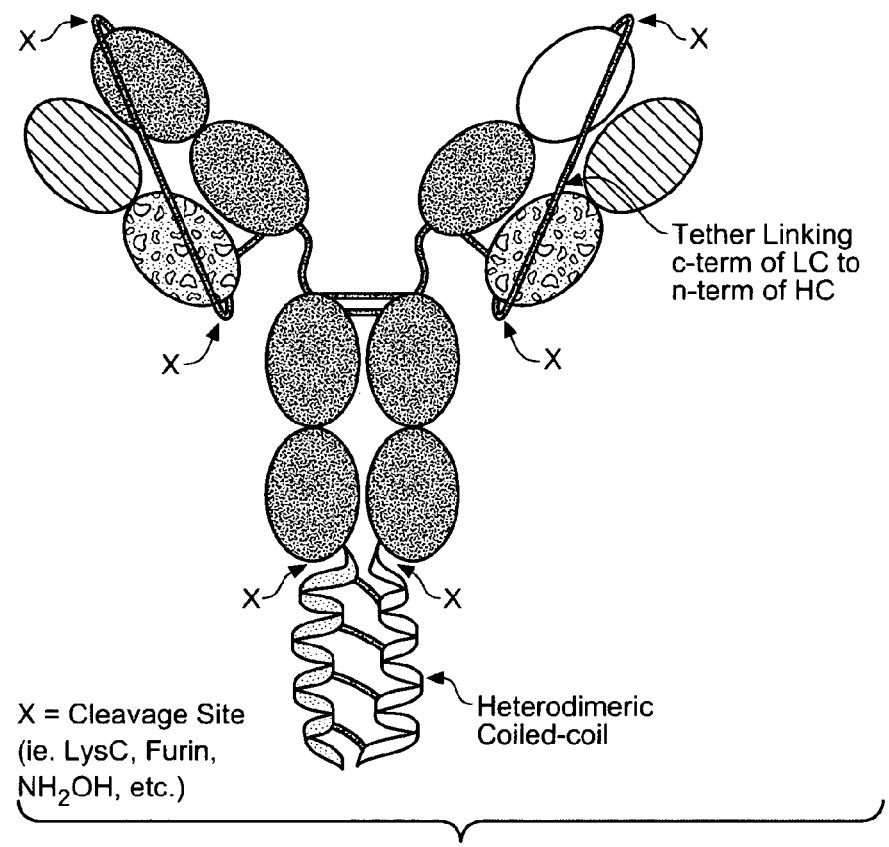
FIG. 7A is a schematic diagram showing the structure of an exemplary antibody containing cleavable tethers and a heterodimeric coiled coil. As indicated in the figure, the exemplary tether links the C-terminus of the light chain (LC) to the N-terminus of the heavy chain (HC). The tether can be cleaved from the antibody at cleavage sites (X) using, for example, Lys-C endopeptidase, Furin (PC1), or NH$_2$OH (hydroxylamine). The exemplary cleavage sites are located at the N- and C-termini of the tether. The exemplary antibody shown in in FIG. 7A also contains a heterodimeric coiled coil, which can be cleaved from the antibody at cleavage sites (X) N-terminal to the coiled coil domains using, for example, Lys-C endopeptidase, Furin (PC1), or NH$_2$OH.

FIG. 7A illustrates the location of exemplary cleavage sites in a tether as well as a linker sequence that joins the coiled coil to the antibody. In general, cleavage sites in the tether are located at or close to the C- and N-terminus of the tether sequence or within the antibody sequence at or close to the site where the antibody and tether are joined. A cleavage site for a linker generally is located at the N-terminus of the linker sequence (or coiled coil) or in the antibody sequence at or close to the site where the antibody and linker (or coiled coil) are joined. If the linker is cleaved using Lys-C endopeptidase (e.g., at a Lysine residue at the C-terminus of the constant heavy chain), the sequence of the antibody may need to be modified to remove Lys-C endopeptidase cleavage sites. An example of such a modification is the mutation of a Lysine in the hinge region to an Alanine (e.g., K222A, Kabat numbering system; K222A, EU numbering system in exemplary antibodies described herein).

Modifications of other cleavage sites may be required and made in a similar manner when different cleavage agents are selected for use in the invention.

Cleavage of amino acid sequences at particular sites is standard in the art and can involve enzymatic cleavage, chemical cleavage, or auto-processing. For example, a tether or linker may be cleaved from an protein using an endopeptidase. Exemplary endopeptidases include, without limitation, Lys-C, Asp-N, Arg-C, V8, Glu-C, Thrombin, Genenase (a variant of subtilisin BPN' protease), Factor Xa, TEV (tobacco etch virus cysteine protease), Enterokinase, HRV C3 (human rhinovirus C3 protease), Kininogenase, chymotrypsin, trypsin, pepsin, and papain, all of which are commercially available (e.g., from Boehringer Mannheim, Thermo Scientific, or New England Biolabs). Lys-C cleaves at the carboxyl side of Lysine residues, V8 and Glu-C cleave at the carboxyl side of Glutamate residues, Arg-C cleaves at the carboxyl side of Arginine residues, Asp-N cleaves at the amino side of Aspartate residues, chymotropsin cleaves at the carboxyl side of Tyrosine, Phenylalanine, Tryptophan, and Leucine residues, and trypsin cleaves at the carboxyl side of Arginine and Lysine residues. TEV cleaved the amino acid sequence GluAsnLeuTyrPheGlnGly (SEQ ID NO:19) between the "Gln" and "Gly" residues. Use of such enzymes is standard in the art and protocols are available from the manufacturers.

Alternatively a tether or linker may be cleaved from an protein using a chemical, such as hydroxylamine. Hydroxylamine cleaves Asparagine-Glycine peptide bonds. If hydroxylamine is used to cleave the tether and linker from a protein, several Glycine or Asparagine residues in the protein may need to be mutated to avoid fragmenting the protein.

Numerous other chemicals that cleave peptide bonds are known in the art. For example, N-chlorosuccinimide cleaves at the C-terminal side of Tryptophan residues (Shechter et al., Biochemistry 15:5071-5075 (1976)). N-bromosuccinimide and cyanogen bromide also cleave at the C-terminal side of Tryptophan residues. In addition, 2-nitrothiocyanobenzoic acid or organophosphines may be used to cleave a protein at the N-terminal side of a Cysteine residue (see, e.g., EP 0339217).

A linker or tether may also be cleaved at dibasic sites (e.g., an Arginine-Arginine, Lysine-Arginine, or Lysine-Lysine site). Enzymes that cleave at dibasic sites are known in the art and include, for example, N-arginine dibasic convertase (Chow et al., JBC 275:19545-19551 (2000)) and subtilisin-like proprotein convertases such as Furin (PC1), PC2, and PC3 (Steiner (1991) in Peptide Biosynthesis and Processing (Fricker ed.) pp. 1-16, CRC Press, Boca Raton, Fla.; Muller et al., JBC 275:39213-39222, (2000)).

Proteins are also known to auto-process. For example, the Hedgehog protein is processed at a Gly.AspTrpAsnAlaArg-Trp.CysPhe cleavage site (SEQ ID NO:20) by a proteolytic activity within the protein. An autoproteolytic cleavage site may also be included in a linker or tether sequence.

G. Other Protein Features

Proteins according to the invention can include sequences from any source, including human or murine sources, or combinations thereof. The sequences of certain portions of the proteins (e.g., the hypervariable regions) can also be artificial sequences, such as sequences identified by screening a library (e.g., a phage display library) including random sequences.

In the case of antibodies including sequences from different sources, the antibodies can be "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. USA 81:6851-6855 (1984)). Such chimeric antibodies may, for example, include murine variable regions (or portions thereof) and human constant regions.

The chimeric antibodies can optionally also be "humanized" antibodies, which contain minimal sequence derived from the non-human antibody. Humanized antibodies typically are human antibodies (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

In more detail, a humanized antibody can have one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework (FR) for the humanized antibody (Sims et al., J. Immunol. 151:2296 (1993); Chothia et al., J. Mol. Biol. 196:901 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA 89:4285 (1992); Presta et al., J. Immnol. 151:2623 (1993)).

It is further important that antibodies be humanized with retention of high affinity for the antigen and other favorable biological properties. To achieve this goal, according to an exemplary method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

III. Vectors, Host Cells, And Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian, but also including fungi (e.g., yeast), insect, plant, and nucleated cells from other multicellular organisms) origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells
  i. Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. An inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker to ligate them to cistrons encoding the target light and heavy chains (Siebenlist et al., (1980) Cell 20:269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA, and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits (Proba and Pluckthun, Gene, 159:203 (1995)).

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ (nmpc-fepE) degP41 kanR (U.S. Pat. No. 5,639,635). Other strains and derivatives thereof, such as *E. coli* 294 (ATCC 31,446), *E. coli* B, *E. coli* λ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well-known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a Mixture with another supplement or medium such as a complex nitrogen source. Optionally the culture medium may contain one or more reducing agents selected from the group consisting of glutathione, cysteine, cystamine, thioglycollate, dithioerythritol, and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD, and/or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells (Chen et al., (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun, (2000) J. Biol. Chem. 275: 17106-17113; Arie et al., (2001) Mol. Microbiol. 39:199-210).

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some *E. coli* protease-deficient strains are available and described in, for example, Joly et al., (1998), Proc. Natl. Acad. Sci. USA 95:2773-2777; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41 kD cell wall protein from *Staphylococcus aureus* which binds with a high affinity to the Fc region of antibodies. Lindmark et al., (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. The antibody of interest may be recovered from the solid phase by elution into a solution containing a chaotropic agent or mild detergent. Exemplary chaotropic agents and mild detergents include, but are not limited to, Guanidine-HC1, urea, lithium perclorate, Arginine, Histidine, SDS (sodium dodecyl sulfate), Tween, Triton, and NP-40, all of which are commercially available. Diluting the antibody into a solution containing a chaotropic agent or mild detergent after elution from the column (e.g., mAbSure column) maintains the stability of the antibody post elution and allows for the efficient removal of the coiled coil by Lys-C endopeptidase.

b. Generating Antibodies Using Eukaryotic Host Cells

The vector components generally include, but are not limited to, one or more of the following: a signal sequence, an origin of replication, one or more marker genes, an enhancer element, a promoter, and a transcription termination sequence.

i. Signal Sequence Component

A vector for use in a eukaryotic host cell may contain a signal sequence or other polypeptide having a specific cleavage site at the N-terminus of the mature protein or polypeptide of interest. The heterologous signal sequence selected can be one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region is ligated in reading frame to DNA encoding the antibody.

ii. Origin of Replication

Generally, an origin of replication component is not needed for mammalian expression vectors. For example, the SV40 origin may typically be used, but only because it contains the early promoter.

iii. Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

iv. Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as, for example, polyoma virus, fowlpox virus, adenovirus (such as Adenovirus 2), bovine papilloma virus, avian sarcoma virus, cytomegalovirus, a retrovirus, hepatitis-B virus, and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

v. Enhancer Element Component

Transcription of DNA encoding an antibody polypeptide by higher eukaryotes can be increased by inserting an enhancer sequence into the vector. Many enhancer sequences are now known from mammalian genes (e.g., globin, elastase, albumin, α-fetoprotein, and insulin genes). Also, one may use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) for a description of elements for enhancing activation of eukaryotic promoters. The enhancer may be spliced into the vector at a position 5' or 3' to the antibody polypeptide-encoding sequence, provided that enhancement is achieved, but is generally located at a site 5' from the promoter.

vi. Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO 94/11026 and the expression vector disclosed therein.

vii. Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

viii. Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

ix. Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In one embodiment, the antibody of interest is recovered from the solid phase of a column by elution into a solution containing a chaotropic agent or mild detergent. Exemplary chaotropic agents and mild detergents include, but are not limited to, Guanidine-HC1, urea, lithium perchlorate, Arginine, Histidine, SDS (sodium dodecyl sulfate), Tween, Triton, and NP-40, all of which are commercially available.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt).

x. Antibody Production Using Baculovirus

Recombinant baculovirus may be generated by co-transfecting a plasmid encoding an antibody or antibody fragment and BaculoGold™ virus DNA (Pharmingen) into an insect cell such as a *Spodoptera frugiperda* cell (e.g., Sf9 cells; ATCC CRL 1711) or a *Drosophila melanogaster* S2 cell using, for example, lipofectin (commercially available from GIBCO-BRL). In a particular example, an antibody sequence is fused upstream of an epitope tag contained within a baculovirus expression vector. Such epitope tags include poly-His tags. A variety of plasmids may be employed, including plasmids derived from commercially available plasmids such as pVL1393 (Novagen) or pAcGP67B (Pharmingen). Briefly, the sequence encoding an antibody or a fragment thereof may be amplified by PCR with primers complementary to the 5' and 3' regions. The 5' primer may incorporate flanking (selected) restriction enzyme sites. The product may then be digested with the selected restriction enzymes and subcloned into the expression vector.

After tranfection with the expression vector, the host cells (e.g., Sf9 cells) are incubated for 4-5 days at 28° C. and the released virus is harvested and used for further amplifications. Viral infection and protein expression may be performed as described, for example, by O'Reilley et al. (Baculovirus expression vectors: A Laboratory Manual. Oxford: Oxford University Press (1994)).

Expressed poly-His tagged antibody can then be purified, for example, by $Ni^{2+}$-chelate affinity chromatography as follows. Extracts can be prepared from recombinant virus-infected Sf9 cells as described by Rupert et al. (Nature 362:175-179 (1993)). Briefly, Sf9 cells are washed, resuspended in sonication buffer (25 mL HEPES pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate; 300 mM NaCl; 10% glycerol pH 7.8) and filtered through a 0.45 μm filter. A $Ni^{2+}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl; 10% glycerol pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged antibody are pooled and dialyzed against loading buffer.

Alternatively, purification of the antibody can be performed using known chromatography techniques, including for instance, Protein A or protein G column chromatography. The antibody of interest may be recovered from the solid phase of the column by elution into a solution containing a chaotropic agent or mild detergent. Exemplary chaotropic agents and mild detergents include, but are not limited to, Guanidine-HC1, urea, lithium perchlorate, Arginine, Histidine, SDS (sodium dodecyl sulfate), Tween, Triton, and NP-40, all of which are commercially available.

c. Optimized Purification Technique

One particular purification approach that may be used for coiled coil containing antibodies is shown below.

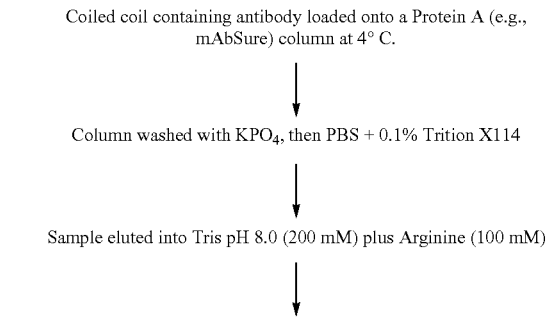

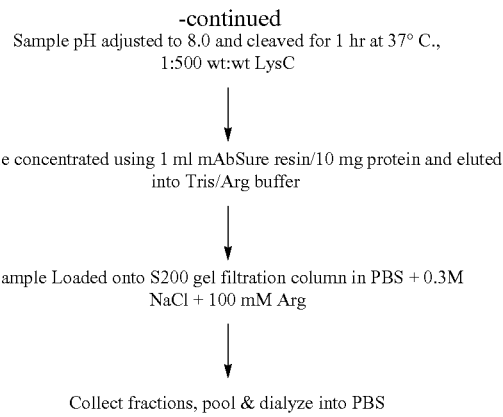

Sample pH adjusted to 8.0 and cleaved for 1 hr at 37° C.,
1:500 wt:wt LysC

Sample concentrated using 1 ml mAbSure resin/10 mg protein and eluted into Tris/Arg buffer Sample Loaded onto S200 gel filtration column in PBS + 0.3M NaCl + 100 mM Arg Collect fractions, pool & dialyze into PBS In addition to Arginine, other chaotropic agents or mild detergents that can be used in the above purification protocol after the initial Protein A column step include, but are not limited to, Guanidine-HCl, urea, lithium perclorate, Histidine, SDS (sodium dodecyl sulfate), Tween, Triton, and NP-40, all of which are commercially available. Diluting the antibody into a solution containing a chaotropic agent or mild detergent after elution from the initial Protein A containing column (e.g., mAbSure column) maintains the stability of the antibody post elution and allows for the efficient removal of the coiled coil by Lys-C endopeptidase.

IV. Conjugated Proteins

The invention also provides conjugated proteins such as conjugated antibodies or immunoconjugates (for example, "antibody-drug conjugates" or "ADC"), comprising any of the antibodies described herein (e.g., a coiled coil containing antibody, a tethered antibody, or an antibody made according to the methods described herein) where one of the constant regions of the light chain or the heavy chain is conjugated to a chemical molecule such as a dye or cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In particular, as described herein, the use of coiled coil domains enables the construction of antibodies containing two different heavy chains (HC1 and HC2) as well as two different light chains (LC1 and LC2). An immunoconjugate constructed using the methods described herein may contain the cytotoxic agent conjugated to a constant region of only one of the heavy chains (HC1 or HC2) or only one of the light chains (LC1 or LC2). Also, because the immunoconjugate can have the cytotoxic agent attached to only one heavy or light chain, the amount of the cytotoxic agent being administered to a subject is reduced relative to administration of an antibody having the cytotoxic agent attached to both heavy or light chains. Reducing the amount of cytotoxic agent being administered to a subject limits adverse side effects associated with the cytotoxic agent.

The use of antibody-drug conjugates for the local delivery of cytotoxic or cytostatic agents, i.e., drugs to kill or inhibit tumor cells in the treatment of cancer (Syrigos and Epenetos, Anticancer Research 19:605-614 (1999); Niculescu-Duvaz and Springer, Adv. Drg. Del. Rev. 26:151-172 (1997); U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., Lancet (Mar. 15, 1986):603-605 (1986); Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., Cancer Immunol. Immunother. 21:183-187 (1986)). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al., Jour. of the Nat. Cancer Inst. 92(19):1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, an $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HC1), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

Conjugates of an antibody and one or more small molecule toxins, such as a calicheamicin, maytansinoids, dolastatins, aurostatins, a trichothecene, and CC 1065, and the derivatives of these toxins that have toxin activity, are also contemplated herein.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3\times10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. Patent Application Publication No. 2005/0169933, the disclosures of which are hereby expressly incorporated by reference. Antibody-maytansinoid conjugates comprising the linker component SMCC may be prepared as disclosed in U.S. Patent Application Publication No. 2005/0169933. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolastatins

In some embodiments, the immunoconjugate comprises an antibody of the invention conjugated to dolastatins or dolostatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al., Antimicrob. Agents and Chemother. 45(12): 3580-3584 (2001)) and have anticancer (U.S. Pat. No. 5,663,149) and antifungal activity (Pettit et al., Antimicrob. Agents Chemother. 42:2961-2965 (1998)). The dolastatin or auristatin drug moiety may be attached to the antibody through the N-(amino) terminus or the C-(carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Application Publication No. 2005/0238649, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., J. Nat. Prod. 44:482-485 (1981); Pettit et al., Anti- Cancer Drug Design 13:47-66 (1998); Poncet, Curr. Pharm. Des. 5:139-162 (1999); and Pettit, Fortschr. Chem. Org. Naturst. 70:1-79 (1997). See also Doronina, Nat. Biotechnol. 21(7):778-784 (2003); and "Monomethylvaline Compounds Capable of Conjugation to Ligands," U.S. Application Publication No. 2005/0238649, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^1$, $\alpha_2^1$, $\alpha_3^1$, N-acetyl-$\gamma_1^1$, PSAG and $\theta^1_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated to is QFA, which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the antibodies of the invention or made according to the methods described herein include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes (see, for example, WO 93/21232, published Oct. 28, 1993).

The present invention further contemplates an immunoconjugate formed between an antibody and a compound with nucleolytic activity (e.g., a ribonuclease or a DNA endonuclease such as a deoxyribonuclease; DNase).

For selective destruction of a tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al., Biochem. Biophys. Res. Commun. 80:49-57 (1978)) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HC1), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Conjugated Antibodies

In the conjugated antibodies of the invention, an antibody is conjugated to one or more moieties (for example, drug moieties), e.g. about 1 to about 20 moieties per antibody, optionally through a linker. The conjugated antibodies may be prepared by several routes, employing organic chemistry reactions, conditions, and reagents known to those skilled in the art, including: (1) reaction of a nucleophilic group of an antibody with a bivalent linker reagent via a covalent bond, followed by reaction with a moiety of interest; and (2) reaction of a nucleophilic group of a moiety with a bivalent linker reagent via a covalent bond, followed by reaction with the nucleophilic group of an antibody. Additional methods for preparing conjugated antibodies are described herein.

The linker reagent may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-1 carboxylate ("SMCC"), and N-Succinimidyl(4-iodo-acetyl)aminobenzoate ("STAB"). Additional linker components are known in the art- and some are described herein. See also "Monomethylvaline Compounds Capable of Conjugation to Ligands," U.S. Application Publication No. 2005/0238649, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Conjugated antibodies of the invention may also be produced by modification of the antibody to introduce electrophilic moieties, which can react with nucleophilic substituents on the linker reagent or drug or other moiety. The sugars of glycosylated antibodies may be oxidized, e.g., with periodate oxidizing reagents, to form aldehyde or ketone groups which may react with the amine group of linker reagents or drug or other moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug or other moiety (Hermanson, Bioconjugate Techniques). In another embodiment, proteins containing N-terminal serine or threonine residues can react with sodium meta-periodate, resulting in production of an aldehyde in place of the first amino acid (Geoghegan and Stroh, Bioconjugate Chem. 3:138-146 (1992); U.S. Pat. No. 5,362,852). Such aldehyde can be reacted with a drug moiety or linker nucleophile.

Likewise, nucleophilic groups on a moiety (such as a drug moiety) include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate. In yet another embodiment, the antibody may be conjugated to a "receptor" (such streptavidin) for utilization in tumor pre-targeting wherein the antibody-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

V. Therapeutic Uses

The protein complexes such as antibodies and antibody fragments described herein (e.g., a coiled coil containing antibody, a tethered antibody, or an antibody made according to the methods described herein) may be used for therapeutic applications. For example, such antibodies and antibody fragments can be used for the treatment of tumors, including pre-cancerous, non-metastatic, metastatic, and cancerous tumors (e.g., early stage cancer), for the treatment of allergic or inflammatory disorders, or for the treatment of autoimmune disease, or for the treatment of a subject at risk for developing cancer (for example, breast cancer, colorectal cancer, lung cancer, renal cell carcinoma, glioma, or ovarian cancer), an allergic or inflammatory disorder, or an autoimmune disease.

The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from where they started and spread to other parts of the body (metastasize), usually through the bloodstream or through the Lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade and cancer cells are described as being well-differentiated, moderately-differentiated, poorly-differentiated, or undifferentiated. Well-differentiated cells are quite normal appearing and resemble the normal cells from which they originated. Undifferentiated cells are cells that have become so abnormal that it is no longer possible to determine the origin of the cells.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia), or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further separated into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors.

Epithelial cancers generally evolve from a benign tumor to a preinvasive stage (e.g., carcinoma in situ), to a malignant cancer, which has penetrated the basement membrane and invaded the subepithelial stroma.

Multispecific protein complexes can also be used in these therapeutic applications, and antibodies that bind HER2 can in particular be used to treat breast cancer, colorectal cancer, lung cancer, renal cell carcinoma, glioma, or ovarian cancer.

Other subjects that are candidates for receiving compositions of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu), osteoarthritis, Paget's disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogren's syndrome, solid tumors, Stargart's disease, Steven's Johnson disease, superior limbic keratitis, syphilis, systemic lupus, Terrien's marginal degeneration, toxoplasmosis, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency, Wegener's sarcoidosis, undesired angiogenesis associated with diabetes, parasitic diseases, abnormal wound healing, hypertrophy following surgery, injury or trauma (e.g., acute lung injury/ARDS), inhibition of hair growth, inhibition of ovulation and corpus luteum formation, inhibition of implantation, and inhibition of embryo development in the uterus.

Examples of allergic or inflammatory disorders or autoimmune diseases or disorders that may be treated using a coiled coil containing antibody, a tethered antibody, or an antibody made according to the methods described herein include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and autoimmune asthma, conditions involving infiltration of T-cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extrarenal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis *nodosa*), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, *pemphigus* (including *pemphigus vulgaris, pemphigus foliaceus, pemphigus* mucus-membrane pemphigoid, and *pemphigus* erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton. myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barre syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes *dorsalis*, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis *acuta*, pyoderma gangrenosum, Quervain's thyreoiditis, acquired spenic atrophy, infertility due to antispermatozoan antobodies, non-malignant thymoma, vitiligo, SCID and Epstein-Barr virus-associated diseases, acquired immune deficiency syndrome (AIDS), parasitic diseases such as *Leishmania*, toxic-shock syndrome, food poisoning, conditions involving infiltration of T-cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

In addition to therapeutic uses, the antibodies of the invention can be used for other purposes, including diagnostic methods, such as diagnostic methods for the diseases and conditions described herein.

VI. Dosages, Formulations, And Duration

The proteins of this invention will be formulated, dosed, and administered in a fashion consistent with good medical practice. Factors for consideration in this context include the particular disorder being treated, the particular mammal being treated, the clinical condition of the individual subject; the cause of the disorder, the site of delivery of the agent, the method of administration, the scheduling of administration, and other factors known to medical practitioners. The "therapeutically effective amount" of the proteins to be administered will be governed by such considerations, and is the minimum amount necessary to prevent, ameliorate, or treat a particular disorder (for example, a cancer, allergic or inflammatory disorder, or autoimmune disorder). The proteins need not be, but are optionally, formulated with one or more agents currently used to prevent or treat the disorder. The effective amount of such other agents depends on the amount of proteins present in the formulation, the type of disorder or treatment, and other factors discussed above. These are generally used in the same dosages and with administration routes as used hereinbefore or about from 1 to 99% of the heretofore employed dosages. Generally, alleviation or treatment of a cancer involves the lessening of one or more symptoms or medical problems associated with the cancer. The therapeutically effective amount of the drug can accomplish one or a combination of the following: reduce (by at least 10%, 20%, 30%, 40%, 50%, 60%, 70%, 80%, 90%, 100% or more) the number of cancer cells; reduce or inhibit the tumor size or tumor burden; inhibit (i.e., to decrease to some extent and/or stop) cancer cell infiltration into peripheral organs; reduce hormonal secretion in the case of adenomas; reduce vessel density; inhibit tumor metastasis; reduce or inhibit tumor growth; and/or relieve to some extent one or more of the symptoms associated with the cancer. In some embodiments, the proteins are used to prevent the occurrence or reoccurrence of cancer or an autoimmune disorder in the subject.

In one embodiment, the present invention can be used for increasing the duration of survival of a human subject susceptible to or diagnosed with a cancer or autoimmune disorder. Duration of survival is defined as the time from first administration of the drug to death. Duration of survival can also be measured by stratified hazard ratio (HR) of the treatment group versus control group, which represents the risk of death for a subject during the treatment.

In yet another embodiment, the treatment of the present invention significantly increases response rate in a group of human subjects susceptible to or diagnosed with a cancer who are treated with various anti-cancer therapies. Response rate is defined as the percentage of treated subjects who responded to the treatment. In one aspect, the combination treatment of the invention using proteins of this invention and surgery, radiation therapy, or one or more chemotherapeutic agents significantly increases response rate in the treated subject group compared to the group treated with surgery, radiation therapy, or chemotherapy alone, the increase having a Chi-square p-value of less than 0.005. Additional measurements of therapeutic efficacy in the treatment of cancers are described in U.S. Patent Application Publication No. 20050186208.

Therapeutic formulations are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The proteins described herein (e.g., a coiled coil containing antibody, a tethered antibody, or an antibody made according to the methods described herein) are administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with antagonism to the target molecule recognized by the proteins. An ex vivo strategy can also be used for therapeutic applications. Ex vivo strategies involve transfecting or transducing cells obtained from the subject with a polynucleotide encoding a protein of this invention. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

In one example, the protein complex is (e.g., a coiled coil containing antibody, a tethered antibody, or an antibody made according to the methods described herein) is administered locally, e.g., by direct injections, when the disorder or location of the tumor permits, and the injections can be repeated periodically. The protein complex can also be delivered systemically to the subject or directly to the tumor cells, e.g., to a tumor or a tumor bed following surgical excision of the tumor, in order to prevent or reduce local recurrence or metastasis.

VII. Articales Of Manufacture

Another embodiment of the invention is an article of manufacture containing one or more protein complexes described herein, and materials useful for the treatment or diagnosis of a disorder (for example, an autoimmune disease or cancer). The article of manufacture comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). At least one active agent in the composition is an antibody or antibody fragment antibody of the invention. The label or package insert indicates that the composition is used for treating the particular condition. The label or package insert will further comprise instructions for administering the antibody composition to the subject. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In certain embodiments, the package insert indicates that the composition is used for treating breast cancer, colorectal cancer, lung cancer, renal cell carcinoma, glioma, or ovarian cancer.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials considered from a commercial and user standpoint, including other buffers, diluents, filters, needles, and syringes.

Kits are also provided that are useful for various purposes, e.g., for purification or immunoprecipitation of an antigen (e.g., HER2 or EGFR) from cells. For isolation and purification of an antigen (e.g., HER2 or EGFR) the kit can contain an antibody (e.g., an EGFR/HER2 antibody) coupled to beads (e.g., sepharose beads). Kits can be provided which contain the antibodies for detection and quantitation of the antigen in vitro, e.g., in an ELISA or a Western blot. As with the article of manufacture, the kit comprises a container and a label or package insert on or associated with the container. The container holds a composition comprising at least one multispecific antibody or antibody fragment of the invention. Additional containers may be included that contain, e.g., diluents and buffers or control antibodies. The label or package insert may provide a description of the composition as well as instructions for the intended in vitro or diagnostic use.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims. ps VII. Target Molecules Examples of molecules that may be targeted by a complex of this invention include, but are not limited to, soluble serum proteins and their receptors and other membrane bound proteins (e.g., adhesins).

In another embodiment the binding protein of the invention is capable of binding one, two or more cytokines, cytokine-related proteins, and cytokine receptors selected from the group consisting of BMP1, BMP2, BMP3B (GDF1O), BMP4, BMP6, BMP8, CSF1 (M-CSF), CSF2 (GM-CSF), CSF3 (G-CSF), EPO, FGF1 (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFNB1, IFNG, IFNW1, FEL1, FEL1 (EPSELON), FEL1 (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, HGF (VEGFD), VEGF, VEGFB, VEGFC, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIF1, HGF, LEP (leptin), PTN, and THPO.

In another embodiment, a target molecule is a chemokine, chemokine receptor, or a chemokine-related protein selected from the group consisting of CCL1 (I-309), CCL2 (MCP-1/MCAF), CCL3 (MIP-Ia), CCL4 (MIP-Ib), CCL5 (RANTES), CCL7 (MCP-3), CCL8 (mcp-2), CCLH (eotaxin), CCL13 (MCP-4), CCL15 (MIP-Id), CCL16 (HCC-4), CCL17 (TARC), CCL18 (PARC), CCL19 (MDP-3b), CCL20 (MIP-3a), CCL21 (SLC/exodus-2), CCL22 (MDC/STC-I), CCL23 (MPIF-1), CCL24 (MPIF-2/eotaxin-2), CCL25 (TECK), CCL26 (eotaxin-3), CCL27 (CTACK/ILC), CCL28, CXCL1 (GRO1), CXCL2 (GRO2), CXCL3 (GRO3), CXCL5 (ENA-78), CXCL6 (GCP-2), CXCL9 (MIG), CXCL1O (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-Ib), BLR1 (MDR15), CCBP2 (D6/JAB61), CCR1 (CKR1/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBB), CCR8 (CMKBR8/TERI/CKR-L1), CCR9 (GPR-9-6), CCRL1 (VSHKI), CCRL2 (L-CCR), XCR1 (GPR5/CCXCR1), CMKLR1, CMKOR1 (RDC1), CX3CR1 (V28), CXCR4, GPR2 (CCR1O), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCP1O, CKLFSF2, CKLFSF3, CKLFSF4, CKLFSF5, CKLFSF6, CKLFSF7, CKLFSF8, BDNF, C5R1, CSF3, GRCC1O (C10), EPO, FY (DARC), GDF5, HDF1A, DL8, PRL, RGS3, RGS13, SDF2, SLIT2, TLR2, TLR4, TREM1, TREM2, and VHL.

In another embodiment the binding proteins of the invention are capable of binding one or more targets selected from the group consisting of ABCF1; ACVR1; ACVR1B; ACVR2; ACVR2B; ACVRL1; AD0RA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF (BLys); BAG1; BAI1; BCL2; BCL6; BDNF; BLNK; BLR1 (MDR15); BMP1; BMP2; BMP3B (GDF1O); BMP4; BMP6; BMP8; BMPR1A; BMPR1B; BMPR2; BPAG1 (plectin); BRCA1; C19orf1O (IL27w); C3; C4A; C5; C5R1; CANT1; CASP1; CASP4; CAV1; CCBP2 (D6/JAB61); CCL1 (1-309); CCLI1 (eotaxin); CCL13 (MCP-4); CCL15 (MIP-Id); CCL16 (HCC-4); CCL17 (TARC); CCL18 (PARC); CCL19 (MIP-3b); CCL2 (MCP-1); MCAF; CCL20 (MIP-3a); CCL21 (MTP-2); SLC; exodus-2; CCL22 (MDC/STC-I); CCL23 (MPIF-1); CCL24 (MPIF-2/eotaxin-2); CCL25 (TECK); CCL26 (eotaxin-3); CCL27 (CTACK/ILC); CCL28; CCL3 (MTP-Ia); CCL4 (MDP-Ib); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-IRB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBB); CCR8 (CMKBR8/TERI/CKR-L1); CCR9 (GPR-9-6); CCRL1 (VSHKI); CCRL2 (L-CCR); CD164; CD19; CD1C; CD20; CD200; CD22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDH1 (E-cadherin); CDH10; CDH12; CDH13; CDH18; CDH19; CDH2O; CDH5; CDH7; CDH8; CDH9; CDK2; CDK3; CDK4; CDK5; CDK6; CDK7; CDK9; CDKN1A (p21Wap1/Cip1); CDKN1B (p27Kip1); CDKN1C; CDKN2A (P16INK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLR1; CMKOR1 (RDC1); CNR1; COL18A1; COLIA1; COL4A3; COL6A1; CR2; CRP; CSF1 (M-CSF); CSF2 (GM-CSF); CSF3 (GCSF); CTLA4; CTNNB1 (b-catenin); CTSB (cathepsin B); CX3CL1 (SCYD1); CX3CR1 (V28); CXCL1 (GRO1); CXCL10 (IP-10); CXCLI1 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB2IP; DES; DKFZp451J0118; DNCL1; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FEL1 (EPSILON); FIL1 (ZETA); FLJ12584; FLJ25530; FLRT1 (fibronectin); FLT1; FOS; FOSL1 (FRA-I); FY (DARC); GABRP (GABAa); GAGEB1; GAGEC1; GALNAC4S-6ST; GATA3; GDF5; GFI1; GGT1; GM-CSF; GNAS1; GNRH1; GPR2 (CCR10); GPR31; GPR44; GPR81 (FKSG80); GRCC1O (C10); GRP; GSN (Gelsolin); GSTP1; HAVCR2; HDAC4; HDAC5; HDAC7A; HDAC9; HGF; HIF1A; HDP1; histamine and histamine receptors; HLA-A; HLA-DRA; HM74; HMOX1; HUMCYT2A; ICEBERG; ICOSL; ID2; IFN-α; IFNA1; IFNA2; IFNA4; IFNA5; IFNA6; IFNA7; IFNB1; IFNgamma; DFNW1; IGBP1; IGF1; IGF1R; IGF2; IGFBP2; IGFBP3; IGFBP6; IL-I; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2; IL1RN; IL2; IL20; IL20RA; IL21R; IL22; IL22R; IL22RA2; IL23; IL24; IL25; IL26; IL27; IL28A; IL28B; IL29; IL2RA; IL2RB;

IL2RG; IL3; IL30; IL3RA; HA; IL4R; IL5; IL5RA; IL6; IL6R; IL6ST (glycoprotein 130); EL7; EL7R; EL8; IL8RA; DL8RB; IL8RB; DL9; DL9R; DLK; INHA; INHBA; INSL3; INSL4; IRAK1; ERAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK1O; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB1; midkine; MEF; MIP-2; MKI67; (Ki-67); MMP2; MMP9; MS4A1; MSMB; MT3 (metallothionectin-III); MTSS1; MUC1 (mucin); MYC; MYD88; NCK2; neurocan; NFKB1; NFKB2; NGFB (NGF); NGFR; NgR-Lingo; NgR-Nogo66 (Nogo); NgR-p75; NgR-Troy; NME1 (NM23A); N0X5; NPPB; NROB1; NR0B2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; P2RX7; PAP; PART1; PATE; PAWR; PCA3; PCNA; PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNFI1O (ZNF144); ROBO2; S100A2; SCGB1D2 (lipophilin B); SCGB2A1 (mammaglobin2); SCGB2A2 (mammaglobin 1); SCYE1 (endothelial Monocyte-activating cytokine); SDF2; SERPINA1; SERPINA3; SERP1NB5 (maspin); SERPINE1 (PAI-I); SERPDMF1; SHBG; SLA2; SLC2A2; SLC33A1; SLC43A1; SLIT2; SPP1; SPRR1B (Spr1); ST6GAL1; STAB1; STAT6; STEAP; STEAP2; TB4R2; TBX21; TCP1O; TDGF1; TEK; TGFA; TGFB1; TGFB1I1; TGFB2; TGFB3; TGFBI; TGFBR1; TGFBR2; TGFBR3; TH1L; THBS1 (thrombospondin-1); THBS2; THBS4; THPO; TIE (Tie-1); TMP3; tissue factor; TLR1O; TLR2; TLR3; TLR4; TLR5; TLR6; TLR7; TLR8; TLR9; TNF; TNF-a; TNFAEP2 (B94); TNFAIP3; TNFRSFI1A; TNFRSF1A; TNFRSF1B; TNFRSF21; TNFRSF5; TNFRSF6 (Fas); TNFRSF7; TNFRSF8; TNFRSF9; TNFSF1O (TRAIL); TNFSF1 1 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1BB ligand); TOLLIP; Toll-like receptors; TOP2A (topoisomerase Ea); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; VLA-4; XCL1 (lymphotactin); XCL2 (SCM-Ib); XCR1(GPR5/CCXCR1); YY1; and ZFPM2.

Preferred molecular target molecules for antibodies encompassed by the present invention include CD proteins such as CD3, CD4, CD8, CD16, CD19, CD20, CD34; CD64, CD200 members of the ErbB receptor family such as the EGF receptor, HER2, HER3 or HER4 receptor; cell adhesion molecules such as LFA-1, Mac1, p150.95, VLA-4, ICAM-1, VCAM, alpha4/beta7 integrin, and alphav/beta3 integrin including either alpha or beta subunits thereof (e.g. anti-CD11a, anti-CD18 or anti-CD11b antibodies); growth factors such as VEGF-A, VEGF-C; tissue factor (TF); alpha interferon (alphaIFN); TNFalpha, an interleukin, such as IL-1beta, IL-3, IL-4, IL-5, IL-8, IL-9, IL-13, IL17A/F, IL-18, IL-13Ralpha1, IL13Ralpha2, IL-4R, IL-5R, IL-9R, IgE; blood group antigens; flk2/flt3 receptor; obesity (OB) receptor; mp1 receptor; CTLA-4; RANKL, RANK, RSV F protein, protein C etc.

In one embodiment, the heteromultimeric complexes of this invention binds to at least two target molecules selected from the group consisting of: IL-1alpha and IL-1beta, IL-12 and IL-18; IL-13 and IL-9; IL-13 and IL-4; IL-13 and IL-5; IL-5 and IL-4; IL-13 and IL-1beta; IL-13 and IL-25; IL-13 and TARC; IL-13 and MDC; IL-13 and MEF; IL-13 and TGF-β; IL-13 and LHR agonist; IL-12 and TWEAK, IL-13 and CL25; IL-13 and SPRR2a; IL-13 and SPRR2b; IL-13 and ADAMS, IL-13 and PED2, IL17A and IL17F, CD3 and CD19, CD138 and CD20; CD138 and CD40; CD19 and CD20; CD20 and CD3; CD38 and CD138; CD38 and CD20; CD38 and CD40; CD40 and CD20; CD-8 and IL-6; CD20 and BR3, TNFalpha and TGF-beta, TNFalpha and IL-1beta; TNFalpha and IL-2, TNF alpha and IL-3, TNFalpha and IL-4, TNFalpha and IL-5, TNFalpha and IL6, TNFalpha and IL8, TNFalpha and IL-9, TNFalpha and IL-10, TNFalpha and IL-11, TNFalpha and IL-12, TNFalpha and IL-13, TNFalpha and IL-14, TNFalpha and IL-15, TNFalpha and IL-16, TNFalpha and IL-17, TNFalpha and IL-18, TNFalpha and IL-19, TNFalpha and IL-20, TNFalpha and IL-23, TNFalpha and IFNalpha, TNFalpha and CD4, TNFalpha and VEGF, TNFalpha and MIF, TNFalpha and ICAM-1, TNFalpha and PGE4, TNFalpha and PEG2, TNFalpha and RANK ligand, TNFalpha and Te38; TNFalpha and BAFF; TNFalpha and CD22; TNFalpha and CTLA-4; TNFalpha and GP130; TNFα and IL-12p40; VEGF and HER2, VEGF-A and HER2, VEGF-A and PDGF, HER1 and HER2, VEGF-A and VEGF-C, VEGF-C and VEGF-D, HER2 and DR5, VEGF and IL-8, VEGF and MET, VEGFR and MET receptor, VEGFR and EGFR, HER2 and CD64, HER2 and CD3, HER2 and CD16, HER2 and HER3; EGFR(HER1) and HER2, EGFR and HER3, EGFR and HER4, IL-13 and CD40L, IL4 and CD40L, TNFR1 and IL-1R, TNFR1 and IL-6R and TNFR1 and IL-18R, EpCAM and CD3, MAPG and CD28, EGFR and CD64, CSPGs and RGM A; CTLA-4 and BTNO2; IGF1 and IGF2; IGF1/2 and Erb2B; MAG and RGM A; NgR and RGM A; NogoA and RGM A; OMGp and RGM A; PDL-I and CTLA-4; and RGM A and RGM B.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

All patents, patent applications, patent application publications, and other publications cited or referred to in this specification are herein incorporated by reference to the same extent as if each independent patent, patent application, patent application publication or publication was specifically and individually indicated to be incorporated by reference. Such patent applications specifically include U.S. provisional application Nos. 61/243,105 and 61/266,992, filed on Sep. 16, 2009 and Dec. 4, 2009, respectively, from which this application claims benefit.

EXAMPLES

Example 1

Construction of Vectors for the Expression of Coiled Coil Containing Antibodies The coiled coil heterodimerization domains described herein can be linked to a constant chain (e.g., the C-terminus of the HC) of any antibody. Numerous antibody sequences that can be used to construct coiled coil containing antibodies are known in the art and techniques required to manipulate DNA sequences are also well known in the art. An exemplary method for constructing coiled coil containing antibodies is described below.

The HC backbone for the generation of antibodies containing a coiled coil was constructed as follows. Sense and anti-sense oligonucleotides were designed and synthesized to encode either the ACID.p1 (GGSAQLEKELQALEK-ENAQLEWELQALEKELAQGAT; SEQ ID NO:33) or BASE.p1 (GGSAQLKKKLQALKKKNAQLK-WKLQALKKKLAQGAT; SEQ ID NO:34) coiled coil domain sequence with 5' AscI and 3' XbaI overhangs. The oligonucleotides were annealed, phosphorylated, and ligated into a digested and dephosphorylated pRK plasmid (Genentech Inc.; Eaton et al., Biochemistry 25:8343-8347 (1986)). The $C_H1$ through $C_H3$ domain of a hIgG1 was prepared using PCR (polymerase chain reaction) to include a 5' multiple cloning site (MCS) (ClaI-BamHI-KpnI-ApaI) and a 3' AscI site and cloned into the previously prepared pRK-ACID.p1 or pRK-BASE.p1 vector using ClaI and AscI. Finally, the Lysine residue at position H222 (Kabat numbering scheme) was mutated into an Alanine residue using Stratagene's Quikchange II XL site-directed mutagenesis kit to prevent Fab release during Lys-C cleavage.

Antibodies containing a coiled coil domain were constructed as follows. For common LC and one-armed antibodies, the $V_H$ domain of the desired antibody was prepared using PCR to include 5' ClaI and 3' ApaI restriction sites. The PCR fragments were digested and cloned into a similarly prepared backbone vector. No changes had to be made to the LC constructs already available for these antibodies.

For tethered antibodies the $V_H$ domain (minus the signal sequence) of the desired antibody was first prepared using PCR where the 5' primer contained the 3' half of a GGS tether and terminated in a 5' BamHI site and the 3' primer terminated in a 3' ApaI site. The fragments were digested and cloned into a similarly prepared backbone vector. The cognate LC of the desired antibody was then prepared using PCR where the 5' primer terminated in a 5' ClaI site and the 3' primer contained the 5' portion of the GGS tether and terminated in a 3' BamHI. The LC fragment was joined to its cognate HC (now in the backbone vector) by cloning the fragment in front of the $V_H$ using ClaI and BamHI. The completed tether sequence linking the LC to the $V_H$ was GGGSGGSGGSGGSGGSGGSGGSGGSG (SEQ ID NO:14). The vectors were transfected into mammalian cells (CHO or 293 cells) using standard transfection techniques.

A bispecific antibody that specifically binds both FcεR1 and FcγR2b and having a common LC was prepared using the methods described herein. This antibody has a "BASE.p1" sequence containing an anti-human FcγR2b HC sequence with a BASE.p1 coiled coil domain sequence and the K222A mutation (SEQ ID NO:1), an "ACID.p1" sequence containing an anti-human FcεR1 HC sequence with an ACID.p1 coiled coil domain sequence and the K222A mutation (SEQ ID NO:2), and a common LC sequence (SEQ ID NO:3) (FIG. 8).

One-armed antibodies that specifically bind either HER2 or EGFR were also prepared. The antibody that specifically binds HER2 contains an anti-HER2 antibody 1 HC sequence with an ACID.p1 coiled coil domain sequence and the K222A mutation (SEQ ID NO:4), an HC region lacking the VH and CH1 domains with a BASE.p1 coiled coil domain sequence (SEQ ID NO:5), and an antib-HER2 antibody 1 LC sequence (SEQ ID NO:6). The antibody that specifically binds EGFR contains an anti-EGFR HC sequence with an ACID.p1 coiled coil domain sequence and the K222A mutation (SEQ ID NO:7), an HC region lacking the VH and CH1 domains with a BASE.p1 coiled coil domain sequence (SEQ ID NO:5), and an anti-EGFR (D1.5) LC sequence (SEQ ID NO:8) (FIGS. 9-1 and 9-2).

Tethered antibodies that specifically bind HER2 and EGFR/HER1 were also prepared (FIGS. 10 and 11). One antibody that specifically binds HER2 and EGFR contains (1) an anti-HER2 antibody 1 LC sequence tethered to an anti-HER2 antibody 1 HC sequence by a 26 amino acid GGS tether, an ACID.p1 coiled coil domain sequence, and the K222A mutation (SEQ ID NO:9) and (2) an anti-EGFR antibody LC sequence tethered to an anti-EGFR antibody HC sequence by a 26 amino acid GGS tether, a BASE.p1 coiled coil domain sequence, and the K222A mutation (SEQ ID NO:10) (FIG. 10). A second antibody that specifically binds HER2 and EGFR contains (1) the anti-HER2 antibody 2 LC sequence tethered to the anti-HER2 antibody 2 HC sequence by a 26 amino acid GGS tether, an ACID.p1 coiled coil domain sequence, and the K222A mutation (SEQ ID NO:11) and (2) an anti-EGFR antibody LC sequence tethered to an anti-EGFR antibody HC sequence by a 26 amino acid GGS tether, a BASE.p1 coiled coil domain sequence, and the K222A mutation (SEQ ID NO:10) (FIG. 11). Anti-HER2 antibody 1 LC and HC sequences used in the construction of the coiled coil containing antibodies are shown in FIGS. 12A and 12B (SEQ ID NOS:15 and 16). The location of various restriction sites used in constructing the vectors encoding these antibodies is also shown in FIGS. 12B1-3.

Example 2

Purification of Coiled Coil Containing Antibodies

An exemplary schema that can be used to purify coiled coil containing antibodies is shown below.

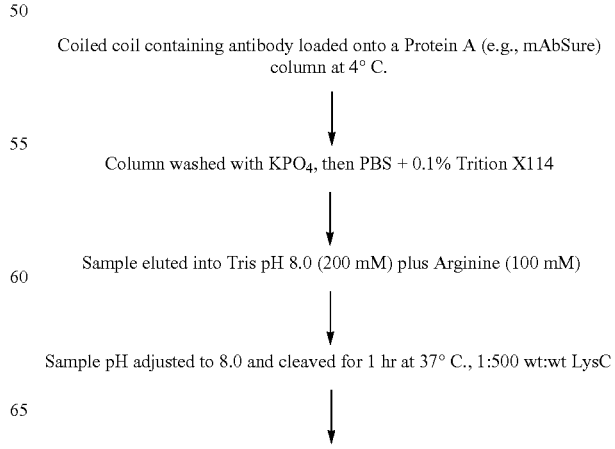

-continued

Sample concentrated using 1 ml mAbSure resin/10 mg protein and eluted into Tris/Arg buffer

↓

Sample Loaded onto S200 gel filtration column in PBS + 0.3M NaCl + 100 mM Arg

↓

Collect fractions, pool & dialyze into PBS

In particular, antibodies were purified from conditioned media using mAbSure Select resin from GE Healthcare (Sweden) overnight at 4° C. The column was washed with two column volumes (CV) of PBS (phosphate buffered saline), followed by 10 CV of PBS+0.1% Triton X114 detergent, followed by 10 CV potassium phosphate buffer. The columns were eluted with 10 mM Acetic Acid (pH 2.9) and immediately diluted with Arginine (100 mM final concentration) and Tris (200 mM final concentration), pH 8.0. Coiled coils were removed from antibodies upon treatment with a 1:500 (weight:weight) ratio of Lys-C endopeptidase (Wako Pure Chemical Laboratories) at 37° C. for 1-5 hours. Cleaved samples were loaded back over an mAbSure resin column to separate cleaved coiled-coils from antibodies and eluted as above. Antibody concentrations were adjusted to 10 mg/ml prior to separation via size exclusion chromatography using a Sephacryl S200 column run in PBS, 150 mM NaCl, 100 mM Arginine, and 1 mM $NaN_3$. Peak fractions were pooled and dialyzed against PBS overnight prior to mass spectrum analysis to ensure identity and purity.

In addition to Arginine, other chaotropic agents or mild detergents that can be used in the above purification protocol after the initial mAbSure resin column step include, but are not limited to, Guanidine-HCl, urea, lithium perclorate, Histidine, SDS (sodium dodecyl sulfate), Tween, Triton, and NP-40, all of which are commercially available. Diluting the antibody into a solution containing a chaotropic agent or mild detergent after elution from the initial Protein A containing column (e.g., mAbSure column) maintains the stability of the antibody post elution and allows for the efficient removal of the coiled coil by Lys-C endopeptidase.

Table 1 shows a summary of the purification results for Anti-HER2 antibody 1/α-EGFR (D 1.5) antibodies.

TABLE 1

| Sample Volume | mAb Sure Column Recovery | S200 Column Recovery | Yield | Aggregation |
|---|---|---|---|---|
| 40 L | 200 mg | 147 mg | 73% | 18% |
| 50 L | 246 mg | 196 mg | 80% | 13% |
| 50 L | 280 mg | 213 mg | 76% | 11% |

The coiled coil was removed from the antibody by Lys-C endopeptidase during the purification process.

An antibody constructed using coiled coil heterdimerization domains, but which no longer contains the coiled coil, is referred to as an "engineered antibody" in the following examples.

Example 3

Cleavage of Coiled Coil Containing Antibodies

Figure 13B:
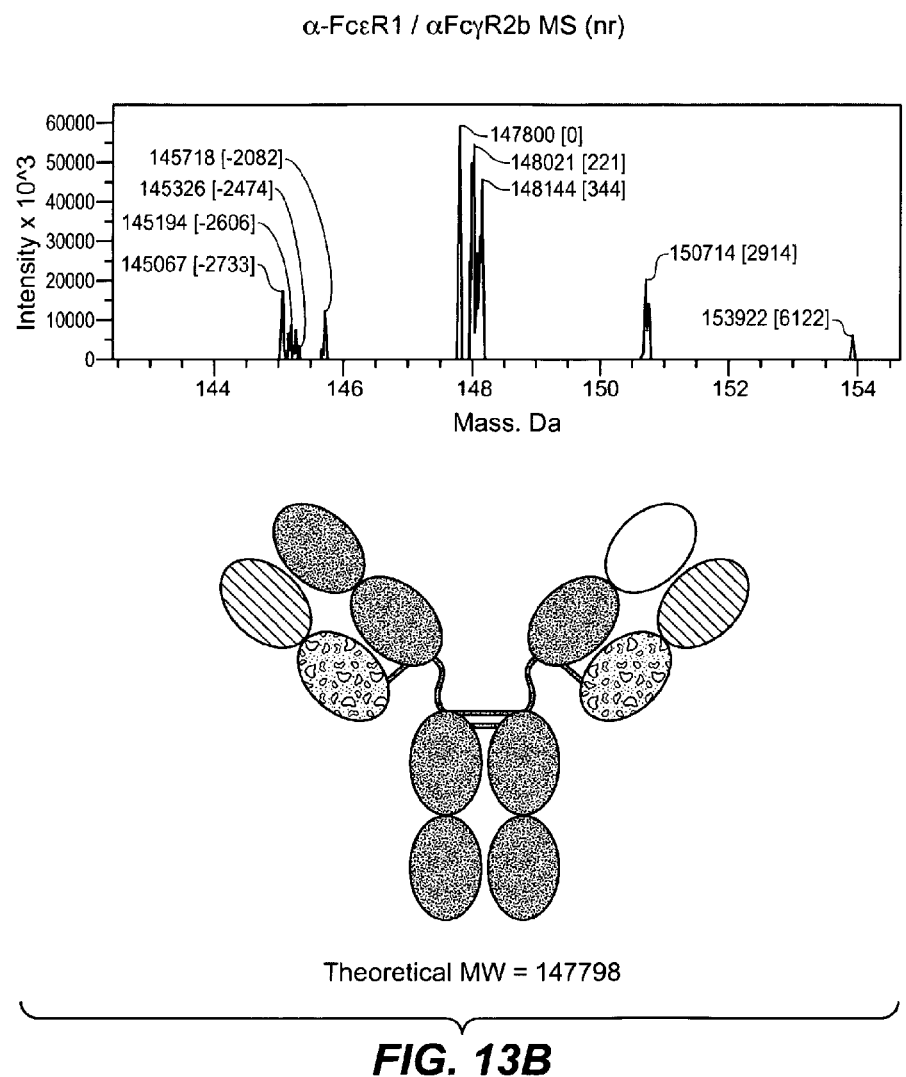

The various coiled coil containing antibodies were subjected to cleavage experiments to show that the coiled coil (and tether, if present) could be cleaved from the antibody sequence while leaving the antibody sequence intact. In particular, FIGS. 13A and B show that the coiled coil was cleaved from an exemplary α-FcεR1/α-FcγR2b antibody using Lys-C endopeptidase and that the antibody remained intact. The theoretical mass for the antibody with the coiled coil is within the margin of error of the mass experimentally observed by mass spectrometry. Similarly, the theoretical mass for the engineered antibody without the coiled coil is within the margin of error of that experimentally observed by mass spectrometry showing that Lys-C cleaved the coiled coil from the antibody.

Figure 14A:
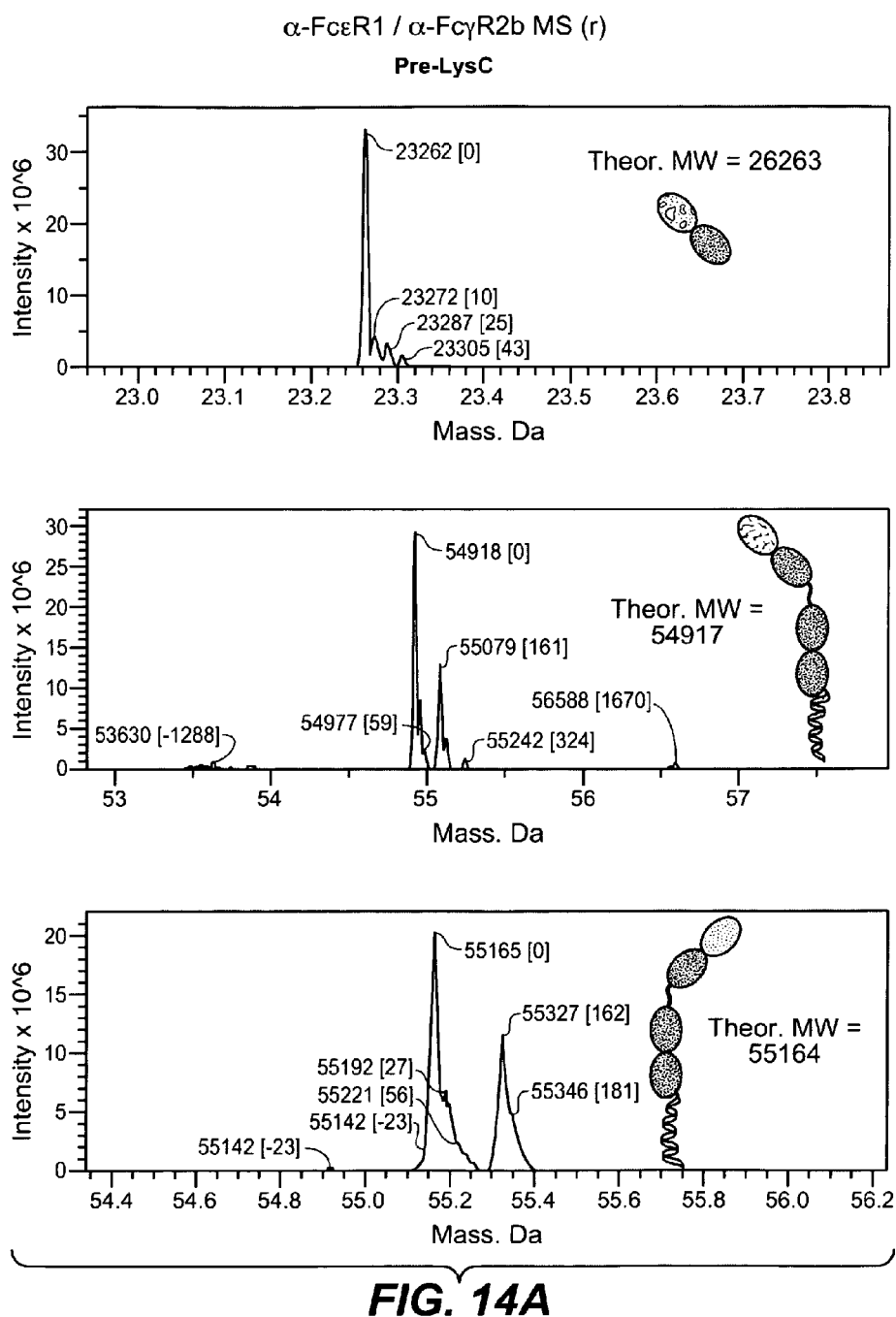
FIGS. 14A and 14B are a series of graphs of mass spectrometry results and schematic diagrams showing that Lys-C endopeptidase (right panels) does not cleave within the LC or HC of an exemplary α-FcεR1/α-FcγR2b bispecific antibody, but does cleave the coiled coil from the HCs (comparison of left two bottom panels and right two bottom panels). The theoretical masses of the light chain (MW=26263), the heavy chain with a coiled coil domain (MW=54917 or 55164), and the heavy chain without a coiled coil domain (MW=50528 and 50767) are within the margin of error of the experimentally observed masses indicated in the graph of the mass spectrometry results for the respective construct.
Figure 14B:
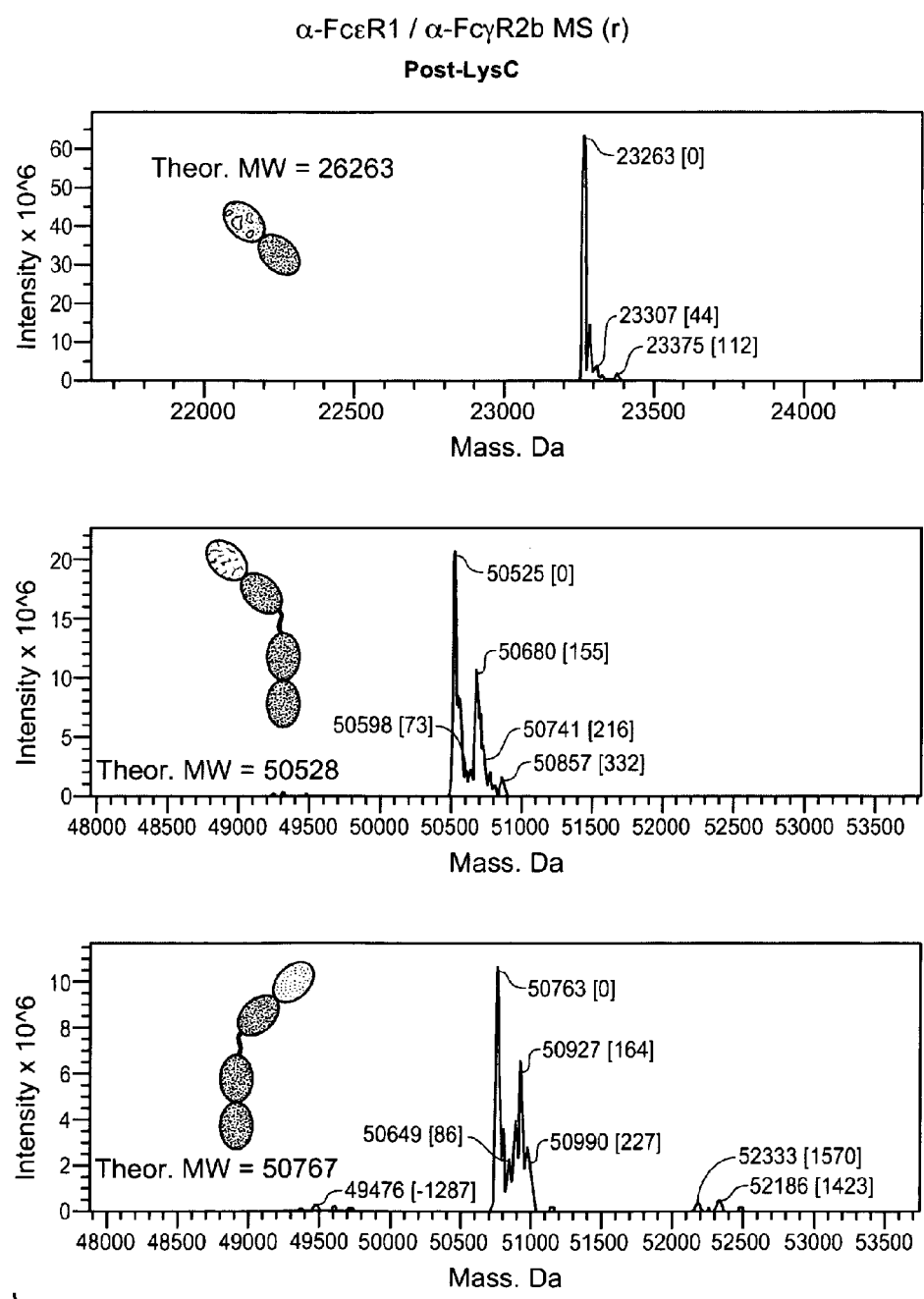

Mass spectrometry results also demonstrated that Lys-C endopeptidase did not cleave the LC or HC of the exemplary α-FcεR1/α-FcγR2b antibody (FIGS. 14A and B). In particular, the molecular mass was determined both pre-Lys-C endopeptidase treatment (left panels) and post-Lys-C endopeptidase treatment (right panels) for the LC (top two panels) and the α-FcεR1 and α-FcγR2b HCs (bottom four panels) using mass spectrometry. The experimentally observed molecular masses are within the margin of error of the theoretical masses for the various contructs showing that Lys-C endopeptidase cleaved the coiled coil domain from the HC, but did not cleave the LC or HC itself.

Figure 18A:
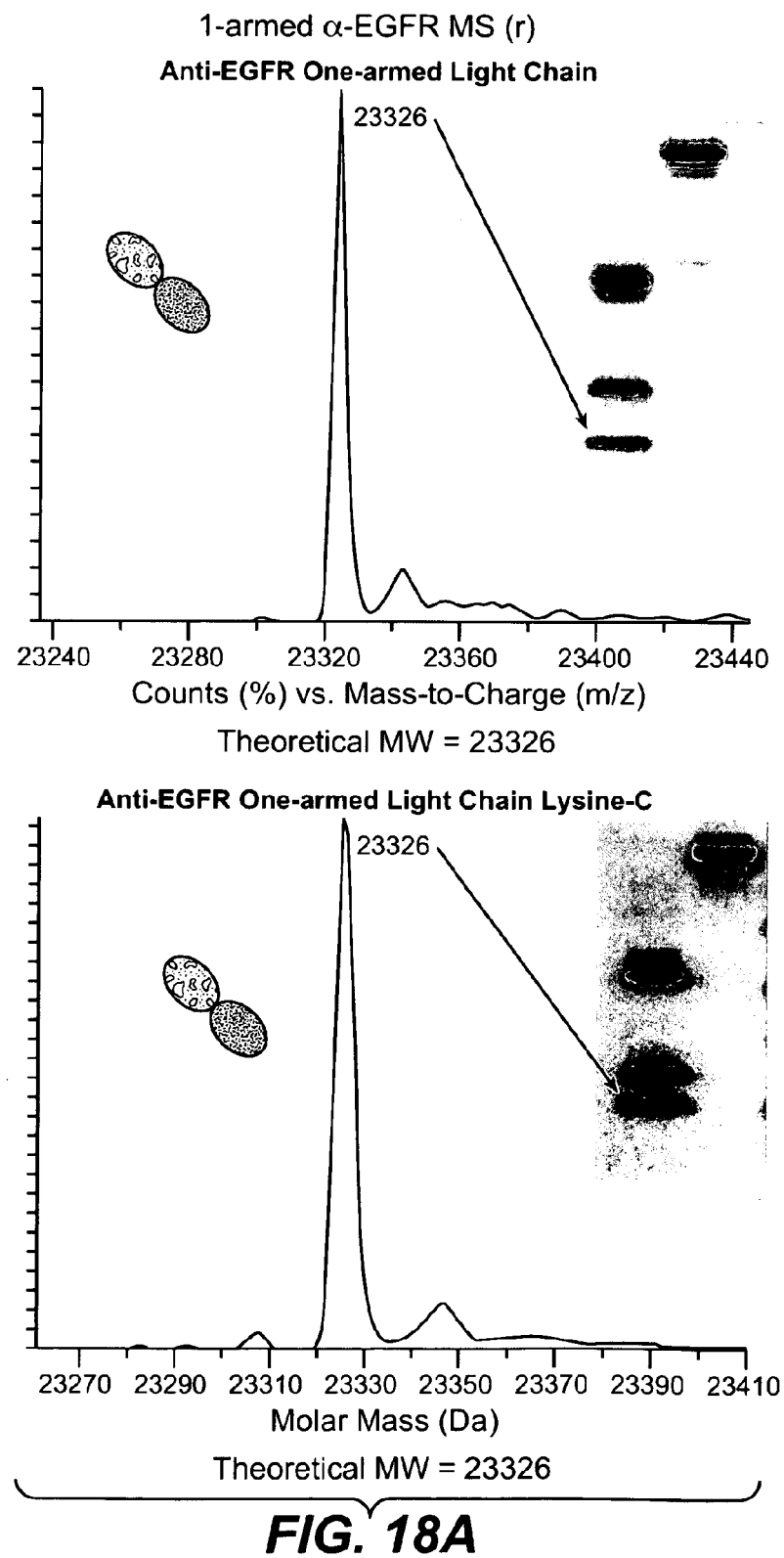
FIGS. 18A, 18B, and 18C are a series of graphs of mass spectrometry results and schematic diagrams showing that Lys-C endopeptidase does not cleave the LC (One-armed Light Chain; left panels), full-length HC (One-armed Heavy Chain; middle panels), or HC lacking the VH and CH1 domains (One-armed Fc; right panels) of an exemplary α-EGFR antibody, but does cleave the coiled coil domain from the HC and the HC lacking the VH and CH1 domains.
Figure 18B:
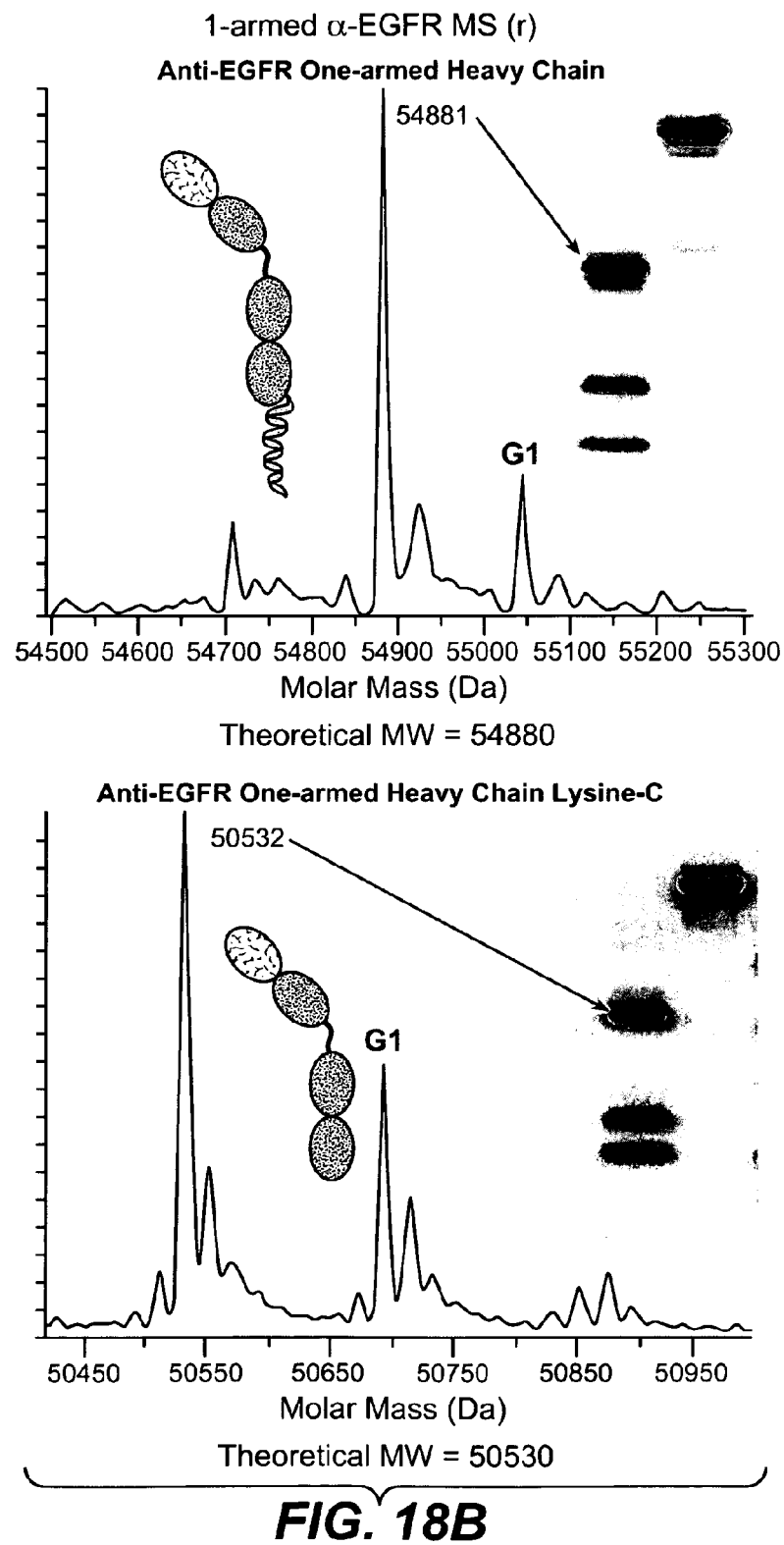
Figure 18C:
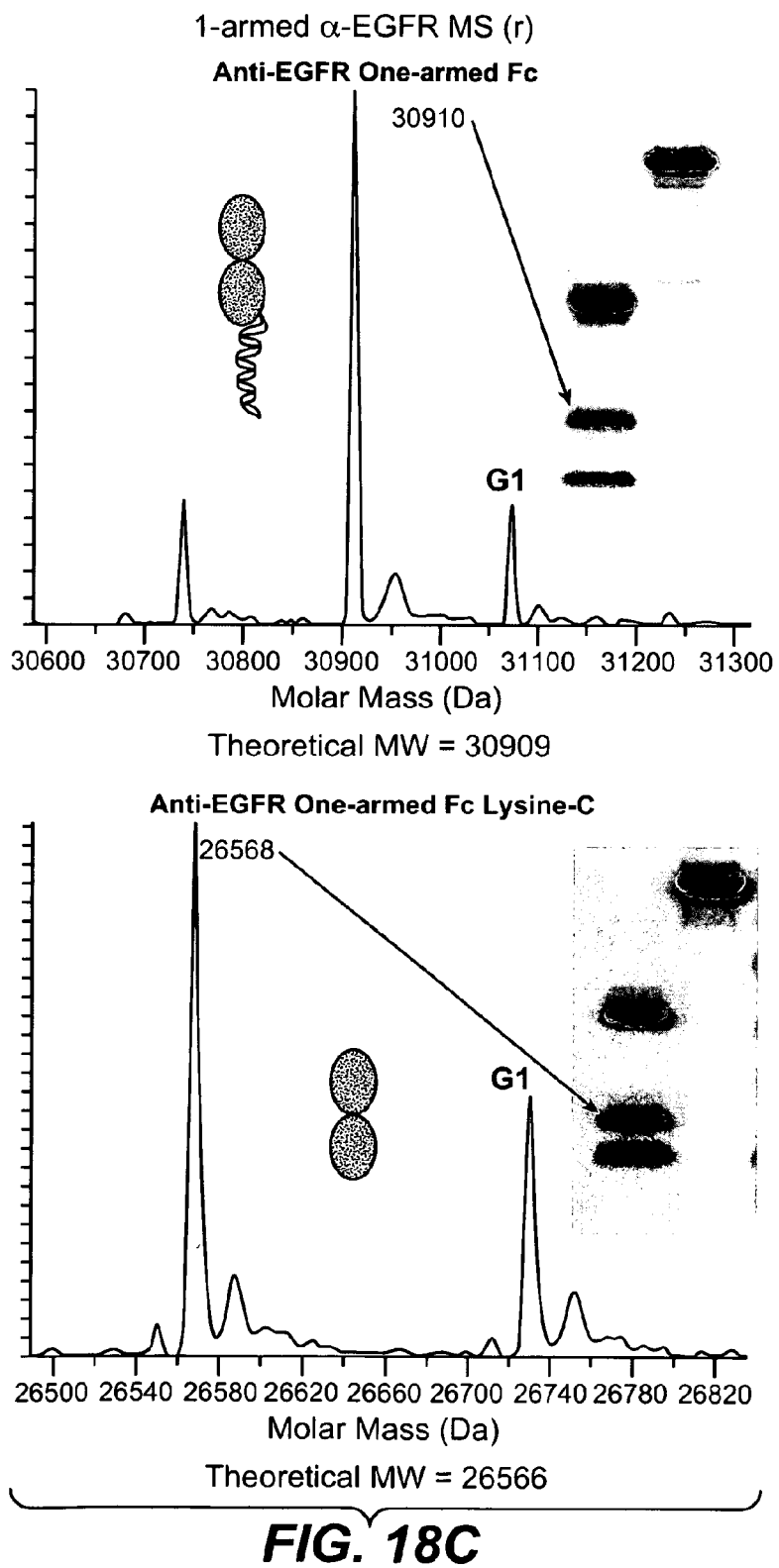

Similarly, mass spectrometry results demonstrated that the coiled coil was cleaved from an exemplary one-armed α-EGFR antibody using Lys-C endopeptidase (FIGS. 17A and B). In particular, the experimentally observed molecular mass was within the margin of error of the theoretical mass for both the one-armed antibody with the coiled coil and for the one-armed antibody without the coiled coil. As shown in FIGS. 18A-C, the theoretical molecular mass was within the margin of error of the experimentally observed molecular mass for each construct, indicating that Lys-C endopeptidase did not cleave the LC, HC, or HC lacking the VH and CH1 domains (one-armed Fc) of the exemplary α-EGFR antibody, but did cleave the coiled coil domains from the HC and HC lacking the VH anc CH1 domains.

In addition, mass spectrometry results showed that the coiled coil was cleaved from an exemplary tethered α-HER2/α-EGFR antibody using Lys-C endopeptidase (FIGS. 19A and B). As shown in FIG. 19B, the theoretical and experimentally observed molecular masses are within the margin of error for each construct. The coiled coil was also cleaved from the exemplary tethered α-HER2/α-EGFR antibody using Lys-C endopeptidase where the antibody had first treated with Lys-C endopeptidase and the sample then was subjected to mass spectrometry analysis (FIGS. 20A-B). The theoretical molecular mass for each construct is within the margin of error of the experimentally observed molecular mass, indicating that the coiled coil is indeed cleaved from the antibody sequence and that the antibody sequence itself is not cleaved. The mass spectrometry results, including the molecular mass (MS), for exemplary coiled coil containing antibodies are summarized in Table 2.

TABLE 2

| Sample | Conc. | LLS Agg. | MS Intact | MS Reduced | MS Cleaved, FL | MS Cleaved, Reduced |
|---|---|---|---|---|---|---|
| Common LC anti-FcεR1/ anti-FcγR2b | 0.64 mg/ml | 5.20% | 156503 | LC 23262 HC-1 54918 HC-2 55165 | 147800 | LC 23263 HC-1 50525 HC-2 50763 |
| One-Armed Anti-HER2 (antibody 1) | 1.0 mg/ml | | 109359 | LC 23440 FC 30907 HC 55016 | 100665 | LC 23440 FC 26568 HC 50665 |
| One-Armed EGFR | 1.0 mg/ml | 5.50% | 109119 | LC 23326 FC 30910 HC 54881 | 100419 | LC 23326 FC 26568 HC 50532 |
| Tethered anti-EGFR(D1.5)/ Anti-HER2 (antibody 1) | 10 mg/ml | 1.80% | 160057 | EGFR 79903 HER 80156 | 151367 | EGFR 75561 HER 75810 |

FL = Full Length;
Conc. = Concentration;
Agg. = Aggregation

Example 4

Characterization of Engineered Antibodies

To determine whether the exemplary engineered antibodies constructed using coiled coil heterodimerization domains retained the binding properties of the antibodies from which their sequences were derived, binding assays were conducted. These binding assays were run using the kinetics wizard program on the ForteBio Octet system. All samples tested were at a concentration of 25 μg/ml, a concentration that indicates saturation of the anti-human IgG probes in repeat experiments and among varying samples. The probes were loaded with the first sample for 15 minutes and washed for 30 seconds in PBS. All associations for the second and third samples were carried out for 10 minutes with 30-second PBS washes between associations.

Figure 15:
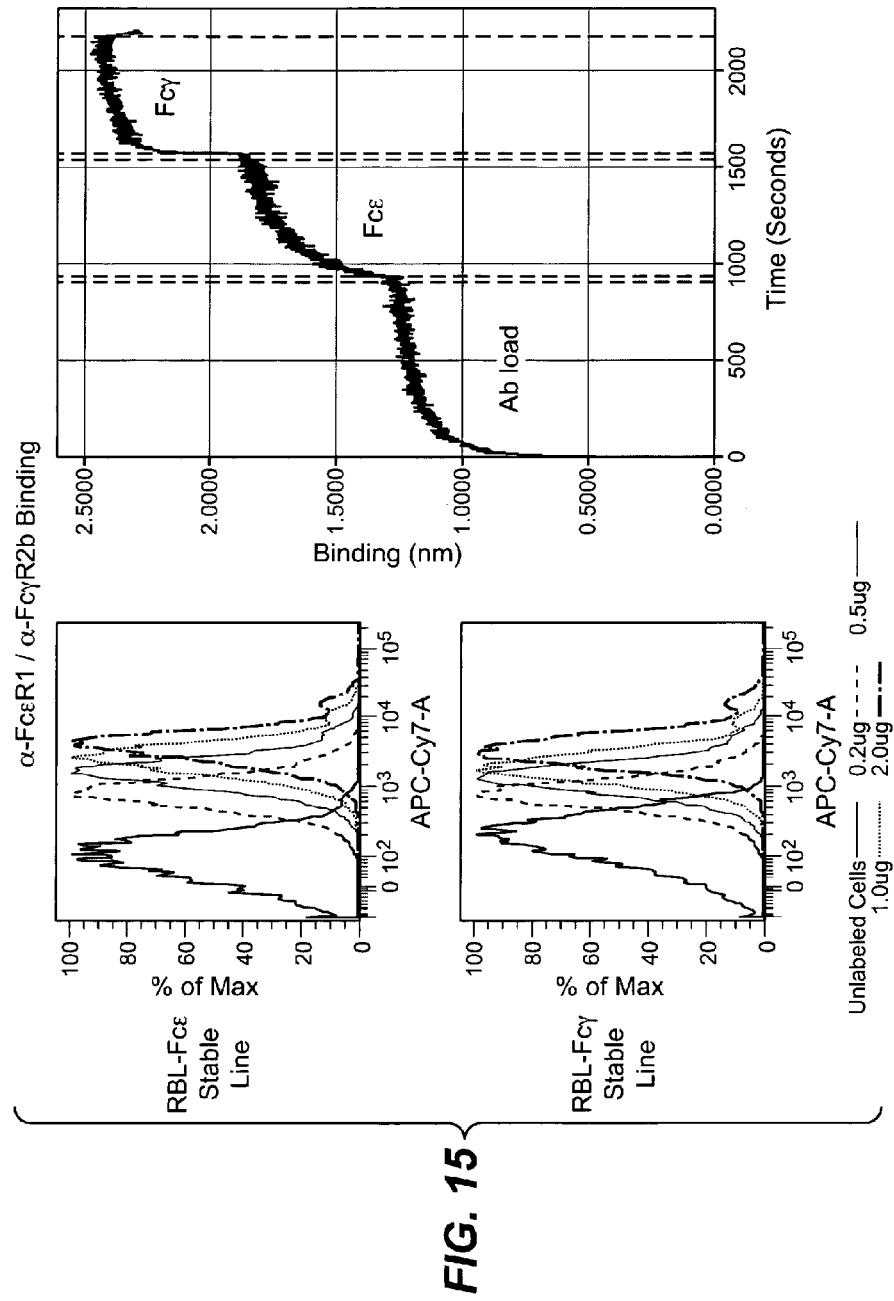
FIG. 15 is a series of graphs showing that an exemplary α-FcεR1/α-FcγR2b bispecific antibody specifically and simultaneously binds both of its antigens.

In particular, the common LC anti-FcεR1/anti-FcγR2b bispecific engineered antibody was loaded onto an anti-human IgG probe (Octet) by incubating the probe with 25 μg/ml of the antibody for 15 minutes followed by a PBS wash step. To evaluate binding, the loaded probe was incubated with 25 μg/ml of FcεR1 and subsequently 25 μg/ml of FcγR2b. A PBS wash step was performed between the two binding incubations. The data represented in FIG. 15 shows that the bispecific, engineered antibody simultaneously bound both of its antigens.

Figure 16:
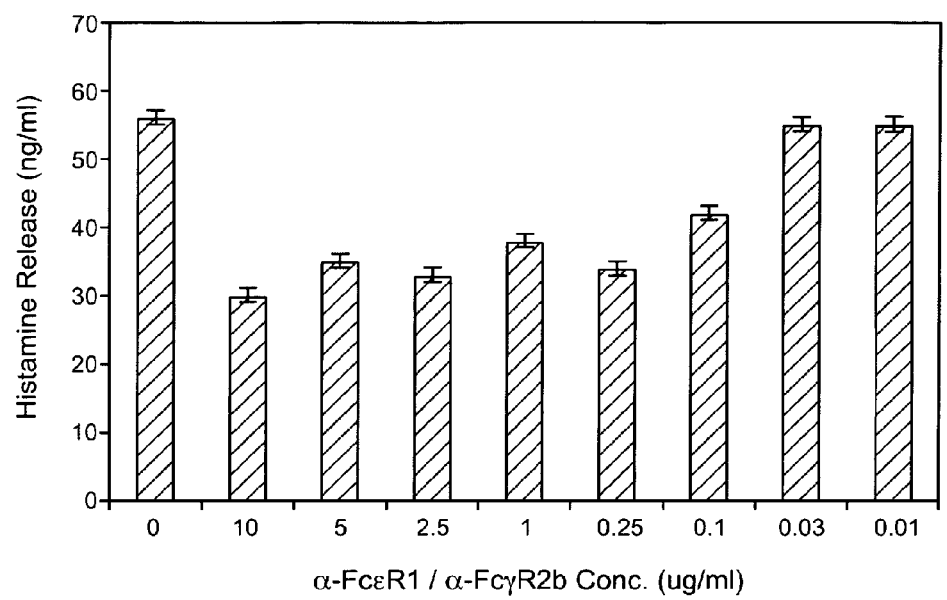
FIG. 16 is a graph showing the results for a histamine release assay with an exemplary common LC α-FcεR1/α-FcγR2b bispecific antibody. The concentration of the antibody used in the assay (in μg/ml) is indicated along the x-axis and the amount in histamine release (in ng/ml) is indicated along the y-axis.

To test the functionality of the engineered antibodies, a rat basophil leukemia (RBL) cell line created to express human FcεRIa and human FcγR2b1 was cultured for 72 hours at 37° C. with 1 μg/ml NP-specific human IgE (JW8.5.13) in complete growth media (MEM with Earle's salts Gibco Cat#11090, 1 mM glutamine (Genentech Inc.), 1 mM sodium pyruvate (Gibco Cat#11360-070), 0.1 mM nonessential amino acids (Gibco Cat#11140-050), 1.5 g/L sodium bicarbonate (Gibco Cat#25080-094), 15% fetal bovine serum (Hyclone Cat# SH30071.03). Cells were trypsinized and plated onto a 96-well, flat bottom tissue culture plate at 3.5×10⁵ cells/ml in 200 μl of complete growth media containing 1 μg/ml NP-specific human IgE and allowed to adhere for 2 hours. Next, the cells were washed three times with fresh media to remove unbound NP-specific human IgE. Cells were treated with 0-10 μg/ml of bispecific antibody and incubated for 1 hour at 37° C., prior to activation with antigen. Cells were activated by incubation with 0.1 μg/ml NP-conjugated ovalbumin (Biosearch Technologies, Inc. Cat. N-5051-10) or 45 minutes at 37° C. Following incubation, the histamine levels in the cell supernatants (cell culture medium) were measured by ELISA (enzyme linked immunosorbent assay) using a Histamine ELISA kit (KMI Diagnostics, Minneapolis, Minn.). Background histamine levels were obtained from cells treated with NP-specific human IgE alone with no activation (FIG. 16).

Octet binding studies were also performed for exemplary one-armed antibodies and tethered engineered antibodies. As a control, octet analysis was used to show that the wild-type anti-HER2 antibody 1 and wild-type α-EGFR antibody did not cross react with each other's antigen, but do bind their respective antigen (FIG. 21). To test the exemplary coiled coil containing antibodies, a one-armed anti-HER2 antibody 1 was loaded at 25 μg/ml onto an anti-human IgG antibody probe for 15 minutes, and the probe was subsequently washed with PBS for 30 seconds. The loaded probe was then incubated with EGFR ECD (extracellular domain) at 25 μg/ml, which showed no binding signal. The probe was then washed for 30 seconds in PBS and incubated with HER2 receptor ECD at 25 μg/ml, which showed a strong binding signal (FIG. 22; top trace).

A one-armed EGFR engineered antibody was loaded at 25 μg/ml onto an anti-human IgG antibody probe for 15 minutes and subsequently washed with PBS for 30 seconds. The probe was then incubated with HER2 ECD at 25 μg/ml, which showed no binding signal. The probe was washed for 30 seconds in PBS and incubated with EGFR ECD at 25 μg/ml, which showed a strong binding signal (FIG. 22; bottom trace).

A tethered bispecific anti-EGFR(D1.5)/anti-HER2 engineered antibody was incubated with an anti-human IgG antibody probe at 25 μg/ml for 15 minutes and subsequently washed with PBS for 30 seconds. This incubation loaded the probe with the bispecific antibody. The probe was then incubated with EGFR ECD at 25 μg/ml for 3 minutes followed by a 30 second PBS wash then subsequently incubated with the HER2 receptor ECD at 25 μg/ml for 3 minutes (FIG. 23A; top trace). For the results shown in the bottom trace of FIG. 23A, the bispecific loaded probe was first incubated with the HER2 receptor ECD then with the EGFR ECD. The data show that the bispecific, engineered antibody bound both the EGF and HER2 receptors simultaneously. As shown in FIG. 23B, the bispecific anti-EGFR (D1.5)/anti-HER2 antibody bound HER2 with a Kd of approximately 0.06 nM and bound EGF receptor with a Kd of approximately 0.660 nM.

To further analyze the binding characteristics of the engineered antibodies, cell based assays were performed on two cell lines, either NR6 expressing EGFR or HER2, or HCA7 cells which co-express both EGFR and HER2. Prior to performing the binding assays, cells were harvested and allowed to cool for 30 minutes on ice in binding buffer (RPMI medium with 1% fetal bovine serum (FBS), 10 mM HEPES, and 0.2% $NaN_3$). Unlabeled antibody was prepared at the desired starting concentration and diluted 1:1 with binding buffer to give multiple data points. Labeled antibody was prepared at one concentration to be used throughout the entire assay. Equilibrium binding studies were carried out using radiolabeled antibody competed with various concentrations of unlabeled antibody. Unlabeled antibody was placed in a 96-well plate, followed by labeled material, and cells were then added to the mixture. The plate was incubated for 2 hours at room temperature. After the incubation, the plate was harvested using Millipore Membrane Multi-Screen Plates to separate the solution from the cells. The cell-bound radiolabeled antibody was then counted on a Perkin Elmer Gamma counter and the data was analyzed using New Ligand software. The results of the affinity binding studies for one-armed and tethered engineered antibody constructs are summarized in Table 3.

TABLE 3

| Antibody | Cell Line | Kd (nM) |
| --- | --- | --- |
| Wt α-EGFR (D1.5) | NR6 expressing EGFR | 0.56 +/− 0.19 |
| α-EGFR Fab | NR6 expressing EGFR | 2.20 +/− 0.23 |
| 1-armed α-EGFR | NR6 expressing EGFR | 1.15 +/− 0.05 |
| Tethered α-EGFR/Anti-HER2 (antibody 1) | NR6 expressing EGFR | 2.79 +/− 0.13 |
| Wt Anti-HER2 (antibody 1) | NR6 expressing HER2 | 0.94 +/− 0.17 |
| Anti-HER2 (antibody 1) Fab | NR6 expressing HER2 | 2.78 +/− 0.11 |
| 1-armed Anti-HER2 (antibody 1) | NR6 expressing HER2 | 1.70 +/− 0.09 |
| Tethered α-EGFR/Anti-HER2 (antibody 1) | NR6 expressing HER2 | 5.13 +/− 0.36 |
| Tethered α-EGFR/Anti-HER2 (antibody 1) | HCA7 co-expressing EGFR and HER2 | 0.93 +/− 0.11 |
| Wt α-EGFR (D1.5) | HCA7 co-expressing EGFR and HER2 | 0.34 +/− 0.06 |
| Wt Anti-HER2 (antibody 1) | HCA7 co-expressing EGFR and HER2 | 0.12 +/− 0.03 |

The functional properties of exemplary engineered antibodies were also characterized biochemically. EGFR-expressing NR6 cells were plated in 12-well plates. Following serum starvation cells were pre-incubated with various concentrations of antibodies for 2 hours at 37° C. Subsequently, cells were stimulated with the TGFα for 12 minutes. Whole cell lysates were subjected to SDS-PAGE analysis, and immunoblots were probed with anti-phosphotyrosine, anti-phosphoAkt, or anti-tubulin as a loading control (FIG. 24). These results show that the exemplary α-EGFR(D1.5)/Anti-HER2 (antibody 1) engineered antibody, like the D1.5 IgG1 control antibody, inhibited TGFα-induced phosphorylation in EGFR-expressing NR6 cells in a dose-dependent manner.

For cell proliferation assays, cells were plated in 96-well plates (EGFR-NR6: 2,000 cells/well) (BT474: 10,000 cells/well) and incubated overnight at 37° C. The next day, the medium was removed and cells were treated in 1% serum containing medium. To compare the effect on cell growth of the α-EGFR(D1.5)/Anti-HER2 (antibody 1) engineered antibody to the D1.5 antibody on EGFR-NR6 cells, 3 nM TGFα was added to the medium, and cells were treated with various concentrations of antibodies. After 3 days Alamar-Blue was added to the wells and fluorescence was read using a 96-well fluorometer with excitation at 530 nm and emission of 590 nm. The results are expressed in relative fluorescence units (RFU) (FIG. 25). To compare the effect on cell growth of the α-EGFR(D1.5)/Anti-HER2 (antibody 1) engineered antibody to the anti-HER2 antibody 1, BT474 cells were treated in 1% serum containing medium with various concentrations of antibody (FIG. 26). After 5 days AlamarBlue assays were performed as described above. These results show that the exemplary α-EGFR(D1.5)/Anti-HER2 (antibody 1) engineered antibody, like the D1.5 IgG1 control antibody, inhibited TGFα-induced phosphorylation in EGFR-expressing NR6 cells in a dose-dependent manner and, like the anti-HER2 antibody 1, inhibited growth of BT474 cells.

Example 5

Pharmacokinetic Analysis of Engineered Antibodies

Pharmacokinetic studies were conducted to compare the pharmacokinetics (PK) of a bispecific engineered antibody with those of typical human IgG (hIgG) antibodies, and to determine the dosing for efficacy experiments. Like the D1.5 hIgG1 control antibody, the HER1/HER2 (D1.5/Anti-HER2 antibody 1) engineered antibody also showed cross-reactivity with mice. The anti-HER2 antibody 2 hIgG1 control antibody did not show cross-reactivity with mice.

The PK of the D1.5 hIgG1 positive control antibody was determined over a 10-day period using SCID Beige mice. In particular, the serum concentration of the antibody over time was determined using an Fc-Fc assay after administration of the antibody at various doses (0.5 mg/kg, 5 mg/kg, and 50 mg/kg). In addition, the serum concentration relative to dose was monitored for ten days using an Fc-Fc ELISA assay (FIG. 27). The area under the curve (AUC), normalized by dose, was also determined and is summarized in Table 4. The D1.5 hIgG1 antibody showed nonlinear PK in mice in the tested dose range.

TABLE 4

| Dose (mg/kg) | AUC till day 10 normalized by dose |
| --- | --- |
| 0.5 | 11.8 |
| 5 | 53.8 |
| 50 | 135 |

In addition, the PK of the anti-HER2 antibody 2 hIgG1 positive control antibodies was also determined over a 10-day period using SCID Beige mice. The serum concentration of the antibody over time was determined using an Fc-Fc ELISA or a HER2-ECD (extracellular domain) ELISA after administration of the antibody at 10 mg/kg. The AUC normalized by dose was also determined and is summarized in Table 5.

TABLE 5

| Molecule | Assay Format | AUC till day 10 normalized by dose |
| --- | --- | --- |
| 10 mg/kg anti-HER2 (antibody 2) hIgG1 | HER2-ECD | 42.9 |
| | Fc-Fc | 63.3 |

Similarly, the PK of the HER1(EGFR)/HER2 (D1.5/Anti-HER2 antibody 1) engineered antibody was determined over a ten-day period in SCID Beige mice. The serum concentration of the antibody over time was determined using an Fc-Fc ELISA or an EGFR-HER2 ELISA after administration of the antibody at various doses (0.5 mg/kg, 5 mg/kg, and 20 mg/kg). In addition, the serum concentration relative to dose was monitored for ten days using an Fc-Fc ELISA or EGFR-HER2 ELISA (FIG. 28). The AUC normalized by dose was also determined and is summarized in Table 6. The HER1(EGFR)/HER2 (D1.5/Anti-HER2 antibody 1) engineered antibody showed nonlinear PK in mice in the tested dose range.

TABLE 6

| Dose mg/kg | Assay format | AUC till day 10 normalized by dose |
|---|---|---|
| 0.5 | EGFR-HER2 | 83.8 |
|  | Fc-Fc | 104 |
| 5 | EGFR-HER2 | 42.6 |
|  | Fc-Fc | 53.2 |
| 20 | EGFR-HER2 | 95.0 |
|  | Fc-Fc | 148 |

Based on the results of the PK assays, the HER1(EGFR)/HER2 (D1.5/Anti-HER2 antibody 1) engineered antibody was determined to have similar or better exposure in mice over the tested time period (until day 10) in comparison to the D1.5 hIgG1 control antibo xzzzdy (FIG. 29).

Example 6

Producing Tethered Antibodies in Mammalian Cell Lines Engineered to Express Enzymes to Cleave Tethers For construction of the 26AA Furin cleavable tethered coiled coil antibodies (FIG. 30A) the VH domain (minus the signal sequence) of the desired antibody was first prepared using PCR wherein the 5' primer contained the 3' half of a GGS-Furin tether and terminated in a 5' BamHI site and the 3' primer terminated in a 3' ApaI site. The fragments were digested and cloned into a similarly prepared antibody-coiled coil backbone vector. The cognate LC of the desired antibody was then prepared using PCR wherein the 5' primer terminated in a 5' ClaI site and the 3' primer contained the 5' portion of the Furin-GGS tether and terminated in a 3' BamHI. The LC fragment was joined to its cognate HC (now in the antibody coiled coil backbone) by cloning the fragment in front of the VH via ClaI and BamHI. The completed tether sequence linking the CL to the VH was RCR-RGSGGSGGSGGSGGSGGSGRSRKRR (SEQ ID NO:35). For construction of the 26AA Furin-cleavable tether (—C) (FIG. 30B), two mutations were introduced into the above mentioned construct. The c-terminal Cys residue of the LC was mutated into and Ala residue using Stratagene's Quikchange II XL site-directed mutagenesis kit. According to the Kabat numbering system, the Cys terminal residue in the CL is at position 214. C220 of the HC was also mutated into an A to eliminate possible mis-folding due to this newly non-disulfide bonded Cys.

The methods used in constructing the 32AA Furin cleavable tether (FIG. 30C) was identical to the construction of the 26AA Furin cleavable tether except that the finished tether sequence was RKRKRRGSGGSGGSGGSGGSGGS-GRSRKRR (SEQ ID NO:36). For Furin over-expression, human or murine Furin was cloned into the pRK vector system and co-transfected with the antibody chain plasmids.

Carboxypeptidase B digestion (FIG. 30D) was carried out in 50 mM Sodium Borate pH8.0 for 1 hr. at 37 C with 1:20 wt:wt of CpB.

FIGS. 30A1-2 is a diagram and reduced Mass Spec (MS) results for the 26 amino acid FURIN cleavable tether. The heavy chain MS trace or graph shows a heavy chain (1) which has fully native n- and c-termini as well as a smaller amount of "full length antibody" (i.e., for these studies, was not cleaved at either Furin site (FL)). The light chain MS trace shows a peak corresponding to the LC plus the entire length of tether (1) and three other peaks (2-4) corresponding to the erosion of the 3' end of the tether, presumably due to Carboxypeptidase B activity in the CHO media. Evidenced by the lack of MS peaks within the region of the bottom trace indicated by the purple oval, there is no cleavage at the n-terminal Furin site. A cartoon of the resulting antibody is provided showing the non-native residues (underlined "R") as well as the 23-26 amino acid tether still attached to the c-terminus of the LC FIG. 30B1-2 is a diagram and reduced Mass Spec (MS) results for the 26 amino acid FURIN cleavable tether ("—C"). In this construct, the C residue was removed and replaced). The heavy chain MS trace shows a heavy chain (1) which has fully native n- and c-termini and no remaining "full length antibody" (FL). The light chain MS trace shows a peak corresponding to the LC plus 2 additional R residues (peak 2) plus one additional R residue (peak 3) and with it's native c-terminus (peak 4), presumably due to Carboxypeptidase B activity in the CHO media. A cartoon of the resulting antibody is provided showing the non-native residues (yellow) as well as the 0, 1 or 2 R residues still attached to the c-terminus of the LC.

FIG. 30C1-5 is a diagram and reduced Mass Spec (MS) results for the 32 amino acid FURIN cleavable tether. FIG. 30C3 shows a Heavy chain (peak 1) which has fully native n- and c-termini as well as a smaller amount of "full length antibody" (FL) which was not cleaved at either Furin site. FIGS. 30C2 and 30C3 show the resulting material obtained from CHO cells expressing native levels of Furin whereas FIGS. 30C4 and 30C5 show the resulting material obtained from CHO cells over-expressing Furin. FIG. 30C2 shows a peak corresponding to the LC plus the entire length of tether (peak 1) and five other peaks (peaks 2-6) corresponding to the erosion of the 3' end of the tether as well as an additional peak showing the LC with only the Furin recognition sequence still attached (peak 7) and five additional peaks (peaks 8-12) corresponding to the erosion of the c-terminal basic residues, presumably due to Carboxypeptidase B activity in the CHO media. FIG. 30C5 shows a heavy chain (1) which has fully native n- and c-termini and no remaining Full length antibody (FL) and FIG. 30C4 shows the LC now fully cleaved at the n-terminal Furin site (7) and four additional peaks (8-11) corresponding to the erosion of the c-terminal basic residues.

FIG. 30D2 is the same as FIG. 30C4. After a 1 hr. incubation at 37 C with 1:20 wt:wt of CpB, the remaining residues (corresponding to peaks 7-11) were completely removed resulting in a LC with a native c-terminus (FIG. 30D3). A cartoon is provided showing the only non-native residues to be the K222A mutation in each HC and an otherwise completely native (compared to parentals) bispecific antibody.

Example 7

Expression of Enzyme-Cleavable Tethered Coiled-Coil Multisecific Antibody in Eukaryotic Cells and Production of Multispecific Antibody without Tethers or Coiled Coils Tethered. coiled coil bispecific antibodies comprising two different VH and VL, each arm recognizing a different target, was produced in CHO cells overexpressing human furin as described above. The antibody, which also contained a K222A mutation, was treated with Lys-C endopeptidase to remove the coiled coil and with Carboxypeptidase B. It was not necessary to mutate the antibody any further in the hinge, and constant regions to achieve the final product. FIG. 31 shows a non-reduced mass spec trace of the finished product. Although a small amount of homodimer is observable in the non-reduced MS, this is due to the imbalance in the expression level of the two Ab chains and is easily corrected by modulating their relative expression levels. FIG. 32 shows a reduced mass spec trace of the finished product. The observed masses of the LCs and HCs confirm that the Ab chains all have native n- and c-termini.

These results show that this platform can be used for the production of several types of one-armed and bispecific antibodies in mammalian cells. In our hands, we have been able to generate mature bispecific antibodies differing from their parental wt Abs only by a single Lys-Ala mutation within the hinge region of each HC. These antibodies retain their specificity, and bispecific variants are able to bind both antigens simultaneously. These antibodies bind their antigens with high affinity.

What is claimed is:

1. An antibody comprising:
   (a) a first polypeptide comprising a VH domain linked to a constant domain and a first coiled coil domain (CC), wherein the first CC comprises a heptad repeat of Formula I:

$(X_1X_2X_3X_4X_5X_6X_7)_n$      (Formula I)(SEQ ID NO:29)

$X_1$ is a hydrophobic amino acid residue or Asparagine,
   $X_2$, $X_3$, and $X_6$ are each any amino acid residue,
   $X_4$ is a hydrophobic amino acid residue, and
   $X_5$ and $X_7$ are each a charged amino acid residue; and
   (b) a second polypeptide comprising a VH domain linked to a constant domain and a second coiled coil domain (CC), wherein the second CC comprises a heptad repeat of Formula II:

$(X'_1X'_2X'_3X'_4X'_5X'_6X'_7)_n$      (Formula II) (SEQ ID NO:30)

$X'_1$ is a hydrophobic amino acid residue or Asparagine,
   $X'_2$, $X'_3$, and $X'_6$ are each any amino acid residue,
   $X'_4$ is a hydrophobic amino acid residue, and
   $X'_5$ and $X'_7$ are each a charged amino acid residue;
   wherein n in Formula I and II is greater than or equal to 2; and
   wherein, in each heptad repeat, the first CC comprises an $X_5$ residue that is opposite in charge to the $X'_7$ residue in the second CC and the first CC comprises an $X_7$ residue that is opposite in charge to the $X'_5$ residue in the second CC;
   wherein the constant domain of a) and the constant domain of b) comprise a CH2 domain and an IgG1 CH3 domain;
   wherein the CC is linked to the C-terminal of the constant domain by a linker and wherein the linker is cleavable.

2. The antibody of claim 1, wherein the first and second polypeptides each comprise a VH and a CH1 domain.

3. The antibody of claim 2, wherein the first and second polypeptides each further comprise a hinge domain.

4. The antibody of claim 1, wherein the first and second polypeptides each comprise VH, CH1, hinge, CH2, and CH3 domains positioned relative to each other in an N-terminal to C-terminal direction: VH-CH1-hinge-CH2-CH3.

5. The antibody of claim 1, wherein said antibody further comprises a third and a fourth polypeptide, wherein said third polypeptide comprises a first VL domain and said fourth polypeptide comprises a second VL domain.

6. The antibody of claim 5, wherein said VH domain of the first polypeptide is linked to the VL domain of the third polypeptide by a tether and the VH domain of the second polypeptide is linked to the VL domain of the fourth polypeptide by a tether.

7. The antibody of claim 5, wherein the third polypeptide further comprises a first CL domain wherein said first VL and CL domains are positioned relative to each other within the third polypeptide in an N-terminal to C-terminal direction: VL-CL, and the fourth polypeptide further comprises a second CL domain, and wherein said second VL and CL domains are positioned relative to each other within the fourth polypeptide in an N-terminal to C-terminal direction: VL-CL.

8. The antibody of claim 5, wherein the sequences of said first VL domain and said second VL domain are the same.

9. The antibody of claim 1, wherein the N-terminus of the VH of at least one of said first or said second polypeptides is connected to the C-terminus of a CL with a tether.

10. An antibody comprising:
    (a) a first polypeptide comprising a VH domain linked to a constant domain comprising a CH2 and an IgG1 CH3 domain and a first coiled coil domain (CC), wherein the first CC comprises a heptad repeat of Formula I:

$(X_1X_2X_3X_4X_5X_6X_7)_n$      (Formula I) (SEQ ID NO:29)

$X_1$ is a hydrophobic amino acid residue or Asparagine,
    $X_2$, $X_3$, and $X_6$ are each any amino acid residue,
    $X_4$ is a hydrophobic amino acid residue, and
    $X_5$ and $X_7$ are each a charged amino acid residue; and
    (b) a second polypeptide comprising a constant domain and a second coiled coil (CC), wherein the constant domain comprises a CH2 and an IgG1 CH3 domain and wherein the second CC comprises a heptad repeat of Formula II:

$(X'_1X'_2X'_3X'_4X'_5X'_6X'_7)_n$      (Formula II) (SEQ ID NO:30)

$X'_1$ is a hydrophobic amino acid residue or Asparagine,
    $X'_2$, $X'_3$, and $X'_6$ are each any amino acid residue,
    $X'_4$ is a hydrophobic amino acid residue, and
    $X'_5$ and $X'_7$ are each a charged amino acid residue;
    wherein n in Formula I and II is greater than or equal to 2; and
    wherein, in each heptad repeat, the first CC comprises an $X_5$ residue that is opposite in charge to the $X'_7$ residue in the second CC and the first CC comprises an $X_7$ residue that is opposite in charge to the $X'_5$ residue in the second CC;
    wherein the CC is linked to the C-terminal of the constant domain by a linker wherein the linker is cleavable.

11. The antibody of claim 10, wherein the first polypeptide comprises a VH and CH1 domain.

12. The antibody of claim 11, wherein the first polypeptide further comprises a hinge domain.

13. The antibody of claim 10, wherein the first polypeptide comprises VH, CH1, hinge, CH2, and CH3 domains positioned relative to each other in an N-terminal to C-terminal direction: VH-CH1-hinge-CH2-CH3.

14. The antibody of claim 10, wherein the antibody further comprises a third polypeptide, wherein the third polypeptide comprises a VL domain.

15. The antibody of claim 14, wherein said third polypeptide further comprises a CL domain, and the VL and CL domains are positioned relative to each other in an N-terminal to C-terminal direction: VL-CL.

16. The antibody of claim 10, wherein the N-terminus of the VH of said first polypeptide is connected to the C-terminus of a CL with a tether.

17. The antibody of claim 1, wherein said hydrophobic amino acid residue in any of $X_1$, $X'_1$, $X_4$, and $X'_4$ is selected from the group consisting of Alanine, Valine, Leucine, Isoleucine, Tryptophan, Phenylalanine, and Methionine.

18. The antibody of claim 1, wherein said charged amino acid residue in any of $X_5$, $X'_5$, $X_7$, and $X'_7$ is selected from the group consisting of Lysine, Arginine, Histidine, Aspartic Acid, and Glutamic Acid.

19. The antibody of claim 1, wherein, in at least one heptad repeat of said first CC, $X_1$ is Asparagine, and wherein the respective $X'_1$ is Asparagine in at least one heptad repeat of said second CC.

20. The antibody of claim 1, wherein
(a) the first CC comprises a heptad repeat wherein
$X_1$ is Leucine or Asparagine,
$X_2$ is Alanine or Glutamine,
$X_3$ is Alanine or Glutamine,
$X_4$ is Leucine,
$X_5$ is Glutamic Acid,
$X_6$ is Lysine or Tryptophan, and
$X_7$ is Glutamic Acid; and
(b) the second CC comprises a heptad repeat wherein
$X'_1$ is Leucine or Asparagine,
$X'_2$ is Alanine or Glutamine,
$X'_3$ is Alanine or Glutamine,
$X'_4$ is Leucine,
$X'_5$ is Lysine,
$X'_6$ is Lysine or Tryptophan, and
$X'_7$ is Lysine.

21. The antibody of claim 1, wherein n is greater than or equal to 3.

22. The antibody of claim 21, wherein n is greater than or equal to 4.

23. The antibody of claim 1, wherein the first CC is linked C-terminal to a CH3 domain of the first polypeptide and the second CC is linked C-terminal to a CH3 domain of the second polypeptide.

24. The antibody of claim 1, wherein a Lys-C endopeptidase cleavage site is located N-terminal to at least one of said first or said second CC.

25. The antibody of claim 1, wherein the antibody is multispecific.

26. The antibody of claim 25, wherein the antibody is capable of binding at least 2 antigens.

27. The antibody of claim 25, wherein the antibody a capable of binding at least 2 epitopes on the same antigen.

28. The antibody of claim 1, wherein said antibody is bispecific.

29. The antibody of claim 6, wherein said tether comprises Glycine (G) and Serine (S) residues.

30. The antibody of claim 6, wherein said tether is between 15 and 50 amino acids in length.

31. The antibody of claim 30, wherein said tether is between 20 and 26 amino acids in length.

32. The antibody of claim 6, wherein said tether comprises GGS repeats.

33. The antibody of claim 6, wherein said tether is cleavable.

34. The antibody of claim 24, wherein said antibody comprises a mutation that removes a Lys-C endopeptidase cleavage site.

35. The antibody of claim 34, wherein said mutation that removes a Lys-C endopeptidase cleavage site is in a hinge domain.

36. The antibody of claim 35, wherein said antibody has a K222A substitution (EU numbering system).

37. The antibody of claim 1, wherein said linker is cleavable by one or more of the following endopeptidases: Furin, Thrombin, Genenase, Lys-C, Arg-C, Asp-N, Glu-C, Factor Xa, Tobacco Etch Virus Protease (TEV), Enterokinase, Human Rhinovirus C3 protease (HRV C3), or Kininogenase.

38. The antibody of claim 1, wherein said linker comprises an Asparagine-Glycine peptide bond.

39. The antibody of claim 38, wherein said Asparagine-Glycine peptide bond is cleavable by hydroxylamine.

40. The antibody of claim 1, wherein said antibody comprises a constant region conjugated to a cytotoxic agent.

41. The antibody of claim 1, wherein said antibody is expressed by a mammalian cell.

42. The antibody of claim 41, wherein said mammalian cell is a CHO cell.

43. The antibody of claim 1, wherein said antibody is expressed by a prokaryotic cell.

44. The antibody of claim 43, wherein said prokaryotic cell is an *E. coli* cell.

45. A method of producing an antibody, said method comprising the step of culturing a cell comprising a vector encoding the antibody of claim 1 in a culture medium.

46. The method of claim 45, wherein said method further comprises recovering said antibody from said cell or said culture medium.

47. The method of claim 46, further comprising the steps of
(a) capturing said antibody on a column comprising Protein A,
(b) eluting said antibody from said column, and
(c) diluting said eluted antibody into a solution containing a chaotropic agent or mild detergent.

48. The method of claim 47, wherein said chaotropic agent or mild detergent is Arginine, Guanidine-HC1, urea, lithium perchlorate, Histidine, Sodium Dodecyl Sulfate (SDS), Tween, Triton, or NP-40.

49. The antibody of claim 33, wherein said tether is cleavable by one or more of the following endopeptidases: Furin, Thrombin, Genenase, Lys-C, Arg-C, Asp-N, Glu-C, Factor Xa, Tobacco Etch Virus Protease (TEV), Enterokinase, Human Rhinovirus C3 protease (HRV C3), or Kininogenase.

50. The antibody of claim 33, wherein said tether comprises an Asparagine-Glycine peptide bond.

* * * * *